(12) United States Patent
Finzel et al.

(10) Patent No.: US 7,041,690 B2
(45) Date of Patent: May 9, 2006

(54) INHIBITORS OF HCV NS5B POLYMERASE

(75) Inventors: Barry Craig Finzel, Dexter, MI (US); Hua Gao, Salem, CT (US); Meredith L. Greene, Detroit, MI (US); Rebecca J. Gross, Kalamazoo, MI (US); Richard Allen Nugent, Ashland, MA (US); Jeffrey A. Pfefferkorn, Ann Arbor, MI (US)

(73) Assignee: Pharmacia & Upjohn Company, LLC, Kalamazoo, MI (US)

( * ) Notice: Subject to any disclaimer, the term of this patent is extended or adjusted under 35 U.S.C. 154(b) by 96 days.

(21) Appl. No.: 10/609,959

(22) Filed: Jun. 30, 2003

(65) Prior Publication Data
US 2004/0142980 A1 Jul. 22, 2004

Related U.S. Application Data

(60) Provisional application No. 60/392,759, filed on Jul. 1, 2002.

(51) Int. Cl.
*A61K 31/426* (2006.01)
*C07D 277/20* (2006.01)
(52) U.S. Cl. ...................... 514/365; 548/204
(58) Field of Classification Search ................ 548/204; 514/365
See application file for complete search history.

(56) References Cited

FOREIGN PATENT DOCUMENTS

| WO | WO 96/35953 | 5/1996 |
|---|---|---|
| WO | WO 09833501 | 1/1998 |
| WO | WO 00/06529 | 7/1999 |
| WO | WO 00/10573 | 8/1999 |
| WO | WO 01/58853 A1 | 2/2001 |
| WO | WO 0177091 A2 | 4/2001 |
| WO | WO 02/04425 A2 | 7/2001 |

OTHER PUBLICATIONS

Vranicar et al(2002): STN International CAPLUS database, Columbus (Ohio), Accession No., 2002:288632.*
XP-002260066 "Analogs of biologically active compounds. V. Synthesis and oxidative decarboxylation of 1-phenyl-3-(4-chlorophenyl)-4-pyrazolylpyruvic acid", Acta Universitatis Palackianae Olomucensis, Fucultas rerum Naturalium, 1990, vol. 97, No. Chem. 29, pp 145-50.
XP-002260067 "The structure of .beta-heteroaryl-.alpha., .beta.-dehydro-alpha.-amino acid derivatives, intermediates in the synthesis of fused pyran-2-ones. Substituted methyl (Z)-benzoylamino-3-(5-oxopyrazoliny-4) propenoates.", J Heterocyclic Chem., , 1991, vol. 28, No. 8, pp 1961-4.
XP-002260068 "Synthesis of 3-methyl-1-phenyl-and 1, 3-diphenyl-5-oxo-, DELTA.2-pyrazoline-4-methylene derivatives", Ind J Chem., Sect. B. 1983, vol. 228, No. 7, pp 637-9.

XP002260069 "Determination of acids and their strength in isobutyl methyl ketone.", Coll. Czech. Chem. Comm., 1982, vol. 47, No. 4, pp 1203-15.
XP002260070 "reactions of 4-'(1,3-diphenyl-4-pyrazolyl) methtlene!-2-phenyl-2-oxazolin-5-one with Grignard reagents and diazoalkanes",J. Prakt. Chem., 1974, vol. 316, No. 3, pp 363-8.
XP-002260071 "Chemical reaction of 4-'4'-(1', 3'-diphenylpyrazolyl) methylene!-2-phenyl-5-oxo(4H)-1, 3-thiazole",Act. Chim. Acad, Sci. Hungar, 1974, vol. 80, No. 1, pp 119-23.
XP-002260065 J. of the Chem Soc, Perkin Trans 1(2002) , vol. 5, 2002, pp 675-681.
XP-004150869 Tetrahedron vol. 55, No. 1, 1999, pp 271-278.
XP-002190259 "Practice of Medicinal Chemistry",Practice of Medicinal Chemistry, 1996, pp 203-237.
Kato et al. Proc. Natl. Acad. Sci. USA (1990), 87; 9524-9528.
Van Doorn, L.J., J. of Medical Virology (1994), 43, 345-356.
Lau, J.Y. et al., J Infect Dis. (1995), 171(2), 281-9.
Behrens et al. EMBO J (1996) 15: 12-22.
Houghton, M., Hepatitis C viruses Fields Virology: (1996), Third Edition, edited by B.N. Fields, D.M. Knoip e, P.M. Howley, et al, Lippincott-Raven Publishers, Philadelphia, pp 1035-1058.
Lohmann et al. (1997) J Viro. 71: 8416-8428.
Ishido et al, Biochem. Biophys. Res. Comm. (1998), 244: 35-40.
Ferrari, E., et at., J.Virol. (1999), 73: 1649-1654.
Webster, G., et al. Balliere's Clinical Gastroenterology (2000), 14, 229-240.

* cited by examiner (Continued)

Primary Examiner—Golam M. M. Shameem
(74) Attorney, Agent, or Firm—Jeffrey H. Tidwell; Bryan C. Zielinski

(57) ABSTRACT

The present invention provides compounds of Formula I, compositions and methods that are useful for treating viral infections and associated diseases, particularly HCV infections and associated diseases

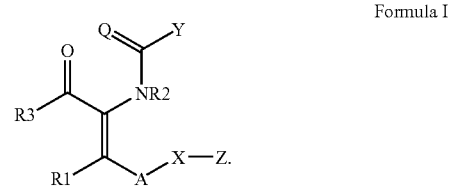

Formula I 2 Claims, No Drawings

INHIBITORS OF HCV NS5B POLYMERASE

CROSS REFERENCE

This application claims the benefit of the following provisional application: U.S. Ser. No. 60/392,759, filed Jul. 1, 2002, under 35 USC 119(e)(i), which is incorporated herein by reference in its entirety.

FIELD OF THE INVENTION

The present invention relates to compounds, process for their synthesis, compositions and methods for the treatment and prevention of hepatitis C virus (HCV) infection. In particular, the present invention provides novel compounds, pharmaceutical compositions containing such compounds and methods for using these compounds in the treatment or prevention of HCV infection. The present invention also provides processes and intermediates for the synthesis of these compounds.

BACKGROUND OF THE INVENTION

Hepatitis C virus (HCV) is the major etiological agent of post-transfusion and community-acquired non-A non-B hepatitis worldwide. It is estimated that over 150 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulins treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy.

Therefore, a need exists for the development of effective antiviral agents for treatment of HCV infection that overcomes the limitations of existing pharmaceutical therapies.

SUMMARY OF THE INVENTION

The present invention provides compounds, compositions and methods that are useful for treating viral infections and associated diseases, particularly HCV infections and associated diseases. The compounds of the invention inhibit viral replication, preferably HCV replication. The methods of the invention comprise administering to an infected or susceptible host a therapeutically or prophylactically effective amount of a compound as represented by Formula 1, or a pharmaceutically acceptable salt or prodrug thereof.

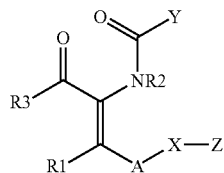

Formula 1

In Formula 1, X represents a covalent bond or is selected from the group NR2, S, O, C=O, C(R2)(R'2), $CF_2$, $CCl_2$, CR2OR'2, CR2NR'2, SO, and $SO_2$;

Y is selected from the group substituted or unsubstituted alkyl, substituted or unsubstituted heteroalkyl, substituted or unsubstituted aryl, and substituted or unsubstituted heteroaryl;

Z is selected from the group substituted or unsubstituted aryl and substituted or unsubstituted heteroaryl;

any two adjacent substiuents of Y or Z may be taken together to form a fused carbocyclic or heterocyclic ring of 5 to 7 members;

Y is selected from the group substituted or unsubstituted alkyl, substituted or unsubstituted heteroalkyl, substituted or unsubstituted aryl, and substituted or unsubstituted heteroaryl; heteroaryl, cycloalkyl and aralkyl;

R2 is H, alkyl, alkenyl, heteroalkyl, cycloalkyl, heterocloalkyl, aryl, aralkyl, heteroaryl or heteroaralkyl;

R3 is selected from the group H, OH, OR2, N(R2)(R'2) and N(R2)-T-W where T represents a substituted or unsubstituted alkyl or cycloalkyl group of 1–8 carbons;

W is selected from the group OH, N(R2)(R'2), CON(R2)(R'2), OCO N(R2)(R'2), NCON(R2)(R'2) and $CO_2R2$ A represents a substituted or unsubstituted aromatic or heteroaromatic ring of 5 or 6 members;

the substituents X and R1C= are connected to A in a 1,2 1,3 or 1,4 spatial relationship;

the substituents A and COR3 have an E (trans) configuration with respect to the double bond to which they are attached.

DETAILED DESCRIPTION OF THE INVENTION

Abbreviations and Definitions

The abbreviations used herein are conventional, unless otherwise defined.

The terms "treat", "treating" and "treatment" refer to a method of alleviating or abrogating a disease and/or its attendant symptoms.

The terms "prevent", "preventing" and "prevention" refer to a method of barring a subject from acquiring a disease. As used herein, "prevent", "preventing" and "prevention" also include reducing a subject's risk of acquiring a disease.

The term "therapeutically effective amount" refers to that amount of the compound being administered sufficient to prevent development of or alleviate to some extent one or more of the symptoms of the disease being treated.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

"Flaviviridae virus", as used herein, refers to a virus of the family Flaviviridae, which family includes the Flavivirus, Pestivirus and Hepacivirus or hepatitis C-like virus genera. Representative species of the genus Flavivirus include yellow fever virus, tick-borne encephalitis virus, Rio Bravo virus, Japanese encephalitis virus, Tyuleniy virus, Ntaya virus, Uganda S virus, Dengue virus and Modoc virus. Representative species of the genus Pestivirus include bovine diarrhea virus, border disease virus and hog cholera virus. A representative species of the genus of hepatitis C-like viruses is hepatitis C virus. Unassigned viruses in the family Flaviviridae are included in the meaning of Flaviviridae virus.

The term "modulate" refers to the ability of a compound to increase or decrease the catalytic activity of a viral polymerase, e.g. a viral RNA polymerase. A modulator preferably activates the catalytic activity of a viral polymerase or more preferably activates or inhibits the catalytic activity of a viral polymerase depending on the concentration of the compound exposed to the viral polymerase or most preferably inhibits the catalytic activity of a viral polymerase.

The term "modify" refers to the act of altering, in whole or in part, the structure of a molecule, e.g., a protein. Modification may be covalent or noncovalent, and includes, but is not limited to, aggregation, association, substitution, conjugation and/or elimination of a chemical group. Modification may alter the function or other properties (e.g., chemical, physical) of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_8$ means 1–8 eight carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, I- and 3-propynyl, 3-butynyl, and the higher homologs and isomers. The term "alkylene" by itself or as part of another substituent means a divalent radical derived from an alkane, as exemplified by —$CH_2CH_2CH_2CH_2$—. A "lower alkyl" or "lower alkylene" is a shorter chain alkyl or alkylene group, having eight or fewer carbon atoms.

The terms "alkoxy", "alkylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NR'15R15" wherein the R groups can be the same or different alkyl groups.

The term "heteroalkyl," by itself or in combination with another term, means, unless otherwise stated, a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$. Also included in the term "heteroalkyl" are those radicals described in more detail below as "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2CH_2$—NH—$CH_2$—. For heteroalkylene groups, heteroatoms can also occupy either or both of the chain termini. Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl, include cyclopentyl, cyclohexyl, 1-cyclohexenyl, 3-cyclohexenyl, cycloheptyl, and the like. Examples of heterocycloalkyl include 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "Fluoroalkyl," are meant to include monofluoroalkyl and polyfluoroalkyl.

The term "aryl," employed alone or in combination with other terms (e.g., aryloxy, arylthioxy, aralkyl) means, unless otherwise stated, an aromatic substituent which can be a single ring or multiple rings (up to three rings) which are fused together or linked covalently. The term "heteroaryl" is meant to include those aryl rings which contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-napthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 1-indolyl, 5-indolyl, 1-isoquinolyl, 5-isoquinolyl, 2-quinoxalinyl, 5-quinoxalinyl, 3-quinolyl, and 6-quinolyl.

Substituents for each of the above noted aryl ring systems are selected from the group of acceptable substituents described below. The term "aralkyl" is meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl . . . heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R"—SR', —halogen, —SiR'R"R, —OC(O)R', —C(O)R', —CO$_2$R', CONR'R", —OC(O)NR'R"—NR'C(O)R', —NR'—C(O)NR"R''', —NR'COOR", —NH—C(NH$_2$)=NH, —NR'C(NH$_2$)=N—H, —NH—C(NH$_2$)=NR', —S(O)R', S(O)$_2$R', —S(O)$_2$NR'R", —CN and —NO$_2$ in a number ranging from zero to (2N+1), where N is the total number of carbon atoms in such radical. R', R" and X" each independently refer to hydrogen, unsubstituted Cl-C0alkyl and heteroalkyl, unsubstituted aryl, aryl substituted with 1–3 halogens, unsubstituted alkyl, alkoxy or thioalkoxy groups, or aryl-(C1–C4)alkyl groups. When R' and R" are attached to the same nitrogen atom, they can be combined with the nitrogen atom to form a 3–7 membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and are selected from: halogen, —OR, —OC(O)R, —NR'R", —SR, —R', —CN, —NO$_2$, —CO$_2$R', —CONR'R:', —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(CI-C4)alkoxy, and perfluoro(CI-C4)alkyl, in a number ranging from zero to the total number of open valences on the aromatic ring system; and where R', R" and R''' are independently selected from hydrogen, (C1–C8)alkyl and heteroalkyl, unsubstituted aryl, (unsubstituted aryl)-(C1–C4)alkyl, and (unsubstituted aryloxy-(C$_1$–C$_4$)alkyl.

Two of the substituents on adjacent atoms of the aryl ring may optionally be replaced with a substituent of the formula —S—C(O)—(CH$_2$)q—R—, wherein S and R are independently —NH—, —O—, —CH$_2$— or a single bond, and the subscript q is an integer of from 0 to 2. Alternatively, two of the substituents on adjacent atoms of the aryl ring may optionally be replaced with a substituent of the formula -A-(CH$_2$)$_w$—B—, wherein A and B are independently —CH$_2$—, —O—, —NH—, —S—, —S(O)—, —S(O)$_2$—, —S(O)$_2$NR'— or a single bond, and w is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_w$-G-(CH$_2$)$_{w'}$—, where w and w' are independently integers of from 0 to 3, and G is —O—, —NR'-, —S—, —S(O)—, —S(O)$_2$—, or —S(O)$_2$NR'—. The substituent R' in —NR'— and —S(O)$_2$NR'— is selected from hydrogen or unsubstituted (C1–C6)alkyl.

As used herein, the term "heteroatom" is meant to include oxygen (O), nitrogen (N),) and sulfur(S).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such . . . as arginate and the like, and salts of organic acids like glucuronic or galactouronic acids and the like (see, for example, Berge, S. M., et. al. (1977) J. Pharm. Sci., 66:1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner.

The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex-vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention unless otherwise stated.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I or carbon-14 ($^{14}$C). All isotopic variations of the compounds of the present invention, whether radioactive or not, are intended to be encompassed within the scope of the present invention.

DESCRIPTION OF THE EMBODIMENTS

General Viral polymerases are attractive targets for antiviral drug development. For example, inhibitors of Viral RNA polymerase activity have been described; see, for example, JAEN, Juan, et.al., WO 0177091, Altamura et. al., WO 00/06529 and Bailey et. al., WO 00/10573, which references are incorporated by reference herein.

The HCV protein NS5B is an RNA dependent RNA polymerase, see, e.g., Lohmann et al. (1997) J Virol. 71:8416–8428, Behrens et al. (1996) EMBO J 15:12–22 and Ishido et al. (1998) Biochem. Biophys. Res. Comm. 244: 35–40, which references are incorporated by reference herein. The sequence of various genotypes of HCV NS5B are known (Kato et al. (1990) Proc. Natl. Acad. Sci. USA. 87:9524–9528; Webster, G., et al. (2000) Balliere's Clinical Gastroenterology 14, 229–240; van Doom, L. J. (1994) J. of Medical Virology 43, 345–356; Houghton, M. (1996) Hepatitis C viruses Fields Virology: Third Edition, edited by B. N. Fields, D. M. Knipe, P. M. Howley, et al. Lippincott-Raven Publishers, Philadelphia, pp. 1035–1058; Lau, J. Y. et.al., J Infect Dis. 1995, 171(2), 281–9). However, NS5B contains sequence motifs that are highly conserved among all the RNA-dependent RNA polymerases characterized to date.

The present invention provides compounds having antiviral activity. It is believed that the compounds of the invention will block viral replication by specifically inhibiting the activity of a viral polymerase. Viral RNA polymerase is required for the transcription of genomic RNA, which process is required for replication of the genome of an RNA virus. Therefore, inhibition of viral RNA polymerase will inhibit viral replication.

Non-limiting examples of the embodiments are given in Table 1.

TABLE 1

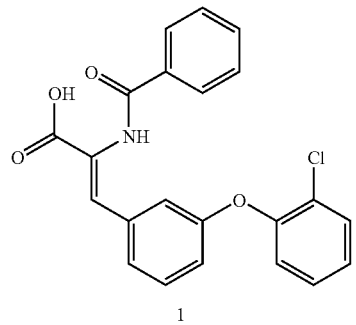

1

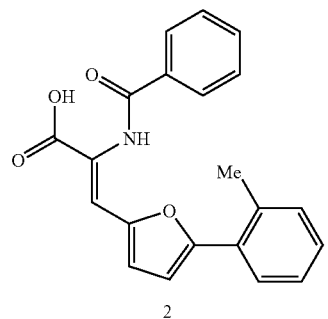

2

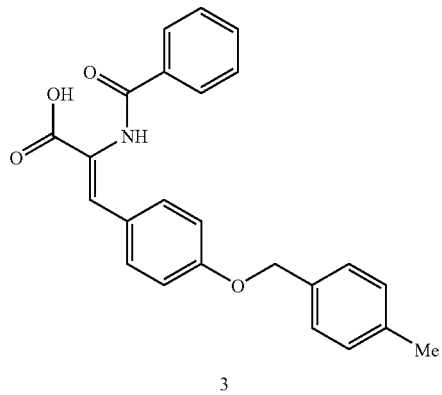

3

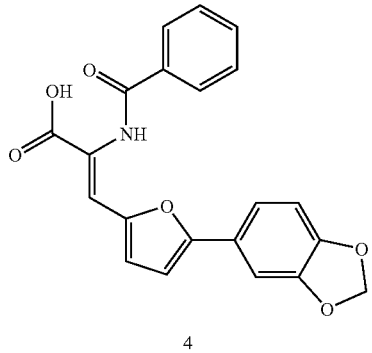

4

TABLE 1-continued
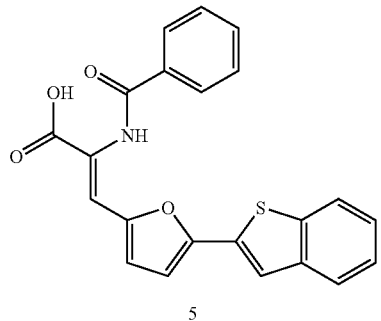
5
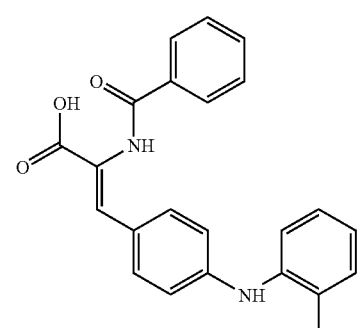
6
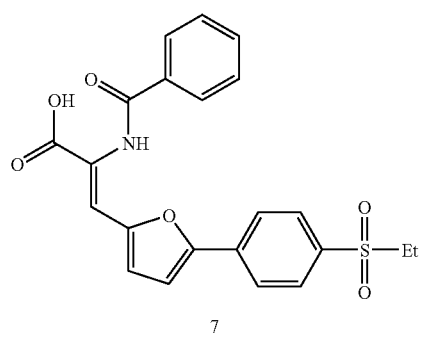
7
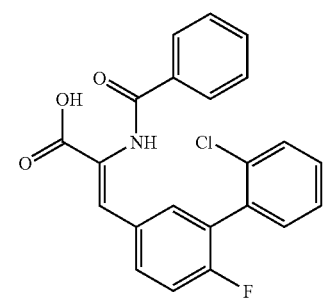
8
TABLE 1-continued
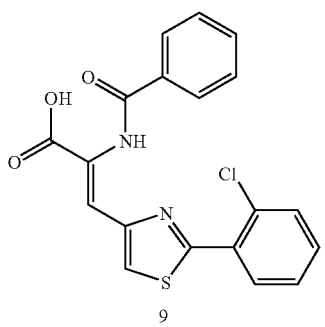
9
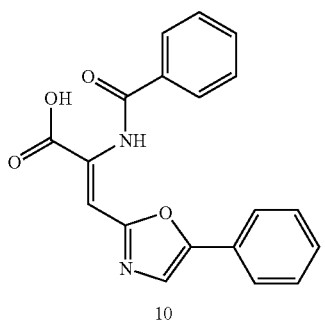
10
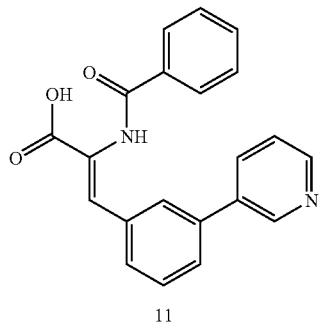
11
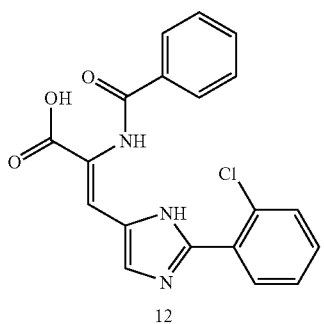
12

TABLE 1-continued

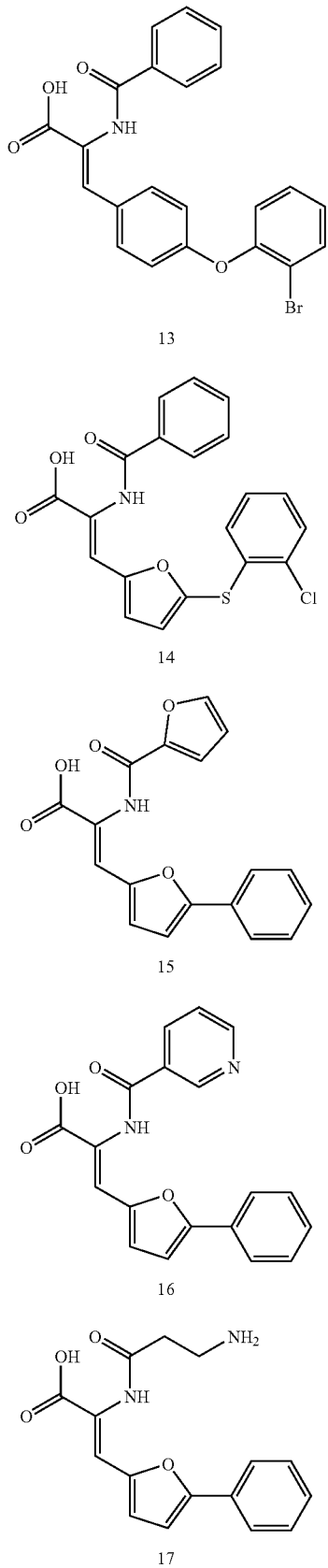

TABLE 1-continued

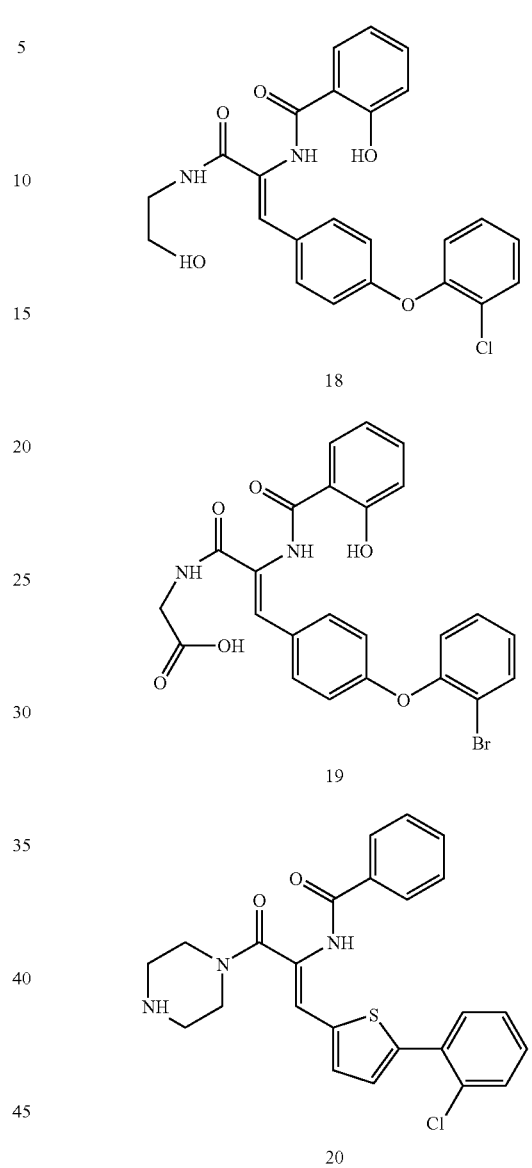

Analysis of the Compounds

The subject compounds and compositions may be demonstrated to have pharmacological activity, e.g, antiviral activity, in in vitro and in vivo assays, as known in the art. See for example Behrens, S. E., et.al EMBO J. 15:12–22; Lohmann, V., et.al., 1997, J. Virol. 71:8416–8428; Ferrari, E., et al., 1999. J. Virol. 73:1649–1654; Bealieu, P. L. et. al., WO0204425 A2; Perni, R. B. et. al., WO9833501; which references are incorporated by reference herein.

The subject compounds and compositions are capable of specifically inhibiting or suppressing a viral infection, e.g., an HCV infection. An in vivo assessment of the antiviral activity of the compounds of the invention may be made using an animal model of viral infection, e.g., a primate model. Cell-based assays may be performed using, e.g, a cell line directly infected with a virus. Cell-based assays for activity against a specific viral component, e.g., a polymerase, may also be performed. Additionally, biochemical or mechanism-based assays, e.g., transcription assays using a purified protein, Northern blot, RT-PCR, etc., may be performed.

The above-described assays are exemplary and not intended to limit the scope of the invention. The skilled practitioner can appreciate that modifications can be made to conventional assays to develop equivalent assays that obtain the same result.

High throughput assays for the presence, absence, quantification, or other properties of particular compounds are well known to those of skill in the art. Such assays may be adapted to identify compounds capable of modifying a viral RNA dependent RNA polymerase protein, e.g., NS5B using functional protein. Preferred assays thus detect enhancement or inhibition of HCV RNA-dependent RNA activity.

Compositions

In view of the antiviral activity associated with the compounds described above, the present invention further provides pharmaceutical compositions comprising one or more of the above compounds in combination with a pharmaceutically acceptable excipient.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a prodrug, which can be metabolically or chemically converted to the subject compound by the recipient host. A wide variety of prodrug derivatives are known in the art such as those that rely on hydrolytic cleavage or oxidative activation of the prodrug.

The compositions may be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

Methods of Use

In yet another aspect, the present invention provides novel methods for the use of the foregoing compounds and compositions. In particular, the invention provides novel methods for treating or preventing viral infections, e.g., HCV infection. The invention also provides novel methods for treating or preventing diseases resulting from, in whole or in part, viral infections, preferably diseases resulting from, in whole or in part, infection, such as hepatitis C, cirrhosis, chronic liver disease and hepatocellular carcinoma. The methods typically involve administering to a patient an effective amount of one or more of the subject compounds or compositions.

The compositions may be advantageously combined and/or used in combination with other antiviral agents which are either therapeutic or prophylactic agents, and different from the subject compounds. The compositions may also be advantageously combined and/or used in combination with agents that treat conditions often associated with the viral infections that are sensitive to the present compounds, such as anti-HIV agents or immunosuppressive agents. In many instances, administration in conjunction with the subject compositions enhances the efficacy of such agents. Accordingly, the present compounds, when combined or administered in combination with other antiviral agents, can be used in dosages which are less than the expected amounts when used alone, or less than the calculated amounts for combination therapy.

Exemplary treatment options for hepatitis C(HCV) include interferons, e.g., interferon alfa-2b, interferon alfa-2a, and interferon alfacon-1. Less frequent interferon dosing can be achieved using pegylated interferon (interferon attached to a polyethylene glycol moiety which significantly improves its pharmacokinetic profile). Combination therapy with interferon alfa-2b (pegylated and unpegylated) and ribavarin has also been shown to be efficacious for some patient populations. Other agents currently being developed include RNA replication inhibitors, antisense agents, therapeutic vaccines, protease inhibitors, helicase inhibitors and antibody therapy (monoclonal and polyclonal).

The compounds and compositions of the present invention may also be used with agents that enhance the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric 5 presentation of antigen and an adjuvant.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

Preparation of the Compounds

The compounds of this invention can be prepared by one or more of the following schemes.

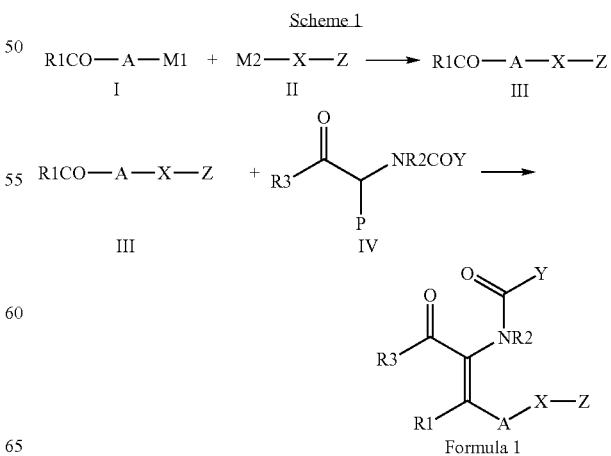

Scheme 2

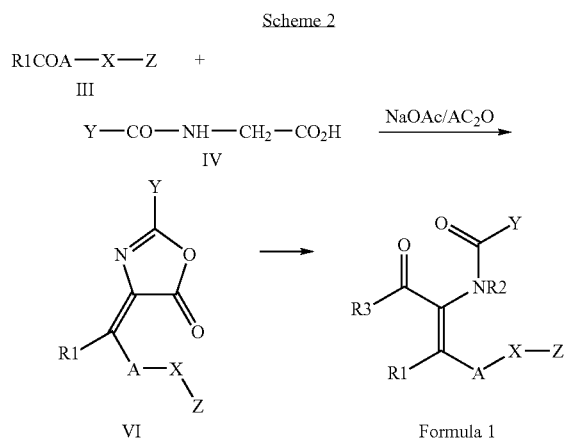

In Scheme 1, R1–3, A, X and Z are as defined above. The reaction of I with II to give III, can be accomplished using palladium catalyzed coupling chemistry well described in the art (Bussalari, J. C., et.al., *Org. Lett.*, 1999, 1, 965; Yeager, G. W., et.al., *Synthesis*, 1991, 61; Hartwig, J. F., et.al., *J. Org. Chem.*, 1999, 64, 5575; Alonso, D. A., et.al., *Org. Lett.*, 2000, 2, 1823; Huff, B. E., et.al. *Org. Synth.*, 1997, 75, 53).

Thus, M1 is selected from the group F, Cl, Br, and I;

M2 is selected from the group $B(OH)_2$, $Sn(R'2)_3$, NHR2 and $OSO_2CF_3$;

alternatively, when M2 is selected from the group F, Cl, Br, and I;

M1 is selected from the group $B(OH)_2$, $Sn(R'2)_3$, NHR2 and $OSO_2CF_3$.

The reaction of I with II may also be accomplished using standard methodology when The reaction of I with II may also be accomplished using standard methodology when M1 is an acid halide, aryl halide, alkyl halide and the like and M2 is OH, SH, or NHR2, or, as appropriate, when M2 is an acid halide aryl halide, alkyl halide and the like and M1 is OH, SH, or NHR2.

In the reaction of IfI with IV to give the title compounds, P represents a substituted phosphorous as found in Wittig, Wittig-Horner, and the like, reagents. Examples of P include dialkoxy phosphonate, dialkyl phosphinate and the like.

Conditions for the reaction of Im with IV to give the compounds of Formula 1 are also well known in the art. See for example Moody, C. J., et.al., *Chem. Commun.* 1997, 2391; Beecher, J. E., et.al., *Tetrahedron Lett.*, (1998), 39, 3927; Dumas, M. et.al., *Tetrahedron Lett.*, (1989), 30, 5121; Schiavi, B. M., et.al., *J. Org. Chem.* (2002), 67, 620.

Scheme 2 represents the well-known azlactone synthesis. See for example Herbst, R. M. et.al. in *Organic Synthesis* Vol. 2, p. 1.

It is obvious to one of ordinary skill in the art that further transformations of the products and intermediates of Schemes 1 and 2 are readily achieved using methods common in the art. These transformations include for example, ester, nitrile and amide hydrolysis; ester, amide and nitrile reduction; primary and secondary amine alkylation, acylation, aroylation; alcohol acylation, aroylation and alkylation; and the like.

EXAMPLES

The following examples further illustrate the preparation and analysis of compounds of the invention. The examples are illustrative only and not intended to limit the scope of the invention in any way. Reagents and solvents can be obtained from commercial sources such as Aldrich Chemical Co. (Milwaukee, Wis., USA). All commercially obtained reagents are used as received without further purification. Solvents are used as received or dried over appropriate drying agents and distilled. Proton NMR experiments are carried out on a Bruker 400 MHz spectrometer, and chemical shifts are reported in ppm downfield from internal TMS. Carbon NMR experiments are carried out on a Bruker 500 MHz spectrometer, and chemical shifts are reported in ppm relative to the central line of deuteriochloroform at 77.0 ppm. Low resolution mass spectra (ESI) are obtained on a Micromass Platform C spectrograph. Low resolution mass spectra (EI) and high resolution mass spectra (FAB), as well as IR spectra and elemental analyses are conducted by the Pharmacia analytical laboratory. Flash column chromatography is carried out on Biotage 40 prepacked columns, while preparative TLC is carried out on Merck silica gel $F_{254}$-coated plates with 0.25 mm or 0.5 mm silica layers. Unless otherwise noted, reactions are carried out in dry glassware under a nitrogen atmosphere.

Example 1

(2Z)-2-(benzoylamino)-3-[5-(2-methylphenyl)-2-furyl]prop-2-enoic acid

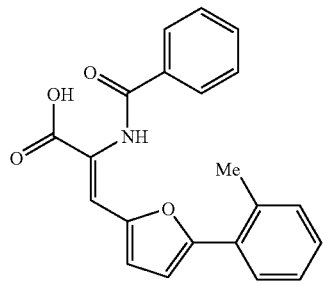

a) As illustrated in Scheme 1, to a mixture of 5-bromo-2-furaldehyde (2.0 g, 11.4 mmol), tetrabutylammonium bromide (3.7 g, 11.4 mmol), potassium carbonate (3.93 g, 28.5 mmol), 2-methylphenyl boronic acid (1.7 g, 12.5 mmol) and palladium (II) acetate (55.2 mg, 0.23 mmol) is added water (20 mL). The reaction mixture is then stirred vigorously for 16 hour at 25° C. Once complete, the reaction mixture is poured into a separatory funnel and diluted with water (50 mL) and ethyl acetate (150 mL). The organic layer is separated and treated with 5.0 g of activated charcoal for 30 min after which time the suspension is filtered through a pad of celite and the filtrate concentrated to afford the crude coupling product as a yellow oil. The crude product is purified by column chromatography (5→10% ethyl acetate in hexanes) to afford 1.8 g of 5-(2'-methylphenyl)-2-furaldehyde.

b) To a solution of N-(benzyloxycarbonyl)-α-phosphonoglycine trimethyl ester (20.0 g, 60.4 mmol) in methanol (300 mL) is added 10% Pd/C (200 mg). The flask is subsequently evacuated and treated with hydrogen gas (3 atm) for 8 hours after which time the flask is evacuated and filled with nitrogen. The reaction mixture is filtered through a pad of celite and concentrated under reduced pressure to afford 11.3 g of α-phosphonoglycine trimethyl ester which is used without further purification.

c) To a solution of α-phosphonoglycine trimethyl ester (11.3 g, 57.4 mmol), prepared as described above, in CH$_2$Cl$_2$ (200 mL) at 0° C. is added triethylamine (16.1 mL, 86.1 mmol) followed by benzoyl chloride (7.3 mL, 63.1 mmol). The reaction is stirred at 0° C. for 1 hour and then at 25° C. for 12 hours. The reaction mixture is then poured into a separatory funnel and washed saturated sodium bicarbonate solution. The organic layer is dried over sodium sulfate before being concentrated under reduced pressure. The crude product is purified by column chromatography (50→100% ethyl acetate in hexanes) to afford 13.9 g of N-benzoyl-α-phosphonoglycine trimethyl ester.

d) To a solution of N-benzoyl-α-phosphonoglycine trimethyl ester (200 mg, 0.66 mmol), prepared as described above, in CH$_2$Cl$_2$ (5 mL) at 25° C. is added 1,8-diazabicyclo[5.4.0]undec-7-ene (108 μl, 0.726 mmol) and the reaction stirred for 10 minutes. A second solution of 5-(2'-methylphenyl)-2-furaldehyde (124 mg, 0.66 mmol), prepared as described above, in CH$_2$Cl$_2$ (5 mL) is added and the combined reaction mixture is stirred at 25° C. for 2 hours. Once complete, the reaction mixture is washed with 10% HCl and the organic layer is dried over sodium sulfate and concentrated to provide the crude product as an oil. This crude product is purified by column chromatography (30% ethyl acetate in hexanes) to afford 104 mg of 1-methyl (Z)-2-(benzoylamino)-3-[4-(2-methylphenoxy)phenyl]prop-2-enoate.

e) To a solution of 1-methyl (Z)-2-(benzoylamino)-3-[4-(2-methylphenoxy)phenyl]prop-2-enoate (104 mg, 0.29 mmol), prepared as described above, in dioxane (5 mL) is added 1 N LiOH (5 mL). The reaction mixture is stirred at 25° C. for 3 hours. The dioxane is then removed under reduced pressure and the remaining reaction mixture poured into a separatory funnel. The aqueous layer is washed with diethyl ether and then acidified (pH=4) by treatment with 10% HCl causing a white precipitate to develop. A portion of ethyl acetate (50 mL) is added and the organic layer is separated, dried over sodium sulfate and concentrated to afford 75 mg of (Z)-2-(benzoylamino)-3-[5-(2-methylphenyl)-2-furyl]prop-2-enoic acid which does not require a further purification.

Example 2

(2Z)-2-(benzoylamiino)-3-(2'-chloro-6-fluoro-1,1'-biphenyl-3-yl)prop-2-enoic acid

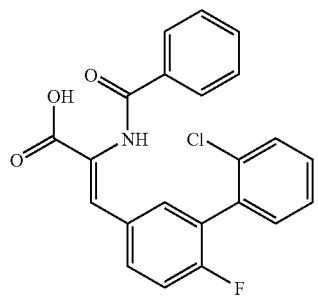

a) To a solution of 2-bromo-4-fluorobenzaldehyde (2.0 g, 9.85 mmol) and 2-chlorophenylboronic acid (2.0 g, 12.1 mmol) in ethylene glycol dimethyl ether (20 mL) is added 2N sodium carbonate (19.7 mL) followed by tetrakis(triphenylphosphine) palladium (0) (573 mg, 0.50 mmol). The reaction is subsequently stirred at 80° C. for 4 hours under an argon atmosphere. Once complete, the reaction mixture is poured into CH$_2$Cl$_2$ and water is added. The organic layer is separated, dried over sodium sulfate and concentrated to provide a crude oil. The crude product is purified by column chromatography (10% ethyl acetate in hexanes) to afford 1.25 g of 3-(2-chlorophenyl)-4-fluorobenzaldehyde.

b) A portion of 3-(2-chlorophenyl)4-fluorobenzaldehyde, prepared as described above, is subsequently converted to Z-2-(benzoylamino)-3-(2'-chloro-6-fluoro-1,1'-biphenyl-3-yl)prop-2-enoic acid using steps (d) and (e) previously described for Example 1.

Example 3

(2Z)-2-(benzoylamino)-3-[2-(2-chlorophenyl)-1,3-thiazol-4-yl]prop-2-enoic acid

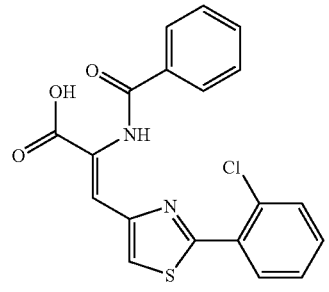

a) According to literature reference (Kelly, T. R.; Lang, F. J. Org. Chem. 1996, 61, 4623–4633), ethyl bromopyruvate (10.0 mL, 79.7 mmol) and thiourea (5.5 g, 72.3 mmol) are combined neat in a 100 mL flask and slowly heated to 100° C. over a 1 hour period. At approximately 70° C. a vigorous reaction occurs and the mixture becomes homogeneous. After reaching 100° C. the reaction is heated for an additional 20 minutes and then cooled to room temperature. Upon cooling the reaction product solidifies affording 19.0 grams of a crude ethyl 2-amino-4-thiazolecarboxylate which is used without further purification.

b) Acording to literature reference (Kelly, T. R.; Lang, F. J. Org. Chem. 1996, 61, 4623–4633), crude ethyl 2-amino-4-thiazolecarboxylate (19.0 g, 111 mmol) is combined with sodium bromide (46.7 g, 444 mmol) and copper (II) sulfate (52.4 g, 333 mmol). A portion of 9N sulfuric acid (225 mL) is then added and the reaction mixture is cooled in an ice/salt bath. A solution of sodium nitrate (8.35 g, 122 mmol) in water (100 mL) is added drop wise to this reaction mixture over 30 minutes while maintaining the reaction temperature at 0° C. Once the addition is complete, the reaction mixture is stirred at 0° C. for 30 minutes and at 25° C. for an additional 1.5 hours. A portion of water (300 mL) is then added and the reaction mixture extracted with diethyl ether. Subsequently, the aqueous layer is made basic (pH 9) by addition of 20% sodium hydroxide and then extracted a second time with diethyl ether. The combined organic extracts are dried over sodium sulfate and concentrated. The crude product is purified by column chromatography (20% ethyl acetate in hexanes) to afford 5.06 g of ethyl 2-bromo-4-thiazolecarboxylate.

c) To a solution of ethyl 2-bromo-4-thiazolecarboxylate (2.0 g, 8.5 mmol), prepared as described above, in ethylene glycol diethyl ether (15 mL) is added 2-chlorophenylboronic acid (1.73 g, 11.1 mmol), 2N sodium carbonate (17 mL) and tetrakis(triphenylphosphine) palladium (0) (492 mg, 0.43 mmol). The reaction is subsequently sealed and heated to 80° C. for 3 hours under an argon atmosphere. Once complete, the reaction mixture is poured into $CH_2Cl_2$ and of water is added. The organic layer is separated, dried over sodium sulfate and concentrated to provide a yellow oil. The crude product is purified by column chromatography (10% ethyl acetate in hexanes) to afford 1.44 g of ethyl 2-(2-chlorophenyl)-4-thiazolecarboxylate.

d) To a solution of ethyl 2-(2-chlorophenyl)-4-thiazolecarboxylate (1.34 g, 5.0 mmol), prepared as described above, in $CH_2Cl_2$ (20 mL) at −78° C. is added diisobutylaluminum hydride (10.5 mL of 1.0 M solution in toluene, 10.5 mmol) and the resulting reaction mixture is stirred at −78° C. for 1 hour after which time sodium fluoride (1.5 g) and water (0.5 mL) are added and the reaction mixture is allowed to warm to room temperature and filtered. The filtrate is concentrated to provide the crude reduction product which is purified by column chromatography (10% ethyl acetate in hexanes) to afford 138 mg of [2-(2-chlorophenyl)-1,3-thiazol-4-yl]carboxyaldehyde and 605 mg of [2-(2-chlorophenyl)-1,3-thiazol-4-yl]methanol. The of [2-(2-chlorophenyl)-1,3-thiazol-4-yl]carboxyaldehyde portion is then used for subsequent steps while the [2-(2-chlorophenyl)-1,3-thiazol-4-yl]methanol portion is converted to [2-(2-chlorophenyl)-1,3-thiazol-4-yl]carboxyaldehyde via standard oxidation conditions.

e) A portion of [2-(2-chlorophenyl)-1,3-thiazol-4-yl]carboxyaldehyde, prepared as described above, is subsequently converted to (2Z)-2-(benzoylamino)-3-[2-(2-chlorophenyl)-1,3-thiazol-4-yl]prop-2-enoic acid using steps (d) and (e) previously described for Example 1.

Example 4

(2Z)-2-(benzoylamino)-3-[2-(2-chlorophenyl)-1H-imidazol-5-yl]prop-2-enoic acid

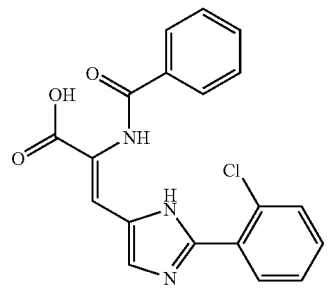

a) According to literature reference (Huang, Y.; Luedtke, R. R.; Freeman, R. A.; Wu, L.; Mach, R. H. Bioorg. Med. Chem. 2001, 9, 3113–3122), to a solution of hexamethyldisilazane (36.7 mL, 175 mmol) in of diethyl ether (300 mL) at 0° C. is added n-butyl lithium (114 mL of 1.6 M solution in hexanes, 182 mmol) and the reaction mixture is stirred at 0° C. for 30 minutes after which time 2-chlorobenzonitrile (10.0 grams, 72.7 mmol) is added and the reaction mixtureis warmed to 25° C. and stirred for 5 hours. Once complete, the reaction is poured into 2 N HCl and the aqueous phase was washed twice with diethyl ether. This aqueous phase is then made basic (pH=12) by addition of 6N sodium hydroxide. Subsequently, the aqueous phase is extracted with $CH_2Cl_2$ and the combined organic extracts are dried over sodium sulfate and concentrated to provide a crude solid. The crude product is then recrystallized from ethyl acetate to afford 5.4 g of 2-chlorobenzenecarboximidamide.

b) According to literature reference (Huang, Y.; Luedtke, R. R.; Freeman, R. A.; Wu, L.; Mach, R. H. Bioorg. Med. Chem. 2001, 9, 3113–3122), to a mixture of 2-chlorobenzenecarboximidamide (5.4 g, 34.8 mmol), 1,3-dihydroxyacetone dimmer (6.2 g, 34.8 mmol) and ammonium chloride (7.5 g, 139 mmol) is added concentrated ammonium hydroxide (40 mL). The reaction mixture is then heated to reflux for 30 minutes after which time it is cooled to room temperature and poured into a ice/water mixture. This aqueous suspension is extracted with $CH_2Cl_2$ and the combined organic extracts are dried over sodium sulfate and concentrated to provide a crude solid. The crude product is recrystallized from ethyl acetate to afford 3.9 g of [2-(2-chlorophenyl)-1H-imidazol-4-yl]methanol.

c) To a solution of [2-(2-chlorophenyl)-1H-imidazol-4-yl]methanol (1.0 g, 4.81 mmol) in $CH_2Cl_2$ (50 mL) at to 25° C. is added sodium bicarbonate (1.21 g, 14.4 mmol) followed by Dess-Martin periodinane (2.29 g, 5.29 mmol). The reaction mixture is then stirred at to 25° C. for 1 hour. Subsequently, the reaction mixture is poured into a separatory funnel, diluted with $CH_2Cl_2$ and washed with a saturated sodium sulfite solution. The organic layer is dried over sodium sulfate and concentrated. The crude product is purified by column chromatography (50% ethyl acetate in hexanes) to afford 182 mg of 2-(2-chlorophenyl)-1H-imidazole-4-carbaldehyde.

d) A portion of 2-(2-chlorophenyl)-1H-imidazole-4-carbaldehyde, prepared as described above, is subsequently converted to (2Z)-2-(benzoylamino)-3-[2-(2-chlorophenyl)-1H-imidazol-5-yl]prop-2-enoic acid using steps (d) and (e) previously described for Example 1.

Example 5

(2Z)-2-(benzoylamino)-3-(5-phenyl-1,3-oxazol-2-yl)prop-2-enoic acid

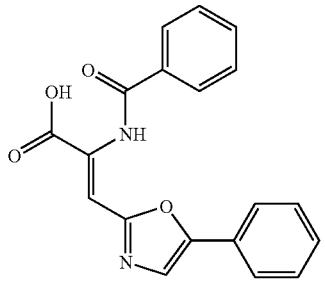

a) According to reference (Synthesis 1984, 1048–1050), to a solution of 5-phenyloxazole (1.5 g, 10.3 mmol) in THF:diethyl ether (2:1, 50 mL) at −78° C. is added n-butyl lithium (7.1 mL of 1.6 M solution in hexanes, 11.4 mmol) .The reaction is stirred at −78° C. for 30 minutes after which time a solution of N-methyl-2-pyridyl formamide (1.85 mL, 15.5 mmol) in THF (20 mL) is added. The reaction mixture is stirred at −78° C. for 30 min and then at 25° C. for 14 hours. It is quenched by addition of water and extracted with ethyl acetate. The combined organic layers are washed with 10% HCl, saturated sodium bicarbonate and brine before being dried over sodium sulfate and concentrated. The resulting oil is purified by column chromatography (5% ethyl acetate in hexanes) to afford 246 ng of 5-phenyl-1,3-oxazole-2-carbaldehyde.

b) A portion of 5-phenyl-1,3-oxazole-2-carbaldehyde, prepared as described above, is subsequently converted to (2Z)-2-(benzoylamino)-3-(5-phenyl-1,3-oxazol-2-yl)prop-2-enoic acid using steps (d) and (e) previously described for Example 1.

Example 6

(2Z)-2-(benzoylamino)-3-[4-(2-bromophenoxy)phenyl]prop-2-enoic acid

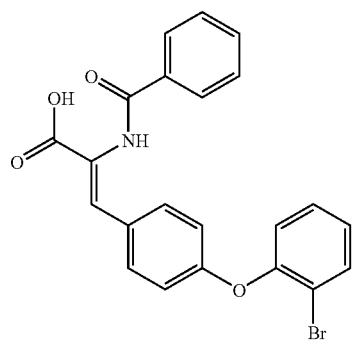

a) To a mixture of 4-fluorobenzaldehyde (2.5 g, 20.2 mmol), 2-bromophenol (3.5 g, 20.2 mmol) and potassium carbonate (3.35 g, 24.3 mmol) is added N,N-dimethylacetamide (20 mL) and the resulting reaction mixture is heated to 150° C. for 12 hours. Once complete, the reaction is cooled to room temperature and diluted with water prior to being extracted with ethyl acetate. The combined extracts are washed with brine and dried over sodium sulfate and concentrated. The resulting yellow oil is purified by column chromatography (5% ethyl acetate in hexanes) to afford 2.1 g of 4-(2-bromophenoxy)benzaldehyde.

b) A portion of 4-(2-bromophenoxy)benzaldehyde, prepared as described above, is subsequently converted to (2Z)-2-(benzoylamino)-3-[4-(2-bromophenoxy)phenyl]prop-2-enoic acid using steps (d) and (e) previously described for Example 1.

Example 7

(2Z)-2-(benzoylamino)-3-[3-(2-chlorophenoxy)phenyl]prop-2-enoic acid

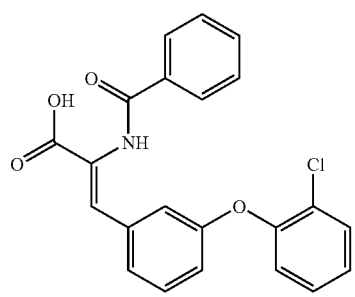

a) To a mixture of 3-cyanophenyl boronic acid (2.84 g, 19.3 mmol), 2-chlorophenol (1.24 g, 9.64 mmol), copper (II) acetate (1.75 g, 9.64 mmol) and 4 Å molecular sieves is added CH$_2$Cl$_2$ (30 mL). While stirring at 25° C., pyridine (3.89 mL, 48.2 mmol) of is added and the reaction mixture stirred at 25° C. for 48 hours. Once complete, the reaction is filtered, and the resulting filtrate is concentrated to afford a crude oil which is purified by column chromatography (5% ethyl acetate in hexanes) to provide 1.92 g of 3-(2-chlorophenoxy)benzonitrile.

b) To a solution of 4-(2-chlorophenoxy)benzonitrile (1.92 g, 8.34 mmol) in toluene:CH$_2$Cl$_2$ (5:1, 100 mL) at −78° C. is added diisobutylaluminum hydride (13.4 mL of 1.0 M solution in toluene, 13.4 mmol). Once addition is complete, the reaction is stirred at −78° C. for 30 minutes and then at 25° C. for 2 hours. The reaction mixture is quenched by drop wise addition of methanol (2 mL) followed by the addition of 10% HCl (10 mL). After stirring at 25° C. for 15 minutes, quenched reaction mixture is extracted with chloroform and the combined organic layers are dried over sodium sulfate and concentrated. The crude product is purified by column chromatography (10% ethyl acetate in hexanes) to afford 593 mg of 3-(2-chlorophenoxy)benzaldehyde.

c) A portion of 3-(2-chlorophenoxy)benzaldehyde, prepared as described above, is subsequently converted to (2Z)-2-(benzoylamino)-3-[3-(2chlorophenoxy)phenyl]prop-2-enoic acid using steps (d) and (e) previously described for Example 1.

Example 8

(2Z)-2-(benzoylamino)-3-{4-[(4-methylbenzyl)oxy]phenyl}prop-2-enoic acid

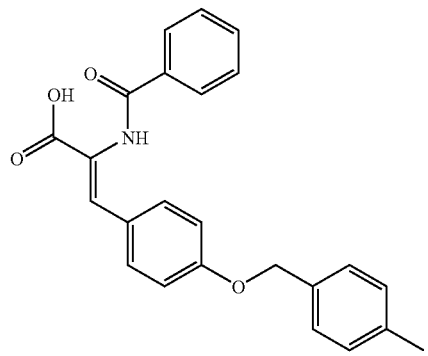

a) To a solution of 4-hydroxybenzaldehyde (2.0 g, 13.9 mmol) in acetone (80 mL) is added potassium carbonate (2.3 g, 16.7 mmol) and 4-methyl benzyl bromide (2.57 g, 13.9 mmol). The reaction mixture is stirred at 25° C. for 12 hours after which time the reaction solvent is removed by evaporation. The residue is taken up in diethyl ether and transferred to a separatory funnel wherein the organic layer is washed with water, 1N sodium hydroxide and brine before being dried over sodium sulfate and concentrated. The resulting crude oil is purified by column chromatography (5% ethyl acetate in hexanes) to 1.4 g of 4-[(4-methylbenzyl)oxy]benzaldehyde.

b) A portion of 4-[(4-methylbenzyl)oxy]benzaldehyde, prepared as described above, is subsequently converted to (2Z)-2-(benzoylamino)-3-{4-[(4-methylbenzyl)oxy]phenyl}prop-2-enoic acid using steps (d) and (e) previously described for Example 1.

Example 9

(2Z)-2-(benzoylamino)-3-{4-[(2-chlorophenyl)amino]phenyl}prop-2-enoic acid

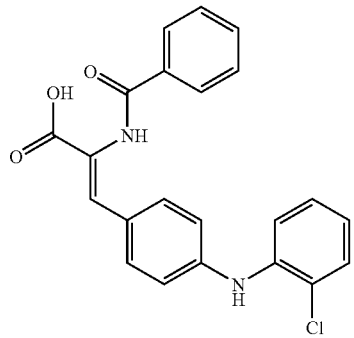

a) To a solution of 4-bromobenzonitrile (3.0 g, 16.4 mmol) in toluene (40 mL) is added 2-chloroaniline (2.09 mL, 19.7 mmol), cesium carbonate (7.5 g, 23.0 mmol), palladium (II) acetate (110 mg, 0.50 mmol) and S-BINAP (460 mg, 0.74 mmol). The reaction mixture is then heated to 100° C. for 12 hours under an argon atmosphere. Once complete, the reaction is cooled to room temperature, diluted with diethyl ether and filtered. The filtrate is then concentrated and purified by column chromatography (6% ethyl acetate in hexanes) to afford 1.35 g of 4-[(2-chlorophenyl)amino]benzonitrile.

b) To a solution of 4-[(2-chlorophenyl)amino]benzonitrile (1.2 g, 5.24 mmol) in toluene:CH$_2$Cl$_2$ (5:1, 50 mL) at −78° C. is added diisobutylaluminum hydride (7.9 mL of 1.0 M solution in toluene, 7.9 mmol). Once addition was complete, the reaction is stirred at −78° C. for 30 minutes and then at 25° C. for 2 hours. The reaction mixture is quenched by drop wise addition of methanol (2 mL) followed by the addition of 10% HCl (10 mL). After stirring at 25° C. for 15 minutes, the quenched reaction mixture is extracted with chloroform and the combined organic layers are dried over sodium sulfate and concentrated. The crude product is purified by column chromatography (15% ethyl acetate in hexanes) to afford 854 mg of 4-[(2-chlorophenyl)amino]benzaldehyde.

c) A portion of 4-[(2-chlorophenyl)amino]benzaldehyde, prepared as described above, is subsequently converted to (2Z)-2-(benzoylamino)-3-{4-[(2-chlorophenyl)amino]phenyl}prop-2-enoic acid using steps (d) and (e) previously described for Example 1.

Example 10

(2Z)-2-(benzoylamino)-3-{5-[(2-chlorophenyl)thio]-2-furyl}prop-2-enoic acid

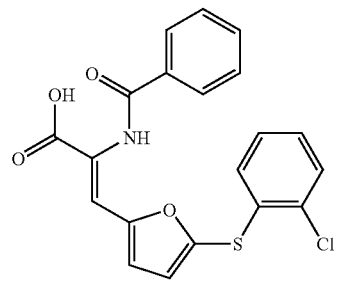

a) To a solution of 2-chlorothiophenol (1.96 g, 13.6 mmol) in THF (20 ML) at 0° C. is slowly added sodium hydride (550 mg of 60% suspension in mineral oil, 13.7 mmol). After gas evolution ceased, 5-bromo-2-furaldehyde (2.0 g, 11.4 mmol) is added and the reaction mixture stirred at 0° C. for 30 minutes and then at 25° C. for 1 hour. Once complete, the reaction is quenched by addition of saturated ammonium chloride and extracted with ethyl acetate. The combined organic extracts are dried over sodium sulfate and concentrated. The resulting yellow oil is purified by column chromatography (3% diethyl ether in hexanes) to afford 1.3 g of 5-[(2-chlorophenyl)thio]-2-furylaldehyde.

b) A portion of 5-[(2-chlorophenyl)thio]-2-furylaldehyde, prepared as described above, is subsequently converted to (2Z)-2-(benzoylamino)-3-{5-[(2-chlorophenyl)thio]-2-furyl}prop-2-enoic acid using steps (d) and (e) previously described for Example 1.

Example 11

(2Z)-2-(2-furoylamino)-3-(5-phenyl-2-furyl)prop-2-enoic acid

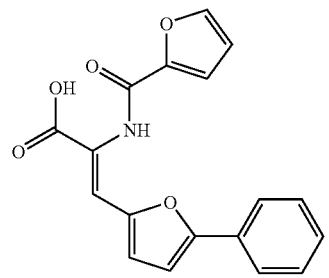

a) As illustrated in Scheme 2, N-2-furoylglycine (131 mg, 0.776 mmol) is suspended in acetic anhydride (1 mL) and sodium acetate (76 mg, 0.931 mmol) and 5-phenylfuraldehyde (170 mg, 1 mmol) are added. The reaction mixture is shaken at 60° C. for one hour, and cooled to 0° C. The resulting orange solid is filtered and washed with ice water (75 mL) and heptane (50 mL). The solid is then dried under vacuum at 40° C. to afford 79 mg of (4Z)-2-(2-furyl)-4-[(5-phenyl-2-furyl)methylene]-1,3-oxazol-5(4H)-one which was used without further purification.

b) 1N NaOH (100 µL) and H$_2$O (500 µL) is added to a solution of (4Z)-2-(2-furyl)-4-[(5-phenyl-2-furyl)methylene]-1,3-oxazol-5(4H)-one (10 mg, 0.0327 mmol), prepared as described above, in acetone (1 mL). The reaction mixture is heated to 75° C. for one hour and then cooled to 25° C. The crude mixture is loaded onto a QAX column, which was pre-treated with MeOH. After 2 minutes the column is washed with MeOH and the product is eluted with 3% HCl/MeOH. Subsequently, the column is washed with MeOH (2 mL) and the combined washings are concentrated under reduced pressure to provide 9.5 mg of (2Z)-2-(2-furoylamino)-3-(5-phenyl-2-furyl)prop-2-enoic acid.

Example 12

N-{(2Z)-3-[4-(2-bromophenoxy)phenyl]-2-[(2-hydroxybenzoyl)amino]prop-2-enoyl}glycine

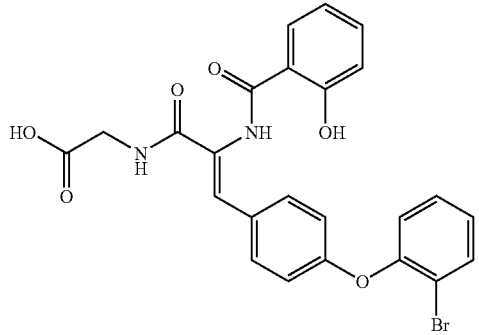

a) A suspension of 4-(2-bromophenoxy)benzaldehyde (0.35 g, 1.26 mmol), 2-hydroxy hippuric acid (0.22 g, 1.14 mmol) and sodium acetate (0.12 g, 1.48 mmol) in acetic anhydride (1 mL) is heated to 60° C. on an orbital shaker for one hour and is then cooled to 0° C. The reaction mixture is then concentrated under reduced pressure at 45° C. to afford a crude yellow solid. This solid is washed with ice water (150 mL) and heptane (100 mL) and then dried under vacuum at 40° C. to provide 0.475 g of 2-{(4Z)-4-[4-(2-bromophenoxy)benzylidene]-5-oxo-4,5-dihydro-1,3-oxazol-2-yl}phenyl acetate.

b) A portion of 2-{(4Z)-4-[4-(2-bromophenoxy)benzylidene]-5-oxo-4,5-dihydro-1,3-oxazol-2-yl}phenyl acetate (0.10 g, 0.229 mmol), prepared as described above, is suspended in DCM (10 mL) and treated with glycine ethyl ester hydrochloride (67 m g, 0.48 mmol). The reaction is heated to 60° C. for 4 hours and then concentrated. The resulting solid is triturated with EtOAc to provide ethyl N-{(2Z)-3-[4-(2-bromophenoxy)phenyl]-2-[(2-hydroxybenzoyl)amino]prop-2-enoyl}glycinate, which is subsequently suspended in 1N NaOH (1 mL) and ethanol (1 mL) and stirred at 25° C. for 3 hours. The ethanol is removed and several drops of concentrated HCl added and a precipitate is formed. Filtration afforded 65 mg of N-{(2Z)-3-[4-(2-bromophenoxy)phenyl]-2-[(2-hydroxybenzoyl)amino]prop-2-enoyl}glycine.

Example 13

N-((Z)-2-[4-(2-chlorophenoxy)phenyl]-1-{[(2-hydroxyethyl)amino]carbonyl}ethenyl)-2-hydroxybenzamide

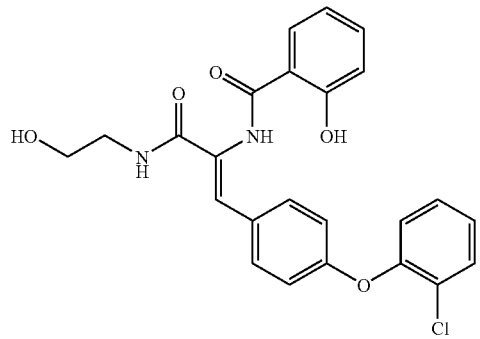

a) A suspension of 4-(2-chlorophenoxy)benzaldehyde (0.193 g, 0.83 mmol, 2-hydroxy hippuric acid (0.147 g, 0.75 mmol) and sodium acetate (0.08 g, 0.975 mmol) in acetic anhydride (0.5 mL) is heated to 60° C. on an orbital shaker for one hour and is cooled to room temperature. The reaction mixture is concentrated under reduced pressure at 45° C. to provide an orange solid. The solid is washed with ice water (150 mL) and heptane (100 mL) and dried under vacuum at 40° C. to provide 0.32 g 2-{(4Z)-4-[4-(2-chlorophenoxy)benzylidene]-5-oxo-4,5-dihydro-1,3-oxazol-2-yl}phenyl acetate.

b) 2-{(4Z)-4-[4-(2-bromophenoxy)benzylidene]-5-oxo-4,5-dihydro-1,3-oxazol-2-yl}phenyl acetate (0.1 g, 0.23 mmol), prepared as described above, was suspended in CH$_2$Cl$_2$ (10 mL) and was treated with ethanol amine (40 µL, 0.66 mmol). The reaction was heated to 60° C. for 3.5 hours and concentrated. The magnesium sulfate and concentrated. The resulting residue was suspended in acetone/1 N NaOH (3:1) and shaken for 1 hr. Acetone is removed and the product extracted ethyl acetate. The organic layer is dried over magnesium sulfate, concentrated and chromatographed on a silica plug, eluting with heptane, 20% ethyl acetate/heptane, 50% ethyl acetate/heptane, ethyl acetate, and methanol (5 mL each). The methanol fraction is concentrated and evaporated from Et$_2$O to provide 15 mg of N-((Z)-2-[4-(2-chlorophenoxy)phenyl]-1-{[(2-hydroxyethyl)amino]carbonyl}ethenyl)-2-hydroxybenzamide as a yellow solid.

Example 14

Further examples of this invention include:
(2Z)-2-(benzoylamino)-3-{5-phenyl-2-furyl}prop-2-enoic acid;
(2Z)-2-(benzoylamino)-3-{5-[2-(trifluoromethyl)phenyl]-2-furyl}prop-2-enoic acid;
(2Z)-2-(benzoylamino)-3-{5-[3-(trifluoromethyl)phenyl]-2-furyl}prop-2-enoic acid;
(2Z)-2-(benzoylamino)-3-{5-[4-(trifluoromethyl)phenyl]-2-furyl}prop-2-enoic acid;
(2Z)-2-(benzoylamino)-3-(5-phenylthien-2-yl)prop-2-enoic acid;
(2Z)-2-(benzoylamino)-3-[5-(4-fluorophenyl)-2-furyl]prop-2-enoic acid;

(2Z)-2-(benzoylamino)-3-[5-(2-chlorophenyl)-2-furyl]prop-2-enoic acid;
(2Z)-2-(benzoylamino)-3-[5-(3-chlorophenyl)-2-furyl]prop-2-enoic acid;
(2Z)-2-(benzoylacino)-3-[5-(4-chlorophenyl)-2-furyl]prop-2-enoic acid;
(2Z)-2-(benzoylamino)-3-[5-(3,4-dichlorophenyl)-2-furyl]prop-2-enoic acid;
(2Z)-2-(benzoylamino)-3-{5-[4-(dimethylamino)phenyl]-2-furyll}prop-2-enoic acid;
(2Z)-2-(benzoylamino)-3-{5-[4-(trifluoromethoxy)phenyl]-2-furyl}prop-2-enoic acid;
(2Z)-2-(benzoylamino)-3-[5-(1,1'-biphenyl-4-yl)-2-furyl]prop-2-enoic acid;
(2Z)-2-(benzoylamino)-3-[5-(2-naphthyl)-2-furyl]prop-2-enoic acid;
(2Z)-2-(benzoylamino)-3-[5-(3-fluorophenyl)-2-furyl]prop-2-enoic acid;
(2Z)-2-(benzoylamino)-3-[5-(3-nitrophenyl)-2-furyl]prop-2-enoic acid;
(2Z)-2-(benzoylamino)-3-[5-(2-nitrophenyl)-2-furyl]prop-2-enoic acid; methyl (2Z)-2-(benzoylamino)-3-(5-phenyl-2-furyl)prop-2-enoate;
(2Z)-2-(benzoylamino)-3-[5-(4-cyanophenyl)-2-furyl]prop-2-enoic acid;
(2Z)-2-(benzoylamino)-3-[5-(4-tert-butylphenyl)-2-furyl]prop-2-enoic acid;
(2Z)-3-{5-[4-(aminosulfonyl)phenyl]-2-furyl}-2-(benzoylamino)prop-2-enoic acid;
(2Z)-2-(benzoylamino)-3-{5-[4-(methylthio)phenyl]-2-furyl}prop-2-enoic acid;
(2Z)-3-[5-(1,3-benzodioxol-5-yl)-2-furyl]-2-(benzoylamino)prop-2-enoic acid;
(2Z)-3-[5-(1-benzothien-2-yl)-2-furyl]-2-(benzoylamino)prop-2-enoic acid;
(2Z)-2-(benzoylamino)-3-[5-(3,5-dibromophenyl)-2-furyl]prop-2-enoic acid;
(2Z)-2-(benzoylamino)-3-[5-(3-cyanophenyl)-2-furyl]prop-2-enoic acid;
(2Z)-2-(benzoylamino)-3-{5-[4-(hydroxymethyl)phenyl]-2-furyl}prop-2-enoic acid;
(2Z)-2-(benzoylamino)-3-[5-(4-butylphenyl)-2-furyl]prop-2-enoic acid;
(2Z)-2-(benzoylamino)-3-[5-(4-hydroxyphenyl)-2-furyl]prop-2-enoic acid;
(2Z)-2-(benzoylamino)-3-{5-[4-(ethylsulfonyl)phenyl]-2-furyl}prop-2-enoic acid;
(2Z)-2-(benzoylamino)-3-{5-[3-(trifluoromethoxy)phenyl]-2-furyl}prop-2-enoic acid;
(2Z)-2-(benzoylamino)-3-{5-[3-(hydroxymethyl)phenyl]-2-furyl}prop-2-enoic acid;
(2Z)-3-[5-(1-benzofuran-2-yl)-2-furyl]-2-(benzoylamino)prop-2-enoic acid;
(2Z)-2-(benzoylamino)-3-[5-(2-chlorophenyl)thien-2-yl]prop-2-enoic acid;
(2Z)-2-(benzoylamino)-3-(2'-chloro-1,1'-biphenyl-4-yl)prop-2-enoic acid;
(2Z)-3-(1-benzofuran-2-yl)-2-(benzoylamino)prop-2-enoic acid;
(2Z)-2-(benzoylamino)-3-(1,1'-biphenyl-3-yl)prop-2-enoic acid;
(2Z)-2-(benzoylamino)-3-(5-phenyl-1,3-oxazol-2-yl)prop-2-enoic acid;
(2Z)-2-(benzoylamino)-3-[5-(2,3-difluorophenyl)-2-furyl]prop-2-enoic acid;
(2Z)-2-(benzoylamino)-3-[5-(2,3-dichlorophenyl)-2-furyl]prop-2-enoic acid;
(2Z)-2-(benzoylamino)-3-[5-(2-methylphenyl)-2-furyl]prop-2-enoic acid;
(2Z)-2-(benzoylamino)-3-[5-(2-ethoxyphenyl)-2-furyl]prop-2-enoic acid;
(2Z)-3-{5-[3-(aminosulfonyl)phenyl]-2-furyl}-2-(benzoylamino)prop-2-enoic acid;
(2Z)-2-(benzoylamino)-3-[5-(2-fluorophenyl)-2-furyl]prop-2-enoic acid;
(2Z)-2-(benzoylamino)-3-[5-(2-methoxyphenyl)-2-furyl]prop-2-enoic acid;
(2Z)-2-(benzoylamino)-3-[5-(2,3-dimethylphenyl)-2-furyl]prop-2-enoic acid;
(2Z)-2-(benzoylamino)-3-[5-(2-methylphenyl)thien-2-yl]prop-2-enoic acid;
(2Z)-3-[5-(2-aminophenyl)-2-furyl]-2-(benzoylamino)prop-2-enoic acid;
(2Z)-2-(benzoylamino)-3-(2-furyl)prop-2-enoic acid;
(2Z)-2-(benzoylamino)-3-(1,1'-biphenyl-4-yl)prop-2-enoic acid;
(2Z)-2-(benzoylamino)-3-[5-(2,3-difluorophenyl)thien-2-yl]prop-2-enoic acid;
(2Z)-2-(benzoylamino)-3-{5-[2-(trifluoromethoxy)phenyl]-2-furyl}prop-2-enoic acid;
(2Z)-2-(benzoylamino)-3-(4-phenylthien-2-yl)prop-2-enoic acid;
(2Z)-2-(benzoylamino)-3-(5-pyridin-2-ylthien-2-yl)prop-2-enoic acid;
(2Z)-2-(benzoylamino)-3-(5-phenylisoxazol-3-yl)prop-2-enoic acid;
(2Z)-3-(5-phenyl-2-furyl)-2-[(pyridin-3-ylcarbonyl)amino]prop-2-enoic acid;
(2Z)-2-[(2-hydroxybenzoyl)amino]-3-(5-phenyl-2-furyl)prop-2-enoic acid;
(2Z)-2-(2-furoylamino)-3-(5-phenyl-2-furyl)prop-2-enoic acid;
(2Z)-2-[(3-methylbenzoyl)amino]-3-(5-phenyl-2-furyl)prop-2-enoic acid;
(2Z)-2-(benzoylamino)-3-[5-(2-fluorophenyl)thien-2-yl]prop-2-enoic acid;
(2Z)-2-(benzoylamino)-3-[5-(2,5-difluorophenyl)thien-2-yl]prop-2-enoic acid;
(2Z)-2-(benzoylamino)-3-{5-[2-(hydroxymethyl)phenyl]thien-2-yl}prop-2-enoic acid;
(2Z)-2-(benzoylamino)-3-[5-(2-methoxyphenyl)thien-2-yl]prop-2-enoic acid;
(2Z)-2-(benzoylamino)-3-(3-methyl-1-benzothien-2-yl)prop-2-enoic acid;
(2Z)-2-[(2-methylbenzoyl)amino]-3-(5-phenyl-2-furyl)prop-2-enoic acid;
(2Z)-2-{[4-(acetylamino)benzoyl]amino}3-3-(5-phenyl-2-furyl)prop-2-enoic acid;
(2Z)-2-[(4-methylbenzoyl)amino]-3-(5-phenyl-2-furyl)prop-2-enoic acid;
(2Z)-2-[(4-nitrobenzoyl)amino]-3-(5-phenyl-2-furyl)prop-2-enoic acid;
(2Z)-3-[5-(2-chlorophenyl)thien-2-yl]-2-[(pyridin-3-ylcarbonyl)amino]prop-2-enoic acid;
(2Z)-3-[5-(2-chlorophenyl)thien-2-yl]-2-[(2-hydroxybenzoyl)amino]prop-2-enoic acid;
(2Z)-3-[5-(2-chlorophenyl)thien-2-yl]-2-(2-furoylamino)prop-2-enoic acid;
(2Z)-3-[5-(2-chlorophenyl)thien-2-yl]-2-[(3-methylbenzoyl)amno]prop-2-enoic acid;
(2Z)-2-(benzoylamino)-3-(5-phenyl-1,3-thiazol-2-yl)prop-2-enoic acid;
(2Z)-2-(benzoylamino)-3-[5-(2-chlorophenyl)-1,3-thiazol-2-yl]prop-2-enoic acid;

(2Z)-2-(benzoylamino)-3-[2-(2-chlorophenyl)-1,3-thiazol-5-yl]prop-2-enoic acid;
(2Z)-2-(benzoylamino)-3-[4-(2-chlorophenyl)-1,3-thiazol-2-yl]prop-2-enoic acid;
(2Z)-2-(benzoylamino)-3-[4-phenyl-5-(trifluoromethyl)thien-2-yl]prop-2-enoic acid;
(2Z)-2-[(4-aminobenzoyl)amino]-3-(5-phenyl-2-furyl)prop-2-enoic acid;
(2Z)-3-[5-(2-chlorophenyl)thien-2-yl]-2-[(4-nitrobenzoyl)amino]prop-2-enoic acid;
(2Z)-2-[(4-aminobenzoyl)amino]-3-[5-(2-chlorophenyl)thien-2-yl]prop-2-enoic acid;
(2Z)-3-[5-(2-chlorophenyl)thien-2-yl]-2-[(2-methylbenzoyl)amino]prop-2-enoic acid;
(2Z)-2-{[4-(acetylamino)benzoyl]amino}-3-[5-(2-chlorophenyl)thien-2-yl]prop-2-enoic acid;
(2Z)-3-[5-(2-chlorophenyl)thien-2-yl]-2-[(4-methylbenzoyl)amino]prop-2-enoic acid;
(2Z)-2-[(2,5-dihydroxybenzoyl)amino]-3-(5-phenyl-2-furyl)prop-2-enoic acid;
(2Z)-3-[5-(2-chlorophenyl)thien-2-yl]-2-[(2,5-dihydroxybenzoyl)amino]prop-2-enoic acid;
(2Z)-2-(beta-alanylamino)-3-(5-phenyl-2-furyl)prop-2-enoic acid trifluoroacetate; (2Z)-2-[(3-hydroxybenzoyl)amino]-3-(5-phenyl-2-furyl)prop-2-enoic acid;
(2Z)-2-[(4-hydroxybenzoyl)amino]-3-(5-phenyl-2-furyl)prop-2-enoic acid;
(2Z)-2-(benzoylamino)-3-{5-[2-chloro-5-(trifluoromethyl)phenyl]-2-furyl}prop-2-enoic acid;
(2Z)-2-(benzoylamino)-3-{5-[2,6-dichloro-4-(trifluoromethyl)phenyl]-2-furyl}prop-2-enoic acid;
(2Z)-2-(benzoylamino)-3-(2'-chloro-1,1'-biphenyl-3-yl)prop-2-enoic acid;
(2Z)-2-(benzoylamino)-3-(1,1'-biphenyl-2-yl)prop-2-enoic acid;
(2Z)-2-[(3,5-dihydroxybenzoyl)amino]-3-(5-phenyl-2-furyl)prop-2-enoic acid;
(2Z)-3-[5-(2-chlorophenyl)thien-2-yl]-2-[(4-hydroxybenzoyl)amino]prop-2-enoic acid;
(2Z)-3-[5-(2-chlorophenyl)thien-2-yl]-2-[(3-hydroxybenzoyl)amino]prop-2-enoic acid;
(2Z)-3-[5-(2-chlorophenyl)thien-2-yl]-2-[(3,5-dihydroxybenzoyl)amino]prop-2-enoic acid;
(2Z)-2-(benzoylamino)-3-[2-(2-chlorophenyl)-1,3-thiazol-4-yl]prop-2-enoic acid;
(2Z)-2-(benzoylamino)-3-[4-(trifluoromethyl)phenyl]prop-2-enoic acid;
methyl (2Z)-2-(benzoylamino)-3-[5-(2-chlorophenyl)thien-2-yl]prop-2-enoate;
(2Z)-2-[(2-hydroxybenzoyl)amino]-3-[5-(2-methylphenyl)thien-2-yl]prop-2-enoic acid;
(2Z)-3-[5-(2,3-difluorophenyl)thien-2-yl]-2-[(2-hydroxybenzoyl)amino]prop-2-enoic acid;
(2Z)-2-[(3-nitrobenzoyl)amino]-3-(5-phenyl-2-furyl)prop-2-enoic acid;
(2Z)-2-[(3-aminobenzoyl)amino]-3-(5-phenyl-2-furyl)prop-2-enoic acid;
(2Z)-2-[(2-aminobenzoyl)amino]-3-(5-phenyl-2-furyl)prop-2-enoic acid;
(2Z)-2-(benzoylamino)-3-(2'-chloro-6-fluoro-1,1'-biphenyl-3-yl)prop-2-enoic acid;
(2Z)-2-(benzoylamino)-3-(2'-chloro-6-methoxy-1,1'-biphenyl-3-yl)prop-2-enoic acid;
(2Z)-2-(benzoylamino)-3-(2'-chloro-5,6-dimethoxy-1,1'-biphenyl-3-yl)prop-2-enoic acid;
(2Z)-2-(benzoylamino)-3-(2',3'-difluoro-1,1'-biphenyl-3-yl)prop-2-enoic acid;
(2Z)-2-(benzoylamino)-3-(2'-chloro-4-fluoro-1,1'-biphenyl-3-yl)prop-2-enoic acid;
(2Z)-2-(benzoylamino)-3-(2'-chloro-4-methoxy-1,1'-biphenyl-3-yl)prop-2-enoic acid;
(2Z)-3-(2'-chloro-6-fluoro-1,1'-biphenyl-3-yl)-2-[(2-hydroxybenzoyl)amino]prop-2-enoic acid;
(2Z)-2-(benzoylamino)-3-[4-chloro-3-(trifluoromethyl)phenyl]prop-2-enoic acid;
(2Z)-2-(benzoylamino)-3-(3-phenoxyphenyl)prop-2-enoic acid;
2-(benzoylamino)-3,3-diphenylacrylic acid;
(2Z)-2-[(3-aminobenzoyl)amino]-3-[5-(2-chlorophenyl)thien-2-yl]prop-2-enoic acid;
(2Z)-2-[(2-aminobenzoyl)amino]-3-[5-(2-chlorophenyl)thien-2-yl]prop-2-enoic acid;
(2Z)-3-[5-(2-chlorophenyl)thien-2-yl]-2-[(2-nitrobenzoyl)amino]prop-2-enoic acid;
(2Z)-3-(2'-chloro-1,1'-biphenyl-3-yl)-2-[(2-hydroxybenzoyl)amino]prop-2-enoic acid;
(2Z)-2-(benzoylamino)-3-(4-methyl-2-phenyl-1,3-thiazol-5-yl)prop-2-enoic acid;
(2Z)-2-(benzoylamino)-3-[6-(2-chlorophenyl)pyridin-2-yl]prop-2-enoic acid;
(2Z)-2-(benzoylamino)-3-[2-(2-chlorophenyl)-1H-imidazol-5-yl]prop-2-enoic acid;
(2Z)-2-(benzoylamino)-3-(2'-chloro-6-hydroxy-1,1'-biphenyl-3-yl)prop-2-enoic acid;
(2Z)-2-(benzoylamino)-3-(1-methyl-1H-indol-2-yl)prop-2-enoic acid;
(2Z)-2-(benzoylamino)-3-(3-pyridin-2-ylphenyl)prop-2-enoic acid;
(2Z)-2-(benzoylamino)-3-(3-pyridin-3-ylphenyl)prop-2-enoic acid;
(2Z)-2-(benzoylamino)-3-(3-pyridin-4-ylphenyl)prop-2-enoic acid;
(2Z)-2-(benzoylamino)-3-(4-phenoxyphenyl)prop-2-enoic acid;
(2Z)-2-(benzoylamino)-3-(2-phenoxyphenyl)prop-2-enoic acid;
(2Z)-2-(enzoylamino)-3-[5-(phenylethynyl)thien-2-yl]prop-2-enoic acid-3-{5-[(Z)-2-(benzoylamino)-2-carboxyethenyl]-2-ffiryl}thiophene-2-carboxylic acid;
(2Z)-2-(benzoylamino)-3-{5-[1-methyl-3-(trifluoromethyl)-1H-pyrazol-5-yl]thien-2-yl}prop-2-enoic acid;
(2Z)-2-(benzoylamino)-3-{5-[1-methyl-5-(trifluoromethyl)-1H-pyrazol-3-yl]thien-2-yl}prop-2-enoic acid;
N-((Z)-2-[5-(2-chlorophenyl)thien-2-yl]-1-{[(2-hydroxyethyl)amino]carbonyl}ethenyl)benzamide;
N-[(Z)-2-[5-(2-chlorophenyl)thien-2-yl]-1-(morpholin-4-ylcarbonyl)ethenyl]benzamide;
(2Z)-2-(benzoylamino)-3-(2',4'-dichloro-1,1'-biphenyl-3-yl)prop-2-enoic acid;
(2Z)-2-(benzoylamino)-3-(2',5'-dichloro-1,1'-biphenyl-3-yl)prop-2-enoic acid;
(2Z)-2-(benzoylamino)-3-(2',4-dichloro-1,1'-biphenyl-3-yl)prop-2-enoic acid;
(2Z)-2-(benzoylamino)-3-[5-(2,5-dichlorophenyl)-2-furyl]prop-2-enoic acid;
(2Z)-2-(benzoylamino)-3-{5-[2-chloro-4-(trifluoromethyl)phenyl]-2-furyl}prop-2-enoic acid;
(2Z)-2-(benzoylamino)-3-[5-(2-chlorophenyl)pyridin-3-yl]prop-2-enoic acid;
(2Z)-2-(benzoylamino)-3-(2-methyl-1,1'-biphenyl-3-yl)prop-2-enoic acid;
2-[(Z)-2-(benzoylamino)-2-carboxyethenyl]-5-(4-chlorophenyl)-3-furoic acid;

(2Z)-2-(benzoylamino)-3-[4-(2-chlorophenoxy)phenyl]
prop-2-enoic acid;
methyl (2Z)-2-(benzoylamino)-3-[2'-(trifluoromethyl)-1,1'-biphenyl-3-yl]prop-2-enoate;
(2Z)-2-(benzoylamino)-3-[2'-(trifluoromethyl)-1,1'-biphenyl-3-yl]prop-2-enoic acid;
N-[(Z)-2-[5-(2-chlorophenyl)thien-2-yl]-1-(piperidin-1-ylcarbonyl)ethenyl]benzamide;
N-[(Z)-2-[5-(2-chlorophenyl)thien-2-yl]-1-(piperazin-1-ylcarbonyl)ethenyl]benzamide;
methyl N-{(2Z)-2-(benzoylamino)-3-[5-(2-chlorophenyl)thien-2-yl]prop-2-enoyl}glycinate;
methyl N-{(2Z)-2-(benzoylamino)-3-[5-(2-chlorophenyl)thien-2-yl]prop-2-enoyl}-beta-alaninate;
(2Z)-2-(benzoylamino)-3-[4-(phenylthio)phenyl]prop-2-enoic acid;
(2Z)-2-(benzoylamino)-3-[4-(phenylsulfonyl)phenyl]prop-2-enoic acid;
(2Z)-2-(benzoylamino)-3-(2-hydroxy-1,1'-biphenyl-3-yl)prop-2-enoic acid;
(2Z)-2-(benzoylamino)-3-[4-phenoxy-2-(trifluoromethyl)phenyl]prop-2-enoic acid;
(2Z)-2-(benzoylamino)-3-[4-phenoxy-3-(trifluoromethyl)phenyl]prop-2-enoic acid;
(2Z)-2-(benzoylamino)-3-(3-cyano-4-phenoxyphenyl)prop-2-enoic acid;
3-{5-[(Z)-2-(benzoylamino)-2-carboxyethenyl]-2-furyl}-4-methylthiophene-2-carboxylic acid;
(2Z)-2-(benzoylamino)-3-[4-(benzyloxy)phenyl]prop-2-enoic acid;
(2Z)-2-(benzoylamino)-3-(2-morpholin-4-ylphenyl)prop-2-enoic acid;
3'-[(Z)-2-(benzoylamino)-2-carboxyethenyl]-1,1'-biphenyl-2-carboxylic acid;
(2Z)-2-(benzoylamino)-3-(2'-cyano-1,1'-biphenyl-3-yl)prop-2-enoic acid;
N-{(2Z)-2-(benzoylaino)-3-[5-(2-chlorohenyl)thien-2-yl]prop-2-enoyl}-beta-alanine;
N-((Z)-2-[5-(2-chlorophenyl)thien-2-yl]-1-{[(3-hydroxypropyl)amino]carbonyl}ethenyl)benzamide;
N-((Z)-2-[5-(2-chlorophenyl)thien-2-yl]-1-{[(4-hydroxybutyl)amino]carbonyl}ethenyl)benzamide;
N-((Z)-2-[5-(2-chlorophenyl)thien-2-yl]-1-{[(2,3-dihydroxypropyl)amino]carbonyl}ethenyl)benzamide;
N-{(Z)-1-{[bis(2-hydroxyethyl)amino]carbonyl}2-[5-(2-chlorophenyl)thien-2-yl]ethenyl}benzamide;
ethyl N-{(2Z)-2-(benzoylamino)-3-[5-(2-chlorophenyl)thien-2-yl]prop-2-enoyl}glycinate;
N-{(2Z)-2-(benzoylamino)-3-[5-(2-chlorophenyl)thien-2-yl]prop-2-enoyl}glycine;
(2Z)-3-[4-(1H-benzimidazol-1-yl)phenyl]-2-(benzoylamino)prop-2-enoic acid;
(2Z)-2-(benzoylamino)-3-[4-(2-fluorophenoxy)phenyl]prop-2-enoic acid;
(2Z)-2-(benzoylamino)-3-[4-(2-bromophenoxy)phenyl]prop-2-enoic acid;
(2Z)-2-(benzoylamino)-3-[4-(2-chlorophenoxy)-3-methylphenyl]prop-2-enoic acid;
(2Z)-2-(benzoylamino)-3-[4-(2-chlorophenoxy)-3-nitrophenyl]prop-2-enoic acid;
(2Z)-2-(benzoylamino)-3-(3-pyrimidin-5-ylphenyl)prop-2-enoic acid;
(2Z)-2-(benzoylamino)-3-[4-(2-cyanophenoxy)phenyl]prop-2-enoic acid;
(2Z)-2-(benzoylamino)-3-[4-(2-chlorophenoxy)-2-(trifluoromethyl)phenyl]prop-2-enoic acid;
(2Z)-2-(benzoylamino)-3-{4-[(2-chlorophenyl)thio]phenyl}prop-2-enoic acid;
2-{5-[(Z)-2-(benzoylamino)-2-carboxyethenyl]thien-2-yl}benzoic acid;
(2Z)-2-(benzoylamino)-3-[5-(2-cyanophenyl)thien-2-yl]prop-2-enoic acid;
(2Z)-2-(benzoylamino)-3-(3'-formyl-1,1'-biphenyl-3-yl)prop-2-enoic acid;
N-[(Z)-1-{[(2-hydroxyethyl)amino]carbonyl}-2-(5-phenyl-2-furyl)ethenyl]benzamide;
N-((Z)-2-[5-(2-chlorophenyl)thien-2-yl]-1-{[(2-hydroxyethyl)amino]carbonyl}ethenyl)-2-hydroxybenzamide;
N-((Z)-2-[4-(2-chlorophenoxy)phenyl]-1-{[(2-hydroxyethyl)amino]carbonyl}ethenyl)benzamide;
(2Z)-3-{4-[(2-chlorophenyl)thio]phenyl}-2-[(2-hydroxybenzoyl)amino]prop-2-enoic acid;
N-((Z)-2-{4-[(2-chlorophenyl)thio]phenyl}-1{[(2-hydroxyethyl)amino]carbonyl}ethenyl)benzamide;
N-((Z)-2-[4-(2-chlorophenoxy)phenyl]-1-{[(2-hydroxyethyl)amino]carbonyl}ethenyl)-2-hydroxybenzamide;
N-((Z)-2-{4-[(2-chlorophenyl)thio]phenyl}-1-{[(2-hydroxyethyl)amino]carbonyl}ethenyl)-2-hydroxybenzamide;
(2Z)-2-(benzoylamino)-3-[4-(3-chlorophenoxy)phenyl]prop-2-enoic acid;
(2Z)-2-(benzoylamino)-3-[3-chloro-4-(2-chlorophenoxy)phenyl]prop-2-enoic acid;
(2Z)-2-(benzoylamino)-3-{4-[(2-chlorobenzyl)oxy]phenyl}prop-2-enoic acid;
(2Z)-2-(benzoylamino)-3-{5-[(2-chlorophenyl)thio]-2-furyl}prop-2-enoic acid;
(2Z)-2-(benzoylamino)-3-{5-[(2-chlorophenyl)thio]thien-2-yl}prop-2-enoic acid;
(2Z)-2-(benzoylamino)-3-[4-(2-phenylethoxy)phenyl]prop-2-enoic acid;
(2Z)-2-(benzoylamino)-3-[4-(2,3-dichlorophenoxy)phenyl]prop-2-enoic acid;
(2Z)-2-(benzoylamino)-3-{4-[(2-bromophenyl)thio]phenyl}prop-2-enoic acid;
(2Z)-2-(benzoylamino)-3-[4-(2-methoxyphenoxy)phenyl]prop-2-enoic acid;
(2Z)-2-(benzoylamino)-3-[4-(2-ethylphenoxy)phenyl]prop-2-enoic acid;
(2Z)-2-(benzoylamino)-3-[4-(2-bromo-4-fluorophenoxy)phenyl]prop-2-enoic acid;
(2Z)-2-(benzoylamino)-3-[4-(2-bromo-5-fluorophenoxy)phenyl]prop-2-enoic acid;
(2Z)-2-(benzoylamino)-3-[4-(2-bromo-4-chlorophenoxy)phenyl]prop-2-enoic acid;
(2Z)-2-(benzoylamino)-3-[4-(2-bromophenoxy)-3-fluorophenyl]prop-2-enoic acid;
(2Z)-2-(benzoylamino)-3-{5-[(2-bromophenyl)thio]-2-furyl}prop-2-enoic acid;
N-{(2Z)-3-[4-(2-bromophenoxy)phenyl]-2-[(2-hydroxybenzoyl)amino]prop-2-enoyl}glycine;
N-{(2Z)-2-(benzoylamino)-3-[4-(2-bromophenoxy)phenyl]prop-2-ernoyl}glycine;
N-((Z)-2-[4-(2-bromophenoxy)phenyl]-1-{[(2-hydroxyethyl)amino]carbonyl}ethenyl)benzamide;
(2Z)-3-(2'-amino-1,1'-biphenyl-3-yl)-2-(benzoylamino)prop-2-enoic acid;
(2Z)-2-(benzoylamino)-3-(2'-hydroxy-1,1'-biphenyl-3-yl)prop-2-enoic acid;
(2Z)-2-(benzoylamino)-3-(2'-nitro-1,1'-biphenyl-3-yl)prop-2-enoic acid;
(2Z)-2-(benzoylamino)-3-[5-(2-nitrophenyl)thien-2-yl]prop-2-enoic acid;

(2Z)-3-[5-(2-aminophenyl)thien-2-yl]-2-(benzoylamino)prop-2-enoic acid;
(2Z)-2-(benzoylamino)-3-{4-[(2-chlorophenyl)amino]phenyl}prop-2-enoic acid;
(2Z)-2-(benzoylamino)-3-[4-(2-methylphenoxy)phenyl]prop-2-enoic acid;
(2Z)-2-(benzoylamino)-3-[4-(2-isopropoxyphenoxy)phenyl]prop-2-enoic acid;
(2Z)-2-(benzoylamino)-3-[4-(2-iodophenoxy)phenyl]prop-2-enoic acid;
(2Z)-2-(benzoylamino)-3-{5-[(2-bromophenyl)thio]thien-2-yl}prop-2-enoic acid;
(2Z)-2-(benzoylamino)-3-{2-[(2-bromophenyl)thio]-1,3-thiazol-4-yl}prop-2-enoic acid;
(2Z)-3-[5-(2-chlorophenyl)thien-2-yl]-2-[(4-methoxybenzoyl)amino]prop-2-enoic acid;
(2Z)-3-[5-(2-chlorophenyl)thien-2-yl]-2-{[4-(trifluoromethyl)benzoyl]amino}prop-2-enoic acid;
(2Z)-3-[5-(2-chlorophenyl)thien-2-yl]-2-[(3,4,5-trimethoxybenzoyl)amino]prop-2-enoic acid;
(2Z)-2-[(4-chlorobenzoyl)amino]-3-[5-(2-chlorophenyl)thien-2-yl]prop-2-enoic acid;
(2Z)-2-[(4-bromobenzoyl)amino]-3-[5-(2-chlorophenyl)thien-2-yl]prop-2-enoic acid;
(2Z)-3-[5-(2-chlorophenyl)thien-2-yl]-2-{[3-(trifluoromethyl)benzoyl]amino}prop-2-enoic acid;
methyl 3'-[(1Z)-2-(benzoylamino)-3-methoxy-3-oxoprop-1-enyl]-1,1'-biphenyl-2-carboxylate;
methyl (2Z)-2-(benzoylamino)-3-(2'-cyano-1,1'-biphenyl-3-yl)prop-2-enoate;
methyl 2-{5-[(1Z)-2-(benzoylamino)-3-methoxy-3-oxoprop-1-enyl]thien-2-yl}benzoate;
methyl (2Z)-2-(benzoylamino)-3-[5-(2-nitrophenyl)thien-2-yl]prop-2-enoate;
methyl (2Z)-2-(benzoylamino)-3-(2'-nitro-1,1'-biphenyl-3-yl)prop-2-enoate;
methyl (2Z)-3-[2'-(acetyloxy)-1,1'-biphenyl-3-yl]-2-(benzoylamino)prop-2-enoate;
N-[4-(2-bromophenoxy)phenyl]benzamide;
(2Z)-2-(benzoylamino)-3-{4-[2-chloro-3-(trifluoromethyl)phenoxy]phenyl}prop-2-enoic acid;
(2Z)-2-(benzoylamino)-3-{4-[2-(methylthio)phenoxy]phenyl}prop-2-enoic acid;
(2Z)-2-(benzoylamino)-3-[4-(2-bromo-4-cyanophenoxy)phenyl]prop-2-enoic acid;
(2Z)-2-(benzoylamino)-3-[4-(2-bromobenzoyl)phenyl]prop-2-enoic acid;
(2Z)-2-(benzoylamino)-3-{4-[(2-chlorophenyl)(methyl)amino]phenyl}prop-2-enoic acid;
(2Z)-2-(benzoylamino)-3-[4-(2-bromo-4-methylphenoxy)phenyl]prop-2-enoic acid;
(2Z)-2-(benzoylamino)-3-[4-(2-cyclopentylphenoxy)phenyl]prop-2-enoic acid;
(2Z)-2-(benzoylamino)-3-{4-[2-(trifluoromethoxy)phenoxy]phenyl}prop-2-enoic acid;
(2Z)-2-(benzoylamino)-3-[4-(1,1'-biphenyl-2-yloxy)phenyl]prop-2-enoic acid;
(2Z)-2-(benzoylamino)-3-[4-(2,3-difluorophenoxy)phenyl]prop-2-enoic acid;
(2Z)-2-(benzoylamino)-3-[4-(2-isopropylphenoxy)phenyl]prop-2-enoic acid;
(2Z)-2-(benzoylamino)-3-[4-(2-chloro-4-methoxyphenoxy)phenyl]prop-2-enoic acid;
(2Z)-2-(benzoylamino)-3-[4-(2-nitrophenoxy)phenyl]prop-2-enoic acid;
(2Z)-2-(benzoylamino)-3-{4-[(1-bromo-2-naphthyl)oxy]phenyl}prop-2-enoic acid;
(2Z)-2-(benzoylamino)-3-(4-{[4-nitro-2-(trifluoromethyl)cyclohexa-1,5-dien-1-yl]oxy}phenyl)prop-2-enoic acid;
(2Z)-3-(4-{[4-amino-2-(trifluoromethyl)cyclohexa-1,5-dien-1-yl]oxy}phenyl)-2-(benzoylamino)prop-2-enoic acid;
(2Z)-2-(benzoylamino)-3-{4-[2-(trifluoromethyl)phenoxy]phenyl}prop-2-enoic acid;
(2Z)-3-[4-(2-bromophenoxy)phenyl]-2-[(2-hydroxybenzoyl)amino]prop-2-enoic acid;
(2Z)-2-[(2-hydroxybenzoyl)amino]-3-[4-(2-iodophenoxy)phenyl]prop-2-enoic acid,
2-hydroxy-N-{(Z)-1-{[(2-hydroxyethyl)amino]carbonyl}-2-[4-(2-iodophenoxy)phenyl]ethenyl}benzamide;
(2Z)-2-(benzoylamino)-3-[4-(2-bromophenoxy)-3-nitrophenyl]prop-2-enoic acid;
(2Z)-2-(benzoylamino)-3-[4-(phenoxymethyl)phenyl]prop-2-enoic acid;
(2Z)-2-(benzoylamino)-3-[4-(pyridin-2-ylmethoxy)phenyl]prop-2-enoic acid;
(2Z)-2-(benzoylamino)-3-{4-[(2-fluorobenzyl)oxy]phenyl}prop-2-enoic acid;
(2Z)-2-(benzoylamino)-3-(4-{[3-(trifluoromethyl)benzyl]oxy}phenyl)prop-2-enoic acid;
(2Z)-3-[3-amino-4-(2-bromophenoxy)phenyl]-2-(benzoylamino)prop-2-enoic acid;
methyl (2Z)-2-(benzoylamino)-3-[4-(2-bromophenoxy)phenyl]prop-2-enoate;
2-[({(Z)-2-[4-(2-bromophenoxy)phenyl]-1-carboxyethenyl}amino)carbonyl]benzoic acid;
(2Z)-2-(benzoylamino)-3-{4-[(4-cyanobenzyl)oxy]phenyl}prop-2-enoic acid;
(2Z)-2-(benzoylamino)-3-[4-(pyridin-3-ylmethoxy)phenyl]prop-2-enoic acid;
(2Z)-2-(benzoylamino)-3-[4-(pyridin-4-ylmethoxy)phenyl]prop-2-enoic acid;
(2Z)-2-(benzoylamino)-3-(4-{[4-(trifluoromethyl)benzyl]oxy}phenyl)prop-2-enoic acid;
(2Z)-2-(benzoylamino)-3-{4-[(4-fluorobenzyl)oxy]phenyl}prop-2-enoic acid;
(2Z)-2-(benzoylamino)-3-{4-[(3-nitrobenzyl)oxy]phenyl}prop-2-enoic acid;
(2Z)-2-(benzoylamino)-3-{4-[(4-methylbenzyl)oxy]phenyl}prop-2-enoic acid;
(2Z)-2-(benzoylamino)-3-{4-[(4-chlorobenzyl)oxy]phenyl}prop-2-enoic acid;
N-{(Z)-1-(aminocarbonyl)-2-[4-(2-bromophenoxy)phenyl]ethenyl}benzamide;
(2Z)-2-(benzoylamino)-3-[3-(benzyloxy)phenyl]prop-2-enoic acid;
(2Z)-2-[benzoyl(methyl)amino]-3-[4-(2-bromophenoxy)phenyl]prop-2-enoic acid;
(2Z)-2-(benzoylamino)-3-[3-(4-chlorophenoxy)phenyl]prop-2-enoic acid;
(2Z)-2-(benzoylamino)-3-[3-(4-methylphenoxy)phenyl]prop-2-enoic acid;
(2Z)-2-(benzoylamino)-3-[3-(4-methoxyphenoxy)phenyl]prop-2-enoic acid;
(2Z)-2-(benzoylamino)-3-{3-[(2-chlorobenzyl)oxy]phenyl}prop-2-enoic acid;
(2Z)-2-(benzoylamino)-3-{4-[(3-methoxybenzyl)oxy]phenyl}prop-2-enoic acid;
(2Z)-2-(benzoylamino)-3-{4-[(3-chlorobenzyl)oxy]phenyl}prop-2-enoic acid;
(2Z)-2-(benzoylamino)-3-(4-{[3-(trifluoromethoxy)benzyl]oxy}phenyl)prop-2-enoic acid;
(2Z)-2-(benzoylamino)-3-[3-(2-chlorophenoxy)phenyl]prop-2-enoic acid;

(2Z)-2-(benzoylamino)-3-[3-(2-bromophenoxy)phenyl]
 prop-2-enoic acid;
(2Z)-2-(benzoylamino)-3-[3-(2-chloro-4-nitrophenoxy)phenyl]prop-2-enoic acid;
(2Z)-2-(benzoylamino)-3-{4-[(3-methylbenzyl)oxy]
 phenyl}prop-2-enoic acid;
(2Z)-2-(benzoylamino)-3-[4-(2-tert-butylphenoxy)phenyl]
 prop-2-enoic acid;
(2Z)-2-(benzoylamino)-3-{4-[(3-fluorobenzyl)oxy]
 phenyl}prop-2-enoic acid;
(2Z)-2-(benzoylamino)-3-{4-[(3-cyanobenzyl)oxy]
 phenyl}prop-2-enoic acid;
(2Z)-2-(benzoylamino)-3-{3-[3-(trifluoromethyl)phenoxy]
 phenyl}prop-2-enoic acid;
(2Z)-2-(benzoylamino)-3-[3-(4-tert-butylphenoxy)phenyl]
 prop-2-enoic acid.

Example 15

Evaluation of Polymerase Activity

Compounds of the present invention are evaluated for inhibition of HCV NS5b RNA dependent RNA polymerase activity in assays comprised of a suitable buffer (e.g. 20 mM Tris-HCl pH 7.6), primed or unprimed RNA templates, GTP, ATP, CTP, and UTP, $MnCl_2$ or $MgCl_2$, and reducing agent such as 10 mM dithiothreitol or 2-mercaptoethanol. The assay buffer may contain salts such as ammonium acetate, KCl, or NaCl, and nonionic or zwitterionic detergents such as Tween or CHAPS. The incorporation of nucleotides into the complementary RNA strand may be monitored by the incorporation of radiolabeled NTP (e.g. $^3$H labeled GTP). Suitable RNA templates for de novo initiation in the presence of 20–50 μM GTP or ATP are the homopolymers poly rC and poly rU, respectively. Heteropolymer RNA templates with 1–3 cytidine (C) bases or 1–3 uridine (U) bases at the 3' terminus of the template may also be used for de novo initiation. Primed RNA templates such as poly rC primed with oligo rG or oligo dG, and poly rA primed with oligo rU may also be used to detect polymerase activity. The primers may be any length greater than 10 bases. A biotin residue may be added to the 5' end of the template or the 5' end of the primer to capture the template and the newly synthesized, complementary strand on avidin coated spheres. One embodiment of this technology consists of a mixture of NS5b polymerase, a poly rC RNA template primed with 5' biotinylated oligo rG, 20 mM Tris HCl pH 7.6, 100 mM ammonium acetate, 10 mM dithiothreitol, 2 mM CHAPS, 1 mM $MgCl_2$, and 150–200 nM $^3$H labeled GTP. Test compounds (inhibitors) may be incorporated in the reaction mixture with up to 10% DMSO. The reaction is run for various times (1–180 minutes) at 22–37° C., and stopped by the addition of 10–140 mM EDTA. Scintillation Proximity Assay avidin-coated beads (Amersham Pharmacia Biotech) are added to capture the ds RNA product; or the reaction mixtures may be transferred to avidin coated Flash Plates (Perkin Elmer Life Sciences). The incorporation of radiolabeled GTP into the complementary strand is measured in 96, 384, or 1536 well plates in scintillation counters such as the Wallac Microbeta and Packard TopCount.

A substantial number of the compounds exhibited IC50 values ranging from less than 1 to about 30 μM or more. In Table 2, the inhibitory activity of representative examples is provided. Activity is listed in Table 2 as +++ if the concentration for 50% inhibition is <10 μM, ++ if activity is 11–30 μM and + if activity is >30 μM.

TABLE 2

| Compound | NS5B Inhibitory Activity |
|---|---|
| 1 | +++ |
| 2 | +++ |
| 3 | ++ |
| 4 | +++ |
| 5 | ++ |
| 6 | ++ |
| 7 | + |
| 8 | +++ |
| 9 | +++ |
| 10 | +++ |
| 11 | + |
| 12 | + |
| 13 | +++ |
| 14 | ++ |
| 15 | ++ |
| 16 | +++ |
| 17 | + |
| 18 | +++ |
| 19 | + |
| 20 | + |

Yet other compounds of this invention are illustrated in Table 3.

| Compound Number | Structure | Name |
|---|---|---|
| 1. | 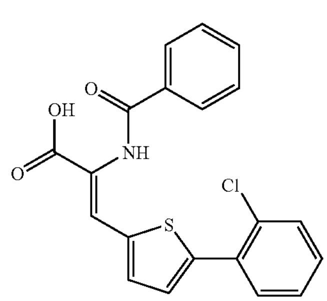 | (2Z)-2-(benzoylamino)-3-[5-(2-chlorophenyl)thien-2-yl]prop-2-enoic acid; |

-continued

| Compound Number | Structure | Name |
|---|---|---|
| 2. | 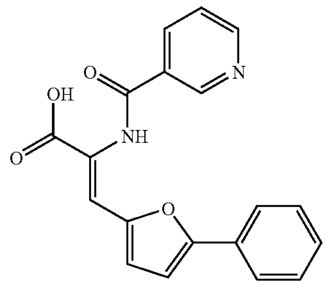 | (2Z)-3-(5-phenyl-2-furyl)-2-[(pyridin-3-ylcarbonyl)amino]prop-2-enoic acid; |
| 3. | 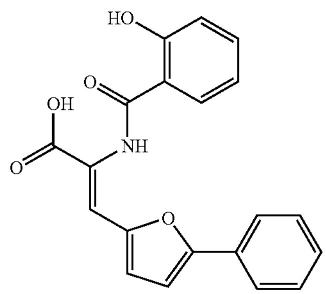 | (2Z)-2-[(2-hydroxybenzoyl)amino]-3-(5-phenyl-2-furyl)prop-2-enoic acid; |
| 4. | 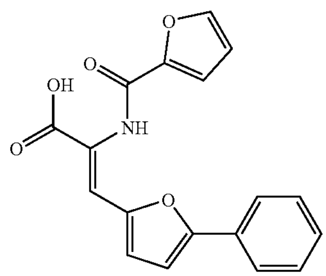 | (2Z)-2-(2-furoylamino)-3-(5-phenyl-2-furyl)prop-2-enoic acid; |
| 5. | 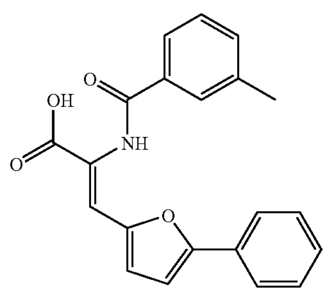 | (2Z)-2-[(3-methylbenzoyl)amino]-3-(5-phenyl-2-furyl)prop-2-enoic acid; |
| 6. | 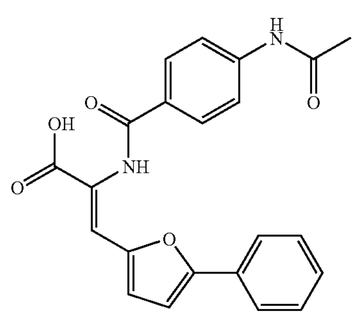 | (2Z)-2-{[4-(acetylamino)benzoyl]amino}-3-(5-phenyl-2-furyl)prop-2-enoic acid; |

-continued

| Compound Number | Structure | Name |
|---|---|---|
| 7. | 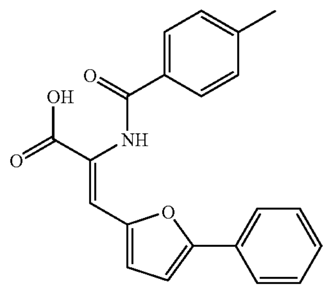 | (2Z)-2-[(4-methylbenzoyl)amino]-3-(5-phenyl-2-furyl)prop-2-enoic acid; |
| 8. | 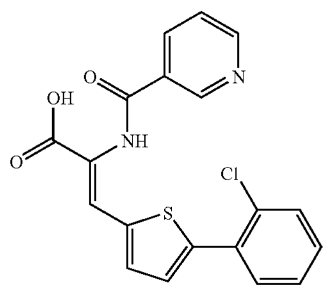 | (2Z)-3-[5-(2-chlorophenyl)thien-2-yl]-2-[(pyridin-3-ylcarbonyl)amino]prop-2-enoic acid; |
| 9. | 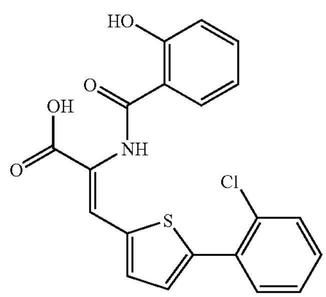 | (2Z)-3-[5-(2-chlorophenyl)thien-2-yl]-2-[(2-hydroxybenzoyl)amino]prop-2-enoic acid; |
| 10. | 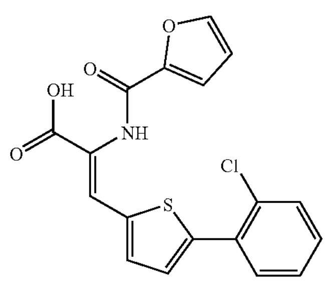 | (2Z)-3-[5-(2-chlorophenyl)thien-2-yl]-2-(2-furoylamino)prop-2-enoic acid; |
| 11. | 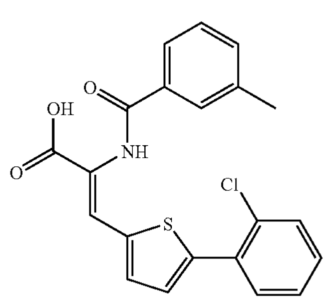 | (2Z)-3-[5-(2-chlorophenyl)thien-2-yl]-2-[(4-methylbenzoyl)amino]prop-2-enoic acid; |

| Compound Number | Structure | Name |
|---|---|---|
| 12. | 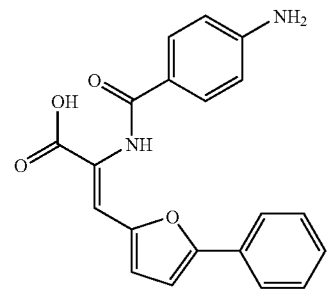 | (2Z)-2-[(4-aminobenzoyl)amino]-3-(5-phenyl-2-furyl)prop-2-enoic acid; |
| 13. | 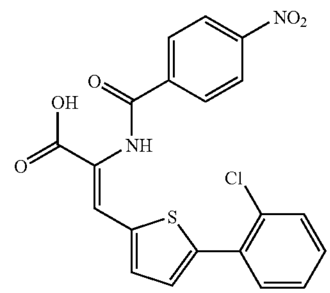 | (2Z)-3-[5-(2-chlorophenyl)thien-2-yl]-2-[(4-nitrobenzoyl)amino]prop-2-enoic acid; |
| 14. | 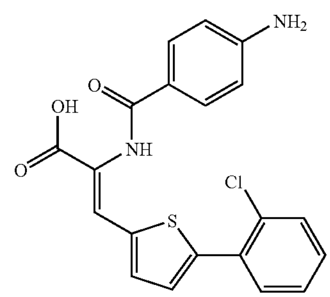 | (2Z)-2-[(4-aminobenzoyl)amino]-3-[5-(2-chlorophenyl)thien-2-yl]prop-2-enoic acid; |
| 15. | 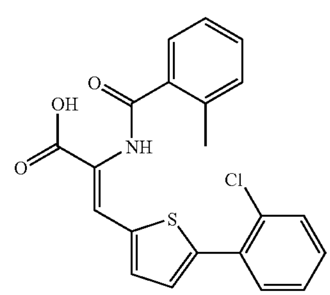 | (2Z)-3-[5-(2-chlorophenyl)thien-2-yl]-2-{(2-methylbenzoyl)amino]prop-2-enoic acid; |
| 16. | 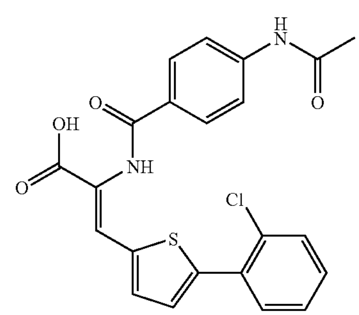 | (2Z)-2-{[4-(acetylamino)benzoyl]amino)-3-[5-(2-chlorophenyl)thien-2-yl]prop-2-enoic acid; |

-continued

| Compound Number | Structure | Name |
|---|---|---|
| 17. | 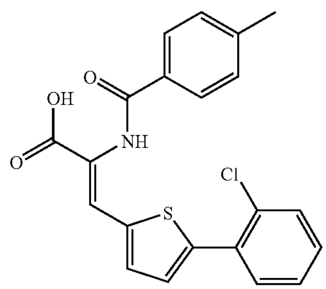 | (2Z)-3-[5-(2-chlorophenyl)thien-2-yl]-2-[(4-methylbenzoyl)amino]prop-2-enoic acid; |
| 18. | 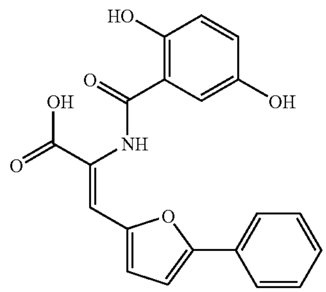 | (2Z)-2-[(2,5-dihydroxybenzoyl)amino]-3-(5-phenyl-2-furyl)prop-2-enoic acid; |
| 19. | 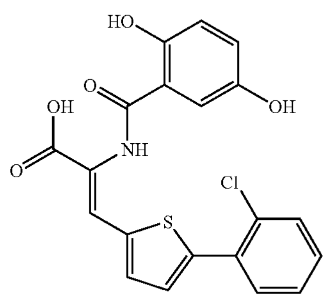 | (2Z)-3-[5-(2-chlorophenyl)thien-2-yl]-2-[(2,5-dihydroxybenzoyl)amino]prop-2-enoic acid; |
| 20. | 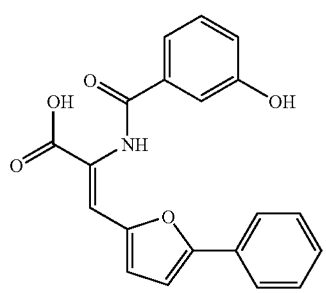 | (2Z)-2-((3-hydroxybenzoyl)amino]-3-(5-phenyl-2-furyl)prop-2-enoic acid; |
| 21. | 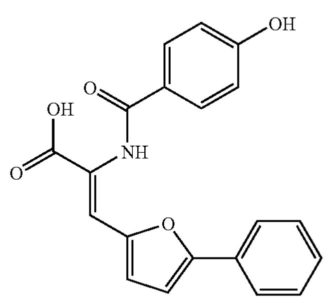 | (2Z)-2-[(4-hydroxybenzoyl)amino]-3-(5-phenyl-2-furyl)prop-2-enoic acid; |

-continued

| Compound Number | Structure | Name |
|---|---|---|
| 22. | 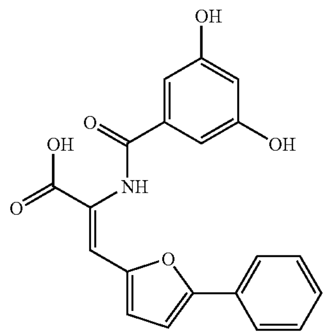 | (2Z)-2-[(3,5-dihydroxybenzoyl)amino]-3-(5-phenyl-2-furyl)prop-2-enoic acid; |
| 23. | 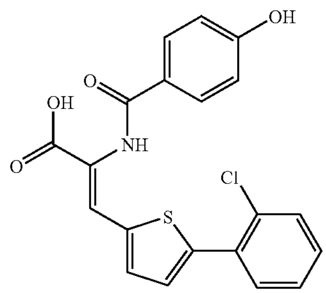 | (2Z)-3-[5-(2-chlorophenyl)thien-2-yl]-2-[(4-hydroxybenzoyl)amino]prop-2-enoic acid; |
| 24. | 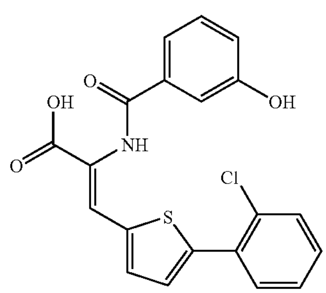 | (2Z)-3-[5-(2-chlorophenyl)thien-2-yl]-2-[(3-hydroxybenzoyl)amino]prop-2-enoic acid; |
| 25. | 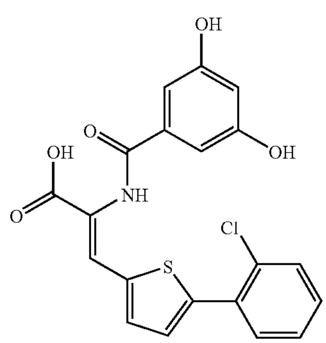 | (2Z)-3-[5-(2-chlorophenyl)thien-2-yl]-2-[(3,5-dihydroxybenzoyl)amino]prop-2-enoic acid; |
| 26. | 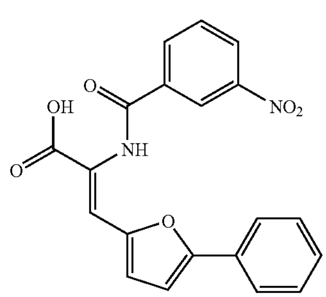 | (2Z)-2-[(3-nitrobenzoyl)amino]-3-(5-phenyl-2-furyl)prop-2-enoic acid; |

-continued

| Compound Number | Structure | Name |
|---|---|---|
| 27. | 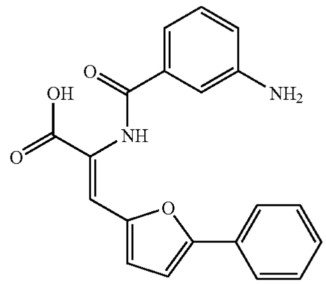 | (2Z)-2-[(3-aminobenzoyl)amino]-3-(5-phenyl-2-furyl)prop-2-enoic acid; |
| 28. | 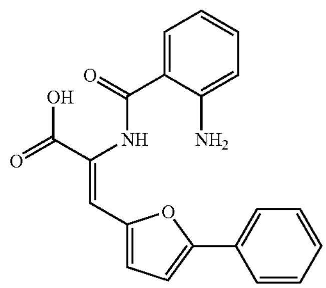 | (2Z)-2-[(2-aminobenzoyl)amino]-3-(5-phenyl-2-furyl)prop-2-enoic acid; |
| 29. | 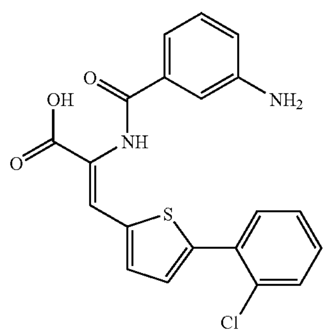 | (2Z)-2-[(3-aminobenzoyl)amino]-3-[5-(2-chlorophenyl)thien-2-yl]prop-2-enoic acid; |
| 30. | 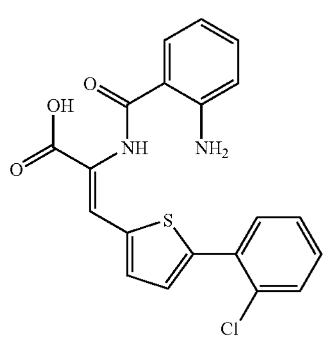 | (2Z)-2-[(2-aminobenzoyl)amino]-3-[5-(2-chlorophenyl)thien-2-yl]prop-2-enoic acid; |

-continued

| Compound Number | Structure | Name |
|---|---|---|
| 31. | 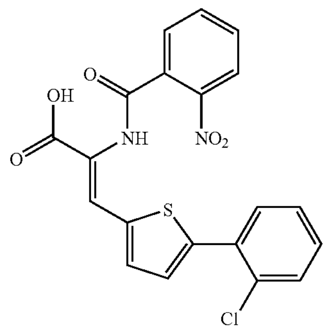 | (2Z)-3-[5-(2-chlorophenyl)thien-2-yl]-2-[(2-nitrobenzoyl)amino]prop-2-enoic acid; |
| 32. | 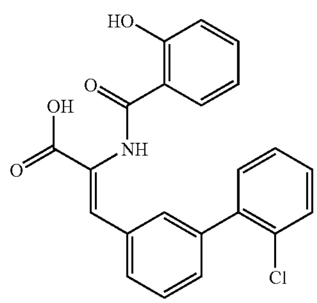 | (2Z)-3-(2'-chloro-1,1'-biphenyl-3-yl)-2-[(2-hydroxybenzoyl)amino]prop-2-enoic acid; |
| 33. | 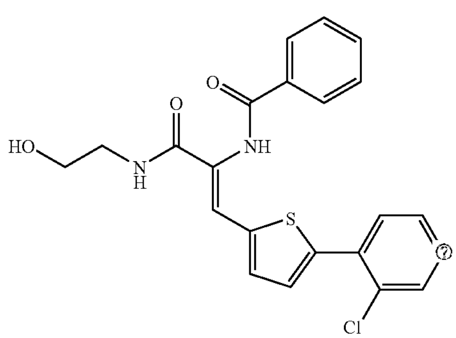 | N-((Z)-2-[5-(2-chlorophenyl)thien-2-yl]-1-{[(2-hydroxyethyl)amino]carbonyl}ethenyl)benzamide; |

ⓘ indicates text missing or illegible when filed

| | | |
|---|---|---|
| 34. | | N-[(Z)-2-[5-(2-chlorophenyl)thien-2-yl]-1-(morpholin-4-ylcarbonyl)ethenyl]benzamide; |

-continued

| Compound Number | Structure | Name |
|---|---|---|
| 35. | 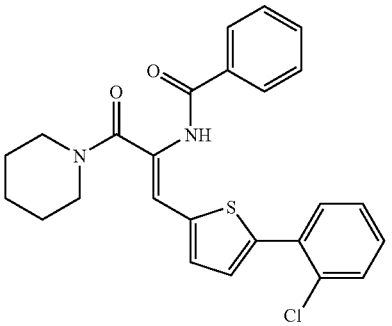 | N-[(Z)-2-[5-(2-chlorophenyl)thien-2-yl]-1-(piperidin-1-ylcarbonyl)ethenyl]benzamide; |
| 36. | 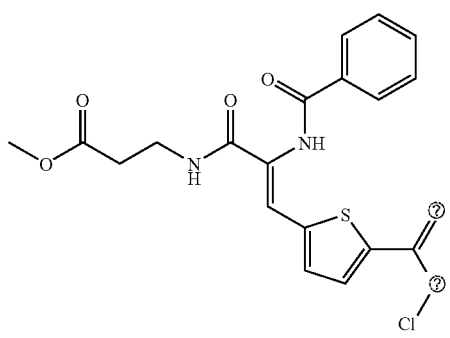<br>⑦ indicates text missing or illegible when filed | methyl N-{(2Z)-2-(benzoylamino)-3-[5-(2-chlorophenyl)thien-2-yl]prop-2-enoyl}-beta-alaninate; |
| 37. | 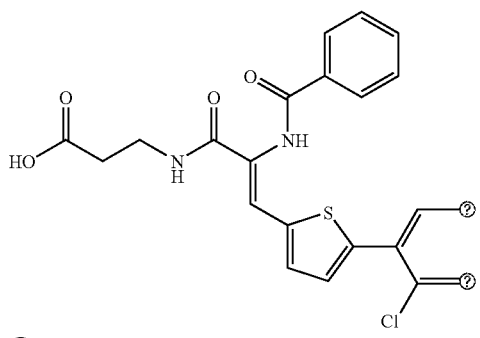<br>⑦ indicates text missing or illegible when filed | N-{(2Z)-2-(benzoylamino)-3-[5-(2-chlorophenyl)thien-2-yl]prop-2-enoyl}-beta-alanine; |
| 38. | 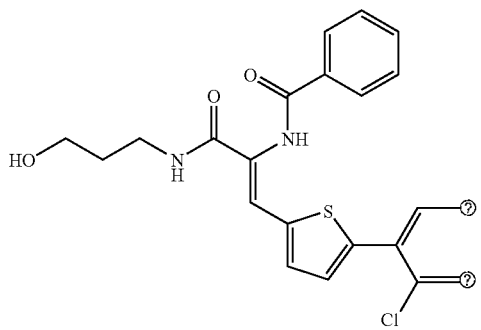<br>⑦ indicates text missing or illegible when filed | N-((Z)-2-[5-(2-chlorophenyl)thien-2-yl]-1-{[(3-hydroxypropyl)amino]carbonyl}ethenyl)benzamide; |

-continued

| Compound Number | Structure | Name |
|---|---|---|
| 39. | 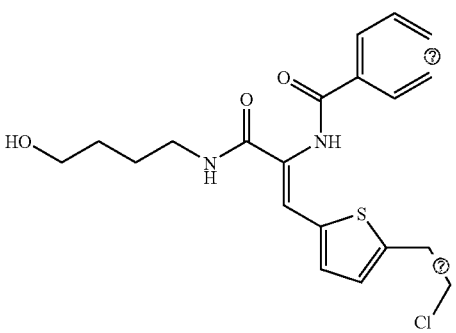 ⓘ indicates text missing or illegible when filed | N-((Z)-2-[5-(2-chlorophenyl)thien-2-yl]-1-{[(4-hydroxybutyl)amino]carbonyl}ethenyl)benzamide; |
| 40. | 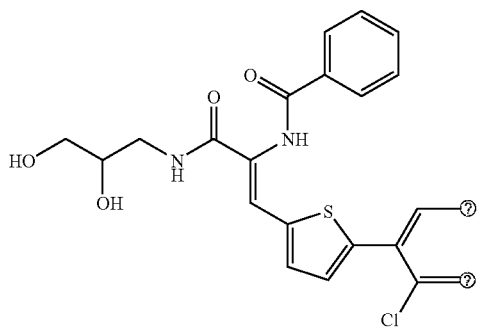 ⓘ indicates text missing or illegible when filed | N-((Z)-2-[5-(2-chlorophenyl)thien-2-yl]-1-{[(2,3-dihydroxypropyl)amino]carbonyl}ethenyl)benzamide; |
| 41. | 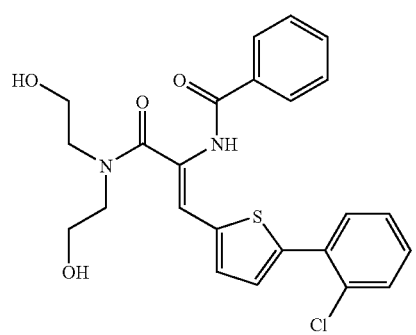 | N-{(Z)-1-{[bis(2-hydroxyethyl)amino]carbonyl}-2-[5-(2-chlorophenyl)thien-2-yl]ethenyl}benzamide; |
| 42. | 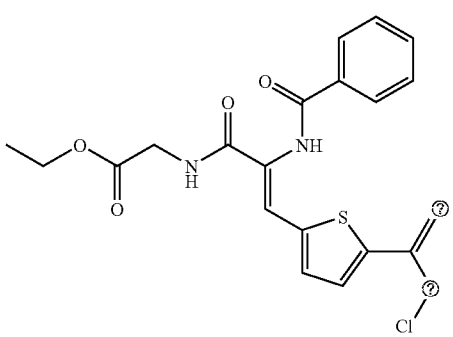 ⓘ indicates text missing or illegible when filed | ethyl N-{(2Z)-2-(benzoylamino)-3-[5-(2-chlorophenyl)thien-2-yl]prop-2-enoyl}glycinate; |

-continued

| Compound Number | Structure | Name |
|---|---|---|
| 43. | 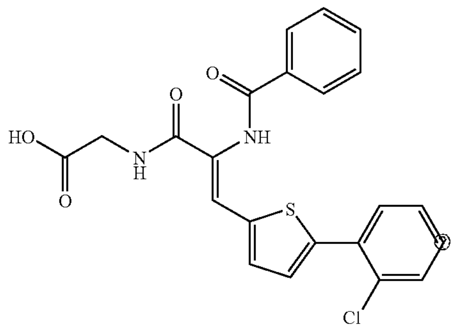 | N-{(2Z)-2-(benzoylamino)-3-[5-(2-chlorophenyl)thien-2-yl]prop-2-enoyl}glycine; |
| 44. | 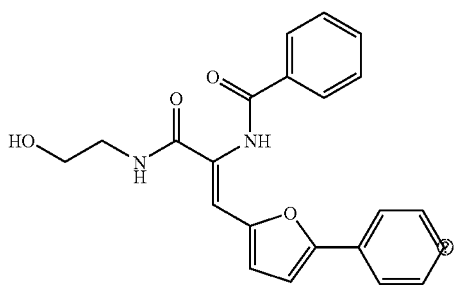 | N-[(Z)-1-{[(2-hydroxyethyl)amino]carbonyl}-2-(5-phenyl-2-furyl)ethenyl]benzamide; |
| 45. | 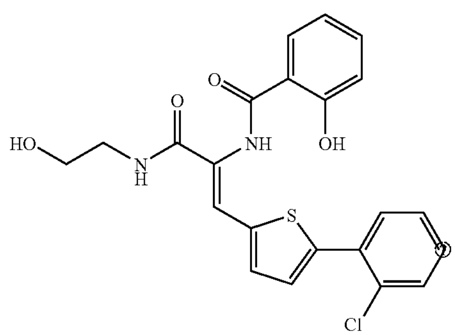 | N-((Z)-2-[5-(2-chlorophenyl)thien-2-yl]-1-{[(2-hydroxyethyl)amino]carbonyl}ethenyl)-2-hydroxybenzamide; |
| 46. | 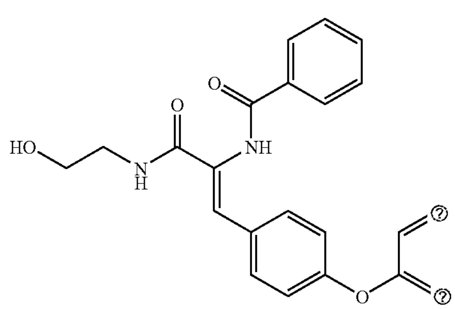 | N-((Z)-2-[4-(2-chlorophenoxy)phenyl]-1-{[(2-hydroxyethyl)amino]carbonyl}ethenyl)benzamide; |

⓪ indicates text missing or illegible when filed

-continued

| Compound Number | Structure | Name |
|---|---|---|
| 47. | 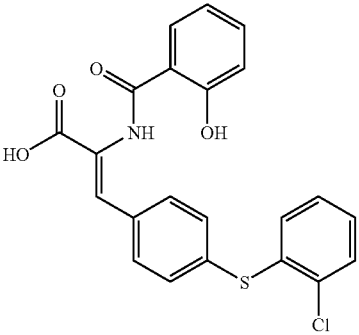 | (2Z)-3-{4-[(2-chlorophenyl)thio]phenyl}-2-[(2-hydroxybenzoyl)amino]prop-2-enoic acid; |
| 48. | 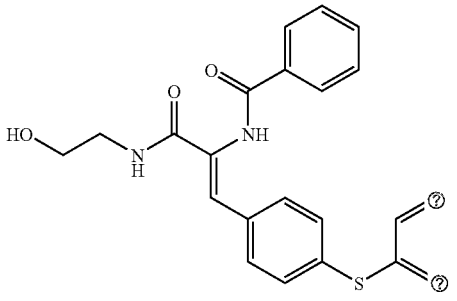<br>⊚ indicates text missing or illegible when filed | N-((Z)-2-{4-[(2-chlorophenyl)thio]phenyl}-1-{[(2-hydroxyethyl)amino]carbonyl}ethenyl)benzamide; |
| 49. | 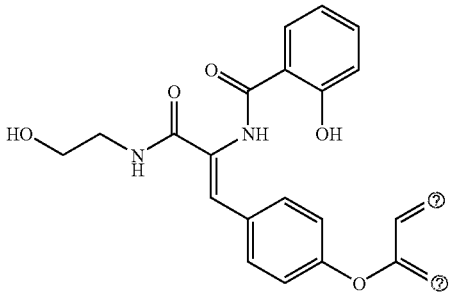<br>⊚ indicates text missing or illegible when filed | N-((Z)-2-[4-(2-chlorophenoxy)phenyl]-1-{[(2-hydroxyethyl)amino]carbonyl}ethenyl)-2-hydroxybenzamide; |
| 50. | 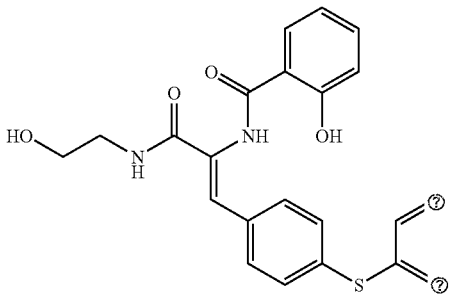<br>⊚ indicates text missing or illegible when filed | N-((Z)-2-{4-[(2-chlorophenyl)thio]phenyl}-1-{[(2-hydroxyethyl)amino]carbonyl}ethenyl)-2-hydroxybenzamide; |

| Compound Number | Structure | Name |
|---|---|---|
| 51. | 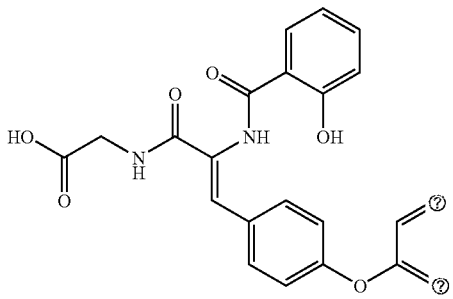 ⓐ indicates text missing or illegible when filed | N-{(2Z)-3-[4-(2-bromophenoxy)phenyl]-2-[(2-hydroxybenzoyl)amino]prop-2-enoyl}glycine; |
| 52. | 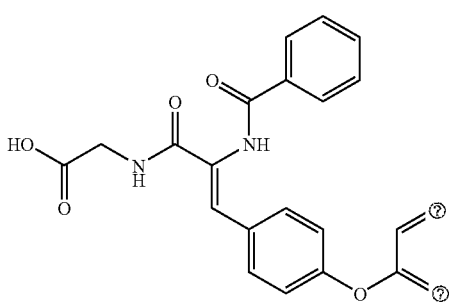 ⓐ indicates text missing or illegible when filed | N-{(2Z)-2-(benzoylamino)-3-[4-(2-bromophenoxy)phenyl]prop-2-enoyl}glycine; |
| 53. | 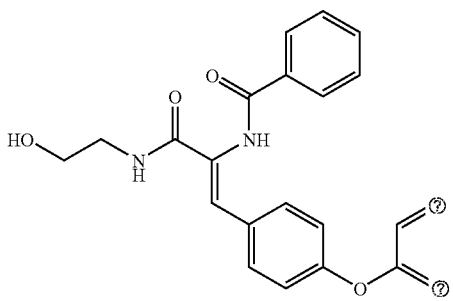 ⓐ indicates text missing or illegible when filed | N-((Z)-2-[4-(2-bromophenoxy)phenyl]-1-{[(2-hydroxyethyl)amino]carbonyl}ethenyl)benzamide; |
| 54. | 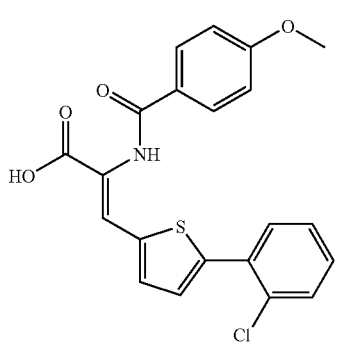 | (2Z)-3-[5-(2-chlorophenyl)thien-2-yl]-2-[(4-methoxybenzoyl)amino]prop-2-enoic acid; |

-continued

| Compound Number | Structure | Name |
|---|---|---|
| 55. | 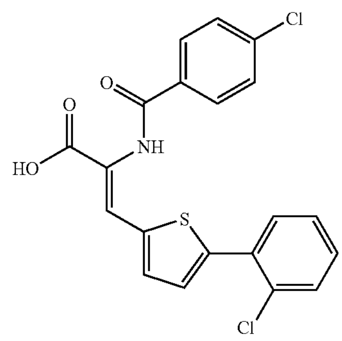 | (2Z)-2-[(4-chlorobenzoyl)amino]-3-[5-(2-chlorophenyl)thien-2-yl]prop-2-enoic acid; |
| 56. | 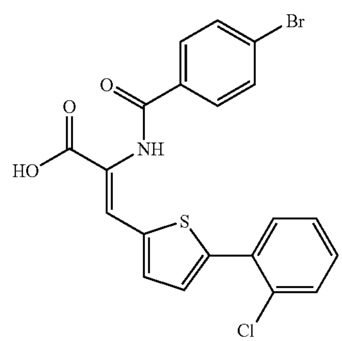 | (2Z)-2-[(4-bromobenzoyl)amino]-3-[5-(2-chlorophenyl)thien-2-yl]prop-2-enoic acid; |
| 57. | 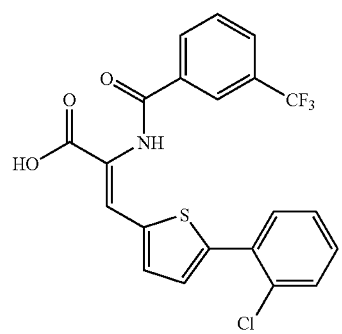 | (2Z)-3-[5-(2-chlorophenyl)thien-2-yl]-2-{[3-(trifluoromethyl)benzoyl]amino}prop-2-enoic acid; |
| 58. | 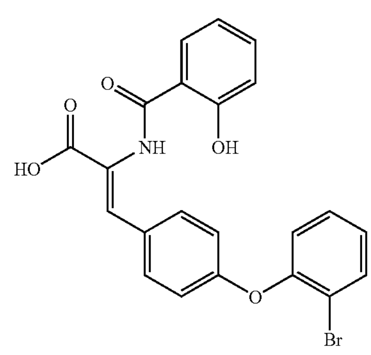 | (2Z)-3-[4-(2-bromophenoxy)phenyl]-2-[(2-hydroxybenzoyl)amino]prop-2-enoic acid; |

-continued

| Compound Number | Structure | Name |
|---|---|---|
| 59. | 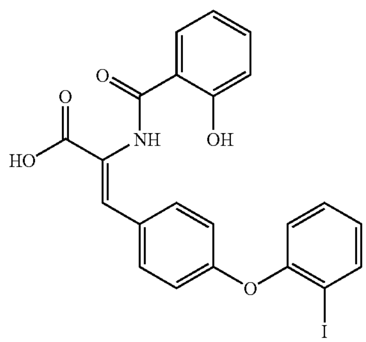 | (2Z)-2-[(2-hydroxybenzoyl)amino]-3-[4-(2-iodophenoxy)phenyl]prop-2-enoic acid; |
| 60. | 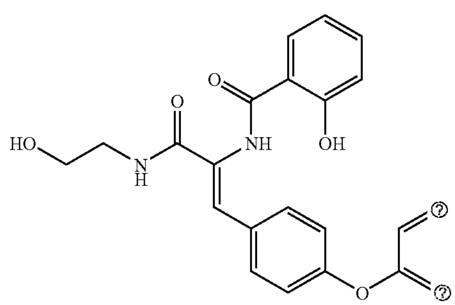 | 2-hydroxy-N-{(Z)-1-{[(2-hydroxyethyl)amino]carbonyl}-2-[4-(2-iodophenoxy)phenyl]ethenyl}benzamide; |
| 61. | 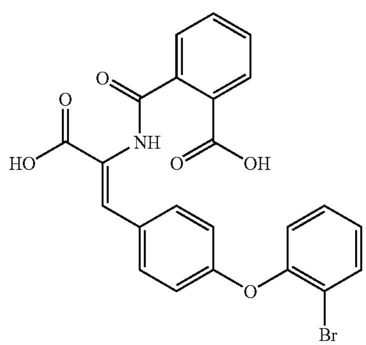 | 2-[({(Z)-2-[4-(2-bromophenoxy)phenyl]-1-carboxyethenyl}amino)carbonyl]benzoic acid; |
| 62. | 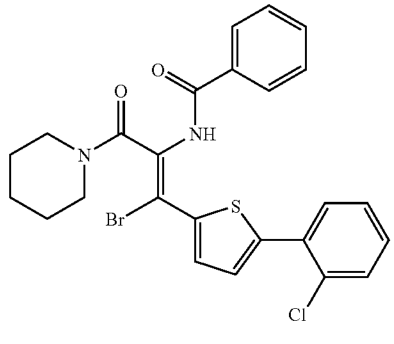 | N-[(E)-2-bromo-2-[5-(2-chlorophenyl)thien-2-yl]-1-(piperidin-1-ylcarbonyl)ethenyl]benzamide; |

? indicates text missing or illegible when filed

-continued

| Compound Number | Structure | Name |
|---|---|---|
| 63. | 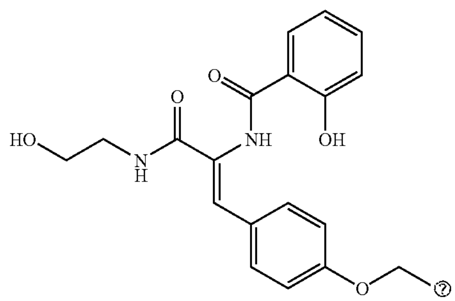 | 2-hydroxy-N-((Z)-1-{[(2-hydroxyethyl)amino]carbonyl}-2-{4-[(3-methoxybenzyl)oxy]phenyl}ethenyl)benzamide; |
| 64. | 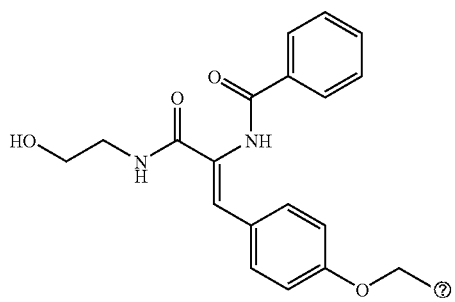 | N-((Z)-1-{[(2-hydroxyethyl)amino]carbonyl}-2-{4-[(3-methoxybenzyl)oxy]phenyl}ethenyl)benzamide; |
| 65. | 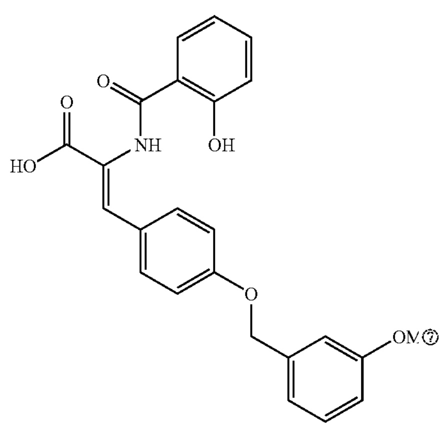 | (2Z)-2-[(2-hydroxybenzoyl)amino]-3-{4-[(3-methoxybenzyl)oxy]phenyl}prop-2-enoic acid; |
| 66. | 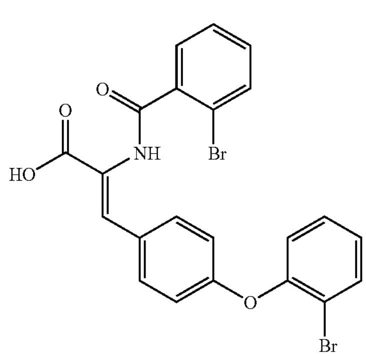 | (2Z)-2-[(2-bromobenzoyl)amino]-3-{4-(2-bromophenoxy)phenyl]prop-2-enoic acid; |

-continued

| Compound Number | Structure | Name |
|---|---|---|
| 67. | 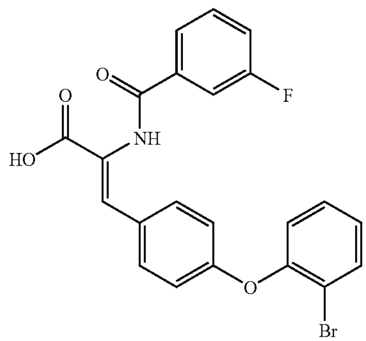 | (2Z)-3-[4-(2-bromophenoxy)phenyl]-2-[(3-fluorobenzoyl)amino]prop-2-enoic acid; |
| 68. | 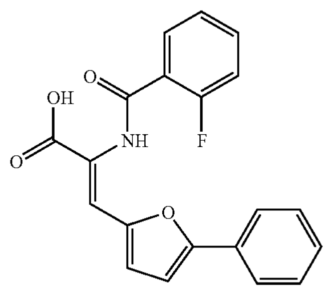 | (2Z)-2-[(2-fluorobenzoyl)amino]-3-(5-phenyl-2-furyl)prop-2-enoic acid; |
| 69. | 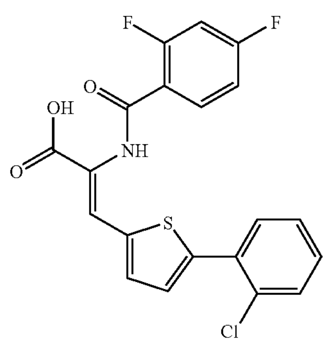 | (2Z)-3-[5-(2-chlorophenyl)thien-2-yl]-2-[(2,4-difluorobenzoyl)amino]prop-2-enoic acid; |
| 70. | 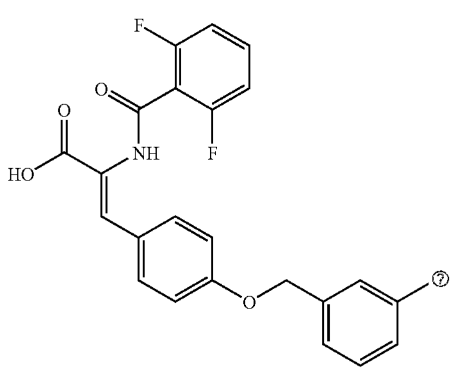 | (2Z)-2-[(2,6-difluorobenzoyl)amino]-3-{4-[(3-methoxybenzyl)oxy]phenyl}prop-2-enoic acid; |

ⓘ indicates text missing or illegible when filed

-continued

| Compound Number | Structure | Name |
|---|---|---|
| 71. | 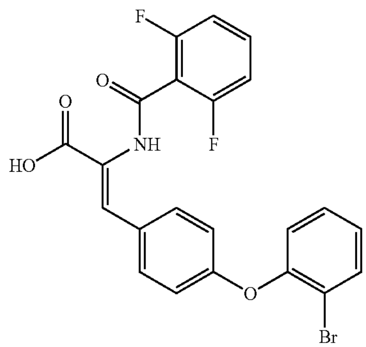 | (2Z)-3-[4-(2-bromophenoxy)phenyl]-2-[(2,6-difluorobenzoyl)amino]prop-2-enoic acid; |
| 72. | 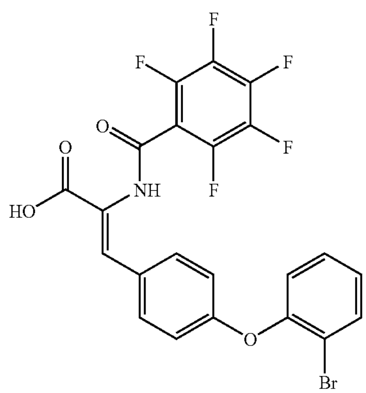 | (2Z)-3-[4-(2-bromophenoxy)phenyl]-2-[(pentafluorobenzoyl)amino]prop-2-enoic acid; |
| 73. | 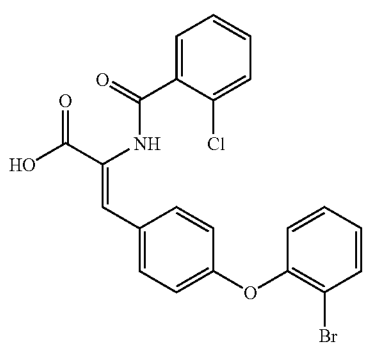 | (2Z)-3-[4-(2-bromophenoxy)phenyl]-2-[(2-chlorobenzoyl)amino]prop-2-enoic acid; |
| 74. | 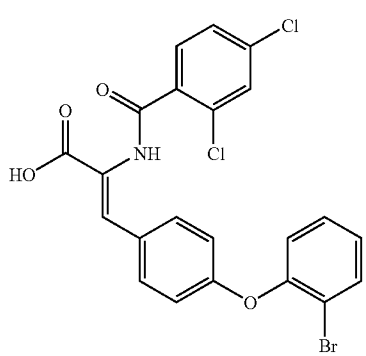 | (2Z)-3-[4-(2-bromophenoxy)phenyl]-2-[(2,4-dichlorobenzoyl)amino]prop-2-enoic acid; |

-continued

| Compound Number | Structure | Name |
|---|---|---|
| 75. | 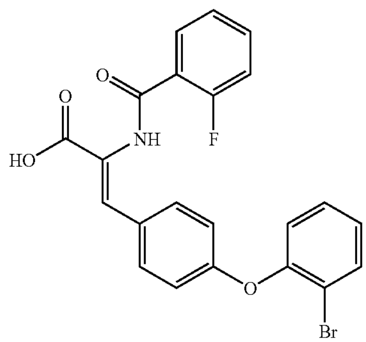 | (2Z)-3-[4-(2-bromophenoxy)phenyl]-2-[(2-fluorobenzoyl)amino]prop-2-enoic acid; |
| 76. | 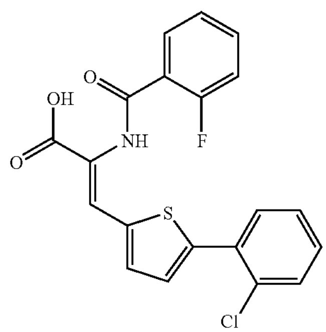 | (2Z)-3-[5-(2-chlorophenyl)thien-2-yl]-2-[(2-fluorobenzoyl)amino]prop-2-enoic acid; |
| 77. | 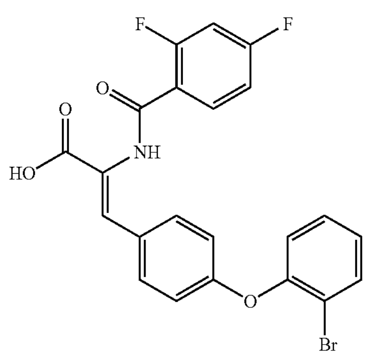 | (2Z)-3-[4-(2-bromophenoxy)phenyl]-2-[(2,4-difluorobenzoyl)amino]prop-2-enoic acid; |
| 78. | 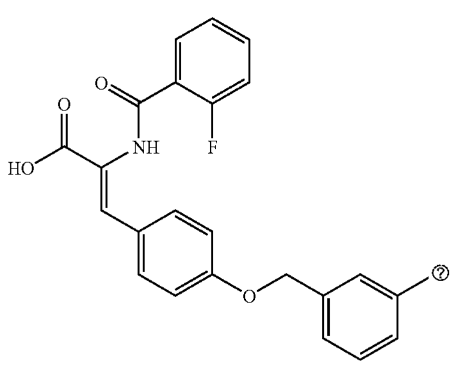 | (2Z)-2-[(2-fluorobenzoyl)amino]-3-{4-[(3-methoxybenzyl)oxy]phenyl}prop-2-enoic acid; |

⑦ indicates text missing or illegible when filed

-continued

| Compound Number | Structure | Name |
|---|---|---|
| 79. | 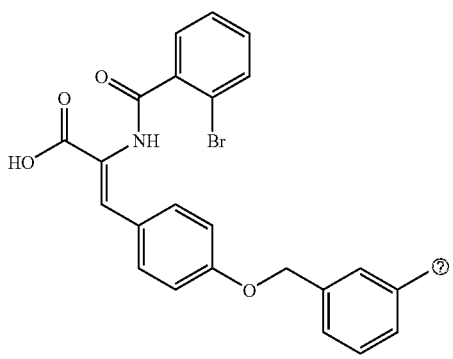<br>⑦ indicates text missing or illegible when filed | (2Z)-2-[(2-bromobenzoyl)amino]-3-{4-[(3-methoxybenzyl)oxy]phenyl}prop-2-enoic acid; |
| 80. | 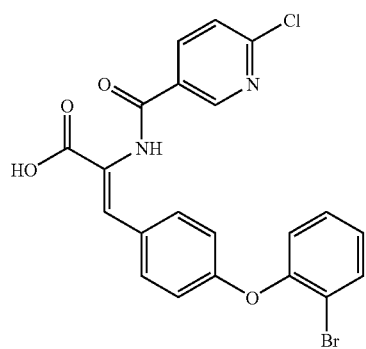 | (2Z)-3-[4-(2-bromophenoxy)phenyl]-2-{[(6-chloropyridin-3-yl)carbonyl]amino}prop-2-enoic acid; |
| 81. | 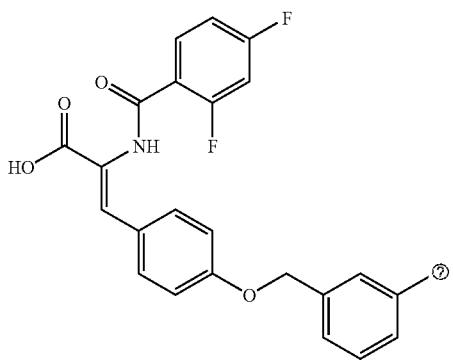<br>⑦ indicates text missing or illegible when filed | (2Z)-2-[(2,4-difluorobenzoyl)amino]-3-{4-[(3-methoxybenzyl)oxy]phenyl}prop-2-enoic acid; |
| 82. | 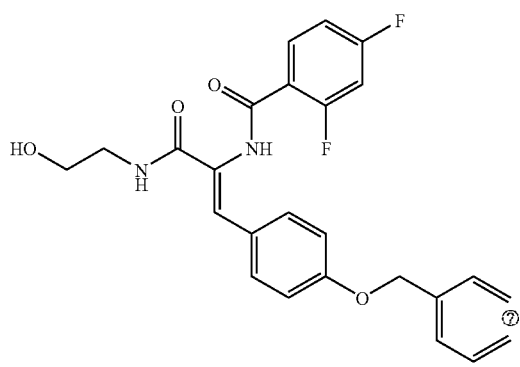<br>⑦ indicates text missing or illegible when filed | |

-continued

| Compound Number | Structure | Name |
|---|---|---|
| 83. | 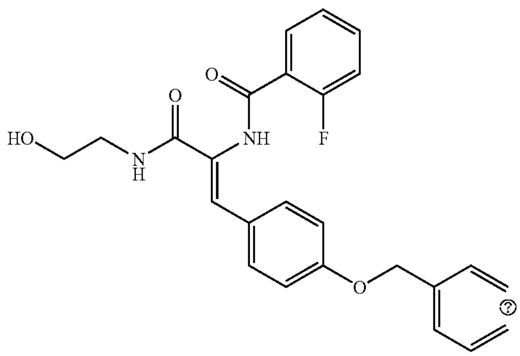 | 2-fluoro-N-((Z)-1-{[(2-hydroxyethyl)amino]-carbonyl}-2-{4-[(3-methoxybenzyl)oxy]phenyl}ethenyl)benzamide; |
| 84. | 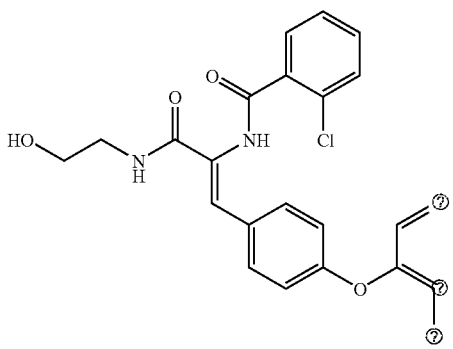 ⓘ indicates text missing or illegible when filed | N-((Z)-2-[4-(2-bromophenoxy)phenyl]-1-{[(2-hydroxyethyl)amino]carbonyl}ethenyl)-3-fluorobenzamide; |
| 85. | 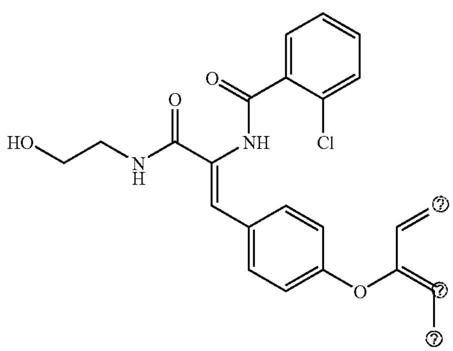 | N-((Z)-2-[4-(2-bromophenoxy)phenyl]-1-{[(2-hydroxyethyl)amino]carbonyl}ethenyl)-2-chlorobenzamide; |
| 86. | 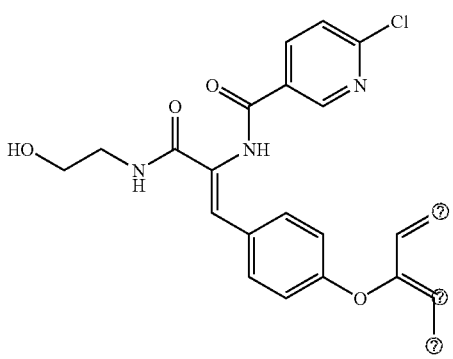 ⓘ indicates text missing or illegible when filed | N-((Z)-2-[4-(2-bromophenoxy)phenyl]-1-{[(2-hydroxyethyl)amino]carbonyl}ethenyl)-6-chloronicotinamide; |

| Compound Number | Structure | Name |
|---|---|---|
| 87. | 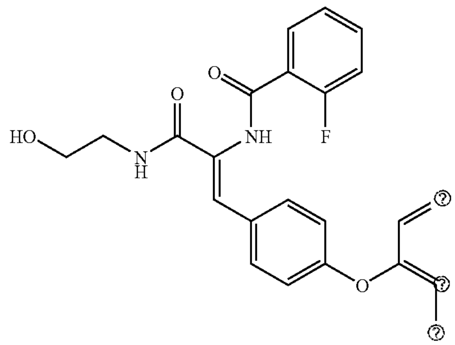 | N-((Z)-2-[4-(2-bromophenoxy)phenyl]-1-{[(2-hydroxyethyl)amino]carbonyl}ethenyl)-2-fluorobenzamide; |
| 88. | 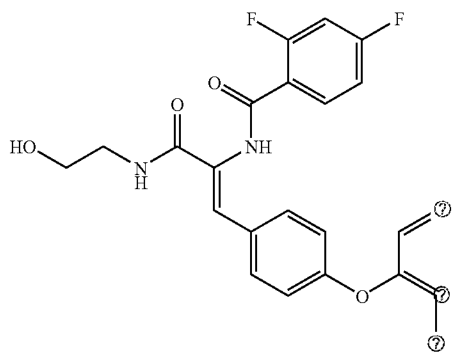 | N-((Z)-2-[4-(2-bromophenoxy)phenyl]-1-{[(2-hydroxyethyl)amino]carbonyl}ethenyl)-2,4-difluorobenzamide; |
| 89. | 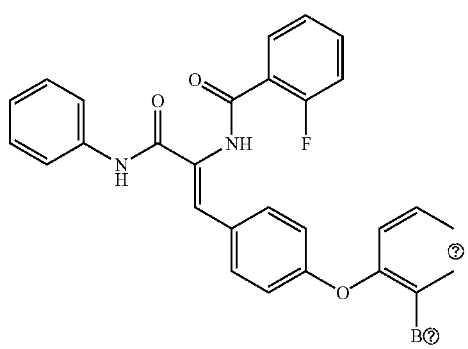 | N-{(Z)-1-(anilinocarbonyl)-2-[4-(2-bromophenoxy)phenyl]ethenyl}-2-fluorobenzamide; |
| 90. | 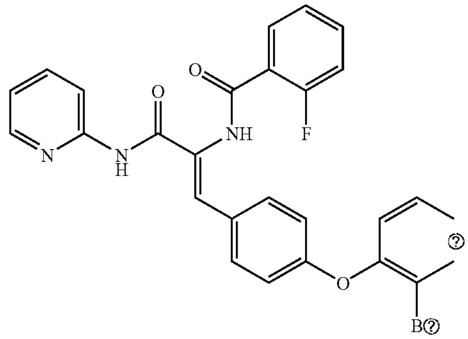 | N-{(Z)-2-[4-(2-bromophenoxy)phenyl]-1-[(pyridin-2-ylamino)carbonyl]ethenyl}-2-fluorobenzamide; |

⑦ indicates text missing or illegible when filed

| Compound Number | Structure | Name |
|---|---|---|
| 91. | 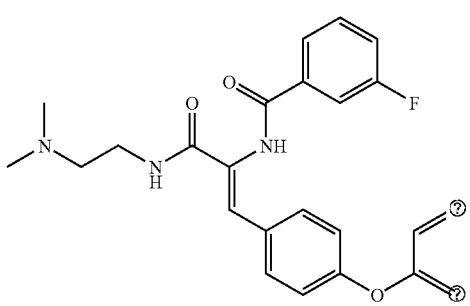 | N-[(Z)-2-[4-(2-bromophenoxy)phenyl]-1-({[2-(dimethylamino)ethyl]amino}carbonyl)ethenyl]-3-fluorobenzamide; |
| 92. | 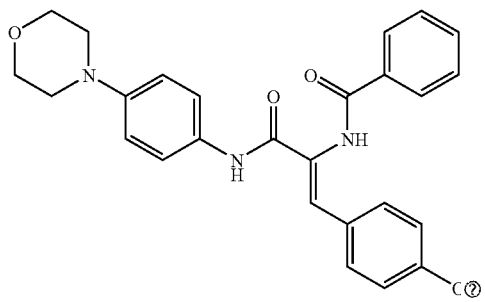 | N-((Z)-2-[4-(2-bromophenoxy)phenyl]-1-{[(4-morpholin-4-ylphenyl)amino]carbonyl}-ethenyl)benzamide; |
| 93. | 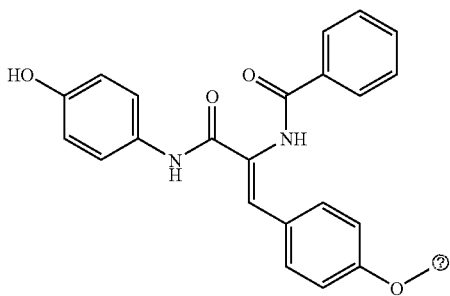 | N-((Z)-2-[4-(2-bromophenoxy)phenyl]-1-{[(4-hydroxyphenyl)amino]carbonyl}ethenyl)benzamide; |
| 94. | 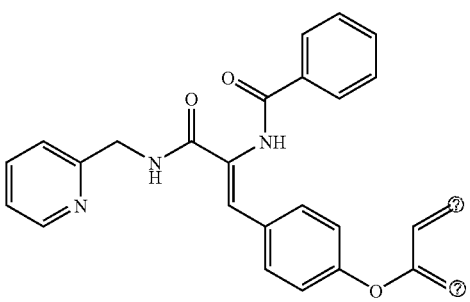 | N-((Z)-2-[4-(2-bromophenoxy)phenyl]-1-{[(pyridin-2-ylmethyl)amino]carbonyl}vinyl)benzamide |

-continued

| Compound Number | Structure | Name |
|---|---|---|
| 95. | 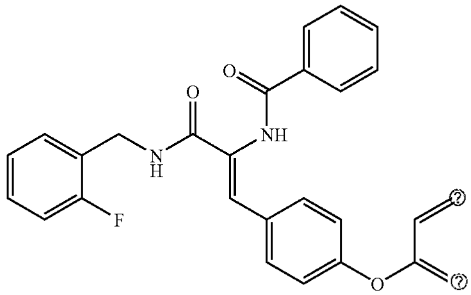 | N-((Z)-2-[4-(2-bromophenoxy)phenyl]-1-{[(2-fluorobenzyl)amino]carbonyl}vinyl)benzamide |
| 96. | 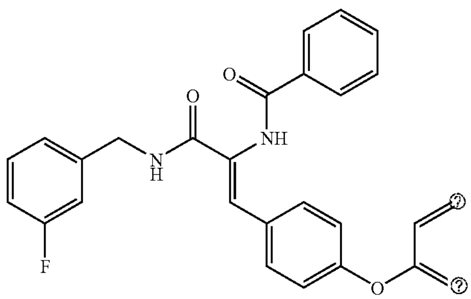 | N-((Z)-2-[4-(2-bromophenoxy)phenyl]-1-{[(3-fluorobenzyl)amino]carbonyl}vinyl)benzamide |
| 97. | 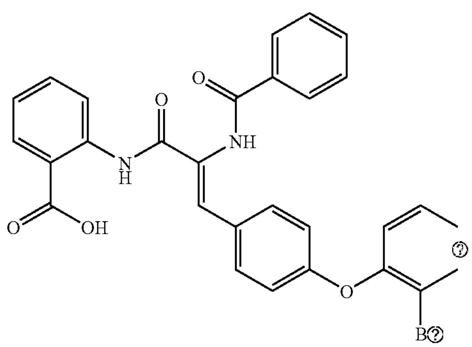 | 2-({(2Z)-2-(benzoylamino)-3-[4-(2-bromophenoxy)phenyl]prop-2-enoyl}amino)-benzoic acid; |
| 98. | 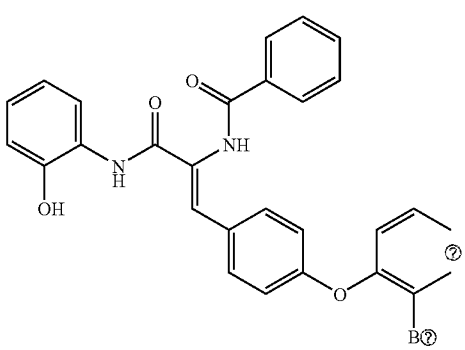 | N-((Z)-2-[4-(2-bromophenoxy)phenyl]-1-{[(2-hydroxyphenyl)amino]carbonyl}vinyl)benzamide; |

-continued
| Compound Number | Structure | Name |
|---|---|---|
| 99. | 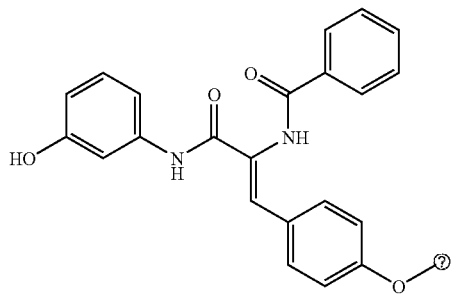 | N-((Z)-2-[4-(2-bromophenoxy)phenyl]-1-{[(3-hydroxyphenyl)amino]carbonyl}vinyl)benzamide; |
| 100. | 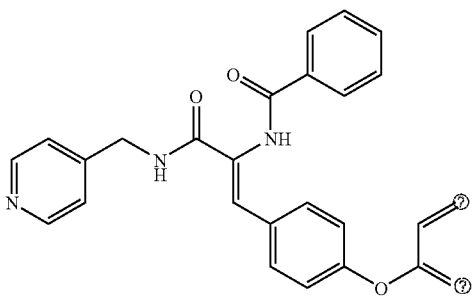 | N-((Z)-2-[4-(2-bromophenoxy)phenyl]-1-{[(pyridin-4-ylmethyl)amino]carbonyl}vinyl)benzamide; |
| 101. | 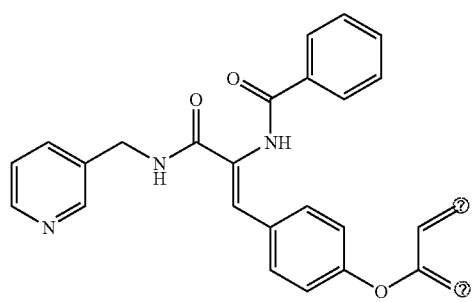 | N-((Z)-2-[4-(2-bromophenoxy)phenyl]-1-{[(pyridin-3-ylmethyl)amino]carbonyl}vinyl)benzamide; |
| 102. | 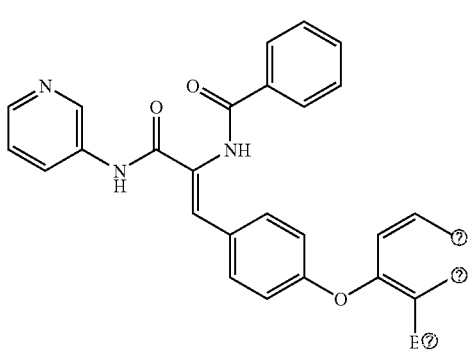 | N-{(Z)-2-[4-(2-bromophenoxy)phenyl]-1-[(pyridin-3-ylamino)carbonyl]vinyl}benzamide; |

-continued

| Compound Number | Structure | Name |
|---|---|---|
| 103. | 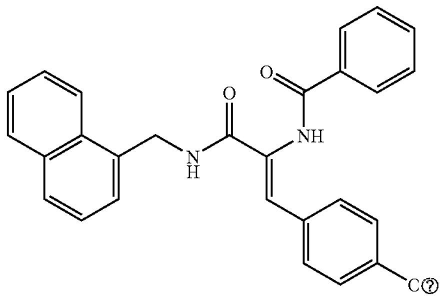 | N-((Z)-2-[4-(2-bromophenoxy)phenyl]-1-{[(1-naphthylmethyl)amino]carbonyl}vinyl)benzamide; |
| 104. | 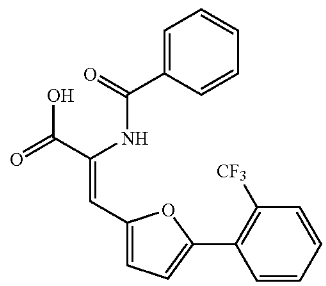 | (2Z)-2-(benzoylamino)-3-{5-[2-(trifluoromethyl)phenyl]-2-furyl}prop-2-enoic acid; |
| 105. | 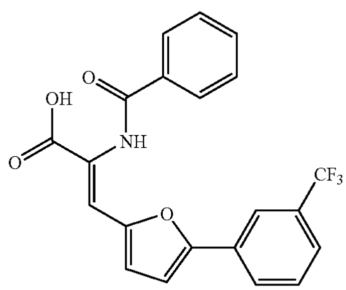 | (2Z)-2-(benzoylamino)-3-{5-[3-(trifluoromethyl)phenyl]-2-furyl}prop-2-enoic acid; |
| 106. | 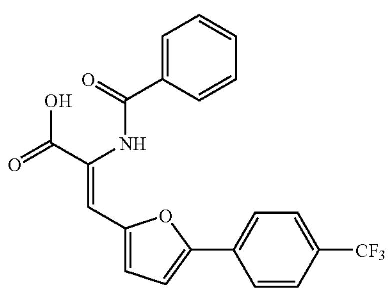 | (2Z)-2-(benzoylamino)-3-{5-[4-(trifluoromethyl)phenyl]-2-furyl}prop-2-enoic acid; |
| 107. | 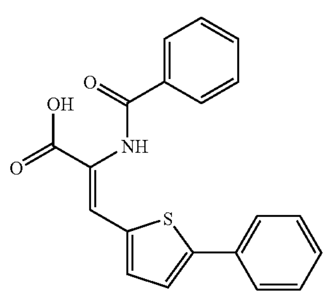 | (2Z)-2-(benzoylamino)-3-(5-phenylthien-2-yl)prop-2-enoic acid; |

⊙ indicates text missing or illegible when filed

-continued

| Compound Number | Structure | Name |
|---|---|---|
| 108. | 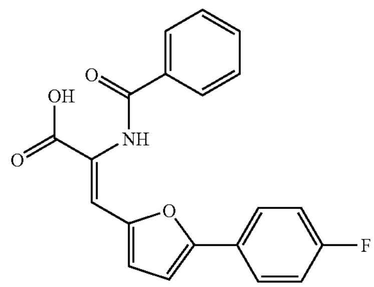 | (2Z)-2-(benzoylamino)-3-[5-(4-fluorophenyl)-2-furyl]prop-2-enoic acid; |
| 109. | 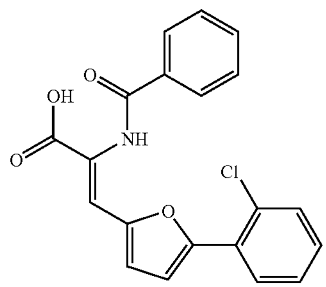 | (2Z)-2-(benzoylamino)-3-[5-(2-chlorophenyl)-2-furyl]prop-2-enoic acid; |
| 110. | 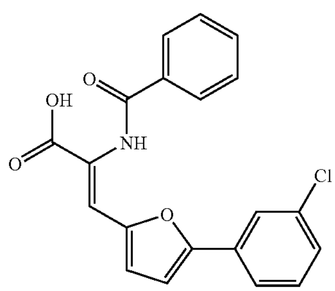 | (2Z)-2-(benzoylamino)-3-[5-(3-chlorophenyl)-2-furyl]prop-2-enoic acid; |
| 111. | 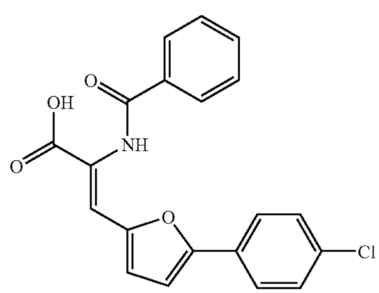 | (2Z)-2-(benzoylamino)-3-[5-(4-chlorophenyl)-2-furyl]prop-2-enoic acid; |
| 112. | 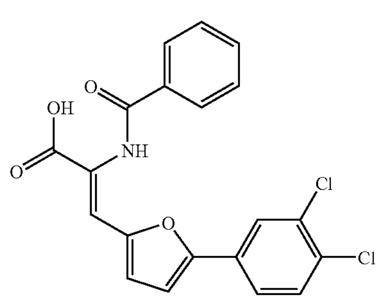 | (2Z)-2-(benzoylamino)-3-[5-(3,4-dichlorophenyl)-2-furyl]prop-2-enoic acid; |

| Compound Number | Structure | Name |
|---|---|---|
| 113. | 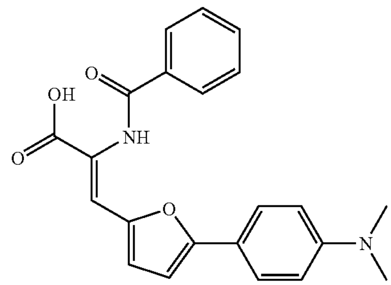 | (2Z)-2-(benzoylamino)-3-{5-[4-(dimethylamino)phenyl]-2-furyl}prop-2-enoic acid; |
| 114. | 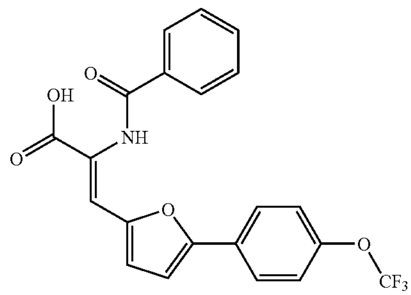 | (2Z)-2-(benzoylamino)-3-{5-[4-(trifluoromethoxy)phenyl]-2-furyl}prop-2-enoic acid; |
| 115. | 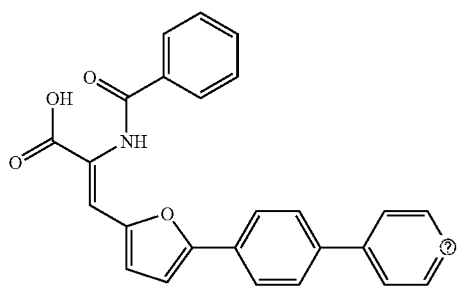 | (2Z)-2-(benzoylamino)-3-[5-(1,1'-biphenyl-4-yl)-2-furyl]prop-2-enoic acid; |
| 116. | 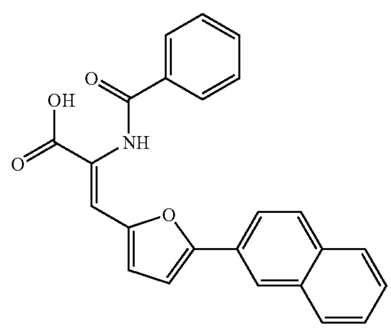 | (2Z)-2-(benzoylamino)-3-[5-(2-naphthyl)-2-furyl]prop-2-enoic acid; |
| 117. | 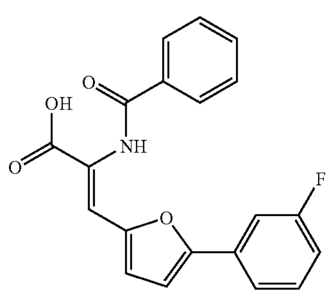 | (2Z)-2-(benzoylamino)-3-[5-(3-fluorophenyl)-2-furyl]prop-2-enoic acid; |

Ⓐ indicates text missing or illegible when filed

-continued

| Compound Number | Structure | Name |
|---|---|---|
| 118. | 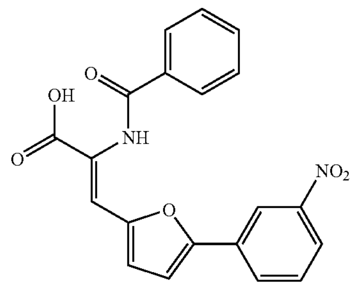 | (2Z)-2-(benzoylamino)-3-[5-(3-nitrophenyl)-2-furyl]prop-2-enoic acid; |
| 119. | 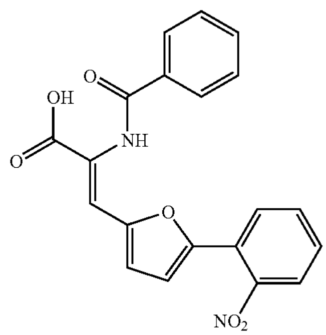 | (2Z)-2-(benzoylamino)-3-[5-(2-nitrophenyl)-2-furyl]prop-2-enoic acid; |
| 120. | 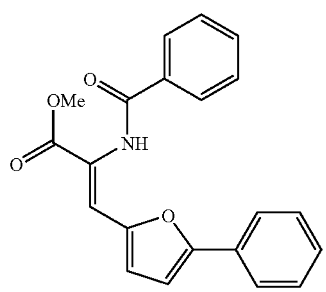 | methyl (2Z)-2-(benzoylamino)-3-(5-phenyl-2-furyl)prop-2-enoate; |
| 121. | 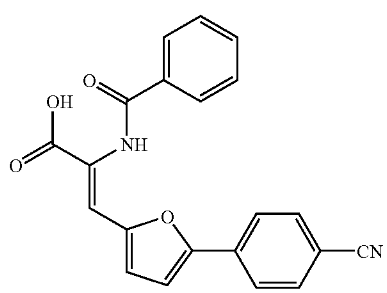 | (2Z)-2-(benzoylamino)-3-[5-(4-cyanophenyl)-2-furyl]prop-2-enoic acid; |
| 122. | 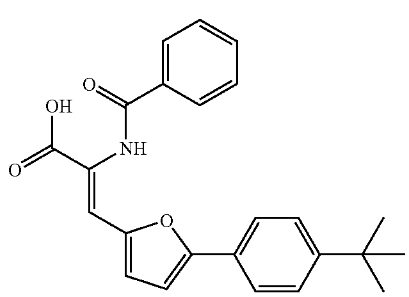 | (2Z)-2-(benzoylamino)-3-[5-(4-tert-butylphenyl)-2-furyl]prop-2-enoic acid; |

-continued

| Compound Number | Structure | Name |
|---|---|---|
| 123. | 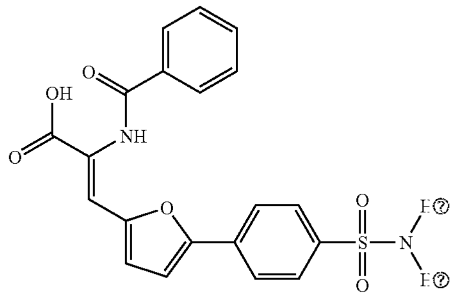 | (2Z)-3-{5-[4-(aminosulfonyl)phenyl]-2-furyl}-2-(benzoylamino)prop-2-enoic acid; |
| 124. | 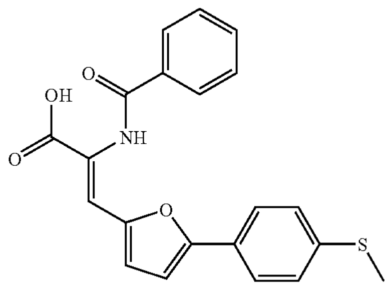 | (2Z)-2-(benzoylamino)-3-{5-[4-(methylthio)phenyl]-2-furyl}prop-2-enoic acid; |
| 125. | 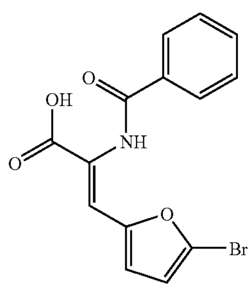 | (2Z)-2-(benzoylamino)-3-(5-bromo-2-furyl)prop-2-enoic acid; |
| 126. | 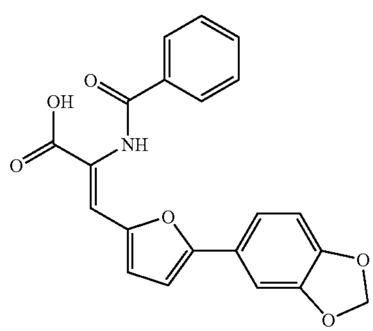 | (2Z)-3-[5-(1,3-benzodioxol-5-yl)-2-furyl]-2-(benzoylamino)prop-2-enoic acid; |
| 127. | 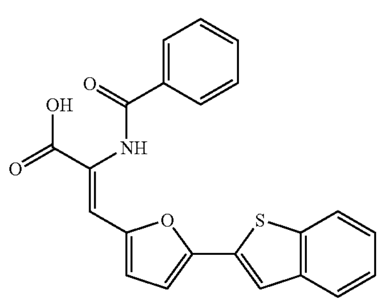 | (2Z)-3-[5-(1-benzothien-2-yl)-2-furyl]-2-(benzoylamino)prop-2-enoic acid; |

? indicates text missing or illegible when filed

-continued

| Compound Number | Structure | Name |
|---|---|---|
| 128. | 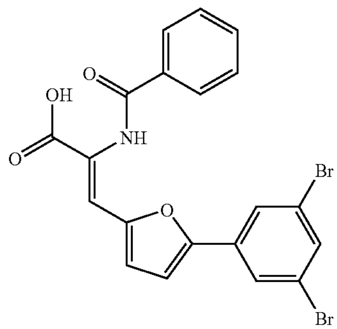 | (2Z)-2-(benzoylamino)-3-[5-(3,5-dibromophenyl)-2-furyl]prop-2-enoic acid; |
| 129. | 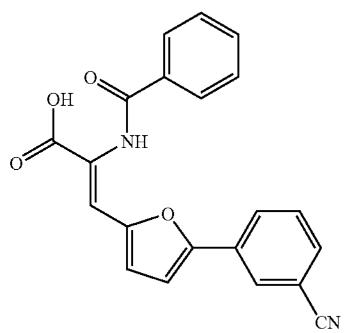 | (2Z)-2-(benzoylamino)-3-[5-(3-cyanophenyl)-2-furyl]prop-2-enoic acid; |
| 130. | 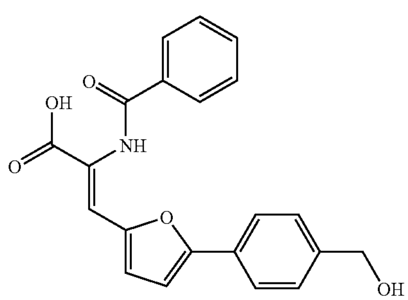 | (2Z)-2-(benzoylamino)-3-{5-[4-(hydroxymethyl)phenyl]-2-furyl}prop-2-enoic acid; |
| 131. | 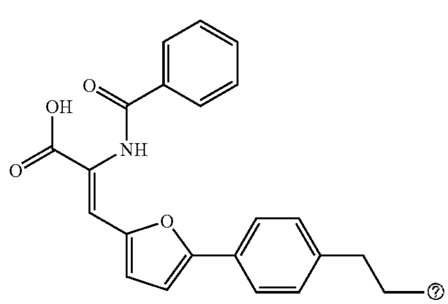 | (2Z)-2-(benzoylamino)-3-[5-(4-butylphenyl)-2-furyl]prop-2-enoic acid; |

⊘ indicates text missing or illegible when filed

| Compound Number | Structure | Name |
|---|---|---|
| 132. | 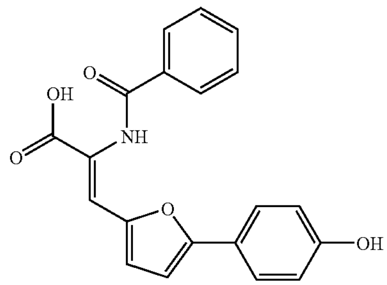 | (2Z)-2-(benzoylamino)-3-[5-(4-hydroxyphenyl)-2-furyl]prop-2-enoic acid; |
| 133. | 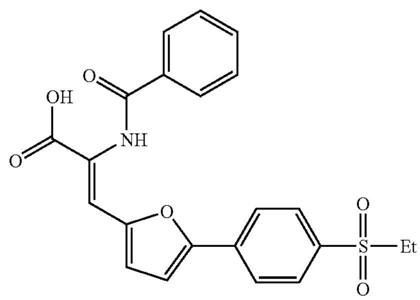 | (2Z)-2-(benzoylamino)-3-{5-[4-(ethylsulfonyl)phenyl]-2-furyl}prop-2-enoic acid; |
| 134. | 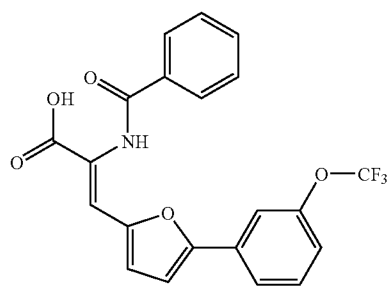 | (2Z)-2-(benzoylamino)-3-{5-[3-(trifluoromethoxy)phenyl]-2-furyl}prop-2-enoic acid; |
| 135. | 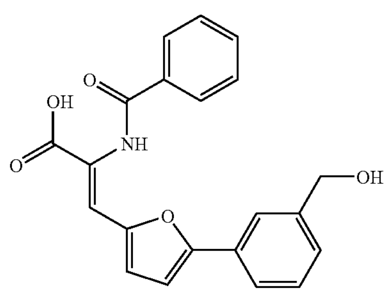 | (2Z)-2-(benzoylamino)-3-{5-[3-(hydroxymethyl)phenyl]-2-furyl}prop-2-enoic acid; |
| 136. | 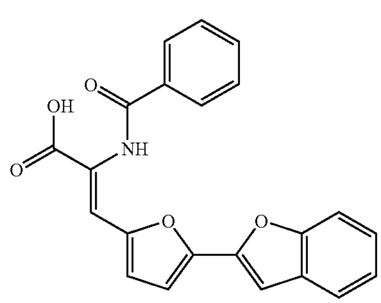 | (2Z)-3-[5-(1-benzofuran-2-yl)-2-furyl]-2-(benzoylamino)prop-2-enoic acid; |

-continued

| Compound Number | Structure | Name |
|---|---|---|
| 137. | 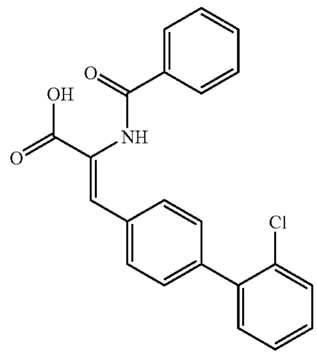 | (2Z)-2-(benzoylamino)-3-(2'-chloro-1,1'-biphenyl-4-yl)prop-2-enoic acid; |
| 138. | 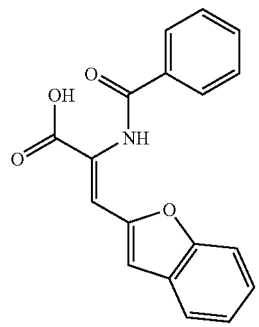 | (2Z)-3-(1-benzofuran-2-yl)-2-(benzoylamino)prop-2-enoic acid; |
| 139. | 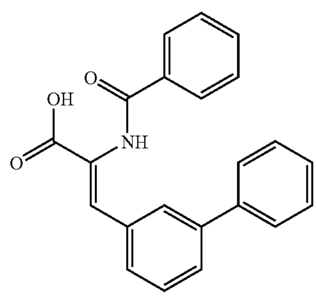 | (2Z)-2-(benzoylamino)-3-(1,1'-biphenyl-3-yl)prop-2-enoic acid; |
| 140. | 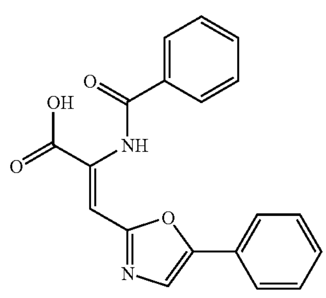 | (2Z)-2-(benzoylamino)-3-(5-phenyl-1,3-oxazol-2-yl)prop-2-enoic acid; |
| 141. | 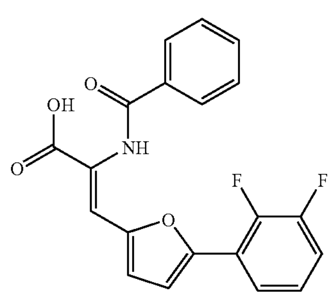 | (2Z)-2-(benzoylamino)-3-[5-(2,3-difluorophenyl)-2-furyl]prop-2-enoic acid; |

-continued

| Compound Number | Structure | Name |
|---|---|---|
| 142. | 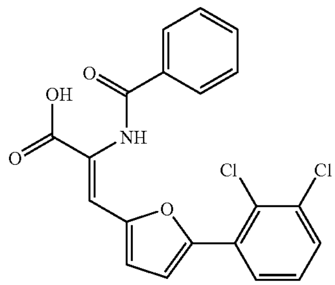 | (2Z)-2-(benzoylamino)-3-[5-(2,3-dichlorophenyl)-2-furyl]prop-2-enoic acid; |
| 143. | 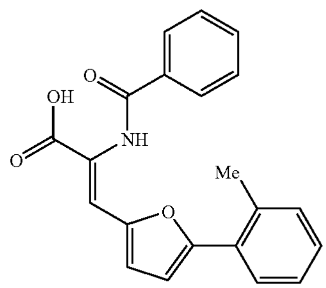 | (2Z)-2-(benzoylamino)-3-[5-(2-methylphenyl)-2-furyl]prop-2-enoic acid; |
| 144. | 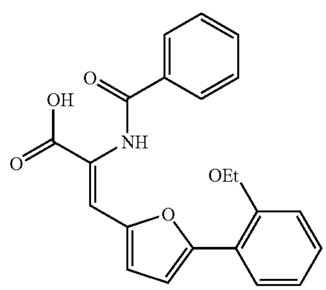 | (2Z)-2-(benzoylamino)-3-[5-(2-ethoxyphenyl)-2-furyl]prop-2-enoic acid; |
| 145. | 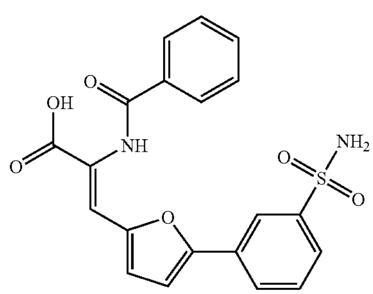 | (2Z)-3-{5-[3-(aminosulfonyl)phenyl]-2-furyl}-2-(benzoylamino)prop-2-enoic acid; |
| 146. | 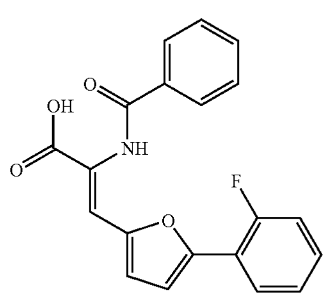 | (2Z)-2-(benzoylamino)-3-[5-(2-fluorophenyl)-2-furyl]prop-2-enoic acid; |

-continued

| Compound Number | Structure | Name |
|---|---|---|
| 147. | 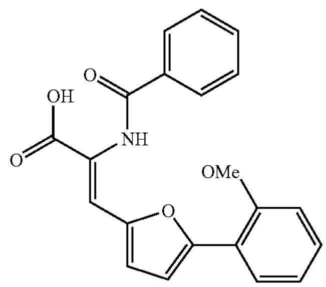 | (2Z)-2-(benzoylamino)-3-[5-(2-methoxyphenyl)-2-furyl]prop-2-enoic acid; |
| 148. | 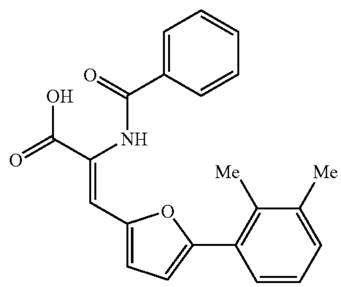 | (2Z)-2-(benzoylamino)-3-[5-(2,3-dimethylphenyl)-2-furyl]prop-2-enoic acid; |
| 149. | 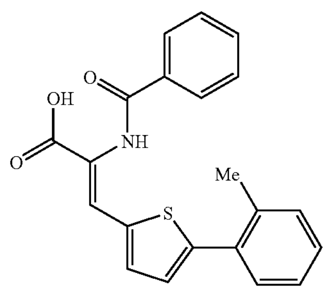 | (2Z)-2-(benzoylamino)-3-[5-(2-methylphenyl)thien-2-yl]prop-2-enoic acid; |
| 150. | 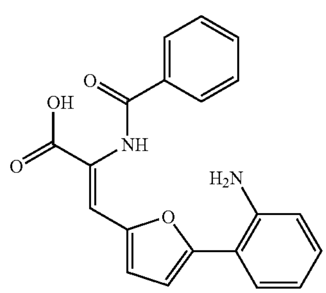 | (2Z)-3-[5-(2-aminophenyl)-2-furyl]-2-(benzoylamino)prop-2-enoic acid; |
| 151. | 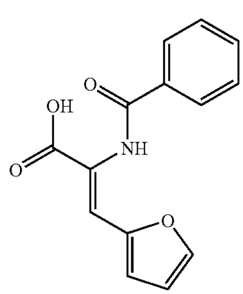 | (2Z)-2-(benzoylamino)-3-(2-furyl)prop-2-enoic acid; |

-continued

| Compound Number | Structure | Name |
|---|---|---|
| 152. | 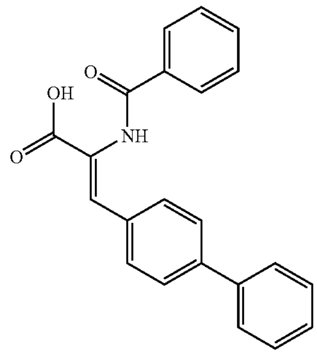 | (2Z)-2-(benzoylamino)-3-(1,1'-biphenyl-4-yl)prop-2-enoic acid; |
| 153. | 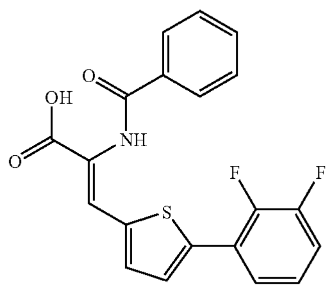 | (2Z)-2-(benzoylamino)-3-[5-(2,3-difluorophenyl)thien-2-yl]prop-2-enoic acid; |
| 154. | 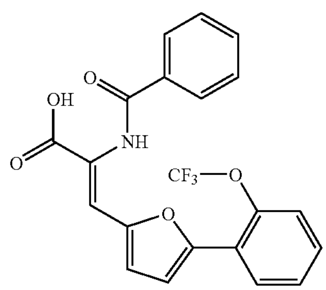 | (2Z)-2-(benzoylamino)-3-{5-[2-(trifluoromethoxy)phenyl]-2-furyl}prop-2-enoic acid; |
| 155. | 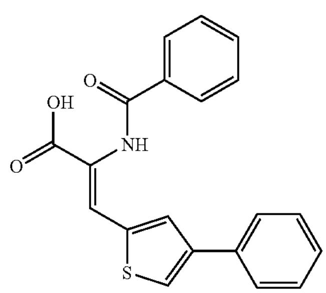 | (2Z)-2-(benzoylamino)-3-(4-phenylthien-2-yl)prop-2-enoic acid; |
| 156. | 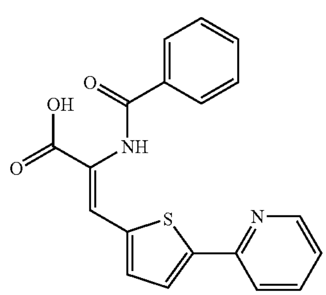 | (2Z)-2-(benzoylamino)-3-(5-pyridin-2-ylthien-2-yl)prop-2-enoic acid; |

-continued

| Compound Number | Structure | Name |
|---|---|---|
| 157. | 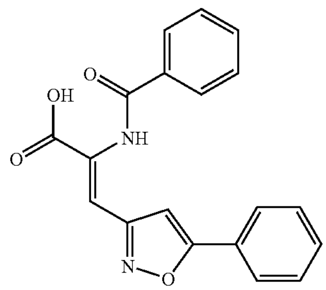 | (2Z)-2-(benzoylamino)-3-(5-phenylisoxazol-3-yl)prop-2-enoic acid; |
| 158. | 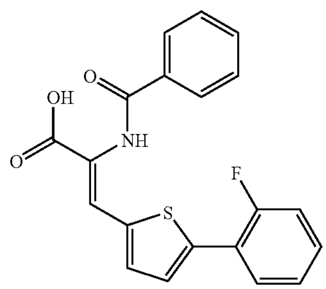 | (2Z)-2-(benzoylamino)-3-[5-(2-fluorophenyl)thien-2-yl]prop-2-enoic acid; |
| 159. | 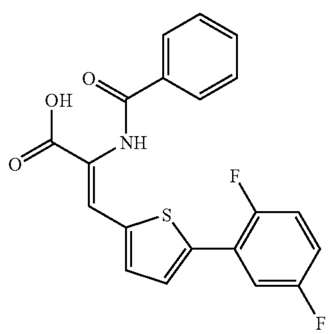 | (2Z)-2-(benzoylamino)-3-[5-(2,5-difluorophenyl)thien-2-yl]prop-2-enoic acid; |
| 160. | 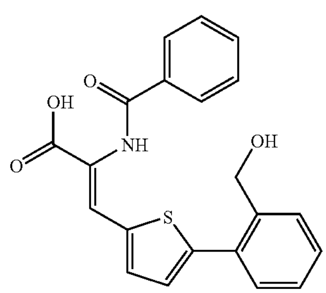 | (2Z)-2-(benzoylamino)-3-{5-[2-(hydroxymethyl)phenyl]thien-2-yl}prop-2-enoic acid; |
| 161. | 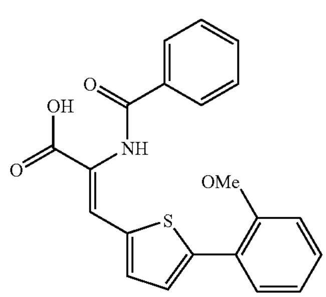 | (2Z)-2-(benzoylamino)-3-{5-(2-methoxyphenyl)-thien-2-yl]prop-2-enoic acid; |

-continued

| Compound Number | Structure | Name |
|---|---|---|
| 162. | 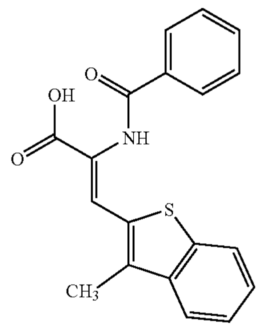 | (2Z)-2-(benzoylamino)-3-(3-methyl-1-benzothien-2-yl)prop-2-enoic acid; |
| 163. | 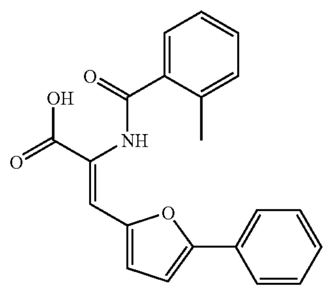 | (2Z)-2-[(2-methylbenzoyl)amino]-3-(5-phenyl-2-furyl)prop-2-enoic acid; |
| 164. | 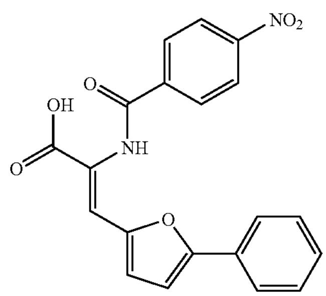 | (2Z)-2-[(4-nitrobenzoyl)amino]-3-(5-phenyl-2-furyl)prop-2-enoic acid; |
| 165. | 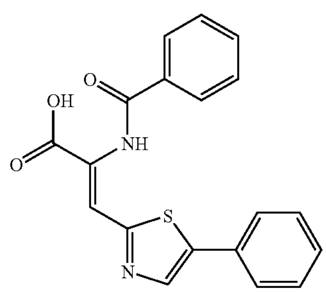 | (2Z)-2-(benzoylamino)-3-(5-phenyl-1,3-thiazol-2-yl)prop-2-enoic acid; |
| 166. | 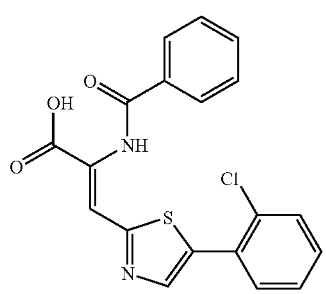 | (2Z)-2-(benzoylamino)-3-[5-(2-chlorophenyl)-1,3-thiazol-2-yl]prop-2-enoic acid; |

-continued

| Compound Number | Structure | Name |
|---|---|---|
| 167. | 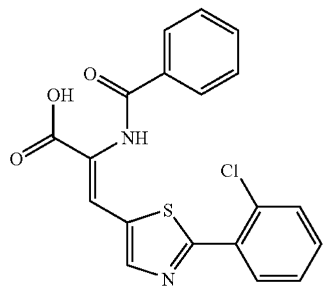 | (2Z)-2-(benzoylamino)-3-[2-(2-chlorophenyl)-1,3-thiazol-5-yl]prop-2-enoic acid; |
| 168. | 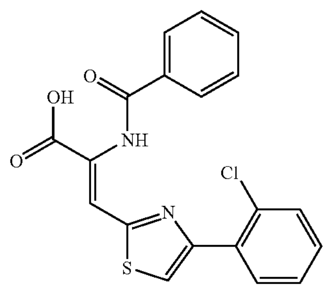 | (2Z)-2-(benzoylamino)-3-[4-(2-chlorophenyl)-1,3-thiazol-2-yl]prop-2-enoic acid; |
| 169. | 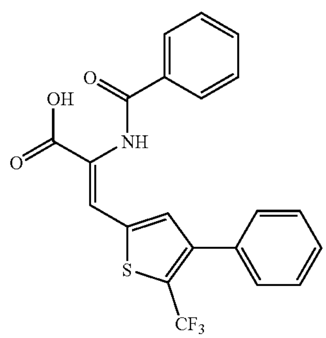 | (2Z)-2-(benzoylamino)-3-[4-phenyl-5-(trifluoromethyl)thien-2-yl]prop-2-enoic acid; |
| 170. | 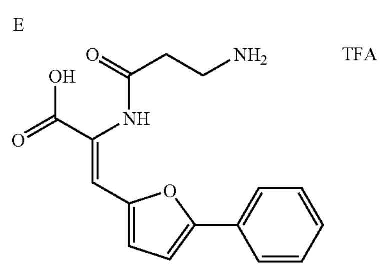 | (2Z)-2-(beta-alanylamino)-3-(5-phenyl-2-furyl)prop-2-enoic acid trifluoroacetate; |
| 171. | 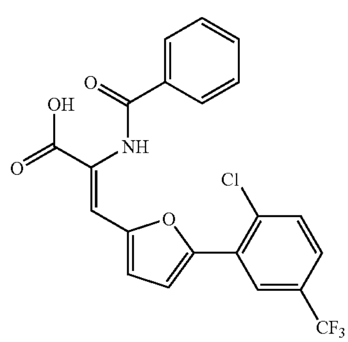 | (2Z)-2-(benzoylamino)-3-{5-[2-chloro-5-(trifluoromethyl)phenyl]-2-furyl}prop-2-enoic acid; |

-continued

| Compound Number | Structure | Name |
|---|---|---|
| 172. | 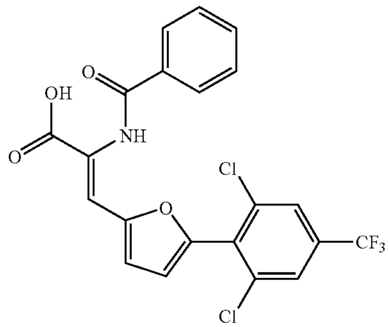 | (2Z)-2-(benzoylamino)-3-{5-[2,6-dichloro-4-(trifluoromethyl)phenyl]-2-furyl}prop-2-enoic acid; |
| 173. | 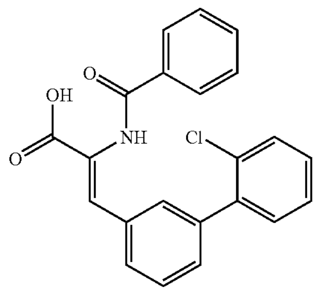 | (2Z)-2-(benzoylamino)-3-(2'-chloro-1,1'-biphenyl-3-yl)prop-2-enoic acid; |
| 174. | 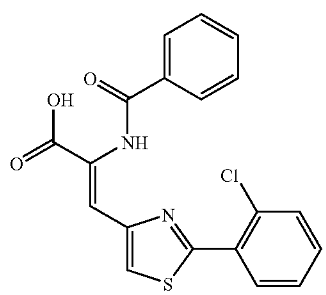 | (2Z)-2-(benzoylamino)-3-[2-(2-chlorophenyl)-1,3-thiazol-4-yl]prop-2-enoic acid; |
| 175. | 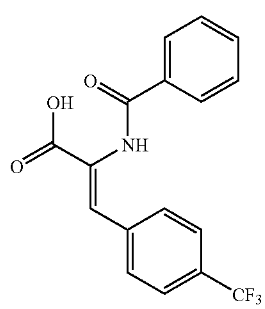 | (2Z)-2-(benzoylamino)-3-[4-(trifluoromethyl)phenyl]prop-2-enoic acid; |
| 176. | 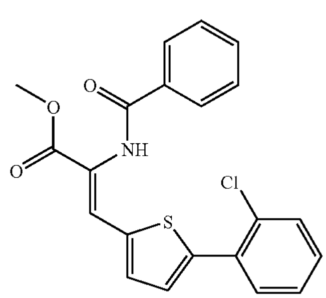 | methyl (2Z)-2-(benzoylamino)-3-[5-(2-chlorophenyl)thien-2-yl)prop-2-enoate; |

-continued

| Compound Number | Structure | Name |
| --- | --- | --- |
| 177. | 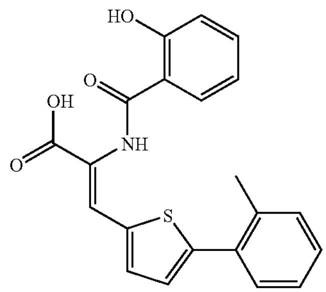 | (2Z)-2-[(2-hydroxybenzoyl)amino]-3-[5-(2-methylphenyl)thien-2-yl]prop-2-enoic acid; |
| 178. | 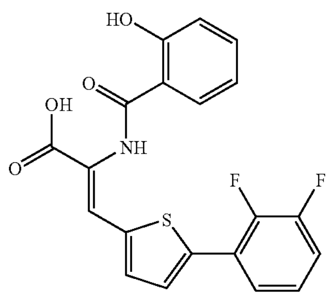 | (2Z)-3-[5-(2,3-difluorophenyl)thien-2-yl]-2-[(2-hydroxybenzoyl)amino]prop-2-enoic acid; |
| 179. | 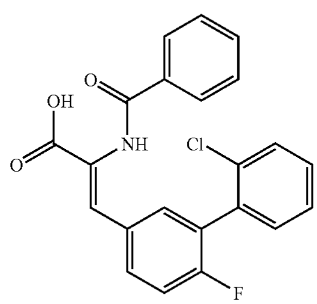 | (2Z)-2-(benzoylamino)-3-(2'-chloro-6-fluoro-1,1'-biphenyl-3-yl)prop-2-enoic acid; |
| 180. | 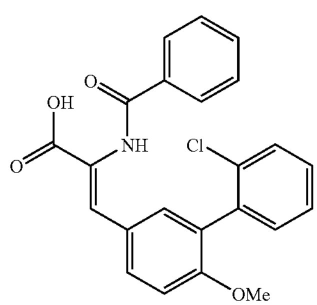 | (2Z)-2-(benzoylamino)-3-(2'-chloro-6-methoxy-1,1'-biphenyl-3-yl)prop-2-enoic acid; |
| 181. | 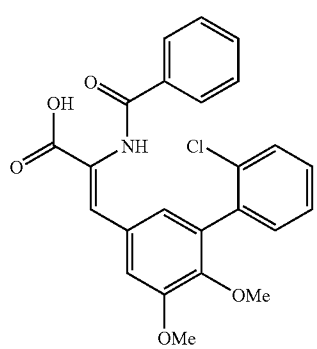 | (2Z)-2-(benzoylamino)-3-(2'-chloro-5,6-dimethoxy-1,1'-biphenyl-3-yl)prop-2-enoic acid; |

-continued

| Compound Number | Structure | Name |
|---|---|---|
| 182. | 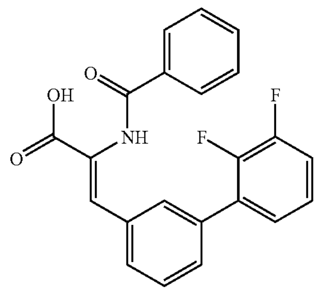 | (2Z)-2-(benzoylamino)-3-(2',3'-difluoro-1,1'-biphenyl-3-yl)prop-2-enoic acid; |
| 183. | 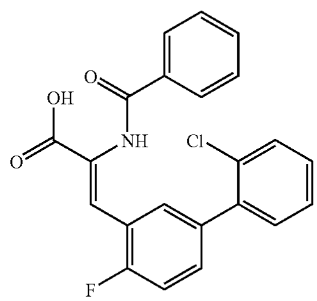 | (2Z)-2-(benzoylamino)-3-(2'-chloro-4-fluoro-1,1'-biphenyl-3-yl)prop-2-enoic acid; |
| 184. | 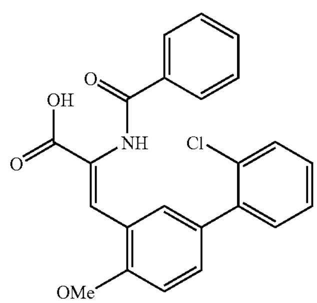 | (2Z)-2-(benzoylamino)-3-(2'-chloro-4-methoxy-1,1'-biphenyl-3-yl)prop-2-enoic acid; |
| 185. | 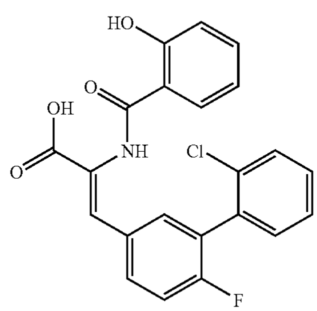 | (2Z)-3-(2'-chloro-6-fluoro-1,1'-biphenyl-3-yl)-2-[(2-hydroxybenzoyl)amino]prop-2-enoic acid; |
| 186. | 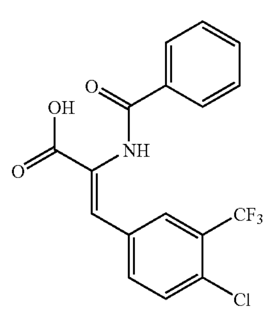 | (2Z)-2-(benzoylamino)-3-[4-chloro-3-(trifluoromethyl)phenyl]prop-2-enoic acid; |

-continued

| Compound Number | Structure | Name |
|---|---|---|
| 187. | 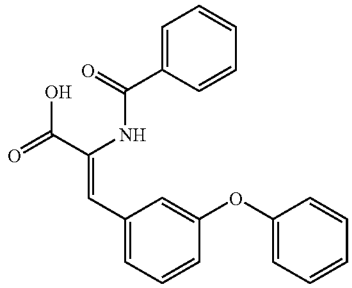 | (2Z)-2-(benzoylamino)-3-(3-phenoxyphenyl)prop-2-enoic acid; |
| 188. | 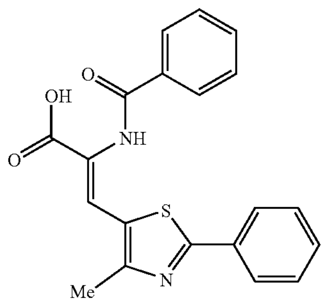 | (2Z)-2-(benzoylamino)-3-(4-methyl-2-phenyl-1,3-thiazol-5-yl)prop-2-enoic acid; |
| 189. | 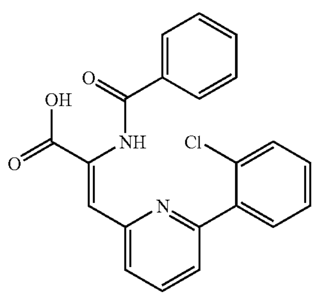 | (2Z)-2-(benzoylamino)-3-[6-(2-chlorophenyl)pyridin-2-yl]prop-2-enoic acid; |
| 190. | 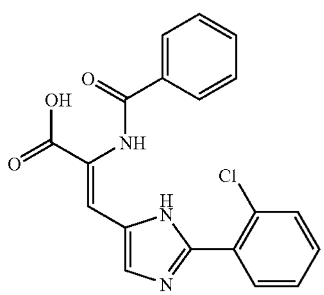 | (2Z)-2-(benzoylamino)-3-[2-(2-chlorophenyl)-1H-imidazol-5-yl]prop-2-enoic acid; |
| 191. | 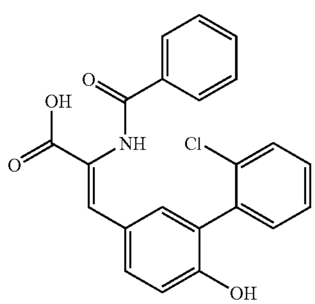 | (2Z)-2-(benzoylamino)-3-(2'-chloro-6-hydroxy-1,1'-biphenyl-3-yl)prop-2-enoic acid; |

-continued

| Compound Number | Structure | Name |
|---|---|---|
| 192. | 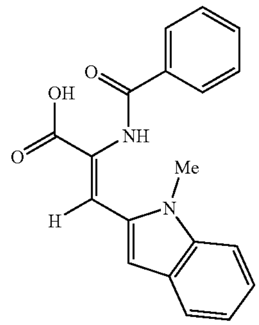 | (2Z)-2-(benzoylamino)-3-(1-methyl-1H-indol-2-yl)prop-2-enoic acid; |
| 193. | 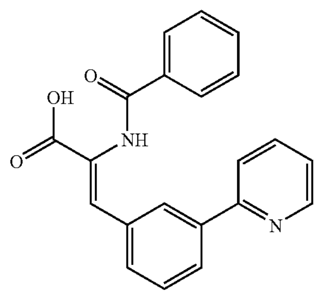 | (2Z)-2-(benzoylamino)-3-(3-pyridin-2-ylphenyl)prop-2-enoic acid; |
| 194. | 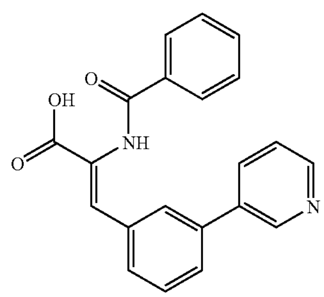 | (2Z)-2-(benzoylamino)-3-(3-pyridin-3-ylphenyl)prop-2-enoic acid; |
| 195. | 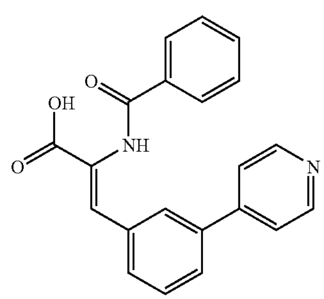 | (2Z)-2-(benzoylamino)-3-(3-pyridin-4-ylphenyl)prop-2-enoic acid; |
| 196. | 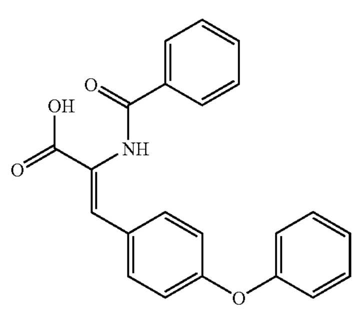 | (2Z)-2-(benzoylamino)-3-(4-phenoxyphenyl)prop-2-enoic acid; |

-continued

| Compound Number | Structure | Name |
|---|---|---|
| 197. | 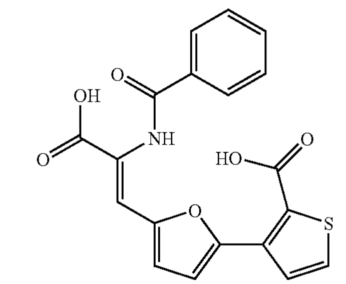 | 3-{5-[(Z)-2-(benzoylamino)-2-carboxyethenyl]-2-furyl}thiophene-2-carboxylic acid; |
| 198. | 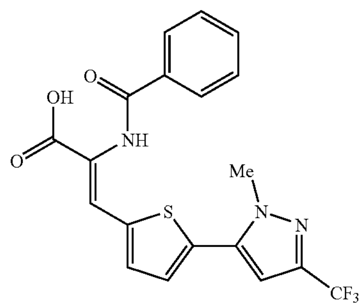 | (2Z)-2-(benzoylamino)-3-{5-[1-methyl-3-(trifluoromethyl)-1H-pyrazol-5-yl]thien-2-yl}prop-2-enoic acid; |
| 199. | 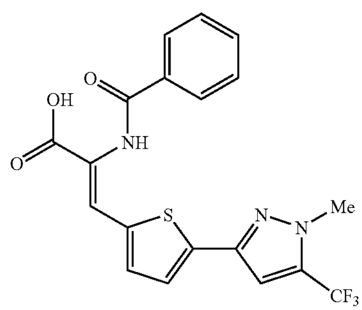 | (2Z)-2-(benzoylamino)-3-{5-[1-methyl-5-(trifluoromethyl)-1H-pyrazol-3-yl]thien-2-yl}prop-2-enoic acid; |
| 200. | 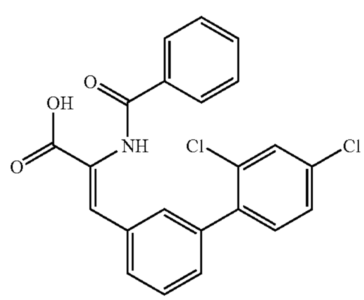 | (2Z)-2-(benzoylamino)-3-(2',4'-dichloro-1,1'-biphenyl-3-yl)prop-2-enoic acid; |
| 201. | 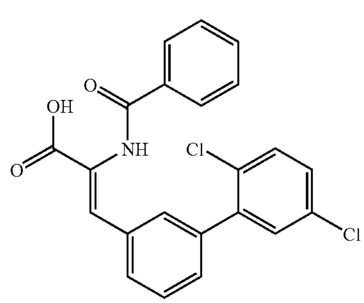 | (2Z)-2-(benzoylamino)-3-(2',5'-dichloro-1,1'-biphenyl-3-yl)prop-2-enoic acid; |

-continued

| Compound Number | Structure | Name |
|---|---|---|
| 202. | 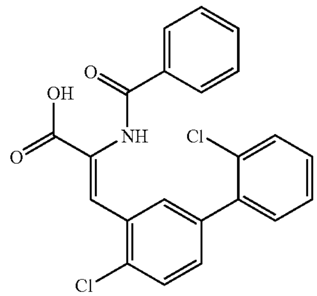 | (2Z)-2-(benzoylamino)-3-(2',4-dichloro-1,1'-biphenyl-3-yl)prop-2-enoic acid; |
| 203. | 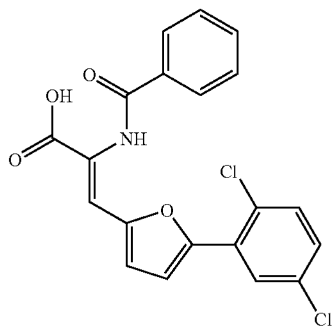 | (2Z)-2-(benzoylamino)-3-[5-(2,5-dichlorophenyl)-2-furyl]prop-2-enoic acid; |
| 204. | 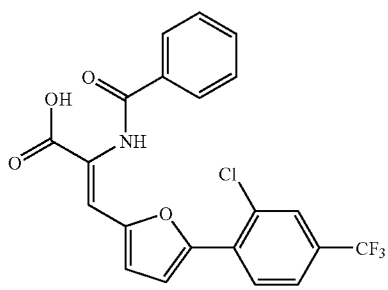 | (2Z)-2-(benzoylamino)-3-{5-[2-chloro-4-(trifluoromethyl)phenyl]-2-furyl}prop-2-enoic acid; |
| 205. | 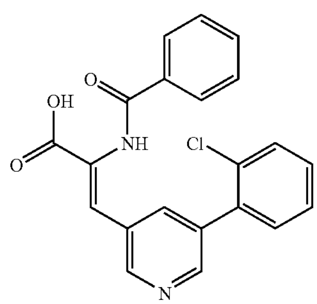 | (2Z)-2-(benzoylamino)-3-[5-(2-chlorophenyl)pyridin-3-yl]prop-2-enoic acid; |
| 206. | 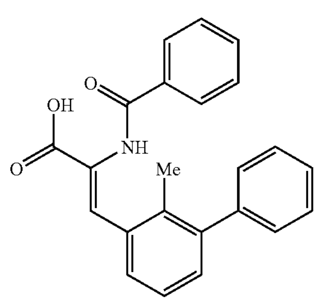 | (2Z)-2-(benzoylamino)-3-(2-methyl-1,1'-biphenyl-3-yl)prop-2-enoic acid; |

-continued

| Compound Number | Structure | Name |
|---|---|---|
| 207. | 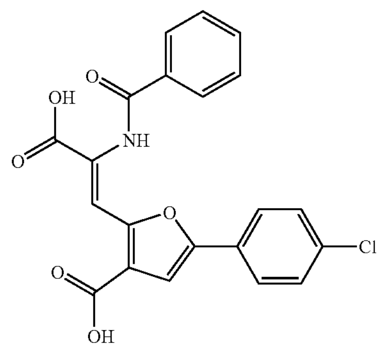 | 2-[(Z)-2-(benzoylamino)-2-carboxyethenyl]-5-(4-chlorophenyl)-3-furoic acid; |
| 208. | 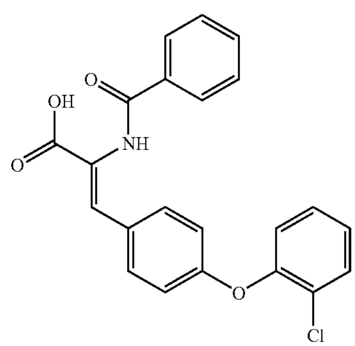 | (2Z)-2-(benzoylamino)-3-[4-(2-chlorophenoxy)phenyl]prop-2-enoic acid; |
| 209. | 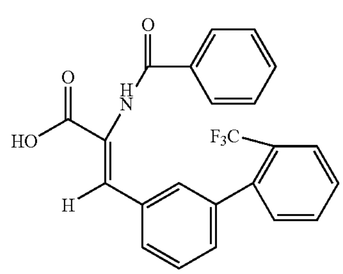 | (2Z)-2-(benzoylamino)-3-[2'-(trifluoromethyl)-1,1'-biphenyl-3-yl]prop-2-enoic acid; |
| 210. | 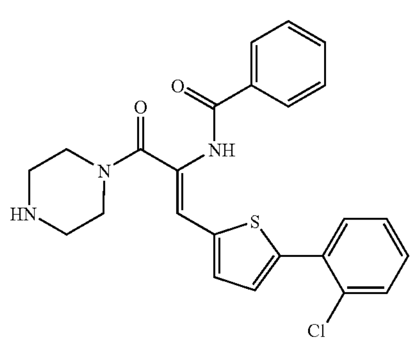 | N-[(Z)-2-[5-(2-chlorophenyl)thien-2-yl]-1-(piperazin-1-ylcarbonyl)ethenyl]benzamide; |

-continued
| Compound Number | Structure | Name |
|---|---|---|
| 211. | 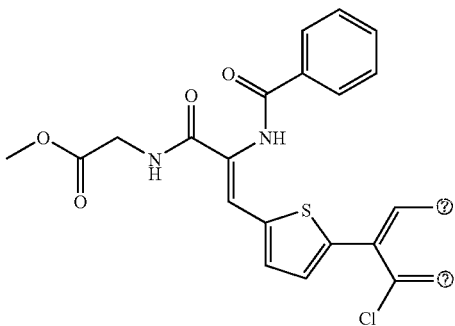 ⓘ indicates text missing or illegible when filed | methyl N-{(2Z)-2-(benzoylamino)-3-[5-(2-chlorophenyl)thien-2-yl]prop-2-enoyl}glycinate; |
| 212. | 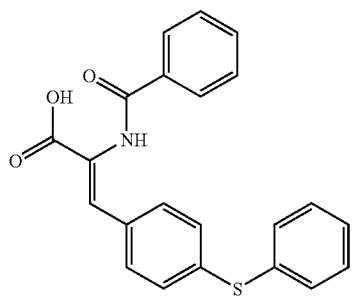 | (2Z)-2-(benzoylamino)-3-[4-(phenylthio)phenyl]prop-2-enoic acid; |
| 213. | 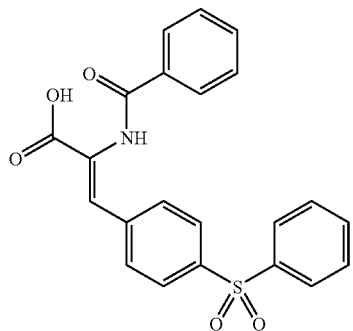 | (2Z)-2-(benzoylamino)-3-[4-(phenylsulfonyl)phenyl]prop-2-enoic acid; |
| 214. | 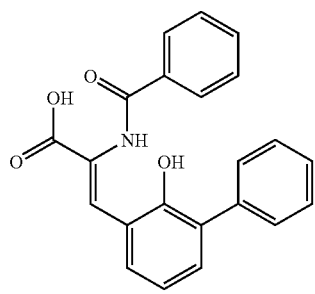 | (2Z)-2-(benzoylamino)-3-(2-hydroxy-1,1'-biphenyl-3-yl)prop-2-enoic acid; |

-continued

| Compound Number | Structure | Name |
|---|---|---|
| 215. | 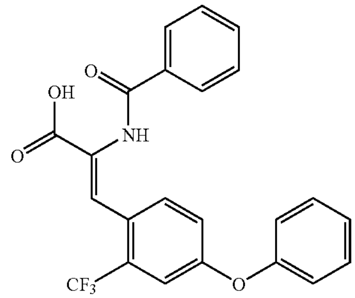 | (2Z)-2-(benzoylamino)-3-[4-phenoxy-2-(trifluoromethyl)phenyl]prop-2-enoic acid; |
| 216. | 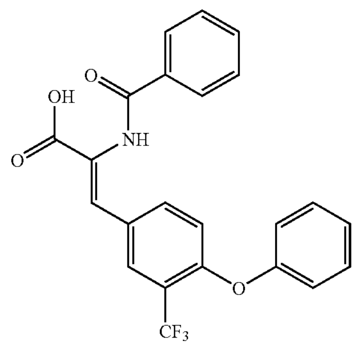 | (2Z)-2-(benzoylamino)-3-[4-phenoxy-3-(trifluoromethyl)phenyl]prop-2-enoic acid; |
| 217. | 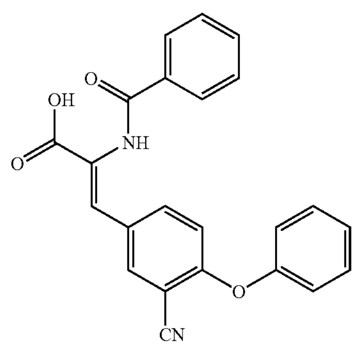 | (2Z)-2-(benzoylamino)-3-(3-cyano-4-phenoxyphenyl)prop-2-enoic acid; |
| 218. | 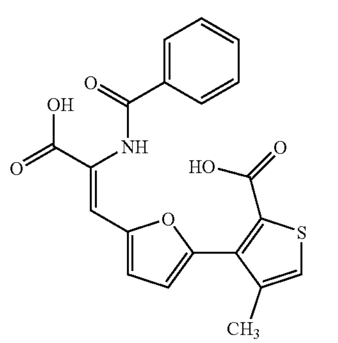 | 3-{5-[(Z)-2-(benzoylamino)-2-carboxyethenyl]-2-furyl}-4-methylthiophene-2-carboxylic acid; |

-continued

| Compound Number | Structure | Name |
| --- | --- | --- |
| 219. | 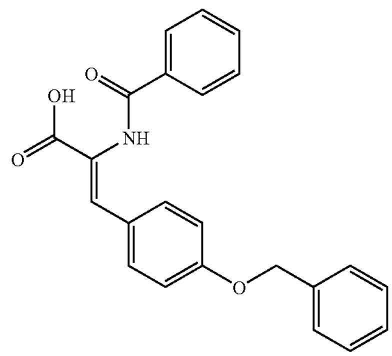 | (2Z)-2-(benzoylamino)-3-[4-(benzyloxy)phenyl]prop-2-enoic acid; |
| 220. | ⓘ indicates text missing or illegible when filed | |
| 221. | 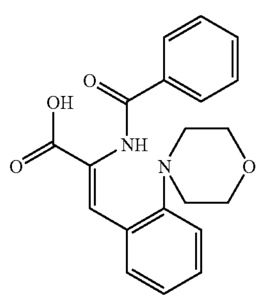 | (2Z)-2-(benzoylamino)-3-(2-morpbolin-4-ylphenyl)prop-2-enoic acid; |
| 222. | 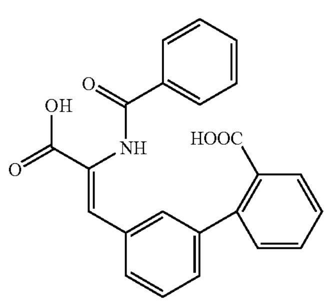 | 3'-[(Z)-2-(benzoylamino)-2-carboxyethenyl]-1,1'-biphenyl-2-carboxylic acid; |

-continued

| Compound Number | Structure | Name |
|---|---|---|
| 223. | 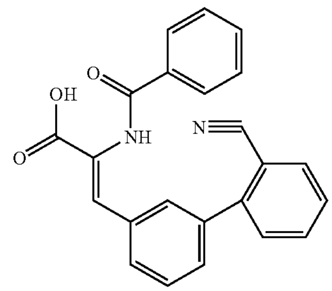 | (2Z)-2-(benzoylamino)-3-(2'-cyano-1,1'-biphenyl-3-yl)prop-2-enoic acid; |
| 224. | 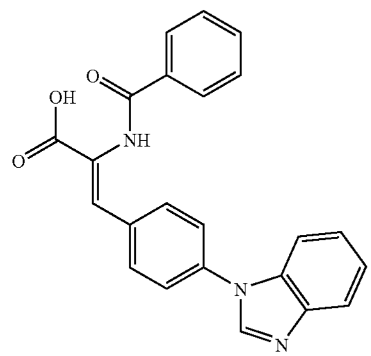 | (2Z)-3-[4-(1H-benzimidazol-1-yl)phenyl]-2-(benzoylamino)prop-2-enoic acid; |
| 225. | 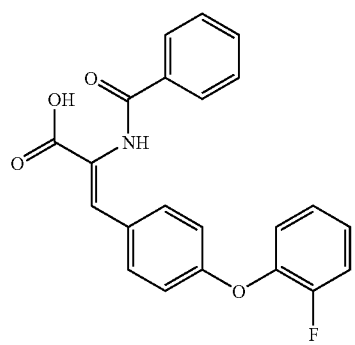 | (2Z)-2-(benzoylamino)-3-[4-(2-fluorophenoxy)phenyl]prop-2-enoic acid; |
| 226. | 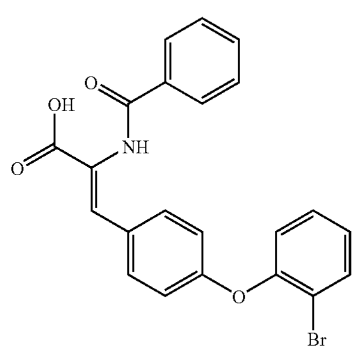 | (2Z)-2-(Benzoylamino)-3-{4-(2-bromophenoxy)phenyl]-2-propenoic acid (uninverted CAS name Sep. 27, 2002) or V00074604 or V00080919 or (2Z)-2-(benzoylamino)-3-[4-(2-bromophenoxy)phenyl]prop-2-enoic acid; |

-continued

| Compound Number | Structure | Name |
|---|---|---|
| 227. | 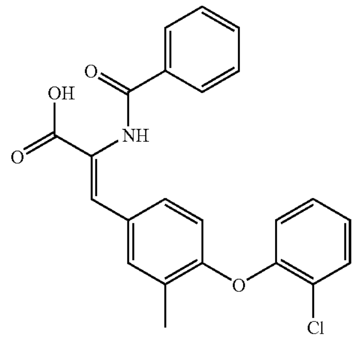 | (2Z)-2-(benzoylamino)-3-[4-(2-chlorophenoxy)-3-methylphenyl]prop-2-enoic acid; |
| 228. | 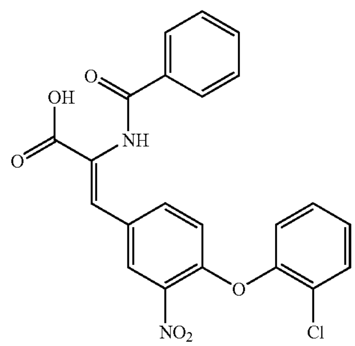 | (2Z)-2-(benzoylamino)-3-[4-(2-chlorophenoxy)-3-nitrophenyl]prop-2-enoic acid; |
| 229. | 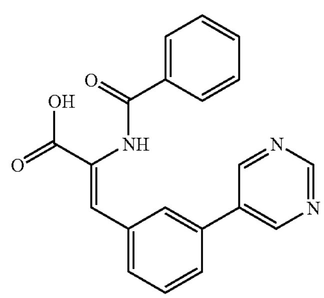 | (2Z)-2-(benzoylamino)-3-(3-pyrimidin-5-ylphenyl)prop-2-enoic acid; |
| 230. | 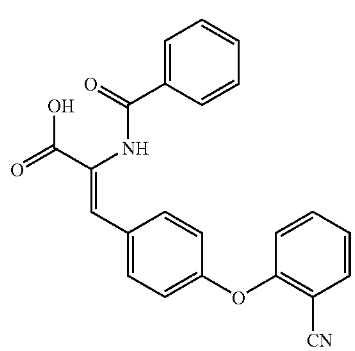 | (2Z)-2-(benzoylamino)-3-[4-(2-cyanophenoxy)phenyl]prop-2-enoic acid; |

-continued

| Compound Number | Structure | Name |
|---|---|---|
| 231. | 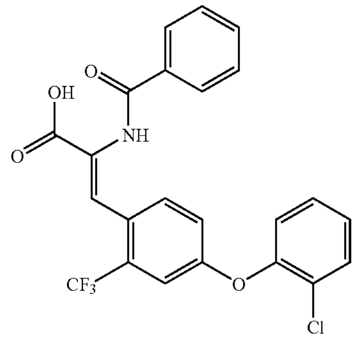 | (2Z)-2-(benzoylamino)-3-[4-(2-chlorophenoxy)-2-(trifluoromethyl)phenyl]prop-2-enoic acid; |
| 232. | 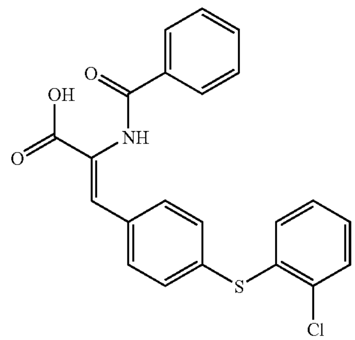 | (2Z)-2-(benzoylamino)-3-{4-[(2-chlorophenyl)thio]phenyl}prop-2-enoic acid; |
| 233. | 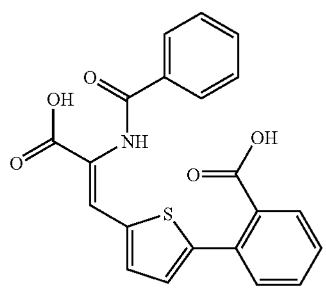 | 2-{5-[(Z)-2-(benzoylamino)-2-carboxyethenyl]thien-2-yl}benzoic acid; |
| 234. | 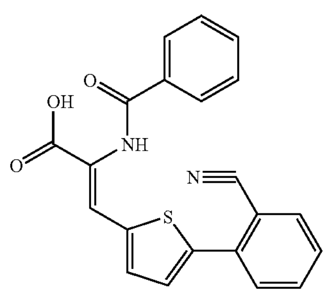 | (2Z)-2-(benzoylamino)-3-[5-(2-cyanophenyl)thien-2-yl]prop-2-enoic acid; |
| 235. | 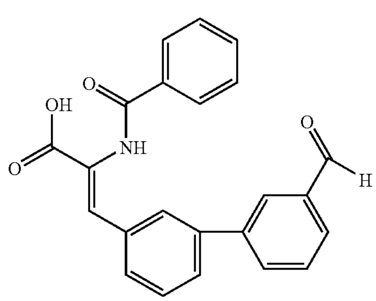 | (2Z)-2-(benzoylamino)-3-(3'-formyl-1,1'-biphenyl-3-yl)prop-2-enoic acid; |

-continued

| Compound Number | Structure | Name |
|---|---|---|
| 236. | 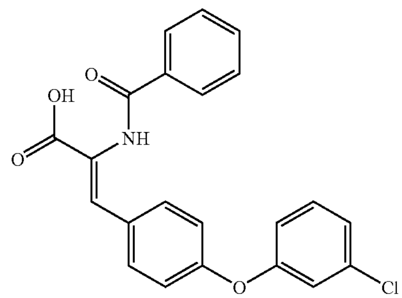 | (2Z)-2-(benzoylamino)-3-[4-(3-chlorophenoxy)phenyl]prop-2-enoic acid; |
| 237. | 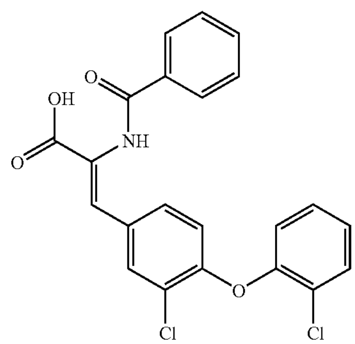 | (2Z)-2-(benzoylamino)-3-[3-chloro-4-(2-chlorophenoxy)phenyl]prop-2-enoic acid; |
| 238. | 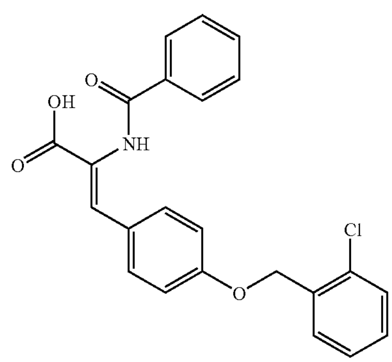 | (2Z)-2-(benzoylamino)-3-{4-[(2-chlorobenzyl)oxy]phenyl}prop-2-enoic acid; |
| 239. | 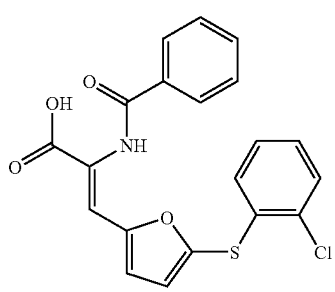 | (2Z)-2-(benzoylamino)-3-{5-[(2-chlorophenyl)thio]-2-furyl}prop-2-enoic acid; |

-continued

| Compound Number | Structure | Name |
|---|---|---|
| 240. | 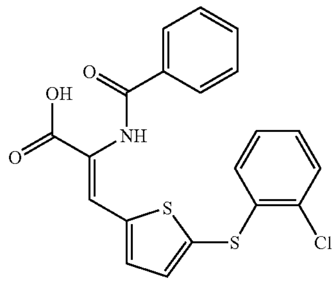 | (2Z)-2-(benzoylamino)-3-{5-[(2-chlorophenyl)thio]thien-2-yl}prop-2-enoic acid; |
| 241. | 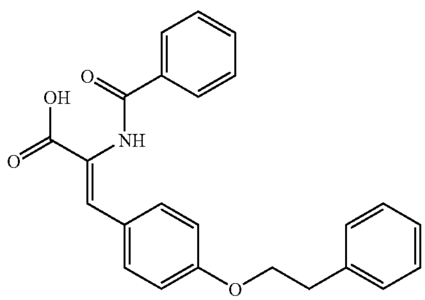 | (2Z)-2-(benzoylamino)-3-[4-(2-phenylethoxy)phenyl]prop-2-enoic acid; |
| 242. | 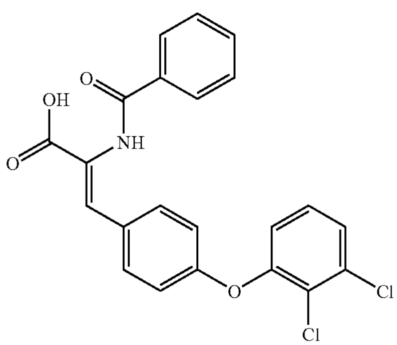 | (2Z)-2-(benzoylamino)-3-[4-(2,3-dichlorophenoxy)phenyl]prop-2-enoic acid; |
| 243. | 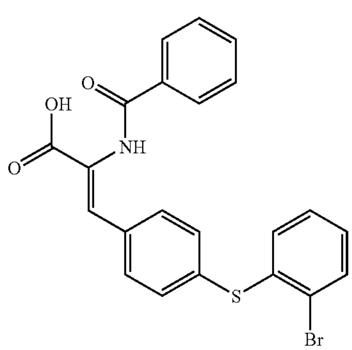 | (2Z)-2-(benzoylamino)-3-{4-[(2-bromophenyl)thio]phenyl}prop-2-enoic acid; |

-continued

| Compound Number | Structure | Name |
|---|---|---|
| 244. | 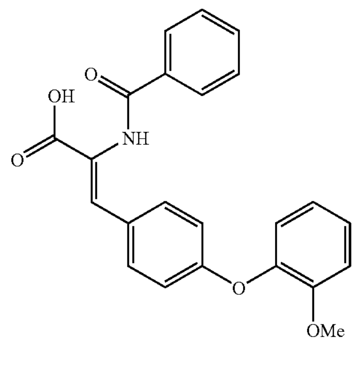 | (2Z)-2-(benzoylamino)-3-[4-(2-methoxyphenoxy)phenyl]prop-2-enoic acid; |
| 245. | 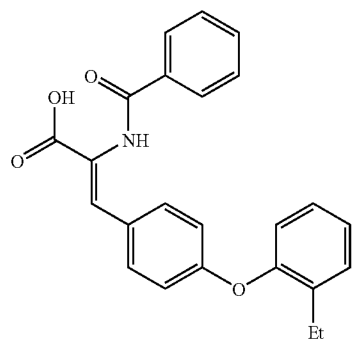 | (2Z)-2-(benzoylamino)-3-[4-(2-ethylphenoxy)phenyl]prop-2-enoic acid; |
| 246. | 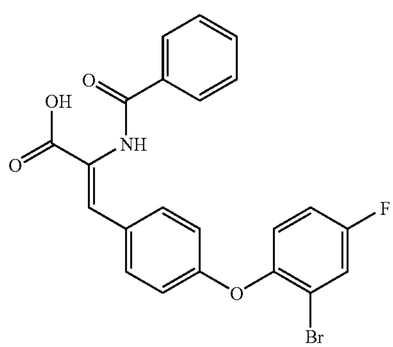 | (2Z)-2-(benzoylamino)-3-[4-(2-bromo-4-fluorophenoxy)phenyl]prop-2-enoic acid; |
| 247. | 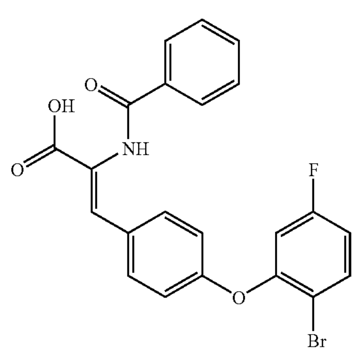 | (2Z)-2-(benzoylamino)-3-[4-(2-bromo-5-fluorophenoxy)phenyl]prop-2-enoic acid; |

-continued

| Compound Number | Structure | Name |
|---|---|---|
| 248. | 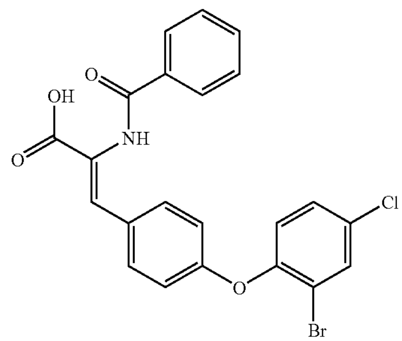 | (2Z)-2-(benzoylamino)-3-[4-(2-bromo-4-chlorophenoxy)phenyl]prop-2-enoic acid; |
| 249. | 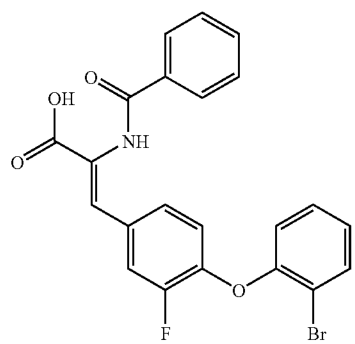 | (2Z)-2-(benzoylamino)-3-[4-(2-bromophenoxy)-3-fluorophenyl]prop-2-enoic acid; |
| 250. | 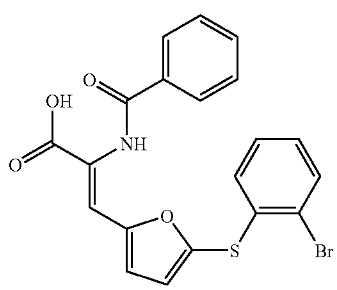 | (2Z)-2-(benzoylamino)-3-{5-[(2-bromophenyl)thio]-2-furyl}prop-2-enoic acid; |
| 251. | 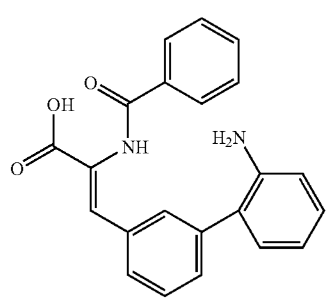 | (2Z)-3-(2'-amino-1,1'-biphenyl-3-yl)-2-(benzoylamino)prop-2-enoic acid; |
| 252. | 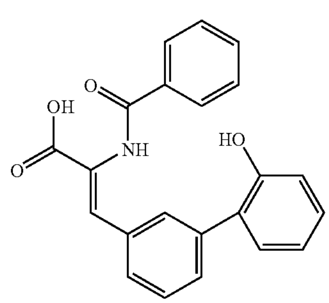 | (2Z)-2-(benzoylamino)-3-(2'-hydroxy-1,1'-biphenyl-3-yl)prop-2-enoic acid; |

-continued

| Compound Number | Structure | Name |
|---|---|---|
| 253. | 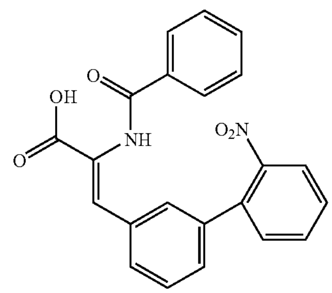 | (2Z)-2-(benzoylamino)-3-(2'-nitro-1,1'-biphenyl-3-yl)prop-2-enoic acid; |
| 254. | 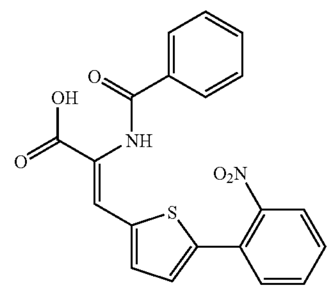 | (2Z)-2-(benzoylamino)-3-[5-(2-nitrophenyl)thien-2-yl]prop-2-enoic acid; |
| 255. | 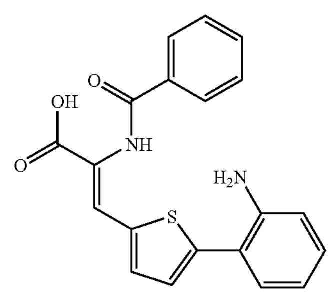 | (2Z)-3-[5-(2-aminophenyl)thien-2-yl]-2-(benzoylamino)prop-2-enoic acid; |
| 256. | 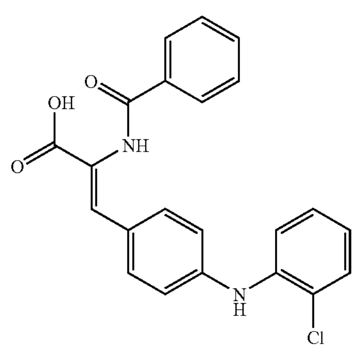 | (2Z)-2-(benzoylamino)-3-{4-[(2-chlorophenyl)amino]phenyl}prop-2-enoic acid; |

| Compound Number | Structure | Name |
|---|---|---|
| 257. | 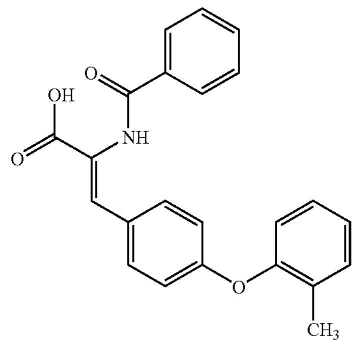 | (2Z)-2-(benzoylamino)-3-[4-(2-methylphenoxy)phenyl]prop-2-enoic acid; |
| 258. | 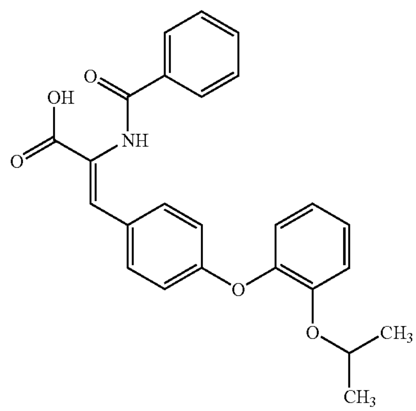 | (2Z)-2-(benzoylamino)-3-[4-(2-isopropoxyphenoxy)phenyl]prop-2-enoic acid; |
| 259. | 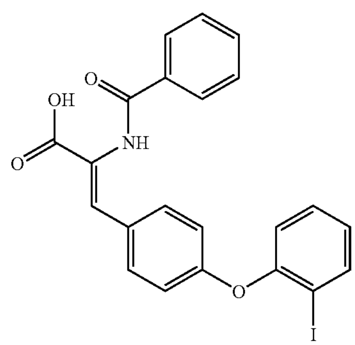 | (2Z)-2-(benzoylamino)-3-[4-(2-iodophenoxy)phenyl]prop-2-enoic acid; |
| 260. | 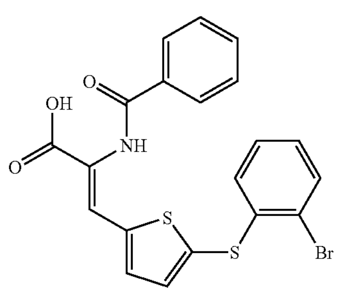 | (2Z)-2-(benzoylamino)-3-{5-[(2-bromophenyl)thio]thien-2-yl}prop-2-enoic acid; |

| Compound Number | Structure | Name |
|---|---|---|
| 261. | 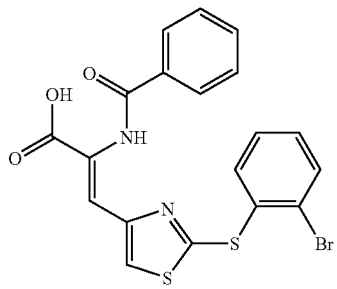 | (2Z)-2-(benzoylamino)-3-{2-[(2-bromophenyl)thio]-1,3-thiazol-4-yl}prop-2-enoic acid; |
| 262. | 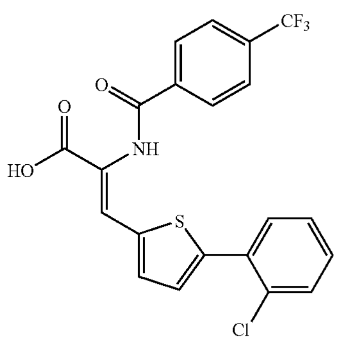 | (2Z)-3-[5-(2-chlorophenyl)thien-2-yl]-2-{[4-(trifluoromethyl)benzoyl]amino}prop-2-enoic acid; |
| 263. | 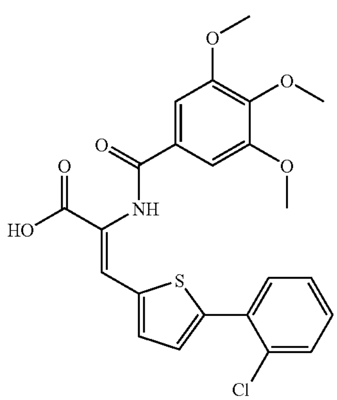 | (2Z)-3-[5-(2-chlorophenyl)thien-2-yl]-2-[(3,4,5-trimethoxybenzoyl)amino]prop-2-enoic acid; |
| 264. | 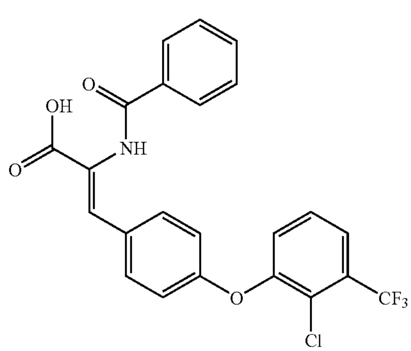 | (2Z)-2-(benzoylamino)-3-{4-[2-chloro-3-(trifluoromethyl)phenoxy]phenyl}prop-2-enoic acid; |

-continued

| Compound Number | Structure | Name |
|---|---|---|
| 265. | 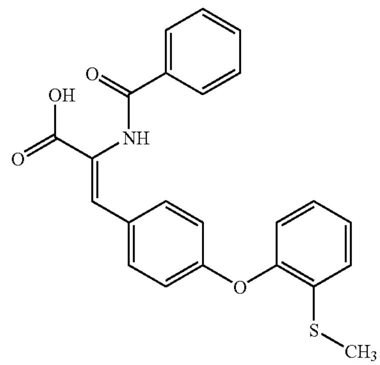 | (2Z)-2-(benzoylamino)-3-{4-[2-(methylthio)phenoxy]phenyl}prop-2-enoic acid; |
| 266. | 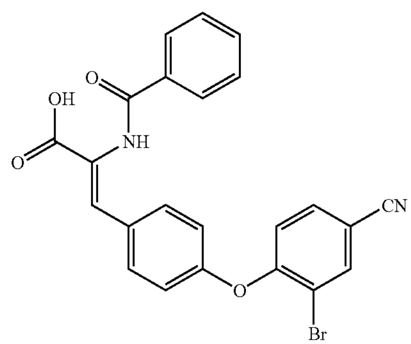 | (2Z)-2-(benzoylamino)-3-[4-(2-bromo-4-cyanophenoxy)phenyl]prop-2-enoic acid; |
| 267. | 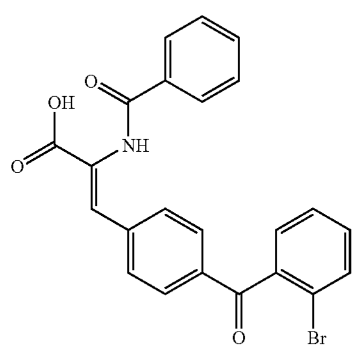 | (2Z)-2-(benzoylamino)-3-[4-(2-bromobenzoyl)phenyl]prop-2-enoic acid; |
| 268. | 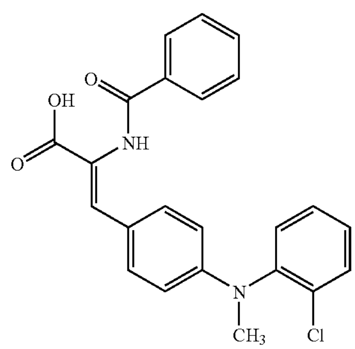 | (2Z)-2-(benzoylamino)-3-{4-[(2-chlorophenyl)(methyl)amino]phenyl}prop-2-enoic acid; |

| Compound Number | Structure | Name |
|---|---|---|
| 269. | 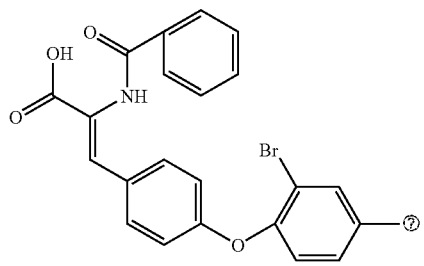 ⓘ indicates text missing or illegible when filed | (2Z)-2-(benzoylamino)-3-[4-(2-bromo-4-methylphenoxy)phenyl]prop-2-enoic acid; |
| 270. | 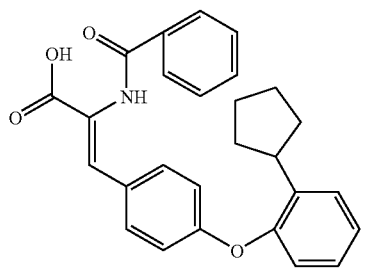 | (2Z)-2-(benzoylamino)-3-[4-(2-cyclopentylphenoxy)phenyl]prop-2-enoic acid; |
| 271. | 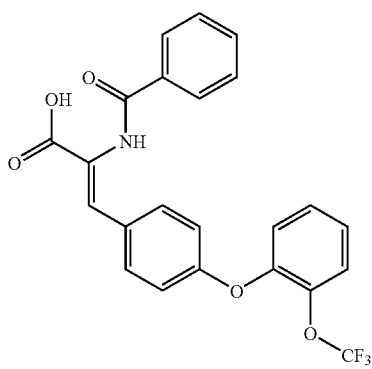 | (2Z)-2-(benzoylamino)-3-{4-[2-(trifluoromethoxy)phenoxy]phenyl}prop-2-enoic acid; |
| 272. | 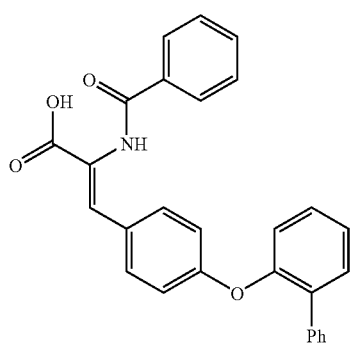 | (2Z)-2-(benzoylamino)-3-[4-(1,1'-biphenyl-2-yloxy)phenyl]prop-2-enoic acid; |

-continued

| Compound Number | Structure | Name |
|---|---|---|
| 273. | 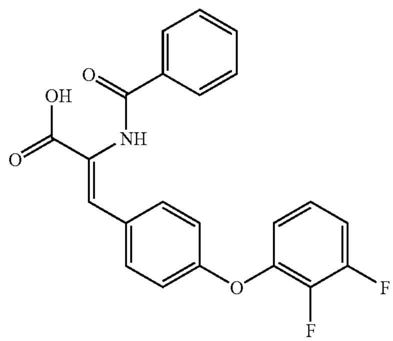 | (2Z)-2-(benzoylamino)-3-[4-(2,3-difluorophenoxy)phenyl]prop-2-enoic acid; |
| 274. | 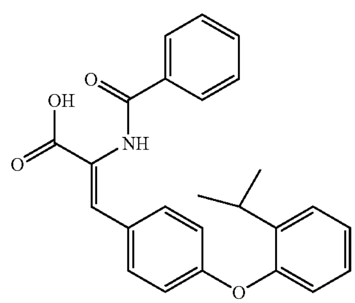 | (2Z)-2-(benzoylamino)-3-[4-(2-isopropylphenoxy)phenyl]prop-2-enoic acid; |
| 275. | 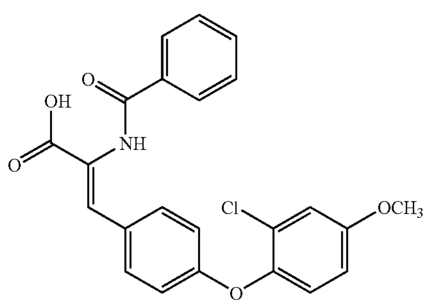 | (2Z)-2-(benzoylamino)-3-[4-(2-chloro-4-methoxyphenoxy)phenyl]prop-2-enoic acid; |
| 276. | 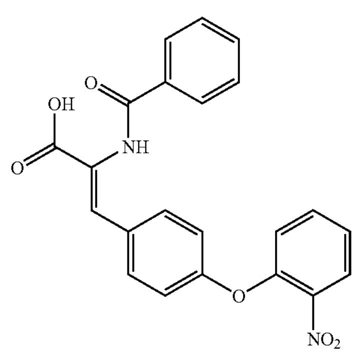 | (2Z)-2-(benzoylamino)-3-[4-(2-nitrophenoxy)phenyl]prop-2-enoic acid; |

-continued

| Compound Number | Structure | Name |
|---|---|---|
| 277. | 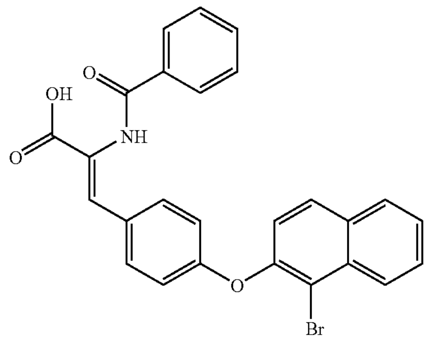 | (2Z)-2-(benzoylamino)-3-{4-[(1-bromo-2-naphthyl)oxy]phenyl}prop-2-enoic acid; |
| 278. | 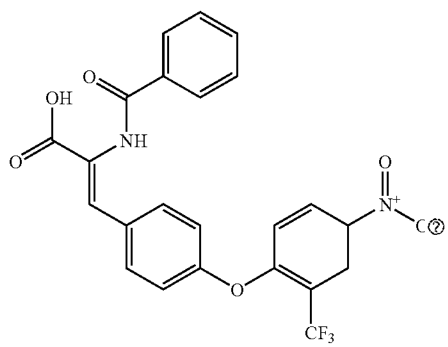 | (2Z)-2-(benzoylamino)-3-(4-{[4-nitro-2-(trifluoromethyl)cyclohexa-1,5-dien-1-yl]oxy}phenyl)prop-2-enoic acid; |
| 279. | 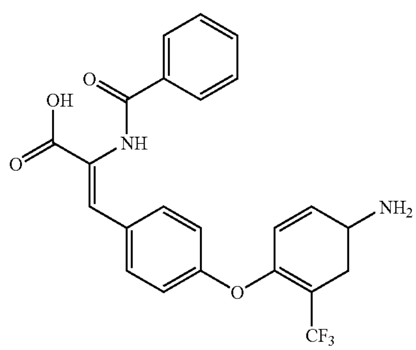 | (2Z)-3-(4-{[4-amino-2-(trifluoromethyl)cyclohexa-1,5-dien-1-yl]oxy}phenyl)-2-(benzoylamino)prop-2-enoic acid; |
| 280. | 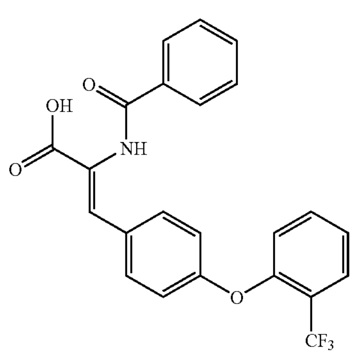 | (2Z)-2-(benzoylamino)-3-{4-[2-(trifluoromethyl)phenoxy]phenyl}prop-2-enoic acid; |

⑦ indicates text missing or illegible when filed

-continued

| Compound Number | Structure | Name |
|---|---|---|
| 281. | 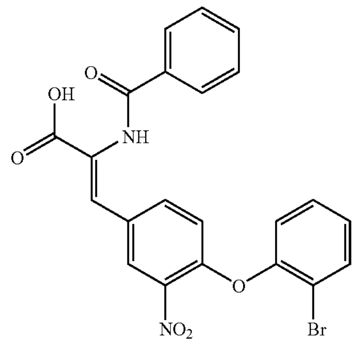 | (2Z)-2-(benzoylamino)-3-[4-(2-bromophenoxy)-3-nitrophenyl]prop-2-enoic acid; |
| 282. | 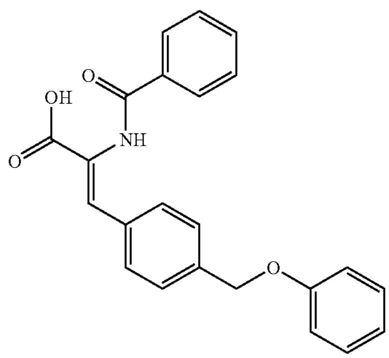 | (2Z)-2-(benzoylamino)-3-[4-(phenoxymethyl)phenyl]prop-2-enoic acid; |
| 283. | 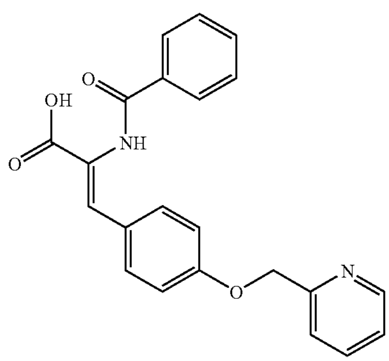 | (2Z)-2-(benzoylamino)-3-[4-(pyridin-2-ylmethoxy)phenyl]prop-2-enoic acid; |
| 284. | 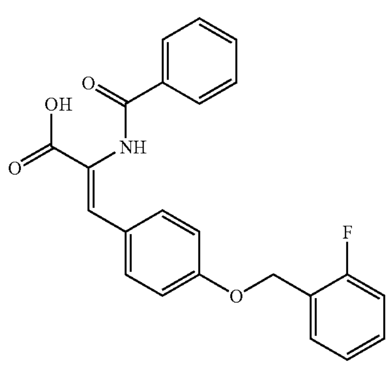 | (2Z)-2-(benzoylamino)-3-{4-[(2-fluorobenzyl)oxy]phenyl}prop-2-enoic acid; |

-continued

| Compound Number | Structure | Name |
|---|---|---|
| 285. | 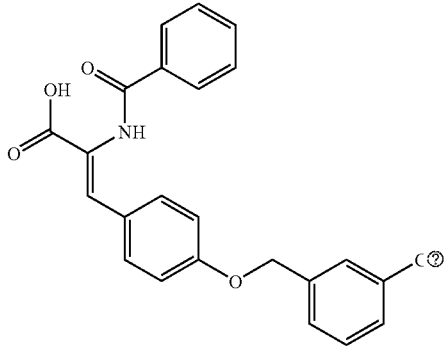 ⑦ indicates text missing or illegible when filed | (2Z)-2-(benzoylamino)-3-(4-{[3-(trifluoromethyl)benzyl]oxy}phenyl)prop-2-enoic acid; |
| 286. | 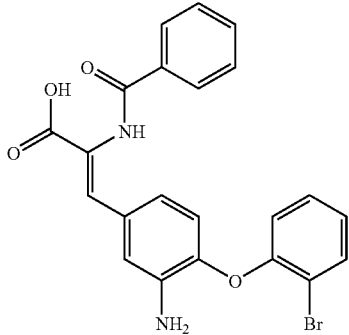 | (2Z)-3-[3-amino-4-(2-bromophenoxy)phenyl]-2-(benzoylamino)prop-2-enoic acid; |
| 287. | 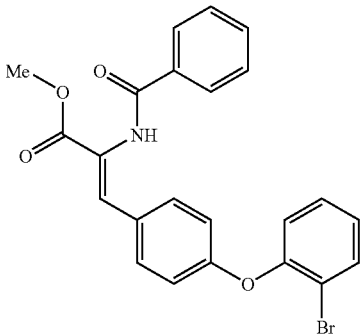 | methyl (2Z)-2-(benzoylamino)-3-[4-(2-bromophenoxy)phenyl]prop-2-enoate; |
| 288. | 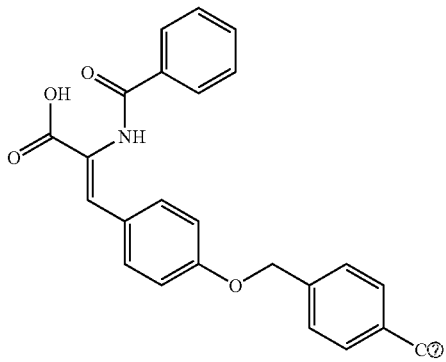 ⑦ indicates text missing or illegible when filed | (2Z)-2-(benzoylamino)-3-{4-[(4-cyanobenzyl)oxy]phenyl}prop-2-enoic acid; |

-continued

| Compound Number | Structure | Name |
|---|---|---|
| 289. | 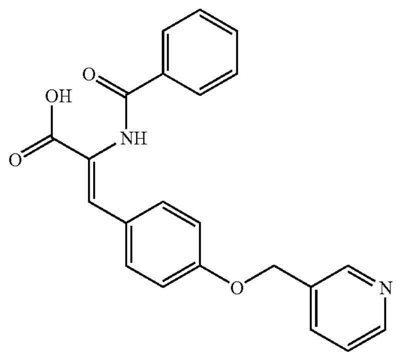 | (2Z)-2-(benzoylamino)-3-[4-(pyridin-3-ylmethoxy)phenyl]prop-2-enoic acid; |
| 290. | 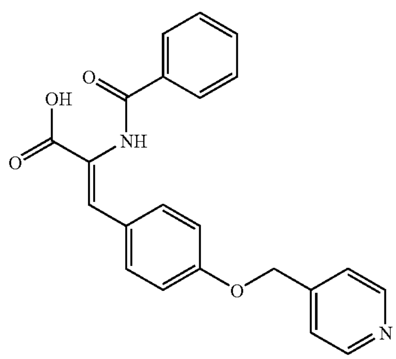 | (2Z)-2-(benzoylamino)-3-[4-(pyridin-4-ylmethoxy)phenyl]prop-2-enoic acid; |
| 291. | 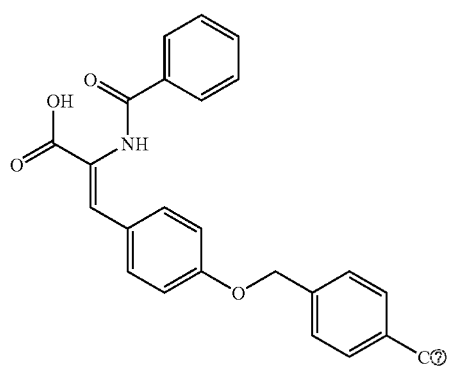 | (2Z)-2-(benzoylamino)-3-(4-{[4-(trifluoromethyl)benzyl]oxy}phenyl)prop-2-enoic acid; |
| 292. | 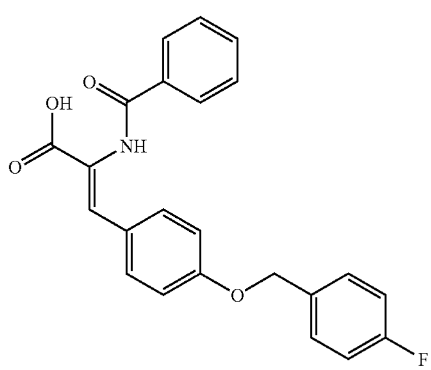 | (2Z)-2-(benzoylamino)-3-{4-[(4-fluorobenzyl)oxy]phenyl}prop-2-enoic acid; |

⑦ indicates text missing or illegible when filed

-continued

| Compound Number | Structure | Name |
| --- | --- | --- |
| 293. | 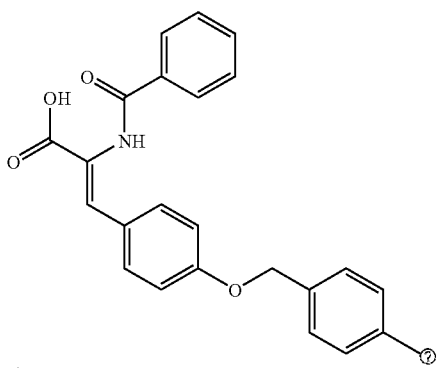 ⑦ indicates text missing or illegible when filed | (2Z)-2-(benzoylamino)-3-{4-[(3-nitrobenzyl)oxy]phenyl}prop-2-enoic acid; |
| 294. | 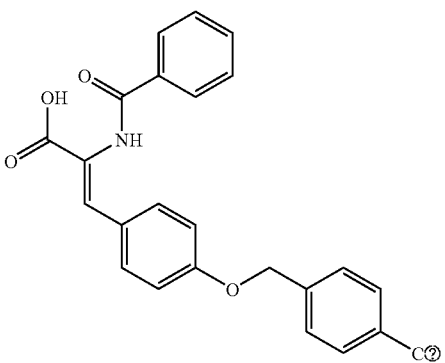 ⑦ indicates text missing or illegible when filed | (2Z)-2-(benzoylamino)-3-{4-[(4-methylbenzyl)oxy]phenyl}prop-2-enoic acid; |
| 295. | 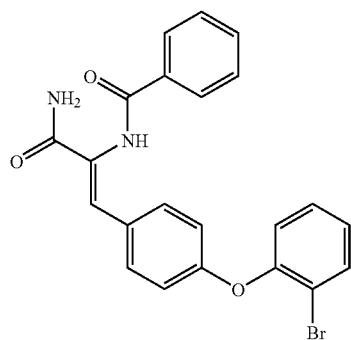 ⑦ indicates text missing or illegible when filed | (2Z)-2-(benzoylamino)-3-{4-[(4-chlorobenzyl)oxy]phenyl}prop-2-enoic acid; |
| 296. | 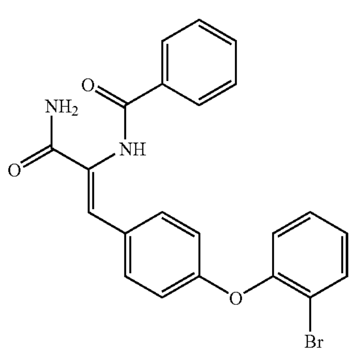 | N-[(1Z)-1-(aminocarbonyl)-2-[4-(2-bromophenoxy)phenyl]ethenyl]benzamide; |

-continued

| Compound Number | Structure | Name |
|---|---|---|
| 297. | 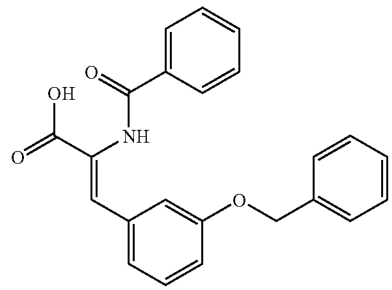 | (2Z)-2-(benzoylamino)-3-[3-(benzyloxy)phenyl]prop-2-enoic acid; |
| 298. | 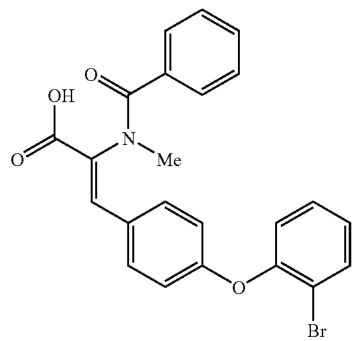 | (2Z)-2-[benzoyl(methyl)amino]-3-[4-(2-bromophenoxy)phenyl]prop-2-enoic acid; |
| 299. | 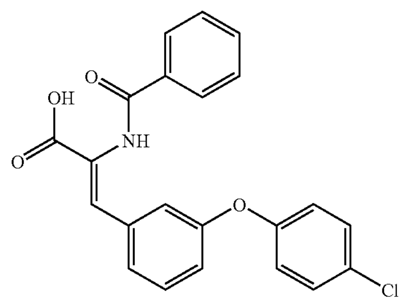 | (2Z)-2-(benzoylamino)-3-[3-(4-chlorophenoxy)phenyl]prop-2-enoic acid; |
| 300. | 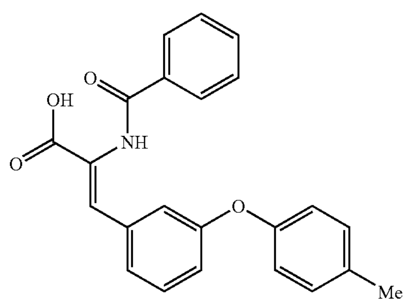 | (2Z)-2-(benzoylamino)-3-[3-(4-methylphenoxy)phenyl]prop-2-enoic acid; |
| 301. | 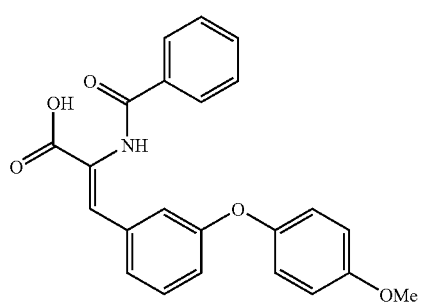 | (2Z)-2-(benzoylamino)-3-[3-(4-methoxyphenoxy)phenyl]prop-2-enoic acid; |

-continued
| Compound Number | Structure | Name |
|---|---|---|
| 302. | 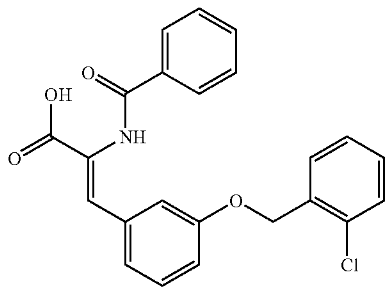 | (2Z)-2-(benzoylamino)-3-{3-[(2-chlorobenzyl)oxy]phenyl}prop-2-enoic acid; |
| 303. | 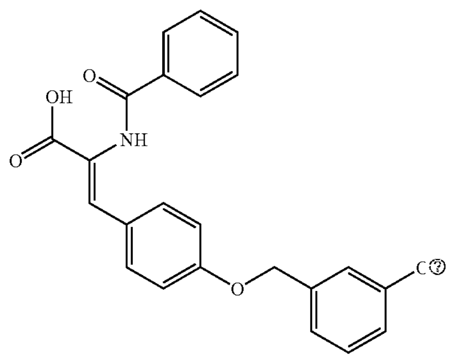 | (2Z)-2-(benzoylamino)-3-{4-[(3-methoxybenzyl)oxy]phenyl}prop-2-enoic acid; |
| 304. | 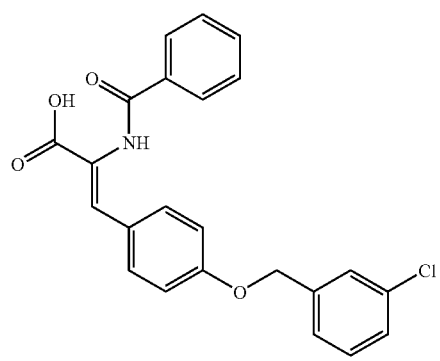 | (2Z)-2-(benzoylamino)-3-{4-[(3-chlorobenzyl)oxy]phenyl}prop-2-enoic acid; |
| 305. | 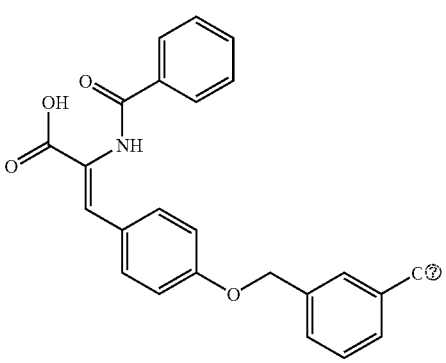 | (2Z)-2-(benzoylamino)-3-(4-{[3-(trifluoromethoxy)benzyl]oxy}phenyl)prop-2-enoic acid; |
? indicates text missing or illegible when filed -continued

| Compound Number | Structure | Name |
|---|---|---|
| 306. | 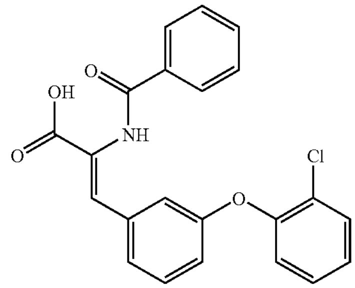 | (2Z)-2-(benzoylamino)-3-[3-(2-chlorophenoxy)phenyl]prop-2-enoic acid; |
| 307. | 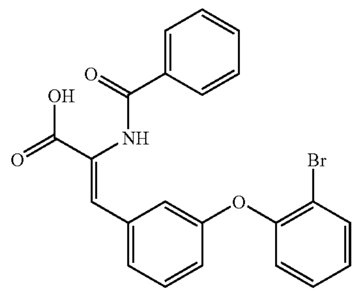 | (2Z)-2-(benzoylamino)-3-[3-(2-bromophenoxy)phenyl]prop-2-enoic acid; |
| 308. | 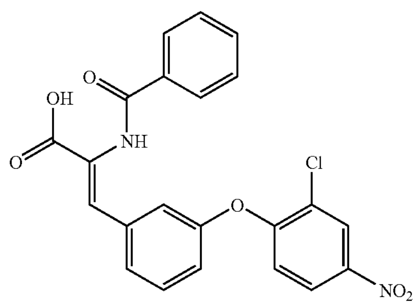 | (2Z)-2-(benzoylamino)-3-[3-(2-chloro-4-nitrophenoxy)phenyl]prop-2-enoic acid; |
| 309. | 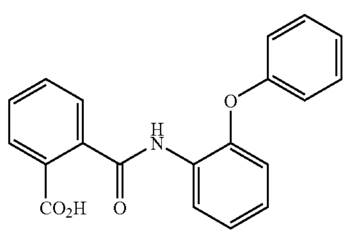 | 2-{[(2-phenoxyphenyl)amino]carbonyl}benzoic acid; |
| 310. | 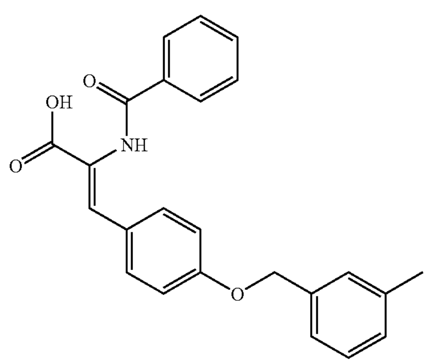 | (2Z)-2-(benzoylamino)-3-{4-[(3-methylbenzyl)oxy]phenyl}prop-2-enoic acid; |

-continued

| Compound Number | Structure | Name |
|---|---|---|
| 311. | 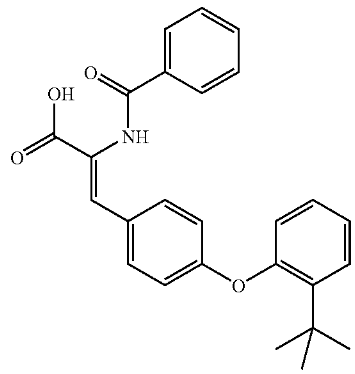 | (2Z)-2-(benzoylamino)-3-[4-(2-tert-butylphenoxy)phenyl]prop-2-enoic acid; |
| 312. | 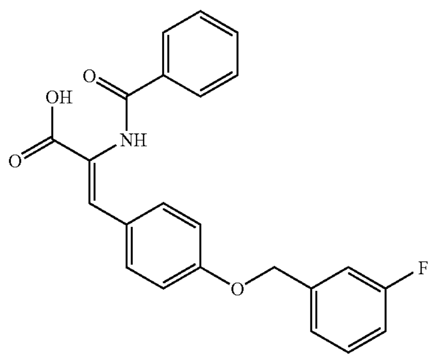 | (2Z)-2-(benzoylamino)-3-{4-[(3-fluorobenzyl)oxy]phenyl}prop-2-enoic acid; |
| 313. | 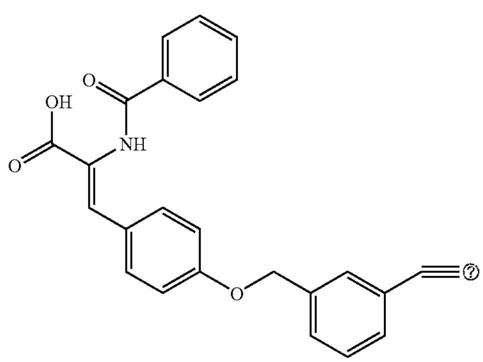 | (2Z)-2-(benzoylamino)-3-{4-[(3-cyanobenzyl)oxy]phenyl}prop-2-enoic acid; |
| 314. | 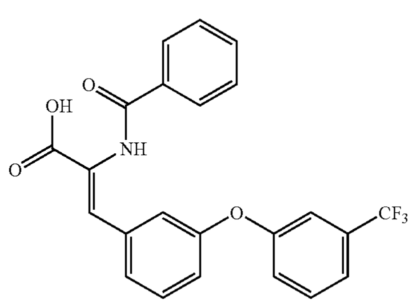 | (2Z)-2-(benzoylamino)-3-{3-[3-(trifluoromethyl)phenoxy]phenyl}prop-2-enoic acid; |

⍰ indicates text missing or illegible when filed

-continued

| Compound Number | Structure | Name |
|---|---|---|
| 315. | 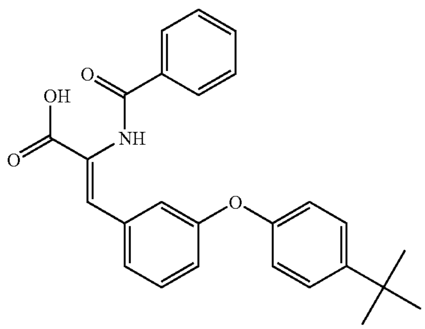 | (2Z)-2-(benzoylamino)-3-[3-(4-tert-butylphenoxy)phenyl]prop-2-enoic acid; |
| 316. | 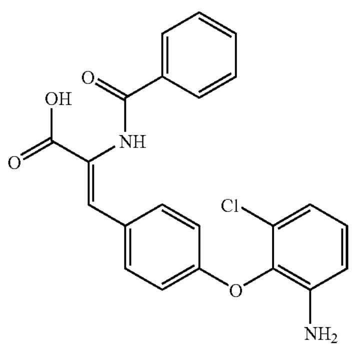 | (2Z)-3-[4-(2-amino-6-chlorophenoxy)phenyl]-2-(benzoylamino)prop-2-enoic acid; |
| 317. | 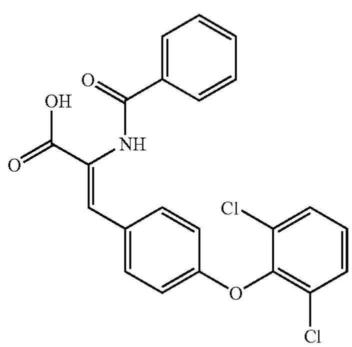 | (2Z)-2-(benzoylamino)-3-[4-(2,6-dichlorophenoxy)phenyl]prop-2-enoic acid; |
| 318. | 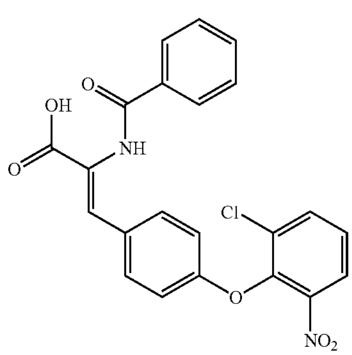 | (2Z)-2-(benzoylamino)-3-[4-(2-chloro-6-nitrophenoxy)phenyl]prop-2-enoic acid; |

-continued

| Compound Number | Structure | Name |
|---|---|---|
| 319. | 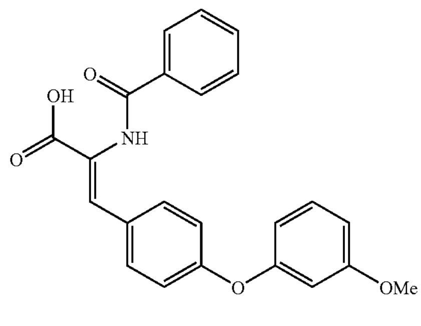 | (2Z)-2-(benzoylamino)-3-[4-(3-methoxyphenoxy)phenyl]prop-2-enoic acid; |
| 320. | 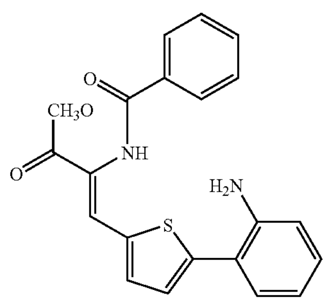 | methyl (2Z)-3-[5-(2-aminophenyl)thien-2-yl]-2-(benzoylamino)prop-2-enoate; |
| 321. | 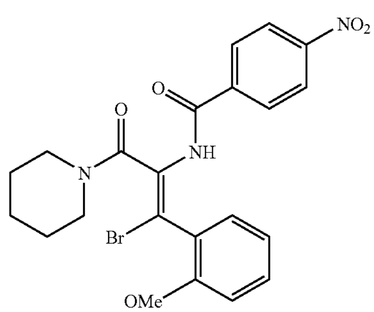 | N-[(E)-2-bromo-2-(2-methoxyphenyl)-1-(piperidin-1-ylcarbonyl)ethenyl]-4-nitrobenzamide; |
| 322. | 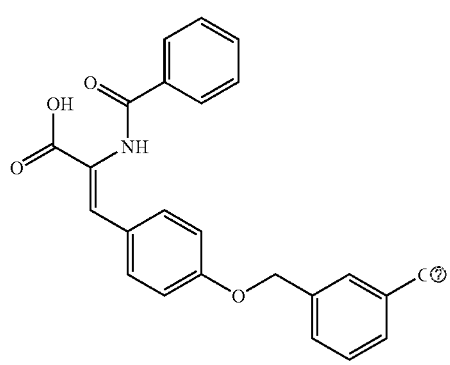 | 3-({4-[(Z)-2-(benzoylamino)-2-carboxyethenyl]phenoxy}methyl)benzoic acid; |

⑦ indicates text missing or illegible when filed

-continued

| Compound Number | Structure | Name |
|---|---|---|
| 323. | 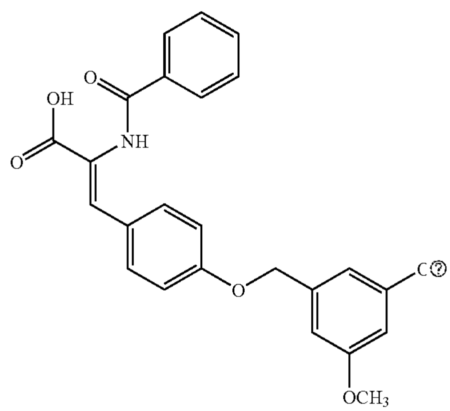 | (2Z)-2-(benzoylamino)-3-{4-[(3,5-dimethoxybenzyl)oxy]phenyl}prop-2-enoic acid; |
| 324. | 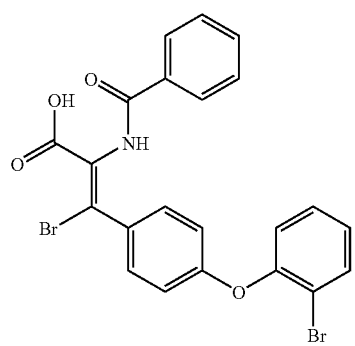 | (2E)-2-(benzoylamino)-3-bromo-3-[4-(2-bromophenoxy)phenyl]prop-2-enoic acid; |
| 325. | 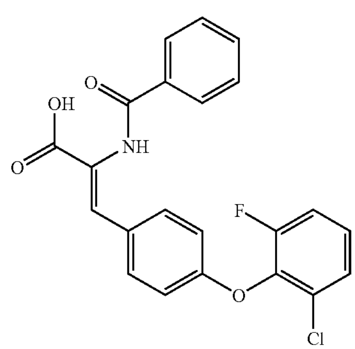 | (2Z)-2-(benzoylamino)-3-[4-(2-chloro-6-fluorophenoxy)phenyl]prop-2-enoic acid; |
| 326. | 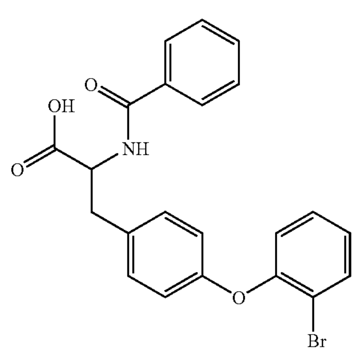 | N-benzoyl-O-(2-bromophenyl)tyrosine; |

⑦ indicates text missing or illegible when filed

-continued

| Compound Number | Structure | Name |
|---|---|---|
| 327. | 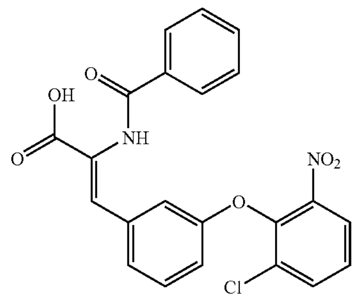 | (2Z)-2-(benzoylamino)-3-[3-(2-chloro-6-nitrophenoxy)phenyl]prop-2-enoic acid; |
| 328. | 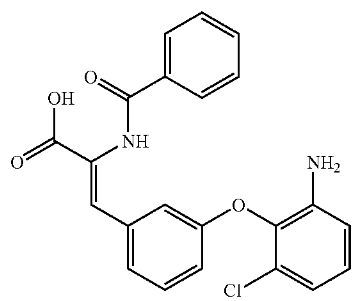 | (2Z)-3-[3-(2-amino-6-chlorophenoxy)phenyl]-2-(benzoylamino)prop-2-enoic acid; |
| 329. | 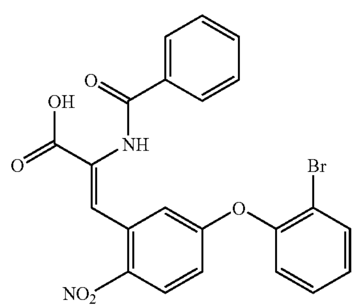 | (2Z)-2-(benzoylamino)-3-[5-(2-bromophenoxy)-2-nitrophenyl]prop-2-enoic acid; |
| 330. | 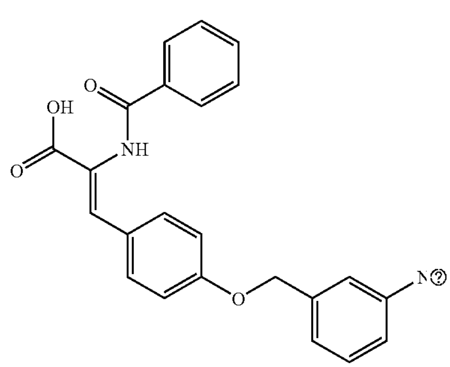 | (2Z)-3-{4-[(3-aminobenzyl)oxy]phenyl}-2-(benzoylamino)prop-2-enoic acid; |

⑦ indicates text missing or illegible when filed

-continued

| Compound Number | Structure | Name |
|---|---|---|
| 331. | 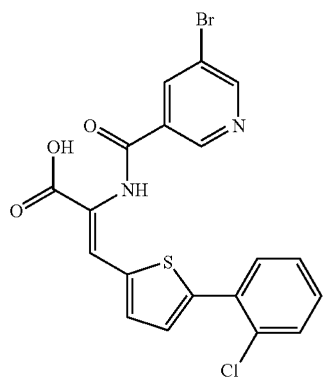 | (2Z)-2-{[(5-bromopyridin-3-yl)carbonyl]amino}-3-[5-(2-chlorophenyl)thien-2-yl]prop-2-enoic acid; |
| 332. | 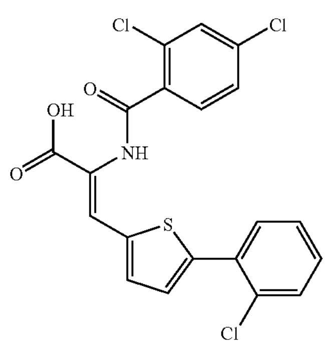 | (2Z)-3-[5-(2-chlorophenyl)thien-2-yl]-2-[(2,4-dichlorobenzoyl)amino]prop-2-enoic acid; |
| 333. | 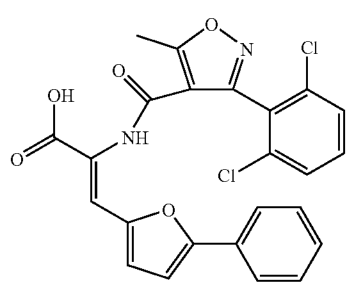 | (2Z)-2-({[3-(2,6-dichlorophenyl)-5-methylisoxazol-4-yl]carbonyl}amino)-3-(5-phenyl-2-furyl)prop-2-enoic acid; |
| 334. | 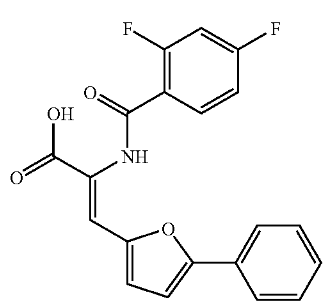 | (2Z)-2-[(2,4-difluorobenzoyl)amino]-3-(5-phenyl-2-furyl)prop-2-enoic acid; |

-continued

| Compound Number | Structure | Name |
|---|---|---|
| 335. | 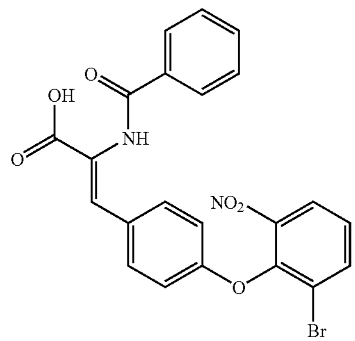 | (2Z)-2-(benzoylamino)-3-[4-(2-bromo-6-nitrophenoxy)phenyl]prop-2-enoic acid; |
| 336. | 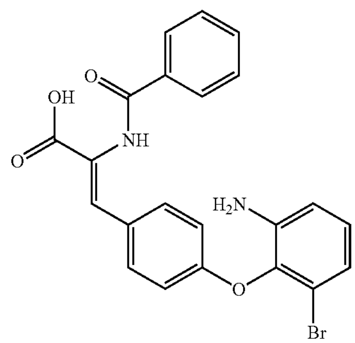 | (2Z)-3-[4-(2-amino-6-bromophenoxy)phenyl]-2-(benzoylamino)prop-2-enoic acid; |
| 337. | 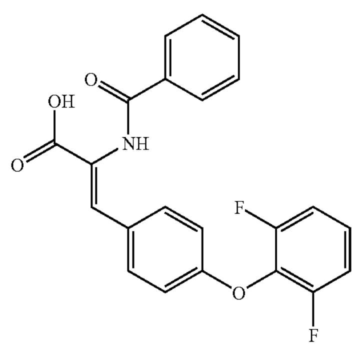 | (2Z)-2-(benzoylamino)-3-[4-(2,6-difluorophenoxy)phenyl]prop-2-enoic acid; |
| 338. | 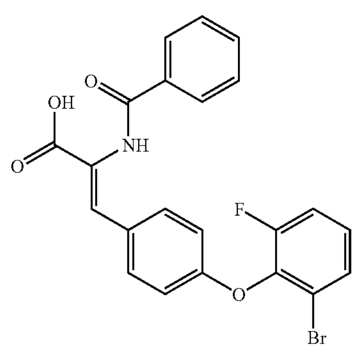 | (2Z)-2-(benzoylamino)-3-[4-(2-bromo-6-fluorophenoxy)phenyl]prop-2-enoic acid; |

| Compound Number | Structure | Name |
|---|---|---|
| 339. | 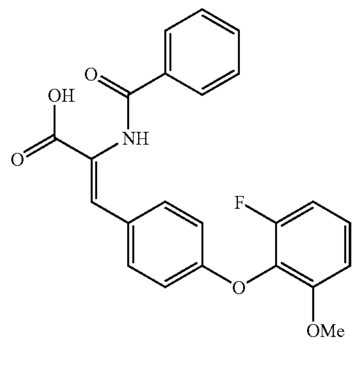 | (2Z)-2-(benzoylamino)-3-[4-(2-fluoro-6-methoxyphenoxy)phenyl]prop-2-enoic acid; |
| 340. | 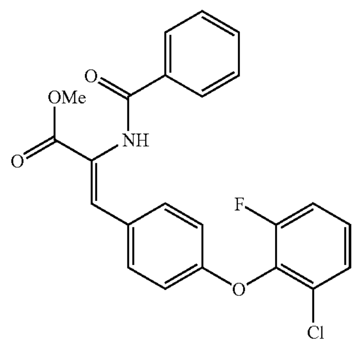 | methyl (2Z)-2-(benzoylamino)-3-[4-(2-chloro-6-fluorophenoxy)phenyl]prop-2-enoate; |
| 341. | 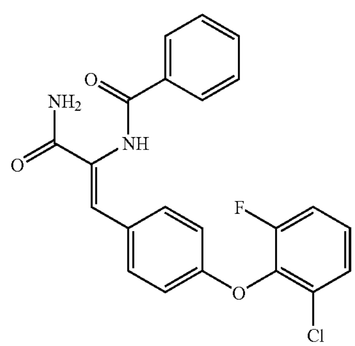 | N-{(Z)-1-(aminocarbonyl)-2-[4-(2-chloro-6-fluorophenoxy)phenyl]ethenyl}benzamide; |
| 342. | 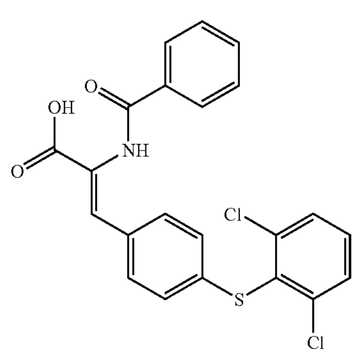 | (2Z)-2-(benzoylamino)-3-{4-[(2,6-dichlorophenyl)thio]phenyl}prop-2-enoic acid; |

-continued

| Compound Number | Structure | Name |
| --- | --- | --- |
| 343. | 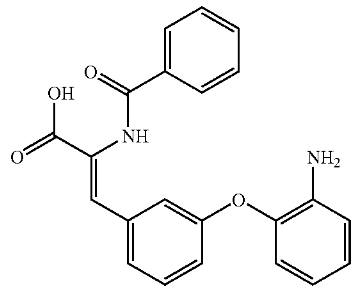 | (2Z)-3-[3-(2-aminophenoxy)phenyl]-2-(benzoylamino)prop-2-enoic acid; |
| 344. | 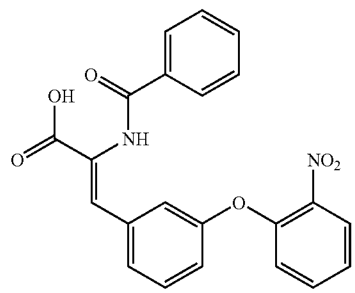 | (2Z)-2-(benzoylamino)-3-[3-(2-nitrophenoxy)phenyl]prop-2-enoic acid; |
| 345. | 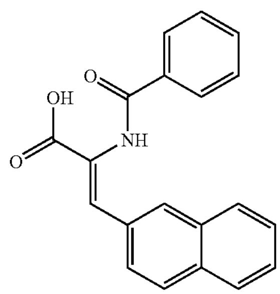 | (2Z)-2-(benzoylamino)-3-(2-naphthyl)prop-2-enoic acid; |
| 346. | 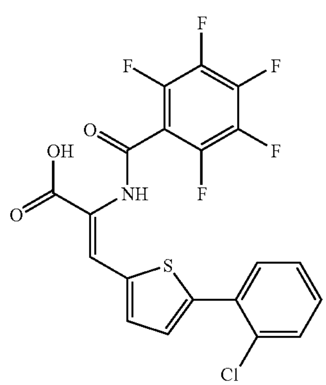 | (2Z)-3-[5-(2-chlorophenyl)thien-2-yl]-2-[(pentafluorobenzoyl)amino]prop-2-enoic acid; |
| 347. | 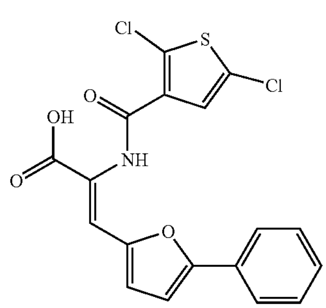 | (2Z)-2-{[(2,5-dichlorothien-3-yl)carbonyl]amino}-3-(5-phenyl-2-furyl)prop-2-enoic acid; |

-continued

| Compound Number | Structure | Name |
|---|---|---|
| 348. | 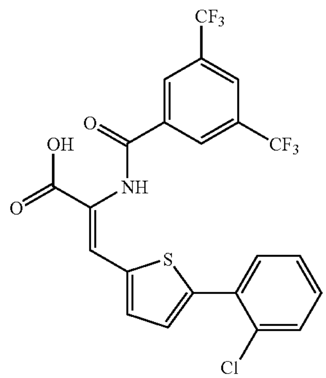 | (2Z)-2-{[3,5-bis(trifluoromethyl)benzoyl]amino}-3-[5-(2-chlorophenyl)thien-2-yl]prop-2-enoic acid; |
| 349. | 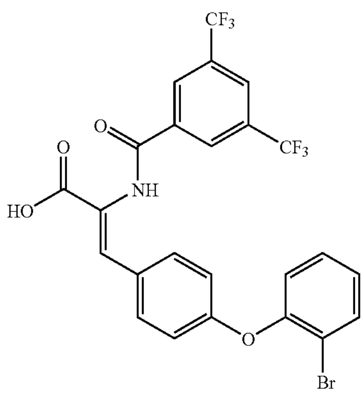 | (2Z)-2-{[3,5-bis(trifluoromethyl)benzoyl]amino}-3-[4-(2-bromophenoxy)phenyl]prop-2-enoic acid; |
| 350. | 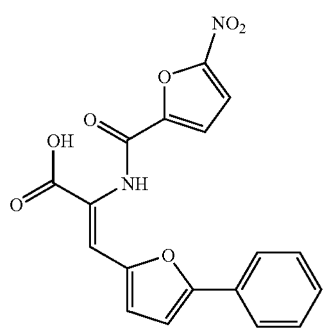 | (2Z)-2-[(5-nitro-2-furoyl)amino]-3-(5-phenyl-2-furyl)prop-2-enoic acid; |
| 351. | 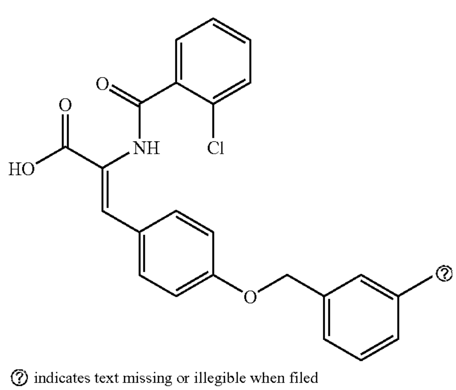 | (2Z)-2-[(2-chlorobenzoyl)amino]-3-{4-[(3-methoxybenzyl)oxy]phenyl}prop-2-enoic acid; |

⊙ indicates text missing or illegible when filed

-continued
| Compound Number | Structure | Name |
|---|---|---|
| 352. | 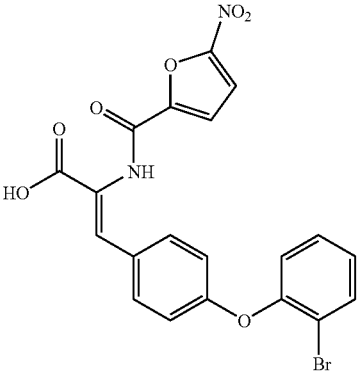 | (2Z)-3-[4-(2-bromophenoxy)phenyl]-2-[(5-nitro-2-furoyl)amino]prop-2-enoic acid; |
| 353. | 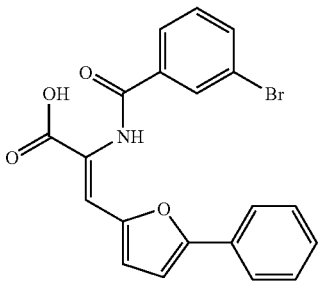 | (2Z)-2-[(3-bromobenzoyl)amino]-3-(5-phenyl-2-furyl)prop-2-enoic acid; |
| 354. | 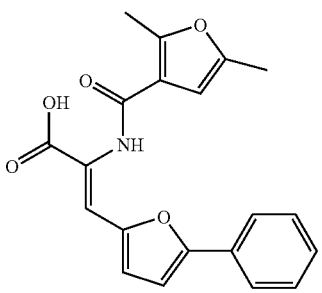 | (2Z)-2-[(2,5-dimethyl-3-furoyl)amino]-3-(5-phenyl-2-furyl)prop-2-enoic acid; |
| 355. | 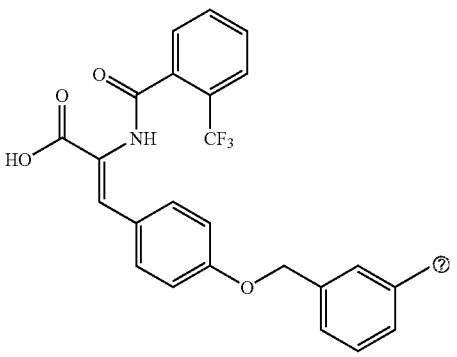 | (2Z)-3-{4-[(3-methoxybenzyl)oxy]phenyl}-2-{[2-(trifluoromethyl)benzoyl]amino}prop-2-enoic acid; |
⊙ indicates text missing or illegible when filed -continued

| Compound Number | Structure | Name |
|---|---|---|
| 356. | 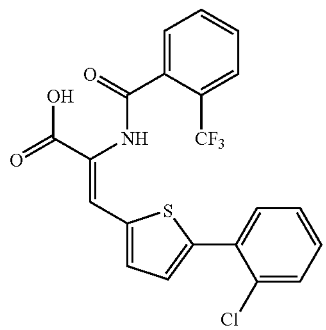 | (2Z)-3-[5-(2-chlorophenyl)thien-2-yl]-2-{[2-(trifluoromethyl)benzoyl]amino}prop-2-enoic acid; |
| 357. | 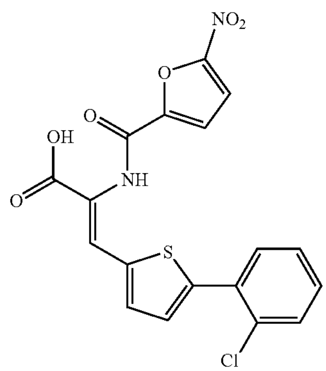 | (2Z)-3-[5-(2-chlorophenyl)thien-2-yl]-2-[(5-nitro-2-furoyl)amino]prop-2-enoic acid; |
| 358. | 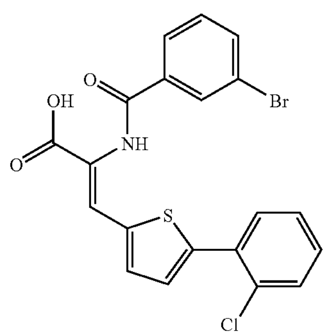 | (2Z)-2-[(3-bromobenzoyl)amino]-3-[5-(2-chlorophenyl)thien-2-yl]prop-2-enoic acid; |
| 359. | 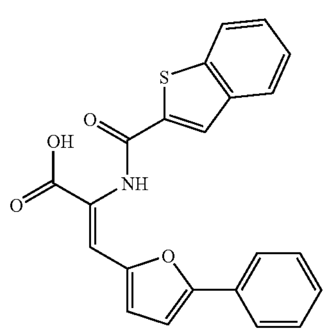 | (2Z)-2-[(1-benzothien-2-ylcarbonyl)amino]-3-(5-phenyl-2-furyl)prop-2-enoic acid; |

-continued

| Compound Number | Structure | Name |
|---|---|---|
| 360. | 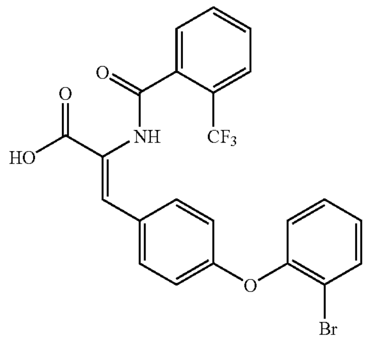 | (2Z)-3-[4-(2-bromophenoxy)phenyl]-2-{[2-(trifluoromethyl)benzoyl]amino}prop-2-enoic acid; |
| 361. | 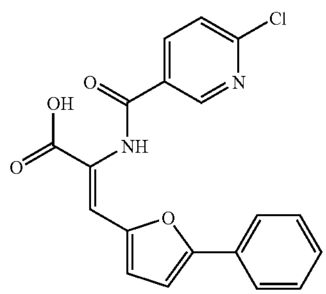 | (2Z)-2-{[(6-chloropyridin-3-yl)carbonyl]amino}-3-(5-phenyl-2-furyl)prop-2-enoic acid; |
| 362. | 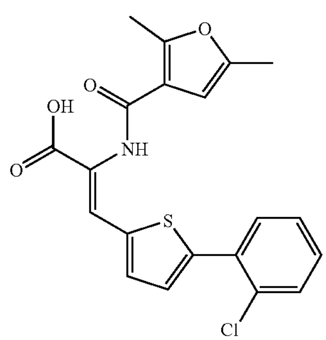 | (2Z)-3-[5-(2-chlorophenyl)thien-2-yl]-2-[(2,5-dimethyl-3-furoyl)amino]prop-2-enoic acid; |
| 363. | 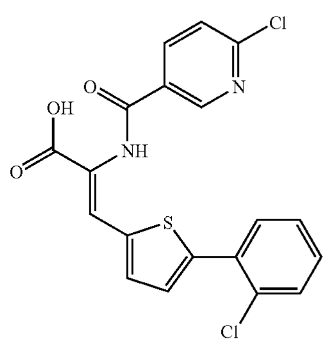 | (2Z)-3-[5-(2-chlorophenyl)thien-2-yl]-2-{[(6-chloropyridin-3-yl)carbonyl]amino}prop-2-enoic acid; |

-continued

| Compound Number | Structure | Name |
|---|---|---|
| 364. | 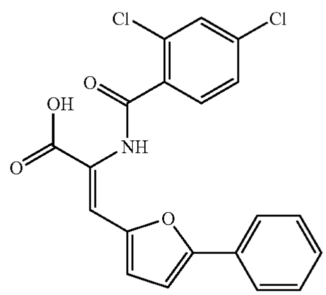 | (2Z)-2-[(2,4-dichlorobenzoyl)amino]-3-(5-phenyl-2-furyl)prop-2-enoic acid; |
| 365. | 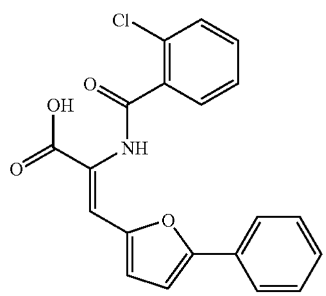 | (2Z)-2-[(2-chlorobenzoyl)amino]-3-(5-phenyl-2-furyl)prop-2-enoic acid; |
| 366. | 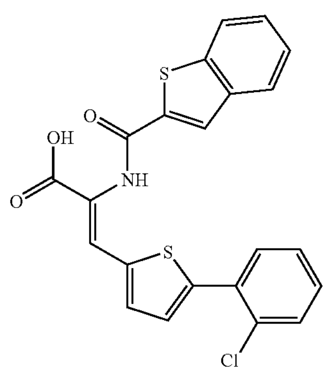 | (2Z)-2-[(1-benzothien-2-ylcarbonyl)amino]-3-[5-(2-chlorophenyl)thien-2-yl]prop-2-enoic acid; |
| 367. | 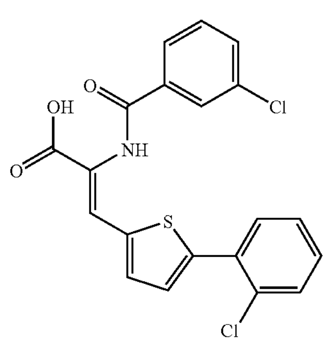 | (2Z)-2-[(3-chlorobenzoyl)amino]-3-[5-(2-chlorophenyl)thien-2-yl]prop-2-enoic acid; |

-continued

| Compound Number | Structure | Name |
|---|---|---|
| 368. | 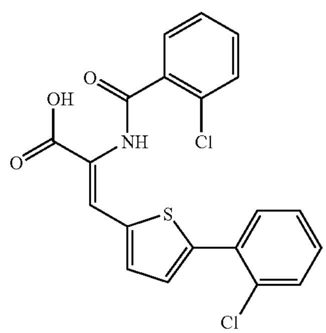 | (2Z)-2-[(2-chlorobenzoyl)amino]-3-[5-(2-chlorophenyl)thien-2-yl]prop-2-enoic acid; |
| 369. | 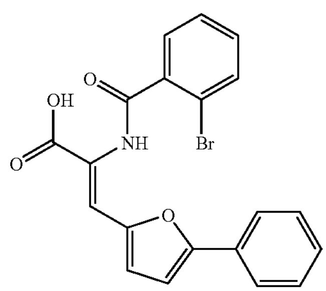 | (2Z)-2-[(2-bromobenzoyl)amino]-3-(5-phenyl-2-furyl)prop-2-enoic acid; |
| 370. | 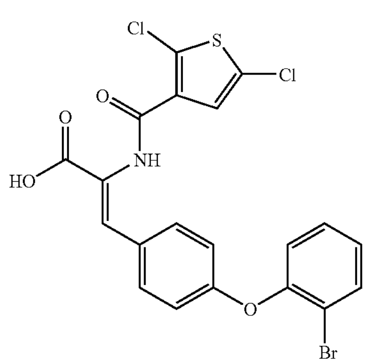 | (2Z)-3-[4-(2-bromophenoxy)phenyl]-2-{[(2,5-dichlorothien-3-yl)carbonyl]amino}prop-2-enoic acid; |
| 371. | 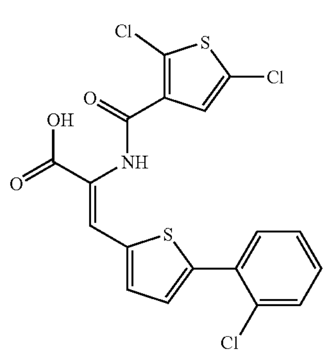 | (2Z)-3-[5-(2-chlorophenyl)thien-2-yl]-2-{[(2,5-dichlorothien-3-yl)carbonyl]amino}prop-2-enoic acid; |

| Compound Number | Structure | Name |
|---|---|---|
| 372. | 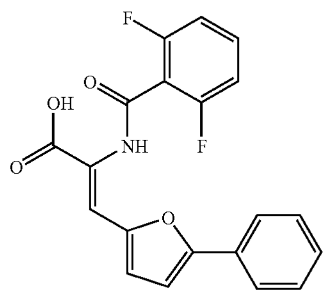 | (2Z)-2-[(2,6-difluorobenzoyl)amino]-3-(5-phenyl-2-furyl)prop-2-enoic acid; |
| 373. | 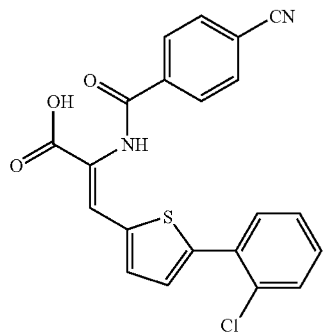 | (2Z)-3-[5-(2-chlorophenyl)thien-2-yl]-2-[(4-cyanobenzoyl)amino]prop-2-enoic acid; |
| 374. | 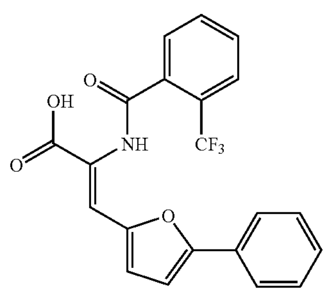 | (2Z)-3-(5-phenyl-2-furyl)-2-{[2-(trifluoromethyl)benzoyl]amino}prop-2-enoic acid; |
| 375. | 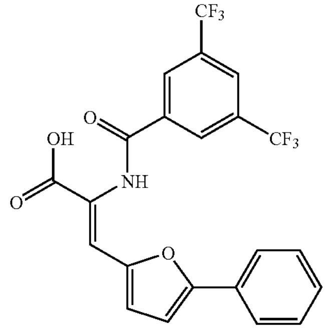 | (2Z)-2-{[3,5-bis(trifluoromethyl)benzoyl]amino}-3-(5-phenyl-2-furyl)prop-2-enoic acid; |

-continued

| Compound Number | Structure | Name |
|---|---|---|
| 376. | 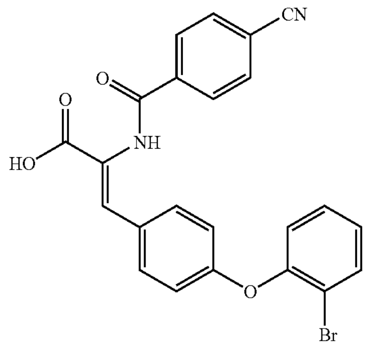 | (2Z)-3-[4-(2-bromophenoxy)phenyl]-2-[(4-cyanobenzoyl)amino]prop-2-enoic acid; |
| 377. | 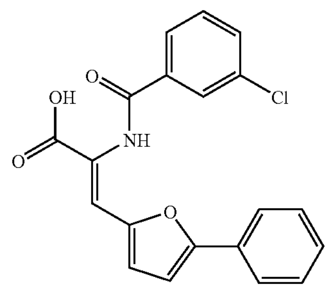 | (2Z)-2-[(3-chlorobenzoyl)amino]-3-(5-phenyl-2-furyl)prop-2-enoic acid; |
| 378. | 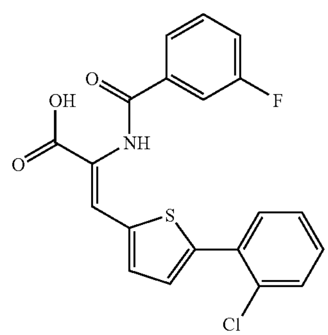 | (2Z)-3-[5-(2-chlorophenyl)thien-2-yl]-2-[(3-fluorobenzoyl)amino]prop-2-enoic acid; |
| 379. | 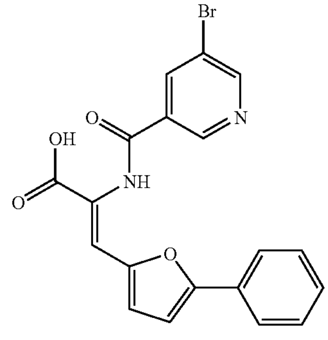 | (2Z)-2-{[(5-bromopyridin-3-yl)carbonyl]amino}-3-(5-phenyl-2-furyl)prop-2-enoic acid; |

-continued

| Compound Number | Structure | Name |
|---|---|---|
| 380. | 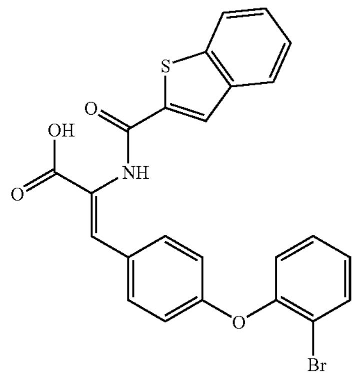 | (2Z)-2-[(1-benzothien-2-ylcarbonyl)amino]-3-[4-(2-bromophenoxy)phenyl]prop-2-enoic acid; |
| 381. | 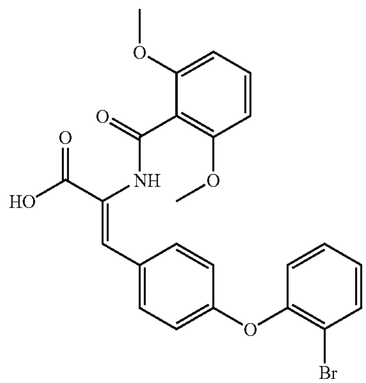 | (2Z)-3-[4-(2-bromophenoxy)phenyl]-2-[(2,6-dimethoxybenzoyl)amino]prop-2-enoic acid; |
| 382. | 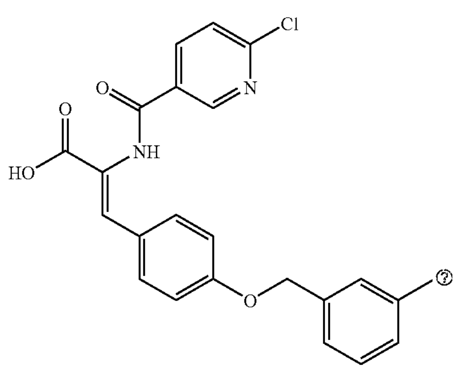 | (2Z)-2-{[(6-chloropyridin-3-yl)carbonyl]amino}-3-{4-[(3-methoxybenzyl)oxy]phenyl}prop-2-enoic acid; |
|  | ⑦ indicates text missing or illegible when filed | |
| 383. | 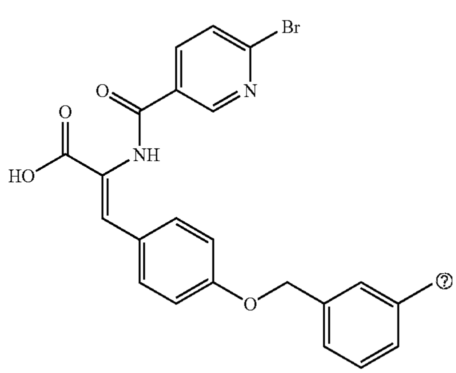 | (2Z)-2-{[(6-bromopyridin-3-yl)carbonyl]amino}-3-{4-[(3-methoxybenzyl)oxy]phenyl]prop-2-enoic acid; |
|  | ⑦ indicates text missing or illegible when filed | |

-continued

| Compound Number | Structure | Name |
|---|---|---|
| 384. | 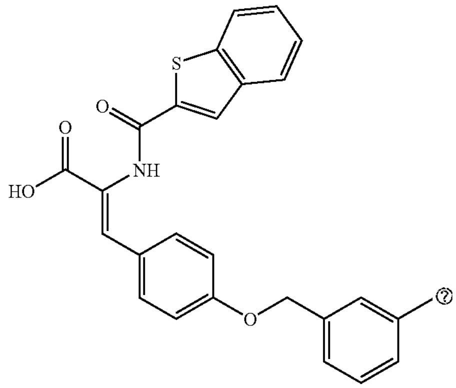 | (2Z)-2-[(1-benzothien-2-ylcarbonyl)amino]-3-{4-[(3-methoxybenzyl)oxy]phenyl}prop-2-enoic acid; |
| 385. | 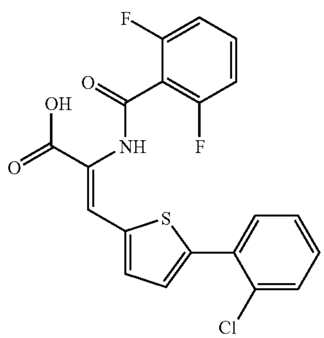 | (2Z)-3-[5-(2-chlorophenyl)thien-2-yl]-2-[(2,6-difluorobenzoyl)amino]prop-2-enoic acid; |
| 386. | 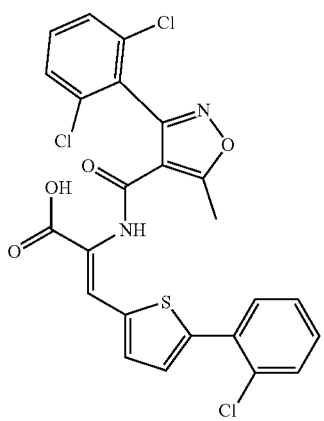 | (2Z)-3-[5-(2-chlorophenyl)thien-2-yl]-2-({[3-(2,6-dichlorophenyl)-5-methylisoxazol-4-yl]carbonyl}amino)prop-2-enoic acid; |
| 387. | | (2Z)-2-[(3-bromobenzoyl)amino]-3-[4-(2-bromophenoxy)phenyl]prop-2-enoic acid; |
| 388. | 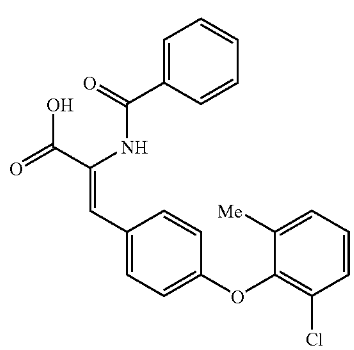 | (2Z)-2-(benzoylamino)-3-[4-(2-chloro-6-methylphenoxy)phenyl]prop-2-enoic acid; |

⑦ indicates text missing or illegible when filed

-continued
| Compound Number | Structure | Name |
|---|---|---|
| 389. | 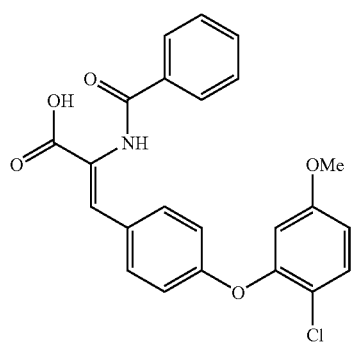 | (2Z)-2-(benzoylamino)-3-[4-(2-chloro-5-methoxyphenoxy)phenyl]prop-2-enoic acid; |
| 390. | 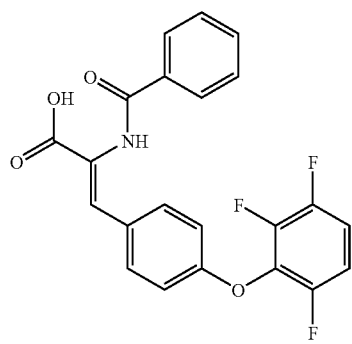 | (2Z)-2-(benzoylamino)-3-[4-(2,3,6-trifluorophenoxy)phenyl]prop-2-enoic acid; |
| 391. | 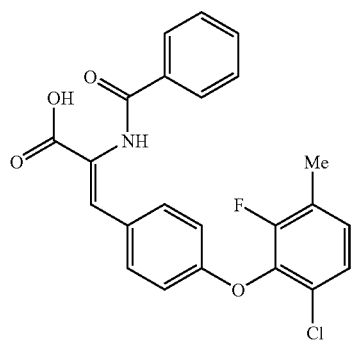 | (2Z)-2-(benzoylamino)-3-[4-(6-chloro-2-fluoro-3-methylphenoxy)phenyl]prop-2-enoic acid; |
| 392. | 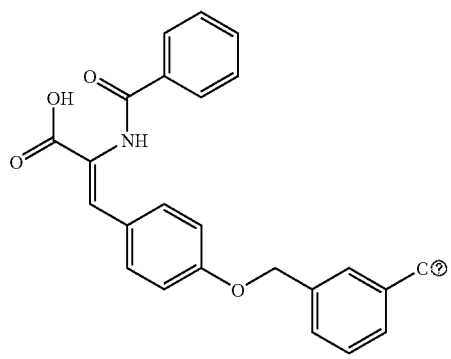 | (2Z)-2-(benzoylamino)-3-{4-[(3-ethoxybenzyl)oxy]phenyl}prop-2-enoic acid; |
⊘ indicates text missing or illegible when filed

| Compound Number | Structure | Name |
|---|---|---|
| 393. | 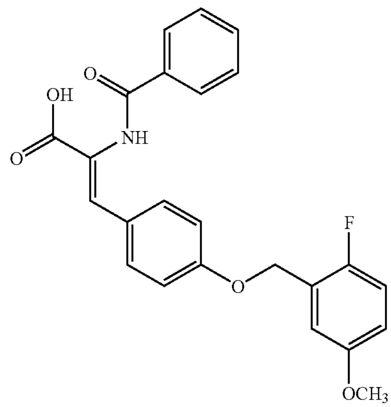 | (2Z)-2-(benzoylamino)-3-{4-[(2-fluoro-5-methoxybenzyl)oxy]phenyl}prop-2-enoic acid; |
| 394. | 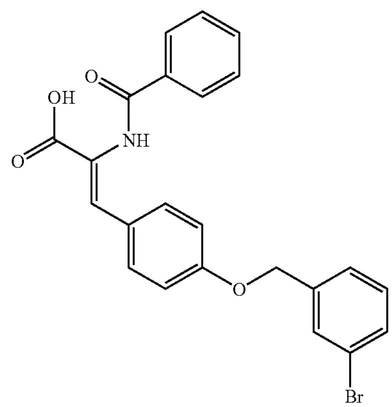 | (2Z)-2-(benzoylamino)-3-{4-[(3-bromobenzyl)oxy]phenyl}prop-2-enoic acid; |
| 395. | 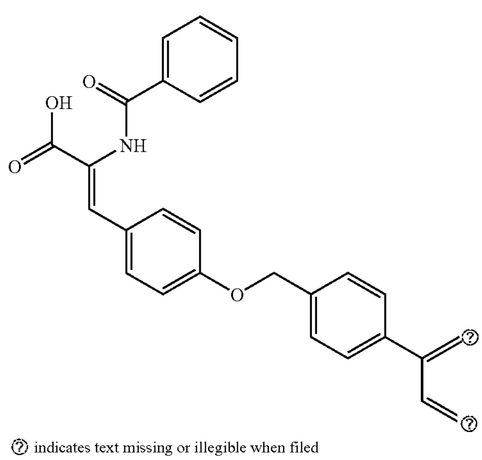 | (2Z)-2-(benzoylamino)-3-{4-[(2'-cyano-1,1'-biphenyl-4-yl)methoxy]phenyl}prop-2-enoic acid; |

⟨?⟩ indicates text missing or illegible when filed

-continued

| Compound Number | Structure | Name |
|---|---|---|
| 396. | 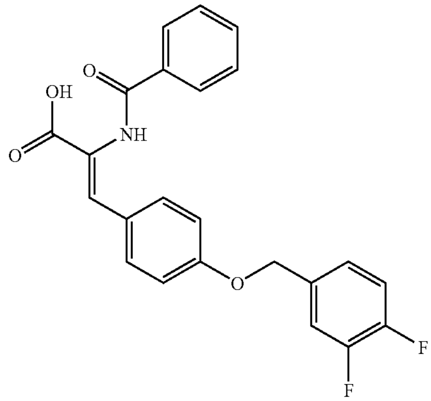 | (2Z)-2-(benzoylamino)-3-{4-[(3,4-difluorobenzyl)oxy]phenyl}prop-2-enoic acid; |
| 397. | 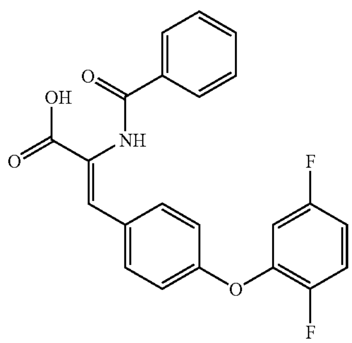 | (2Z)-2-(benzoylamino)-3-[4-(2,5-difluorophenoxy)phenyl]prop-2-enoic acid; |
| 398. | 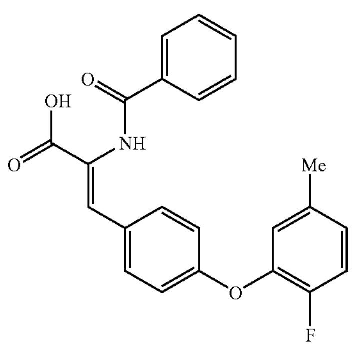 | (2Z)-2-(benzoylamino)-3-[4-(2-fluoro-5-methylphenoxy)phenyl]prop-2-enoic acid; |
| 399. | 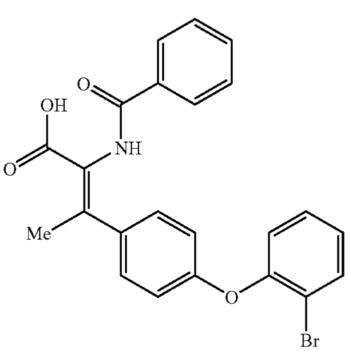 | (2Z)-2-(benzoylamino)-3-[4-(2-bromophenoxy)phenyl]but-2-enoic acid; |

-continued

| Compound Number | Structure | Name |
|---|---|---|
| 400. | 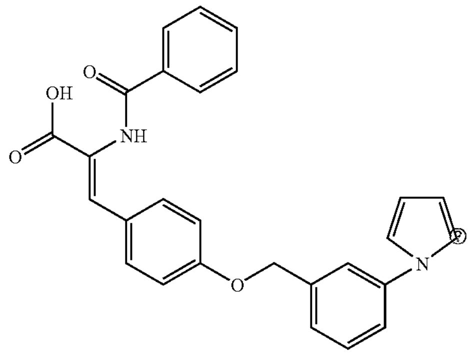 | (2Z)-2-(benzoylamino)-3-(4-{[3-(1H-pyrrol-1-yl)benzyl]oxy}phenyl)prop-2-enoic acid; |
| 401. | 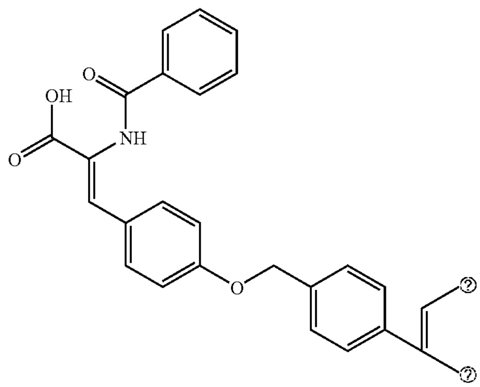 | (2Z)-2-(benzoylamino)-3-(4-{[4-(1,2,3-thiadiazol-4-yl)benzyl]oxy}phenyl)prop-2-enoic acid; |
| 402. | 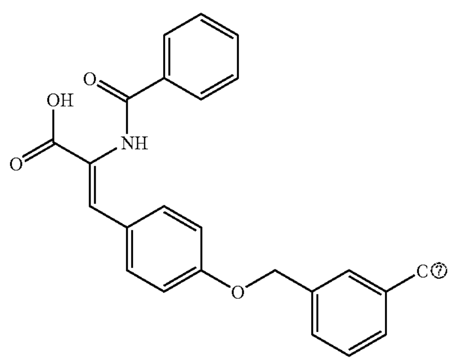 | (2Z)-2-(benzoylamino)-3-(4-{[3-(difluoromethoxy)benzyl]oxy}phenyl)prop-2-enoic acid; |
| 403. | 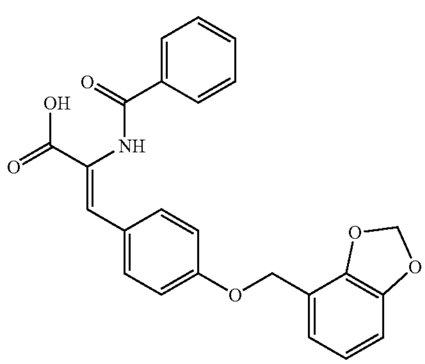 | (2Z)-3-[4-(1,3-benzodioxol-4-ylmethoxy)phenyl]-2-(benzoylamino)prop-2-enoic acid; |

-continued

| Compound Number | Structure | Name |
|---|---|---|
| 404. | 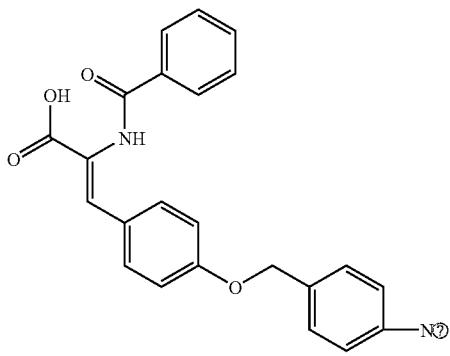 ⑦ indicates text missing or illegible when filed | (2Z)-2-(benzoylamino)-3-(4-{[4-(1H-1,2,4-triazol-1-yl)benzyl]oxy}phenyl)prop-2-enoic acid; |
| 405. | 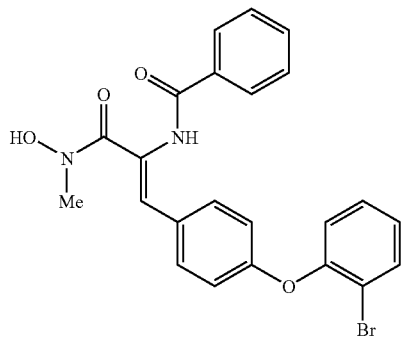 | N-((Z)-2-[4-(2-bromophenoxy)phenyl]-1-{[hydroxy(methyl)amino]carbonyl}ethenyl)benzamide; or V00086354 |
| 406. | 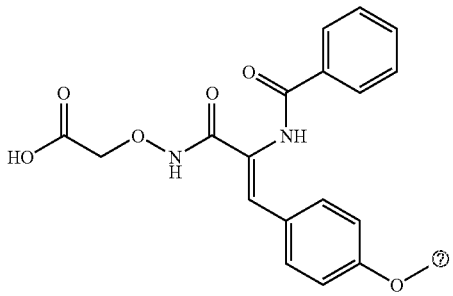 ⑦ indicates text missing or illegible when filed | [({(2Z)-2-(benzoylamino)-3-[4-(2-bromophenoxy)phenyl]prop-2-enoyl}amino)oxy]acetic acid; |
| 407. | 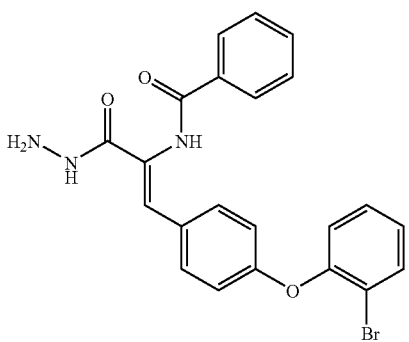 | N-[(Z)-2-[4-(2-bromophenoxy)phenyl]-1-(hydrazinocarbonyl)ethenyl]benzamide; or V00086355 |

-continued

| Compound Number | Structure | Name |
|---|---|---|
| 408. | 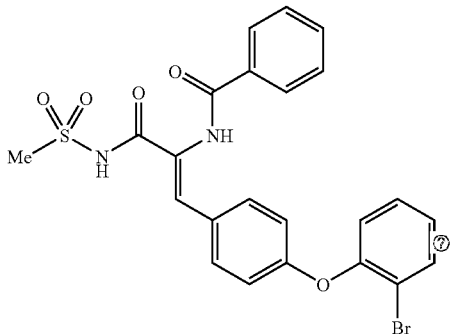 ⊘ indicates text missing or illegible when filed | N-((Z)-2-[4-(2-bromophenoxy)phenyl]-1-{[(methylsulfonyl)amino]carbonyl}ethenyl)benzamide; or V00086363 |
| 409. | 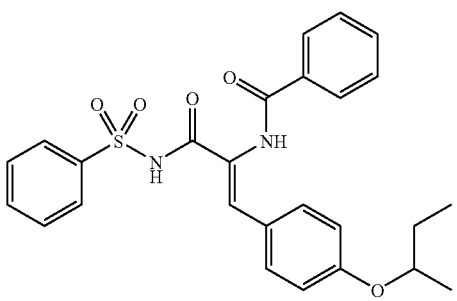 | N-((Z)-2-[4-(2-bromophenoxy)phenyl]-1-{[(phenylsulfonyl)amino]carbonyl}ethenyl)benzamide; |
| 410. | 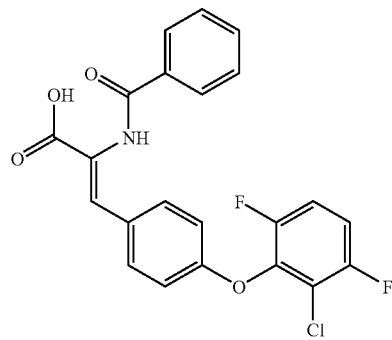 | (2Z)-2-(benzoylamino)-3-[4-(2-chloro-3,6-difluorophenoxy)phenyl]prop-2-enoic acid; |
| 411. | 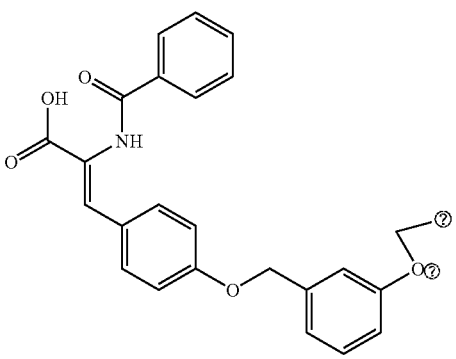 ⊘ indicates text missing or illegible when filed | (2Z)-2-(benzoylamino)-3-(4-{[3-(methoxymethoxy)benzyl]oxy}phenyl)prop-2-enoic acid; |

-continued

| Compound Number | Structure | Name |
|---|---|---|
| 412. | 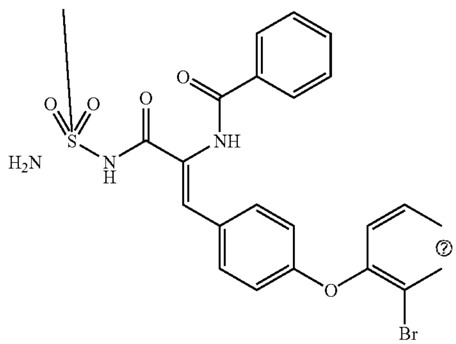 | N-{(Z)-1-{[(aminosulfonyl)amino]carbonyl}-2-[4-(2-bromophenoxy)phenyl]ethenyl}benzamide; or V00086468 |
| 413. | 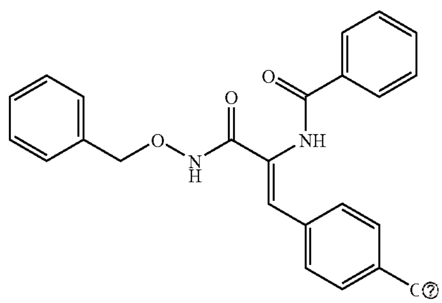 | N-{(Z)-1-{[(benzyloxy)amino]carbonyl}-2-[4-(2-bromophenoxy)phenyl]ethenyl}benzamide; |
| 414. | 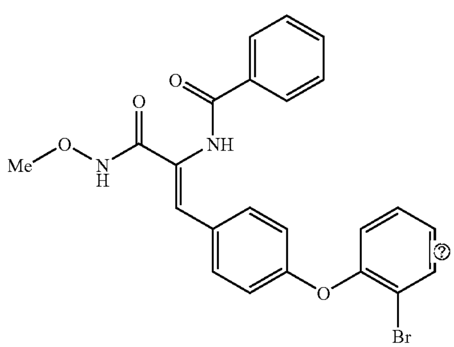 | N-{(Z)-2-{4-(2-bromophenoxy)phenyl]-1-[(methoxyamino)carbonyl]ethenyl}benzamide; |
| 415. | 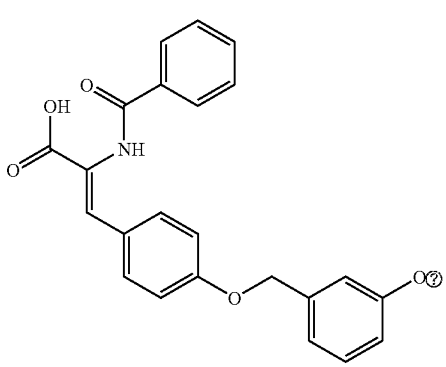 | (2Z)-2-(benzoylamino)-3-{4-[(3-hydroxybenzyl)oxy]phenyl}prop-2-enoic acid; |

⑦ indicates text missing or illegible when filed

-continued

| Compound Number | Structure | Name |
|---|---|---|
| 416. | 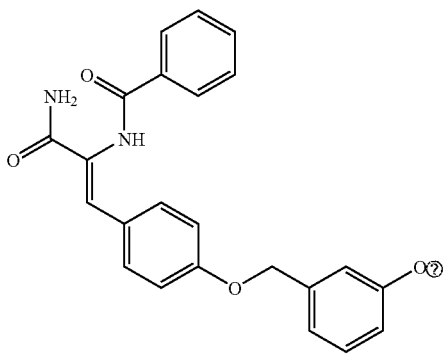 ⓘ indicates text missing or illegible when filed | N-((Z)-1-(aminocarbonyl)-2-{4-[(3-methoxybenzyl)oxy]phenyl}ethenyl)benzamide; |
| 417. | 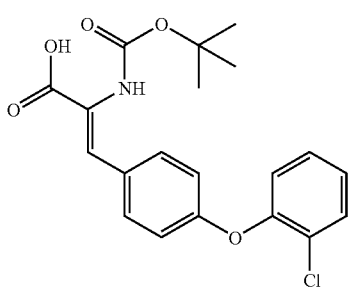 | (2Z)-2-[(tert-butoxycarbonyl)amino]-3-[4-(2-chlorophenoxy)phenyl]prop-2-enoic acid; |
| 418. | 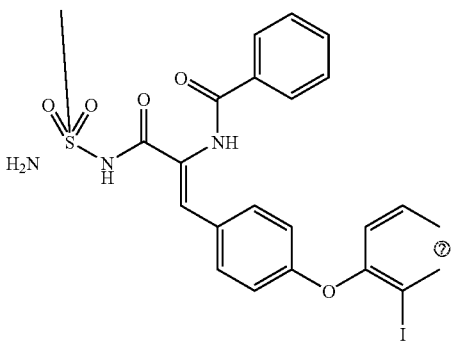 ⓘ indicates text missing or illegible when filed | N-{(Z)-1-{[(aminosulfonyl)amino]carbonyl}-2-[4-(2-iodophenoxy)phenyl]ethenyl}benzamide; |
| 419. | 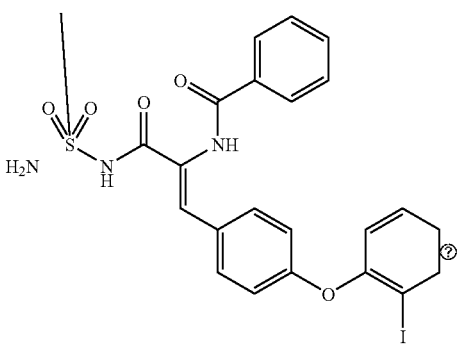 ⓘ indicates text missing or illegible when filed | N-((Z)-2-[4-(2-iodophenoxy)phenyl]-1-{[(methylsulfonyl)amino[carbonyl}ethenyl)benzamide; |

| Compound Number | Structure | Name |
|---|---|---|
| 420. | 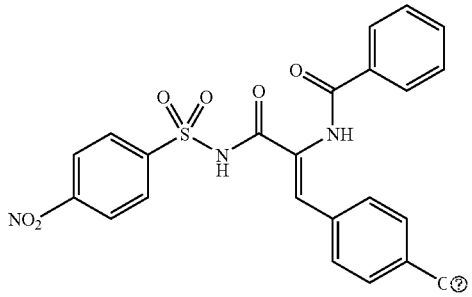 ⓘ indicates text missing or illegible when filed | N-[(Z)-2-[4-(2-iodophenoxy)phenyl]-1-({[(4-nitrophenyl)sulfonyl]amino}carbonyl)ethenyl]-benzamide; |
| 421. | 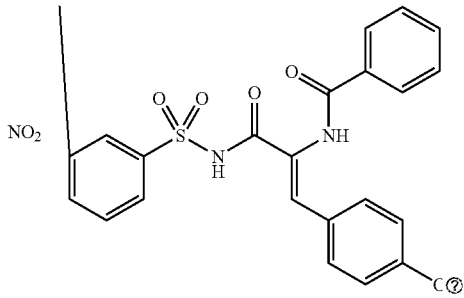 ⓘ indicates text missing or illegible when filed | N-[(Z)-2-[4-(2-iodophenoxy)phenyl]-1-({[(3-nitrophenyl)sulfonyl]amino}carbonyl)ethenyl]-benzamide; |
| 422. | 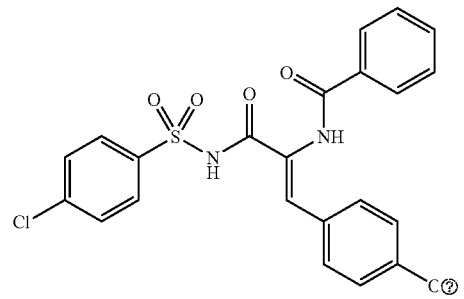 ⓘ indicates text missing or illegible when filed | N-[(Z)-2-[4-(2-bromophenoxy)phenyl]-1-({[(4-chlorophenyl)sulfonyl]amino}carbonyl)ethenyl]-benzamide; |
| 423. | 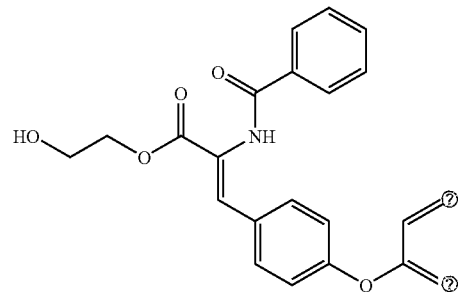 ⓘ indicates text missing or illegible when filed | 2-hydroxyethyl (2Z)-2-(benzoylamino)-3-[4-(2-bromophenoxy)phenyl]prop-2-enoate; |

-continued

| Compound Number | Structure | Name |
|---|---|---|
| 424. | 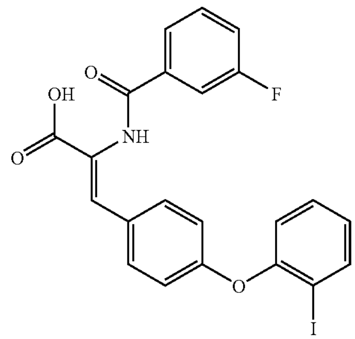 | (2Z)-2-[(3-fluorobenzoyl)amino]-3-[4-(2-iodophenoxy)phenyl]prop-2-enoic acid; |
| 425. | 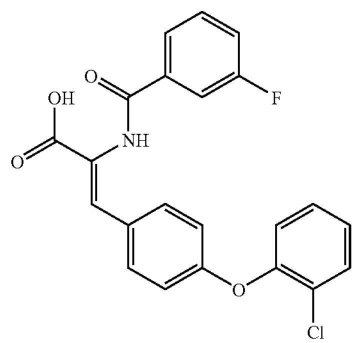 | (2Z)-3-[4-(2-chlorophenoxy)phenyl]-2-[(3-fluorobenzoyl)amino]prop-2-enoic acid; |
| 426. | 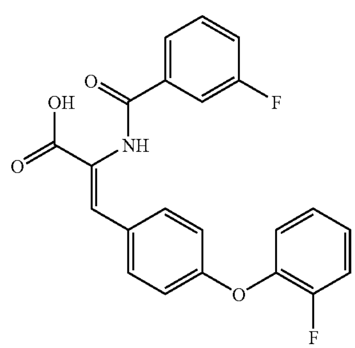 | (2Z)-2-[(3-fluorobenzoyl)amino]-3-[4-(2-fluorophenoxy)phenyl]prop-2-enoic acid; |
| 427. | 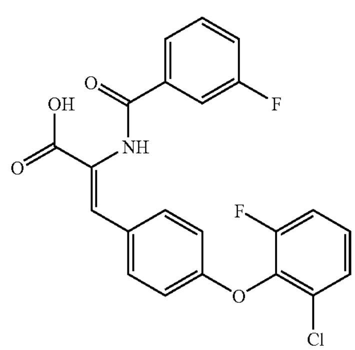 | (2Z)-3-[4-(2-chloro-6-fluorophenoxy)phenyl]-2-[(3-fluorobenzoyl)amino]prop-2-enoic acid; |

-continued

| Compound Number | Structure | Name |
|---|---|---|
| 428. | 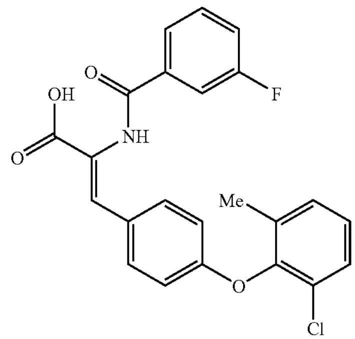 | (2Z)-3-[4-(2-chloro-6-methylphenoxy)phenyl]-2-[(3-fluorobenzoyl)amino]prop-2-enoic acid; |
| 429. | 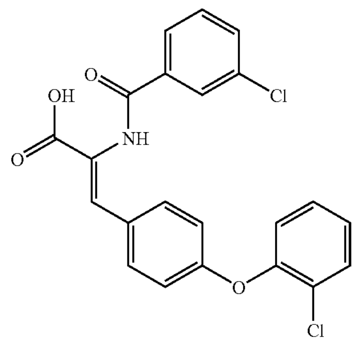 | (2Z)-2-[(3-chlorobenzoyl)amino]-3-[4-(2-chlorophenoxy)phenyl]prop-2-enoic acid; |
| 430. | 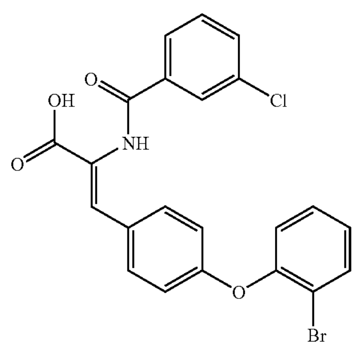 | (2Z)-3-[4-(2-bromophenoxy)phenyl]-2-[(3-chlorobenzoyl)amino]prop-2-enoic acid; |
| 431. | 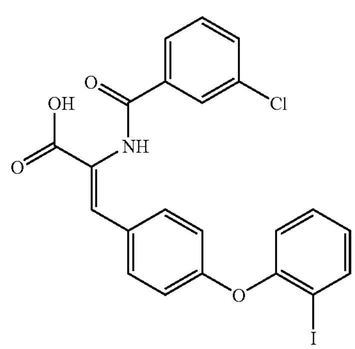 | (2Z)-2-[(3-chlorobenzoyl)amino]-3-[4-(2-iodophenoxy)phenyl]prop-2-enoic acid; |

-continued

| Compound Number | Structure | Name |
|---|---|---|
| 432. | 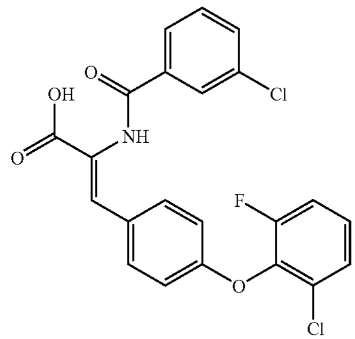 | (2Z)-2-[(3-chlorobenzoyl)amino]-3-[4-(2-chloro-6-fluorophenoxy)phenyl]prop-2-enoic acid; |
| 433. | 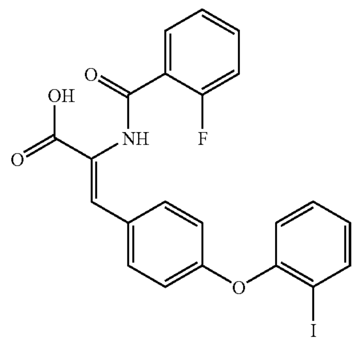 | (2Z)-2-[(2-fluorobenzoyl)amino]-3-[4-(2-iodophenoxy)phenyl]prop-2-enoic acid; |
| 434. | 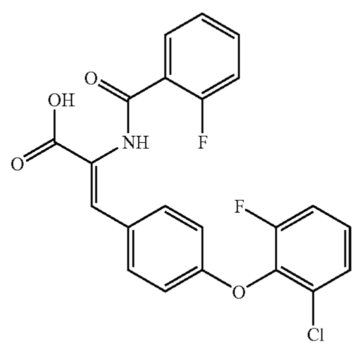 | (2Z)-3-[4-(2-chloro-6-fluorophenoxy)phenyl]-2-[(2-fluorobenzoyl)amino]prop-2-enoic acid; |
| 435. | 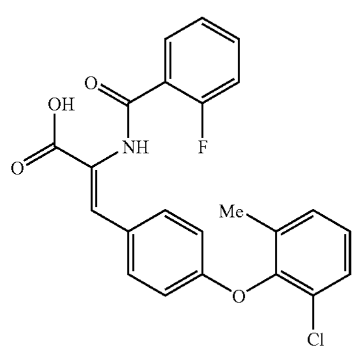 | (2Z)-3-[4-(2-chloro-6-methylphenoxy)phenyl]-2-[(2-fluorobenzoyl)amino]prop-2-enoic acid; |

-continued

| Compound Number | Structure | Name |
|---|---|---|
| 436. | 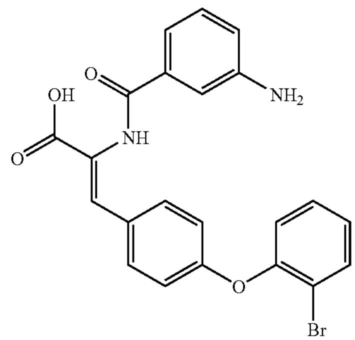 | (2Z)-2-[(3-aminobenzoyl)amino]-3-[4-(2-bromophenoxy)phenyl]prop-2-enoic acid; |
| 437. | 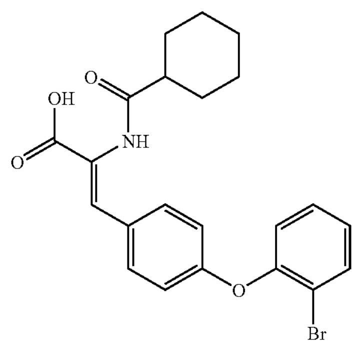 | (2Z)-3-[4-(2-bromophenoxy)phenyl]-2-[(cyclohexylcarbonyl)amino]prop-2-enoic acid; |
| 438. | 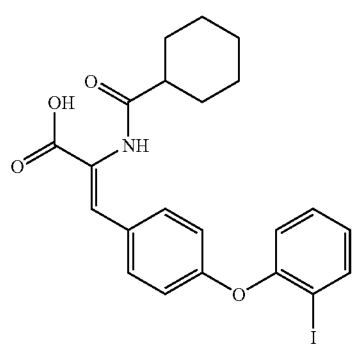 | (2Z)-2-[(cyclohexylcarbonyl)amino]-3-[4-(2-iodophenoxy)phenyl]prop-2-enoic acid; |
| 439. | 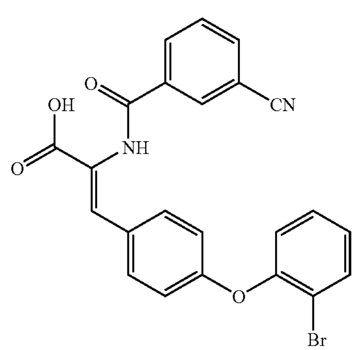 | (2Z)-3-[4-(2-bromophenoxy)phenyl]-2-[(3-cyanobenzoyl)amino]prop-2-enoic acid; |

-continued

| Compound Number | Structure | Name |
|---|---|---|
| 440. | 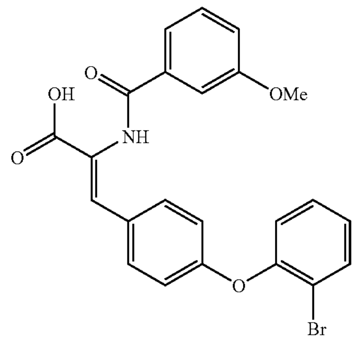 | (2Z)-3-[4-(2-bromophenoxy)phenyl]-2-[(3-methoxybenzoyl)amino]prop-2-enoic acid; |
| 441. | 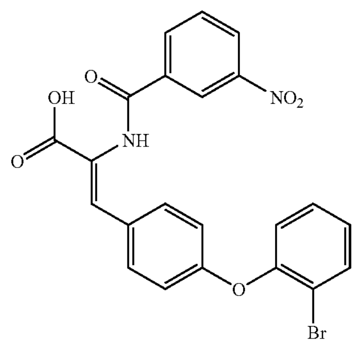 | (2Z)-3-[4-(2-bromophenoxy)phenyl]-2-[(3-nitrobenzoyl)amino]prop-2-enoic acid; |
| 442. | 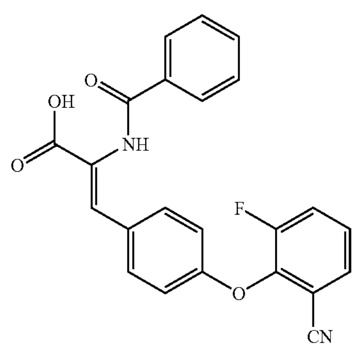 | (2Z)-2-(benzoylamino)-3-[4-(2-cyano-6-fluorophenoxy)phenyl]prop-2-enoic acid; |
| 443. | 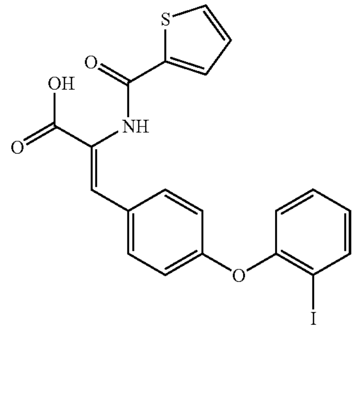 | (2Z)-3-[4-(2-iodophenoxy)phenyl]-2-[(thien-2-ylcarbonyl)amino]acrylic acid; |

-continued
| Compound Number | Structure | Name |
|---|---|---|
| 444. | 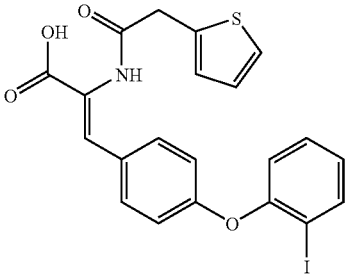 | (2Z)-3-[4-(2-iodophenoxy)phenyl]-2-[(thien-2-ylacetyl)amino]acrylic acid; |
| 445. | 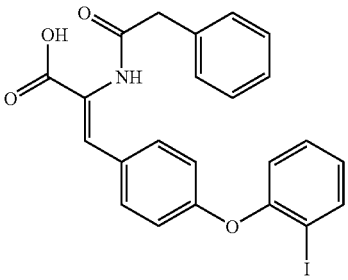 | (2Z)-3-[4-(2-iodophenoxy)phenyl]-2-[(phenylacetyl)amino]acrylic acid; |
| 446. | 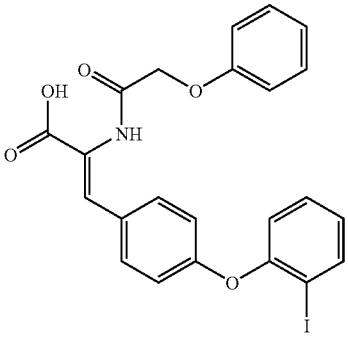 | (2Z)-3-[4-(2-iodophenoxy)phenyl]-2-[(phenoxyacetyl)amino]acrylic acid; |
| 447. | 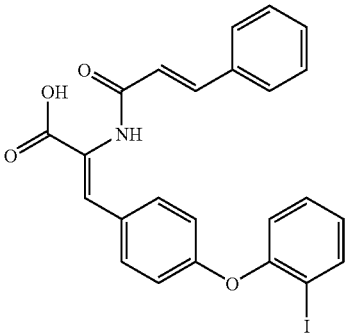 | (2Z)-3-[4-(2-iodophenoxy)phenyl]-2-{[(2E)-3-phenylprop-2-enoyl]amino}prop-2-enoic acid; |

-continued

| Compound Number | Structure | Name |
|---|---|---|
| 448. | 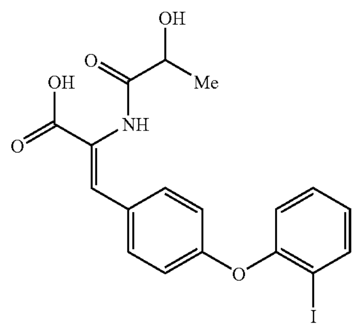 | (2Z)-3-[4-(2-iodophenoxy)phenyl]-2-(lactoylamino)prop-2-enoic acid; |
| 449. | 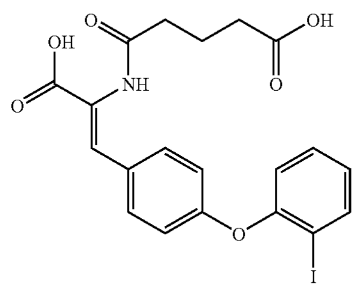 | (2Z)-2-[(4-carboxybutanoyl)amino]-3-[4-(2-iodophenoxy)phenyl]prop-2-enoic acid; |
| 450. | 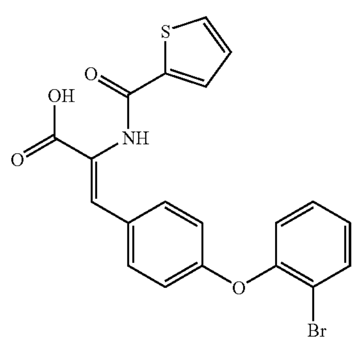 | (2Z)-3-[4-(2-bromophenoxy)phenyl]-2-[(thien-2-ylcarbonyl)amino]prop-2-enoic acid; |
| 451. | 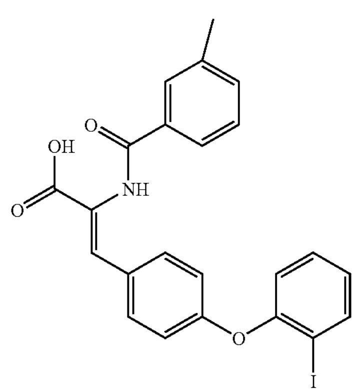 | (2Z)-3-[4-(2-iodophenoxy)phenyl]-2-[(3-methylbenzoyl)amino]prop-2-enoic acid; |

-continued

| Compound Number | Structure | Name |
|---|---|---|
| 452. | 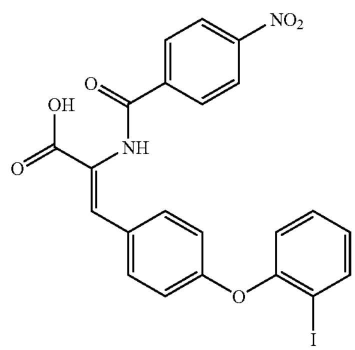 | (2Z)-3-[4-(2-iodophenoxy)phenyl]-2-[(4-nitrobenzoyl)amino]prop-2-enoic acid; |
| 453. | 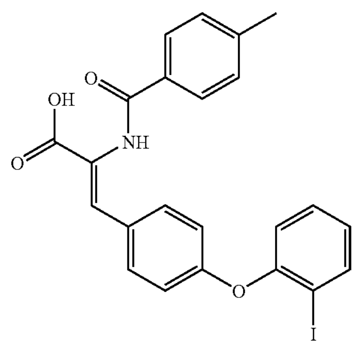 | (2Z)-3-[4-(2-iodophenoxy)phenyl]-2-[(4-methylbenzoyl)amino]prop-2-enoic acid; |
| 454. | 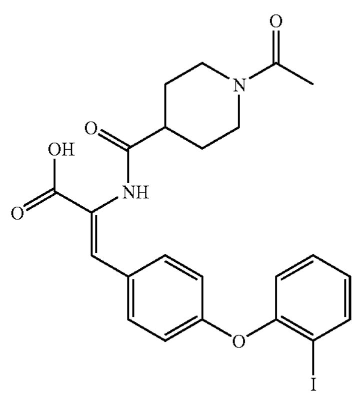 | (2Z)-2-{[(1-acetylpiperidin-4-yl)carbonyl]amino}-3-[4-(2-iodophenoxy)phenyl]prop-2-enoic acid; |
| 455. | 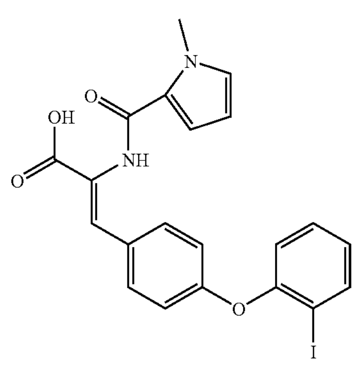 | (2Z)-3-[4-(2-iodophenoxy)phenyl]-2-{[(1-methyl-1H-pyrrol-2-yl)carbonyl]amino}prop-2-enoic acid; |

-continued

| Compound Number | Structure | Name |
|---|---|---|
| 456. | 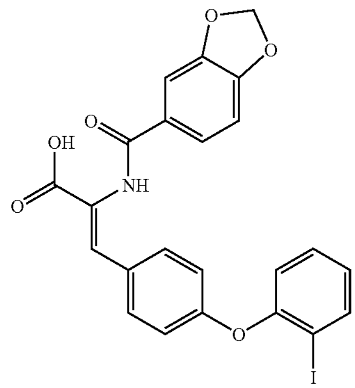 | (2Z)-2-[(1,3-benzodioxol-5-ylcarbonyl)amino]-3-[4-(2-iodophenoxy)phenyl]prop-2-enoic acid; |
| 457. | 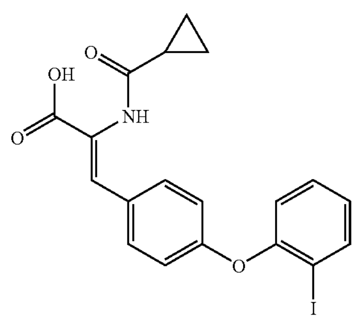 | (2Z)-2-[(cyclopropylcarbonyl)amino]-3-[4-(2-iodophenoxy)phenyl]prop-2-enoic acid; |
| 458. | 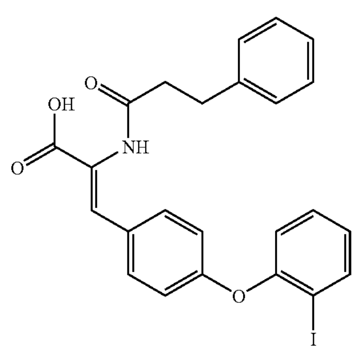 | (2Z)-3-[4-(2-iodophenoxy)phenyl]-2-[(3-phenylpropanoyl)amino]prop-2-enoic acid; |
| 459. | 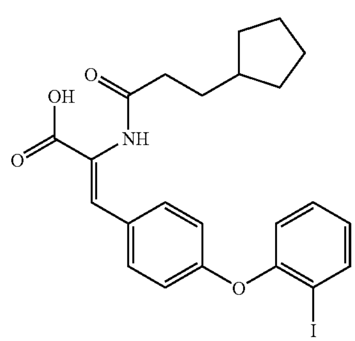 | (2Z)-2-[(3-cyclopentylpropanoyl)amino]-3-[4-(2-iodophenoxy)phenyl]prop-2-enoic acid; |

-continued

| Compound Number | Structure | Name |
|---|---|---|
| 460. | A | sodium (2Z)-2-[(3-cyclopentylpropanoyl)amino]-3-[4-(2-iodophenoxy)phenyl]acrylate; |
| 461. | 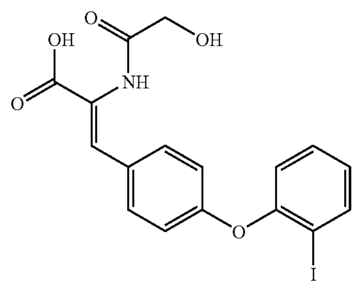 | (2Z)-2-(glycoloylamino)-3-[4-(2-iodophenoxy)phenyl]prop-2-enoic acid; |
| 462. | 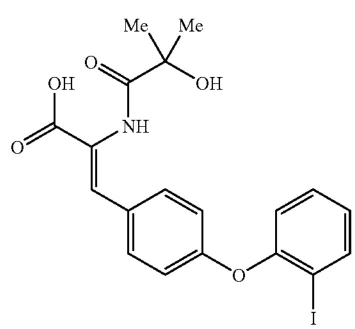 | (2Z)-2-[(2-hydroxy-2-methylpropanoyl)amino]-3-[4-(2-iodophenoxy)phenyl]prop-2-enoic acid; |
| 463. | racemic | (2Z)-3-[4-(2-iodophenoxy)phenyl]-2-[(2-phenylbutanoyl)amino]prop-2-enoic acid; |

-continued

| Compound Number | Structure | Name |
|---|---|---|
| 464. | 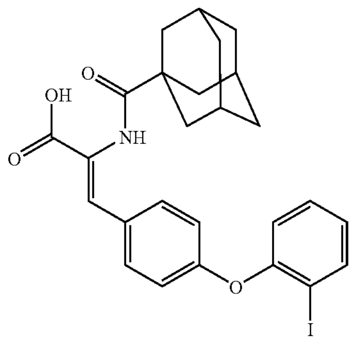 | (2Z)-2-[(1-adamantylcarbonyl)amino]-3-[4-(2-iodophenoxy)phenyl]prop-2-enoic acid; |
| 465. | Racemic | (2Z)-3-[4-(2-iodophenoxy)phenyl]-2-({[(1S,2S)-2-phenylcyclopropyl]carbonyl}amino)prop-2-enoic acid; |
| 466. | Racemic | (2Z)-3-[4-(2-bromophenoxy)phenyl]-2-{[hydroxy(phenyl)acetyl]amino}prop-2-enoic acid; |
| 467. | 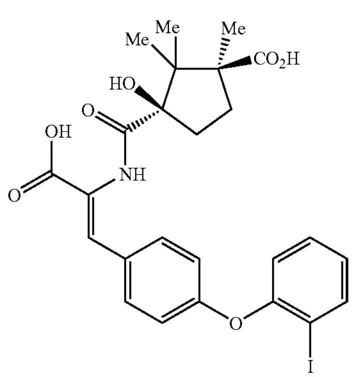 | (1S,3R)-3-[({(Z)-1-carboxy-2-[4-(2-iodophenoxy)phenyl]ethenyl}amino)carbonyl]-2-ethyl-3-hydroxy-1,2-dimethylcyclopentanecarboxylic acid; |

-continued

| Compound Number | Structure | Name |
|---|---|---|
| 468. | 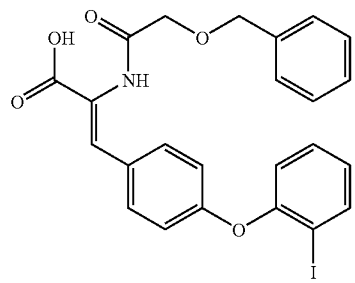 | (2Z)-2-{[(benzyloxy)acetyl]amino}-3-[4-(2-iodophenoxy)phenyl]prop-2-enoic acid; |
| 469. | 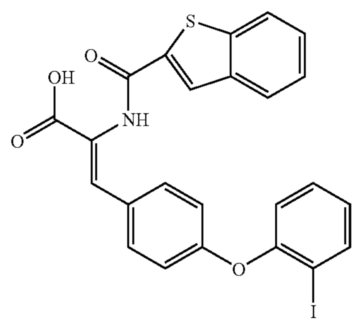 | (2Z)-2-[(1-benzothien-2-ylcarbonyl)amino]-3-[4-(2-iodophenoxy)phenyl]prop-2-enoic acid; |
| 470. | 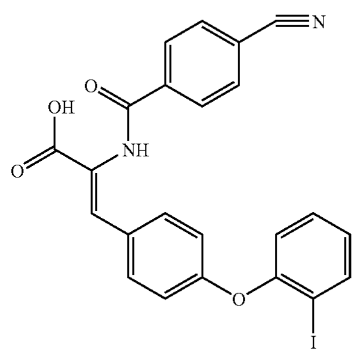 | (2Z)-2-[(4-cyanobenzoyl)amino]-3-[4-(2-iodophenoxy)phenyl]prop-2-enoic acid; |
| 471. | 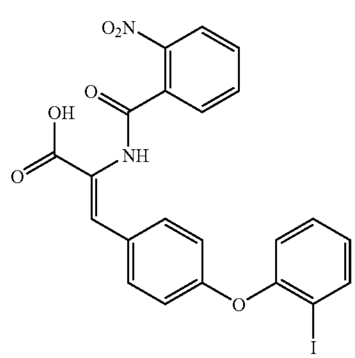 | (2Z)-3-[4-(2-iodophenoxy)phenyl]-2-[(2-nitrobenzoyl)amino]prop-2-enoic acid; |

-continued

| Compound Number | Structure | Name |
|---|---|---|
| 472. | 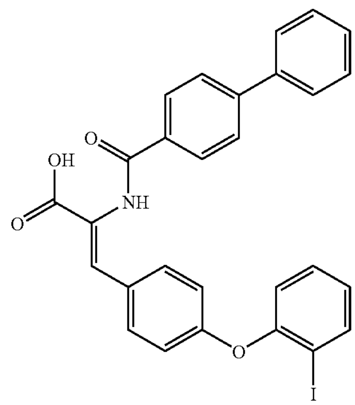 | (2Z)-2-[(1,1'-biphenyl-4-ylcarbonyl)amino]-3-[4-(2-iodophenoxy)phenyl]prop-2-enoic acid; |
| 473. | 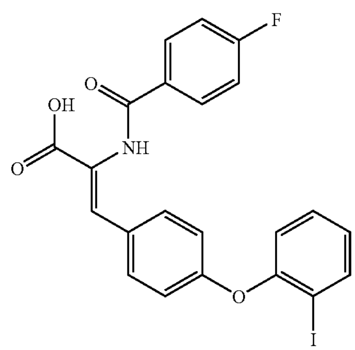 | (2Z)-2-[(4-fluorobenzoyl)amino]-3-[4-(2-iodophenoxy)phenyl]prop-2-enoic acid; |
| 474. | 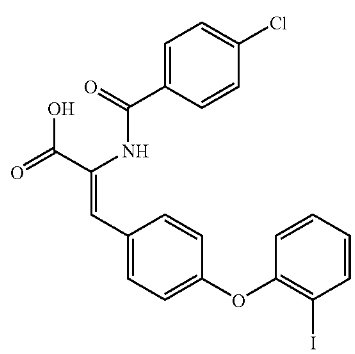 | (2Z)-2-[(4-chlorobenzoyl)amino]-3-[4-(2-iodophenoxy)phenyl]prop-2-enoic acid; |
| 475. | 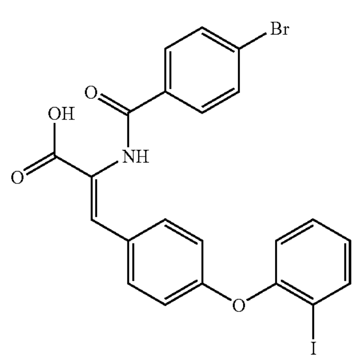 | (2Z)-2-[(4-bromobenzoyl)amino]-3-[4-(2-iodophenoxy)phenyl]prop-2-enoic acid; |

-continued

| Compound Number | Structure | Name |
|---|---|---|
| 476. | 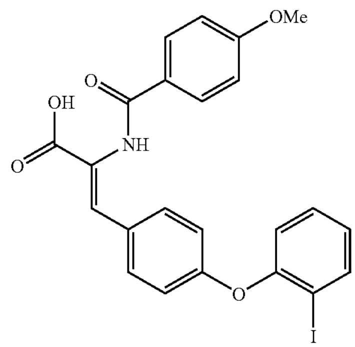 | (2Z)-3-[4-(2-iodophenoxy)phenyl]-2-[(4-methoxybenzoyl)amino]prop-2-enoic acid; |
| 477. | 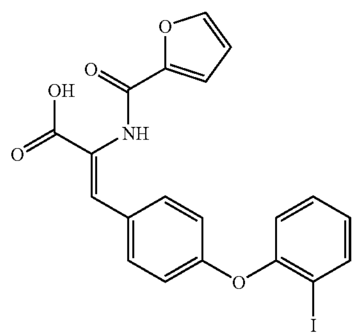 | (2Z)-2-(2-furoylamino)-3-[4-(2-iodophenoxy)phenyl]prop-2-enoic acid; |
| 478. | 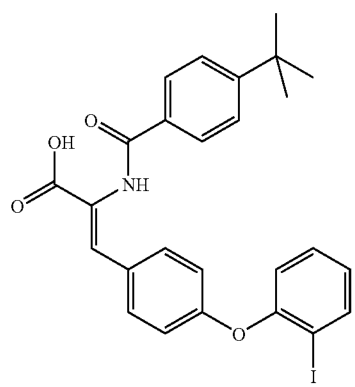 | (2Z)-2-[(4-tert-butylbenzoyl)amino]-3-[4-(2-iodophenoxy)phenyl]prop-2-enoic acid; |
| 479. | 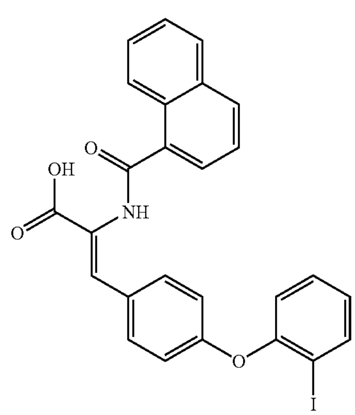 | (2Z)-3-[4-(2-iodophenoxy)phenyl]-2-(1-naphthoylamino)prop-2-enoic acid; |

-continued
| Compound Number | Structure | Name |
|---|---|---|
| 480. | 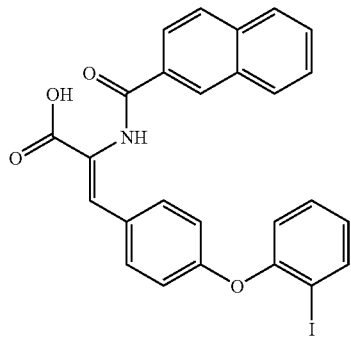 | (2Z)-3-[4-(2-iodophenoxy)phenyl]-2-(2-naphthoylamino)prop-2-enoic acid; |
| 481. | 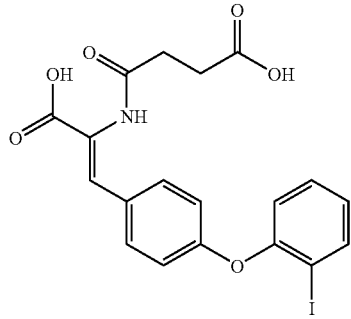 | (2Z)-2-[(3-carboxypropanoyl)amino]-3-[4-(2-iodophenoxy)phenyl]prop-2-enoic acid; |
| 482. | 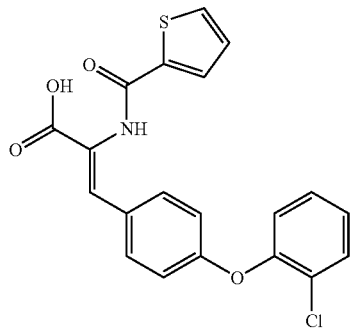 | (2Z)-3-[4-(2-chlorophenoxy)phenyl]-2-[(thien-2-ylcarbonyl)amino]prop-2-enoic acid; |
| 483. | 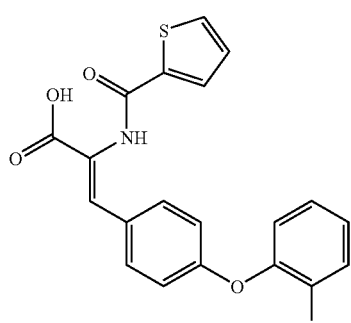 | (2Z)-3-[4-(2-fluorophenoxy)phenyl]-2-[(thien-2-ylcarbonyl)amino]prop-2-enoic acid; |

-continued
| Compound Number | Structure | Name |
|---|---|---|
| 484. | 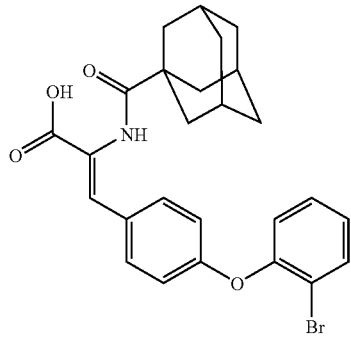 | (2Z)-2-[(1-adamantylcarbonyl)amino]-3-[4-(2-bromophenoxy)phenyl]prop-2-enoic acid; |
| 485. | 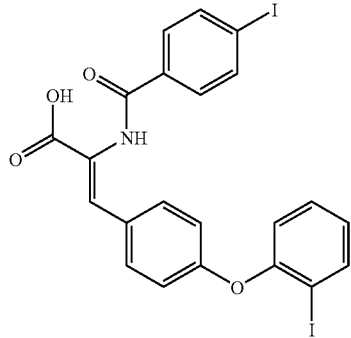 | (2Z)-2-[(4-iodobenzoyl)amino]-3-[4-(2-iodophenoxy)phenyl]prop-2-enoic acid; |
| 486. | 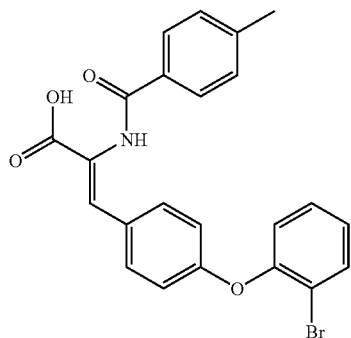 | (2Z)-3-[4-(2-bromophenoxy)phenyl]-2-[(4-methylbenzoyl)amino]prop-2-enoic acid; |
| 487. | 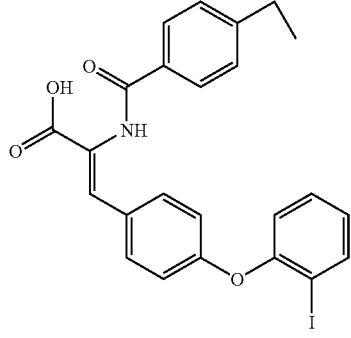 | (2Z)-2-[(4-ethylbenzoyl)amino]-3-[4-(2-iodophenoxy)phenyl]prop-2-enoic acid; |

-continued

| Compound Number | Structure | Name |
|---|---|---|
| 488. | 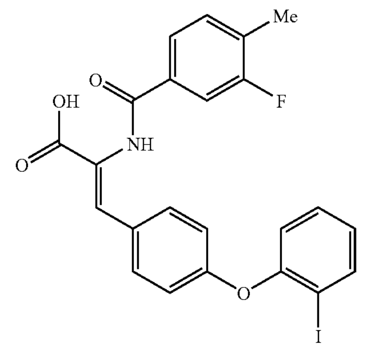 | (2Z)-2-[(3-fluoro-4-methylbenzoyl)amino]-3-[4-(2-iodophenoxy)phenyl]prop-2-enoic acid; |
| 489. | 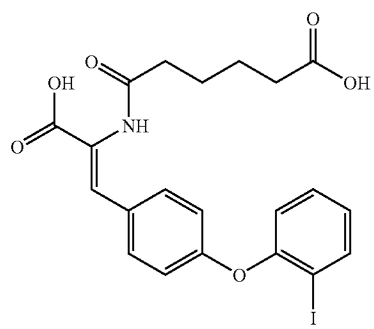 | (2Z)-2-[(5-carboxypentanoyl)amino]-3-[4-(2-iodophenoxy)phenyl]prop-2-enoic acid; |
| 490. | 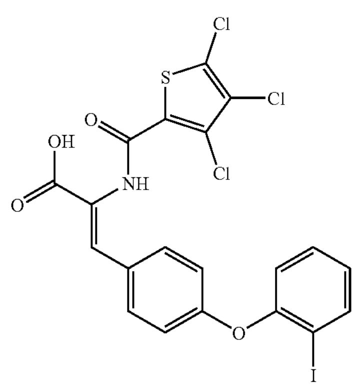 | (2Z)-3-[4-(2-iodophenoxy)phenyl]-2-{[(3,4,5-trichlorothien-2-yl)carbonyl]amino}prop-2-enoic acid; |
| 491. | 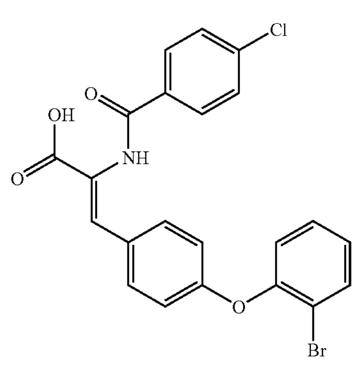 | (2Z)-3-[4-(2-bromophenoxy)phenyl]-2-[(4-chlorobenzoyl)amino]prop-2-enoic acid; |

-continued

| Compound Number | Structure | Name |
|---|---|---|
| 492. | 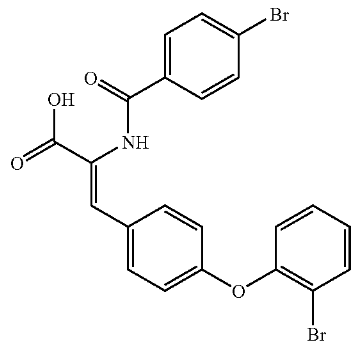 | (2Z)-2-[(4-bromobenzoyl)amino]-3-[4-(2-bromophenoxy)phenyl]prop-2-enoic acid; |
| 493. | 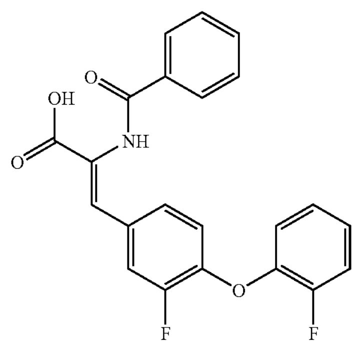 | (2Z)-2-(benzoylamino)-3-[3-fluoro-4-(2-fluorophenoxy)phenyl]prop-2-enoic acid; |
| 494. | 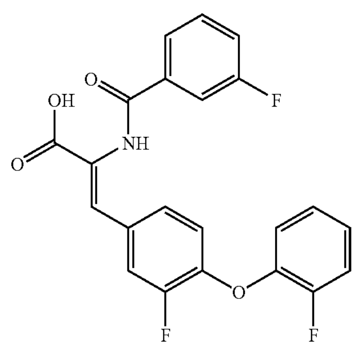 | (2Z)-2-[(3-fluorobenzoyl)amino]-3-[3-fluoro-4-(2-fluorophenoxy)phenyl]prop-2-enoic acid; |
| 495. | 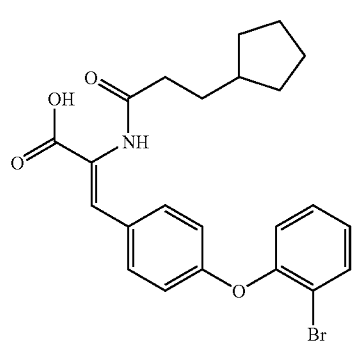 | (2Z)-3-[4-(2-bromophenoxy)phenyl]-2-[(3-cyclopentylpropanoyl)amino]acrylic acid; |

-continued

| Compound Number | Structure | Name |
|---|---|---|
| 496. | A | sodium (2Z)-3-[4-(2-bromophenoxy)phenyl]-2-[(3-cyclopentylpropanoyl)amino]acrylate; |
| 497. | 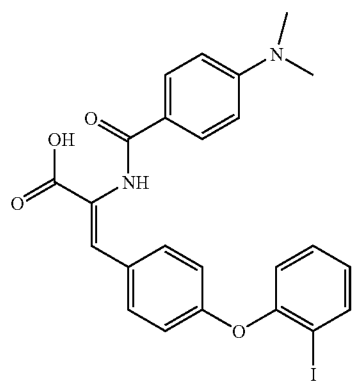 | (2Z)-2-{[4-(dimethylamino)benzoyl]amino}-3-[4-(2-iodophenoxy)phenyl]prop-2-enoic acid; |
| 498. | 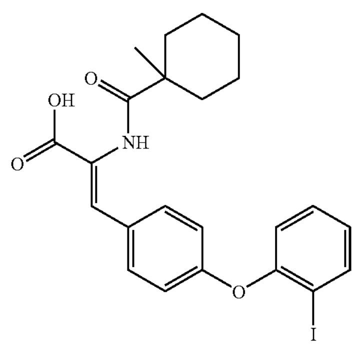 | (2Z)-3-[4-(2-iodophenoxy)phenyl]-2-{[(1-methylcyclohexyl)carbonyl]amino}prop-2-enoic acid; |
| 499. | 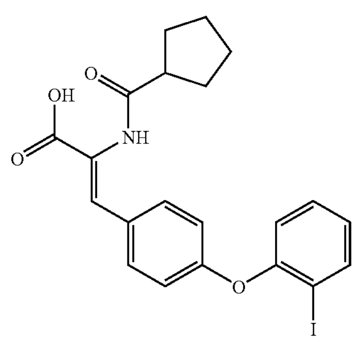 | (2Z)-2-[(cyclopentylcarbonyl)amino]-3-[4-(2-iodophenoxy)phenyl]prop-2-enoic acid; |

-continued

| Compound Number | Structure | Name |
|---|---|---|
| 500. | 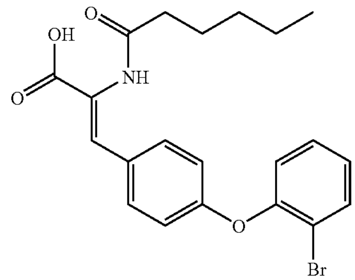 | (2Z)-3-[4-(2-bromophenoxy)phenyl]-2-(hexanoylamino)prop-2-enoic acid; |
| 501. | 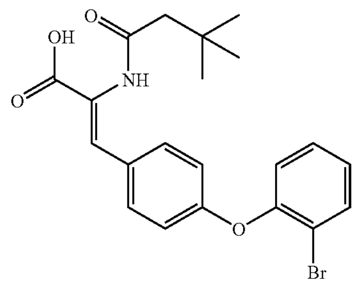 | (2Z)-3-[4-(2-bromophenoxy)phenyl]-2-[(3,3-dimethylbutanoyl)amino]prop-2-enoic acid; |
| 502. | 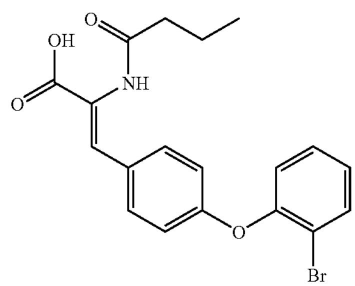 | (2Z)-3-[4-(2-bromophenoxy)phenyl]-2-(butyrylamino)prop-2-enoic acid; |
| 503. | 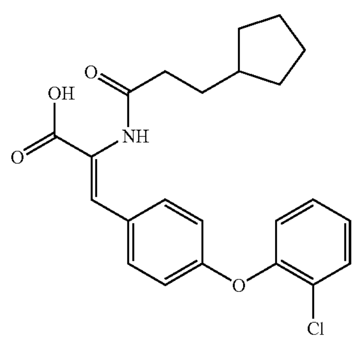 | (2Z)-3-[4-(2-chlorophenoxy)phenyl]-2-[(3-cyclopentylpropanoyl)amino]prop-2-enoic acid; |
| 504. | 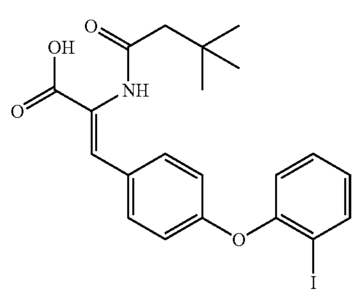 | (2Z)-2-[(3,3-dimethylbutanoyl)amino]-3-[4-(2-iodophenoxy)phenyl]prop-2-enoic acid; |

-continued

| Compound Number | Structure | Name |
|---|---|---|
| 505. | 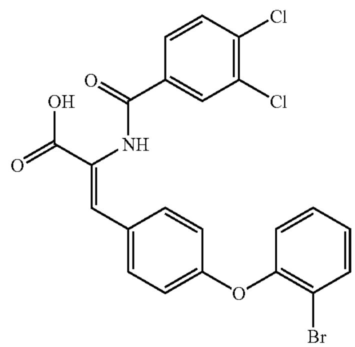 | (2Z)-3-[4-(2-bromophenoxy)phenyl]-2-[(3,4-dichlorobenzoyl)amino]prop-2-enoic acid; |
| 506. | 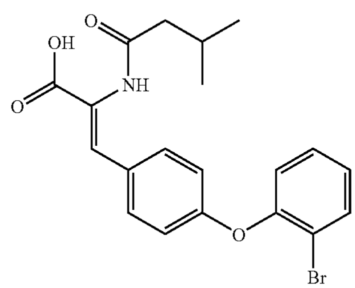 | (2Z)-3-[4-(2-bromophenoxy)phenyl]-2-[(3-methylbutanoyl)amino]prop-2-enoic acid; |
| 507. | 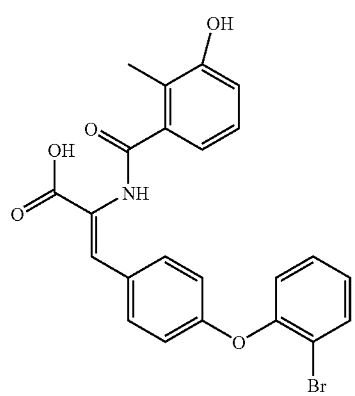 | (2Z)-3-[4-(2-bromophenoxy)phenyl]-2-[(3-hydroxy-2-methylbenzoyl)amino]prop-2-enoic acid; |
| 508. | 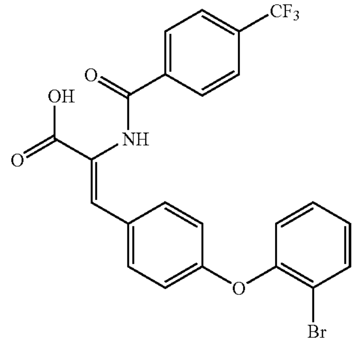 | (2Z)-3-[4-(2-bromophenoxy)phenyl]-2-{[4-(trifluoromethyl)benzoyl]amino}prop-2-enoic acid; |

-continued

| Compound Number | Structure | Name |
|---|---|---|
| 509. | 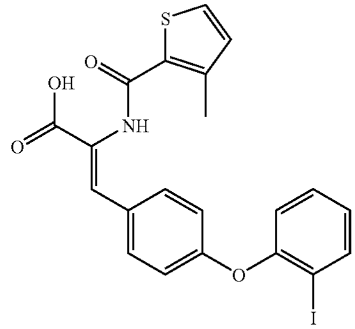 | (2Z)-3-[4-(2-iodophenoxy)phenyl]-2-{[(3-methylthien-2-yl)carbonyl]amino}prop-2-enoic acid; |
| 510. | 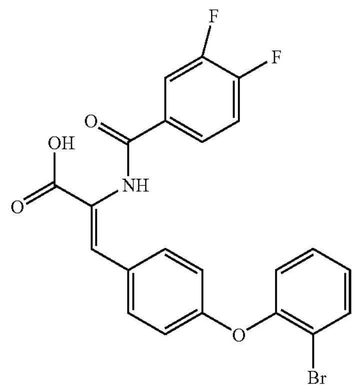 | (2Z)-3-[4-(2-bromophenoxy)phenyl]-2-[(3,4-difluorobenzoyl)amino]prop-2-enoic acid; |
| 511. | 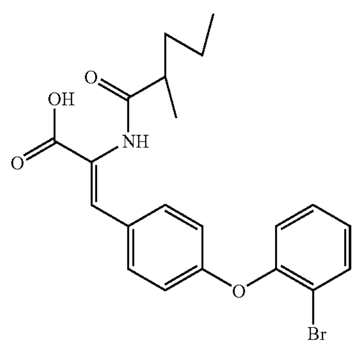 | (2Z)-3-[4-(2-bromophenoxy)phenyl]-2-[(2-methylpentanoyl)amino]prop-2-enoic acid; |
| 512. | 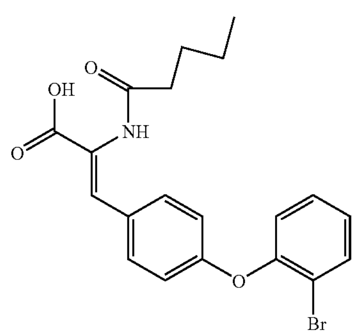 | (2Z)-3-[4-(2-bromophenoxy)phenyl]-2-(pentanoylamino)prop-2-enoic acid; |

-continued

| Compound Number | Structure | Name |
|---|---|---|
| 513. | 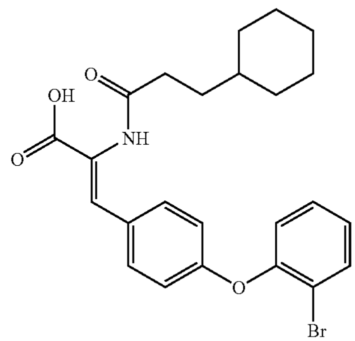 | (2Z)-3-[4-(2-bromophenoxy)phenyl]-2-[(3-cyclohexylpropanoyl)amino]prop-2-enoic acid; |
| 514. | 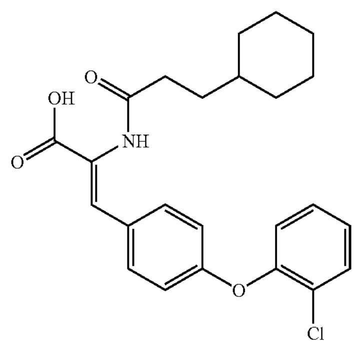 | (2Z)-3-[4-(2-chlorophenoxy)phenyl]-2-[(3-cyclohexylpropanoyl)amino]prop-2-enoic acid; |
| 515. | 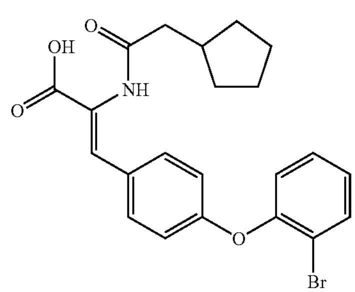 | (2Z)-3-{4-(2-bromophenoxy)phenyl]-2-[(cyclopentylacetyl)amino]prop-2-enoic acid; |
| 516. | 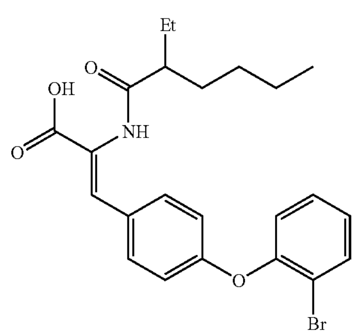 | (2Z)-3-[4-(2-bromophenoxy)phenyl]-2-[(2-ethylhexanoyl)amino]prop-2-enoic acid; |

-continued

| Compound Number | Structure | Name |
|---|---|---|
| 517. | | (2Z)-3-[4-(2-bromophenoxy)phenyl]-2-(pent-4-enoylamino)prop-2-enoic acid; |
| 518. | 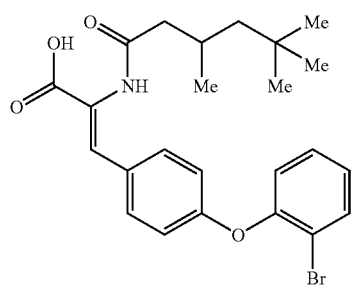<br>Racemic | (2Z)-3-[4-(2-bromophenoxy)phenyl]-2-[(3,5,5-trimethylhexanoyl)amino]prop-2-enoic acid; |
| 519. | 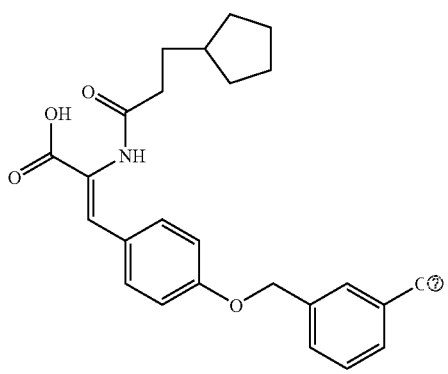<br>⑦ indicates text missing or illegible when filed | (2Z)-2-[(3-cyclopentylpropanoyl)amino]-3-{4-[(3-methoxybenzyl)oxy]phenyl}prop-2-enoic acid; |
| 520. | A<br>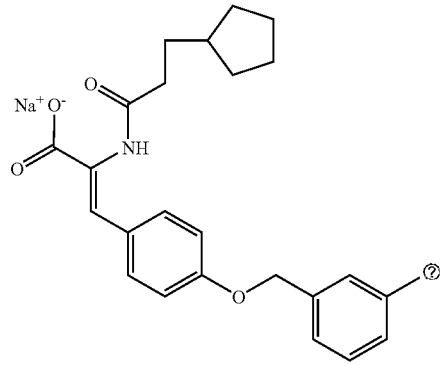<br>⑦ indicates text missing or illegible when filed | sodium (2Z)-2-[(3-cyclopentylpropanoyl)amino]-3-{4-[(3-methoxybenzyl)oxy]phenyl}acrylate; |

-continued

| Compound Number | Structure | Name |
|---|---|---|
| 521. | Racemic | V00116684 |
| 522. | 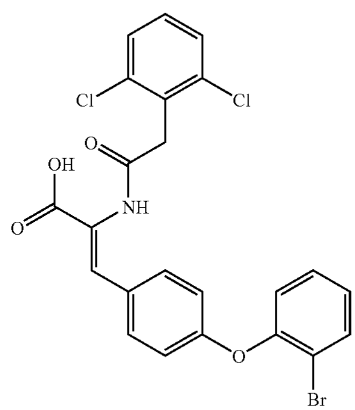 | V00116682 |
| 523. | 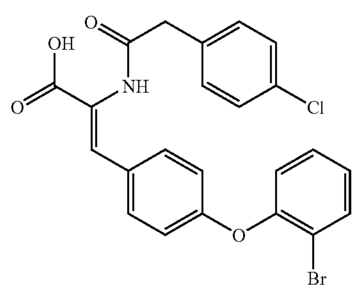 | V00116736 or (2Z)-3-[4-(2-bromophenoxy)phenyl]-2-{[(4-chlorophenyl)acetyl]amino}acrylic acid; or V00116736 |
| 524. | | V00116637 |
| 525. | 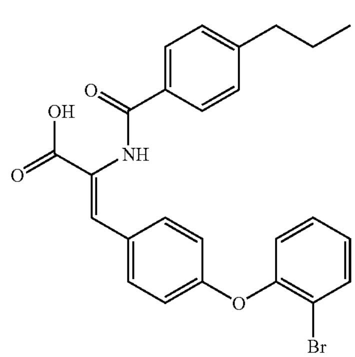 | V00116735 |

-continued

| Compound Number | Structure | Name |
|---|---|---|
| 526. | Diastereomeric Mixture | V00116612 |
| 527. | 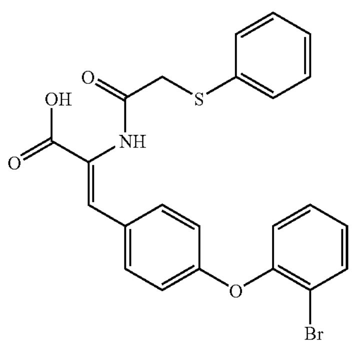 | V00116739 |
| 528. | 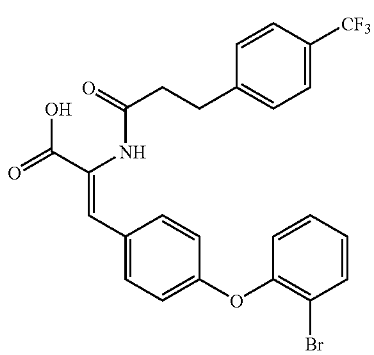 | V00116636 |
| 529. | Cyclohexane is (cis/trans) mixture | V00116660 or (2Z)-3-[4-(2-bromophenoxy)phenyl]-2-{[(4-methylcyclohexyl)acetyl]amino}acrylic acid; |

-continued
| Compound Number | Structure | Name |
|---|---|---|
| 530. | 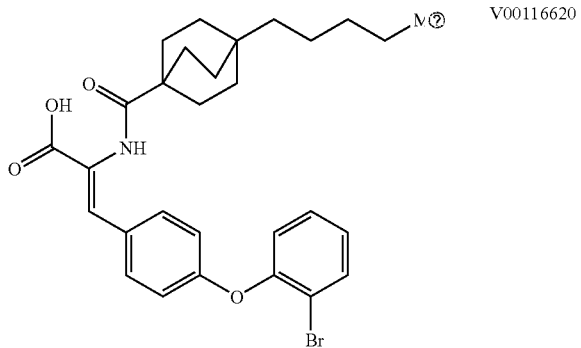<br>⑦ indicates text missing or illegible when filed | V00116620 |
| 531. | 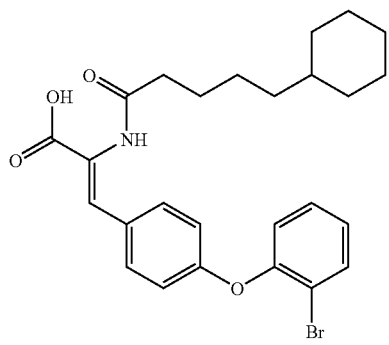<br>Racemic | V00116614 |
| 532. | 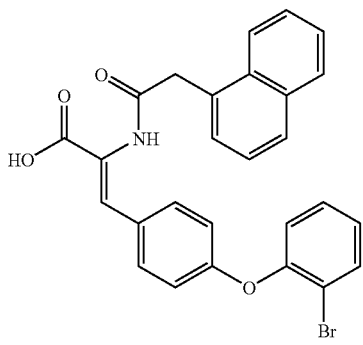 | (2Z)-3-[4-(2-bromophenoxy)phenyl]-2-[(1-naphthylacetyl)amino]acrylic acid; or V00116661 |
| 533. | 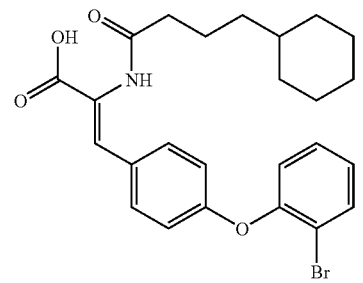 | (2Z)-3-[4-(2-bromophenoxy)phenyl]-2-[(4-cyclohexylbutanoyl)amino]acrylic acid; or V00116623 |

-continued

| Compound Number | Structure | Name |
|---|---|---|
| 534. | 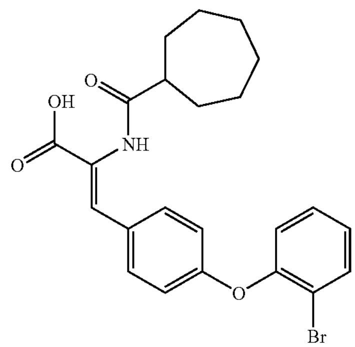 | (2Z)-3-[4-(2-bromophenoxy)phenyl]-2-[(cycloheptylcarbonyl)amino]acrylic acid; or V00116630 |
| 535. | 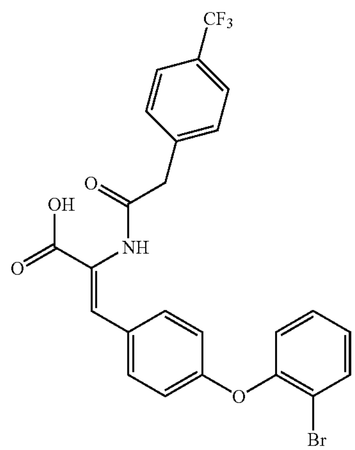 | (2Z)-3-[4-(2-bromophenoxy)phenyl]-2-({[4-(trifluoromethyl)phenyl]acetyl}amino)acrylic acid; or V00116641 |
| 536. | 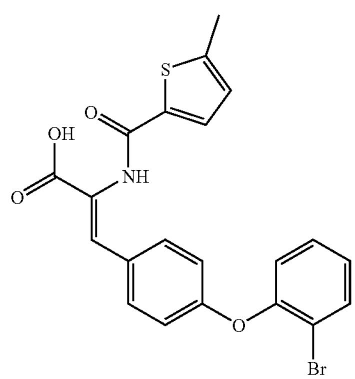 | (2Z)-3-[4-(2-bromophenoxy)phenyl]-2-{[(5-methylthien-2-yl)carbonyl]amino}acrylic acid; |
| 537. | 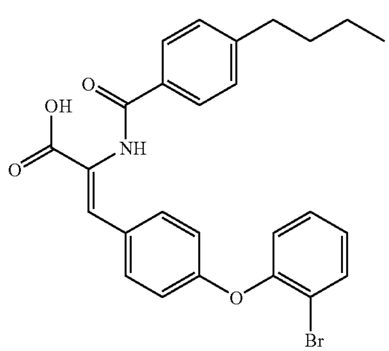 | (2Z)-3-[4-(2-bromophenoxy)phenyl]-2-[(4-butylbenzoyl)amino]acrylic acid; or V00116733 |

-continued

| Compound Number | Structure | Name |
|---|---|---|
| 538. | racemate | (2Z)-3-[4-(2-bromophenoxy)phenyl]-2-[(3-methylpentanoyl)amino]acrylic acid; or V00116693 |
| 539. | 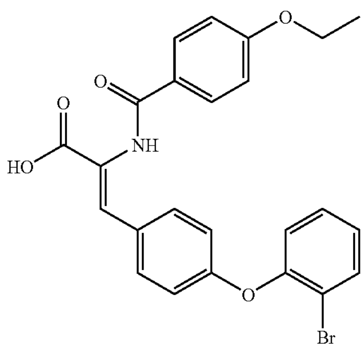 | (2Z)-3-[4-(2-bromophenoxy)phenyl]-2-[(4-ethoxybenzoyl)amino]acrylic acid; or V00116738 |
| 540. | mixture of isomers | (2Z)-3-[4-(2-bromophenoxy)phenyl]-2-{[(4-tert-butylcyclohexyl)carbonyl]amino}acrylic acid; or V00116692 |
| 541. | mixture of isomers | (2Z)-3-[4-(2-bromophenoxy)phenyl]-2-{[(4-methylcyclohexyl)carbonyl]amino}acrylic acid; or V00116679 |

-continued

| Compound Number | Structure | Name |
|---|---|---|
| 542. | 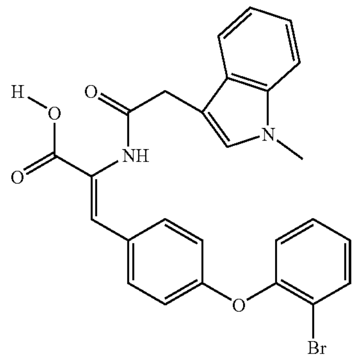 | (2Z)-3-[4-(2-bromophenoxy)phenyl]-2-{[(1-methyl-1H-indol-3-yl)acetyl]amino}acrylic acid; or V00116691 |
| 543. | 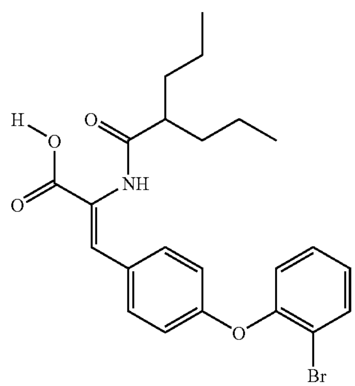 | (2Z)-3-[4-(2-bromophenoxy)phenyl]-2-[(2-propylpentanoyl)amino]acrylic acid; or V00116624 |
| 544. | 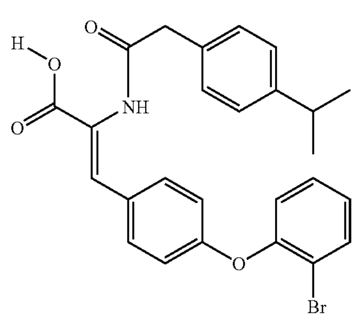 | (2Z)-3-[4-(2-bromophenoxy)phenyl]-2-{[(4-isopropylphenyl)acetyl]amino}acrylic acid; or V00116663 |
| 545. | 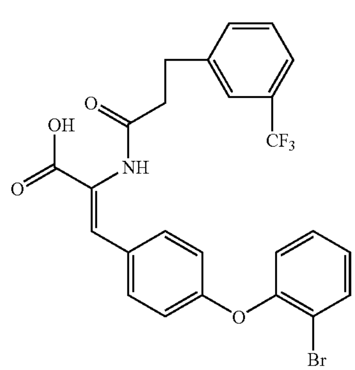 | (2Z)-3-[4-(2-bromophenoxy)phenyl]-2-({3-[3-(trifluoromethyl)phenyl]propanoyl}amino)acrylic acid; or V00116646 |

-continued

| Compound Number | Structure | Name |
|---|---|---|
| 546. | 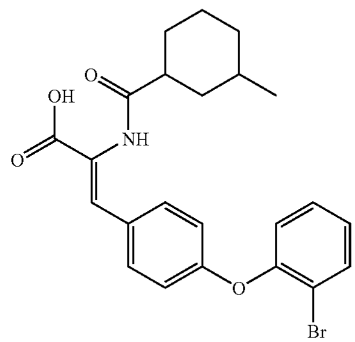 | (2Z)-3-[4-(2-bromophenoxy)phenyl]-2-{[(3-methylcyclohexyl)carbonyl]amino}acrylic acid; or V00116694 |
| 547. | 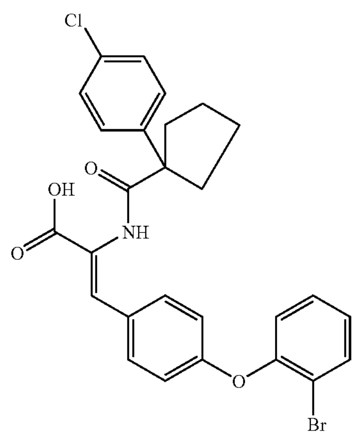 | (2Z)-3-[4-(2-bromophenoxy)phenyl]-2-({[1-(4-chlorophenyl)cyclopentyl]carbonyl}amino)acrylic acid; |
| 548. | 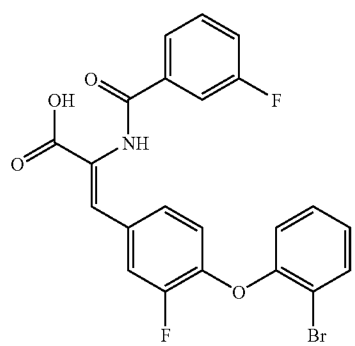 | (2Z)-3-[4-(2-bromophenoxy)-3-fluorophenyl]-2-[(3-fluorobenzoyl)amino]acrylic acid; |
| 549. | 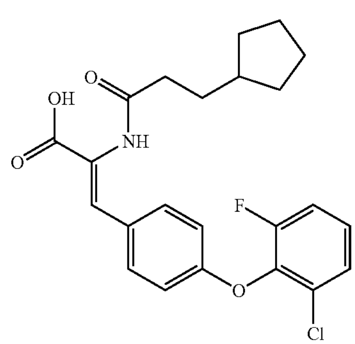 | (2Z)-3-[4-(2-chloro-6-fluorophenoxy)phenyl]-2-[(3-cyclopentylpropanoyl)amino]acrylic acid; |

-continued

| Compound Number | Structure | Name |
|---|---|---|
| 550. | 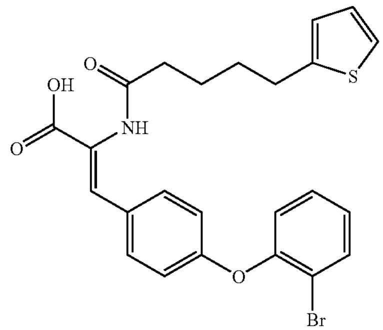 | (2Z)-3-[4-(2-bromophenoxy)phenyl]-2-[(5-thien-2-ylpentanoyl)amino]acrylic acid; or V00116671 |
| 551. | 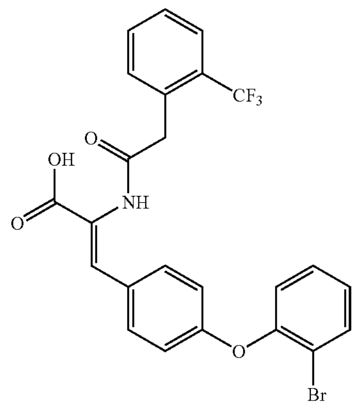 | (2Z)-3-[4-(2-bromophenoxy)phenyl]-2-({[2-(trifluoromethyl)phenyl]acetyl}amino)acrylic acid; or V00116644 |
| 552. | 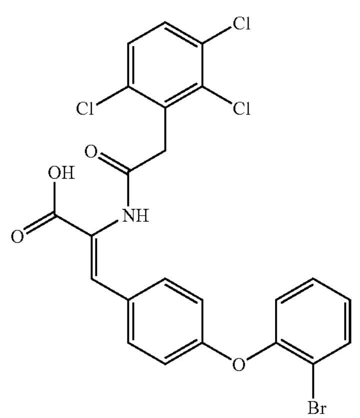 | (2Z)-3-[4-(2-bromophenoxy)phenyl]-2-{[(2,3,6-trichlorophenyl)acetyl]amino}acrylic acid; or V00116621 |
| 553. | Diastereomeric Mixture | (2Z)-3-[4-(2-bromophenoxy)phenyl]-2-{[(4-propylcyclohexyl)carbonyl]amino}acrylic acid; or V00116711 |

-continued

| Compound Number | Structure | Name |
|---|---|---|
| 554. | 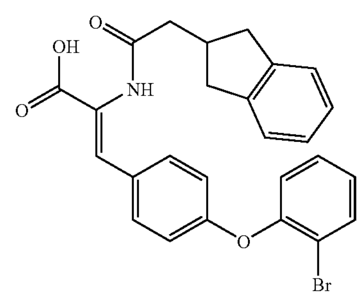 | (2Z)-3-[4-(2-bromophenoxy)phenyl]-2-[(2,3-dihydro-1H-inden-2-ylacetyl)amino]acrylic acid; or V00116705 |
| 555. | 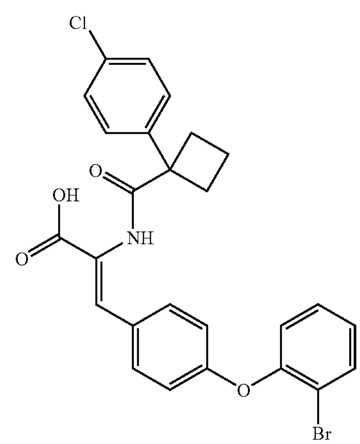 | (2Z)-3-[4-(2-bromophenoxy)phenyl]-2-({[1-(4-chlorophenyl)cyclobutyl]carbonyl}amino)acrylic acid; or V00116653 |
| 556. | 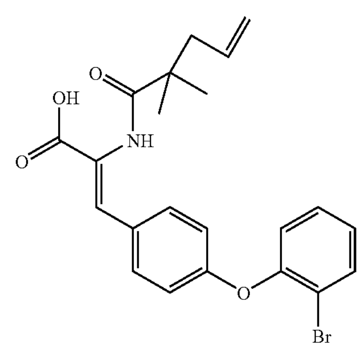 | (2Z)-3-[4-(2-bromophenoxy)phenyl]-2-[(2,2-dimethylpent-4-enoyl)amino]acrylic acid; or V00116667 |
| 557. | 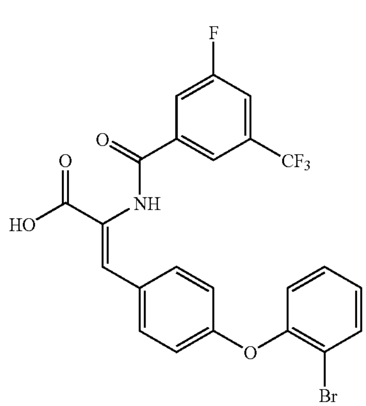 | (2Z)-3-[4-(2-bromophenoxy)phenyl]-2-{[3-fluoro-5-(trifluoromethyl)benzoyl]amino}acrylic acid; or V00116734 |

| Compound Number | Structure | Name |
|---|---|---|
| 558. | 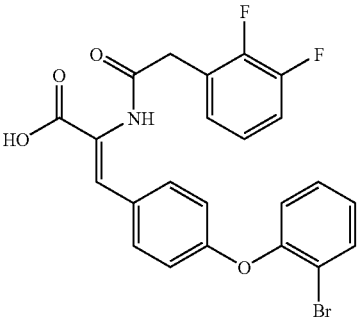 | (2Z)-3-[4-(2-bromophenoxy)phenyl]-2-{[(2,3-difluorophenyl)acetyl]amino}acrylic acid; or V00116657 |
| 559. | 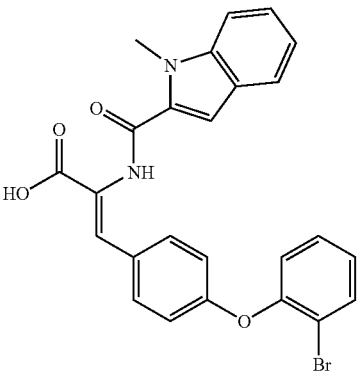 | (2Z)-3-[4-(2-bromophenoxy)phenyl]-2-{[(1-methyl-1H-indol-2-yl)carbonyl]amino}acrylic acid; or V00116645 |
| 560. | 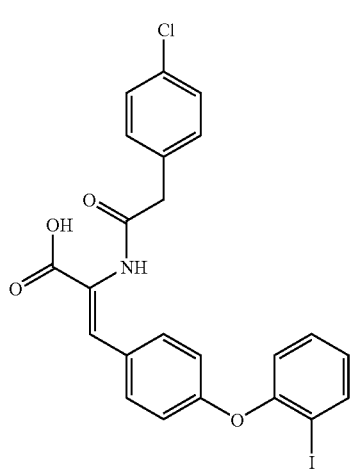 | (2Z)-2-{[(4-chlorophenyl)acetyl]amino}-3-[4-(2-iodophenoxy)phenyl]acrylic acid; |

-continued

| Compound Number | Structure | Name |
|---|---|---|
| 561. | 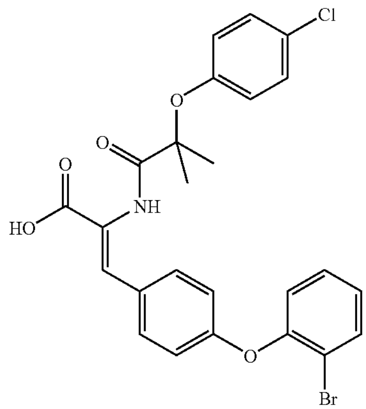 | V00116676 or (2Z)-3-[4-(2-bromophenoxy)phenyl]-2-{[2-(4-chlorophenoxy)-2-methylpropanoyl]amino}acrylic acid; or V00116676 |
| 562. | 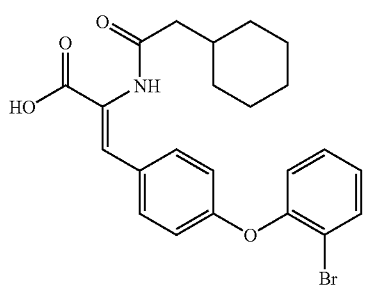 | (2Z)-3-[4-(2-bromophenoxy)phenyl]-2-[(cyclohexylacetyl)amino]acrylic acid; or V00116643 |
| 563. | 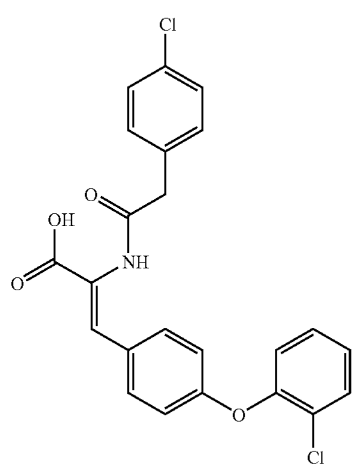 | (2Z)-3-[4-(2-chlorophenoxy)phenyl]-2-{[(4-chlorophenyl)acetyl]amino}acrylic acid; |

-continued
| Compound Number | Structure | Name |
|---|---|---|
| 564. | 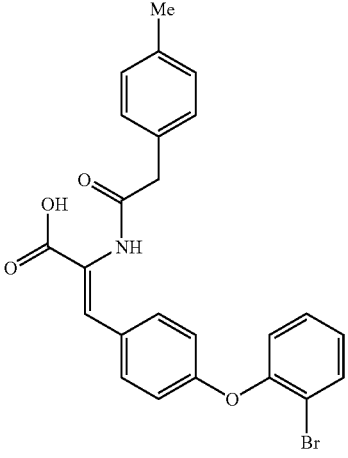 | (2Z)-3-[4-(2-bromophenoxy)phenyl]-2-{[(4-methylphenyl)acetyl]amino}acrylic acid; |
| 565. | 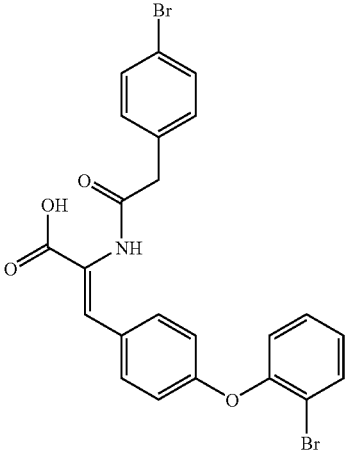 | (2Z)-3-[4-(2-bromophenoxy)phenyl]-2-{[(4-bromophenyl)acetyl]amino}acrylic acid; |
| 566. | 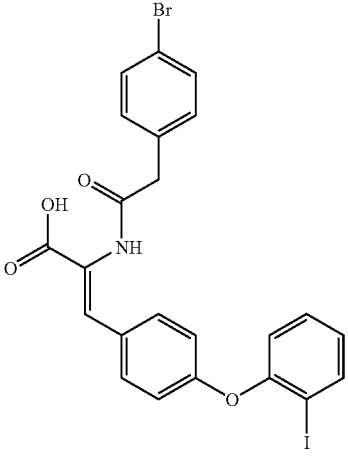 | (2Z)-2-{[(4-bromophenyl)acetyl]amino}-3-[4-(2-iodophenoxy)phenyl]acrylic acid; |

-continued

| Compound Number | Structure | Name |
|---|---|---|
| 567. | 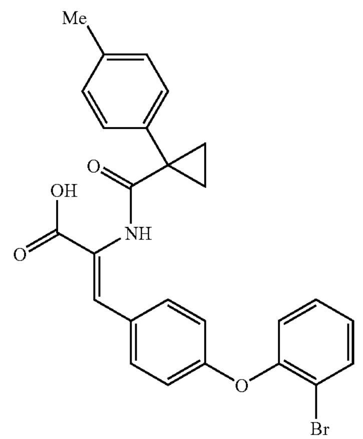 | (2Z)-3-[4-(2-bromophenoxy)phenyl]-2-({[1-(4-methylphenyl)cyclopropyl]carbonyl}amino)acrylic acid; or V00116670 |
| 568. | 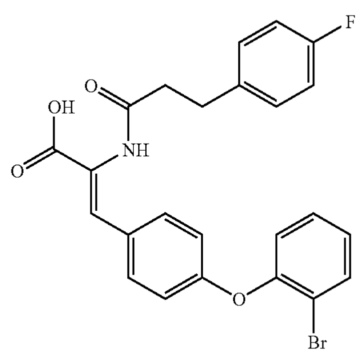 | (2Z)-3-[4-(2-bromophenoxy)phenyl]-2-{[3-(4-fluorophenyl)propanoyl]amino}acrylic acid; |
| 569. | 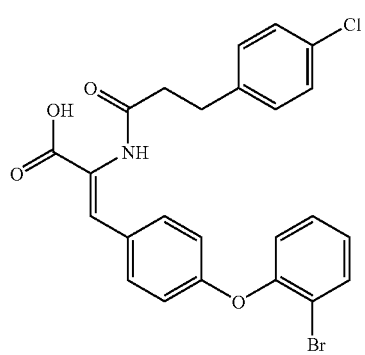 | (2Z)-3-[4-(2-bromophenoxy)phenyl]-2-{[3-(4-chlorophenyl)propanoyl]amino}acrylic acid; |
| 570. | 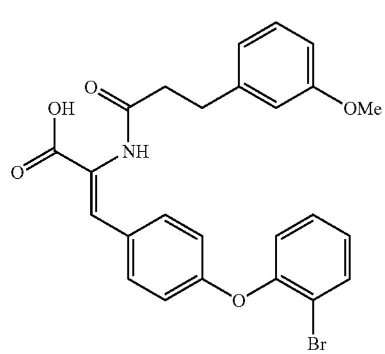 | (2Z)-3-[4-(2-bromophenoxy)phenyl]-2-{[3-(3-methoxyphenyl)propanoyl]amino}acrylic acid; |

-continued

| Compound Number | Structure | Name |
|---|---|---|
| 571. | 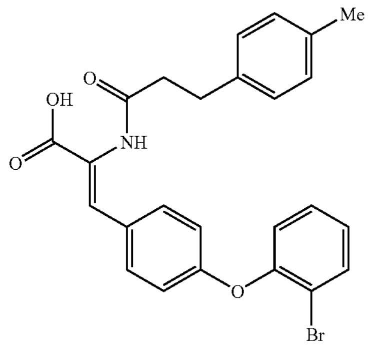 | (2Z)-3-[4-(2-bromophenoxy)phenyl]-2-{[3-(4-methylphenyl)propanoyl]amino}acrylic acid; |
| 572. | 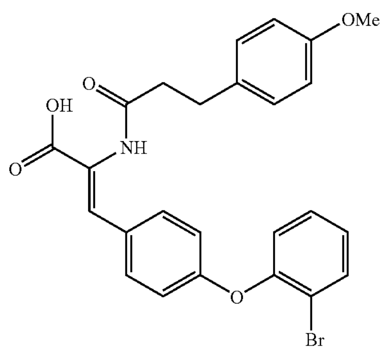 | (2Z)-3-[4-(2-bromophenoxy)phenyl]-2-{[3-(4-methoxyphenyl)propanoyl]amino}acrylic acid; |
| 573. | 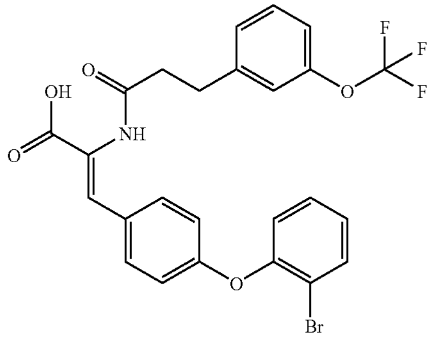 | (2Z)-3-[4-(2-bromophenoxy)phenyl]-2-({3-[3-(trifluoromethoxy)phenyl]propanoyl}amino)acrylic acid; |
| 574. | Diastereomeric Mixture | (2Z)-3-[4-(2-iodophenoxy)phenyl]-2-{[(4-methylcyclohexyl)acetyl]amino}acrylic acid; |

| Compound Number | Structure | Name |
|---|---|---|
| 575. | 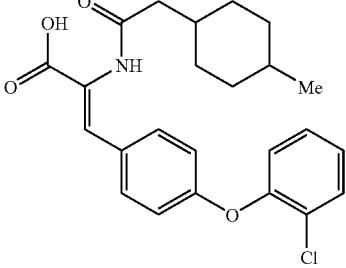<br>Diastereomeric Mixture | (2Z)-3-[4-(2-chlorophenoxy)phenyl]-2-{[(4-methylcyclohexyl)acetyl]amino}acrylic acid; |
| 576. | 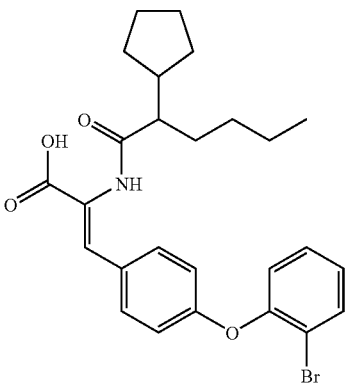<br>Racemic | (2Z)-3-[4-(2-bromophenoxy)phenyl]-2-[(2-cyclopentylhexanoyl)amino]acrylic acid; or V00116617 |
| 577. | 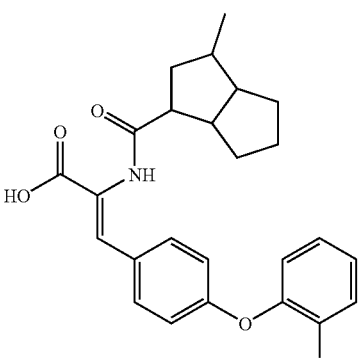<br>stereochemistry not determined | (2Z)-3-[4-(2-bromophenoxy)phenyl]-2-{[(3-methyloctahydropentalen-1-yl)carbonyl]amino}acrylic acid; |

-continued
| Compound Number | Structure | Name |
|---|---|---|
| 578. | 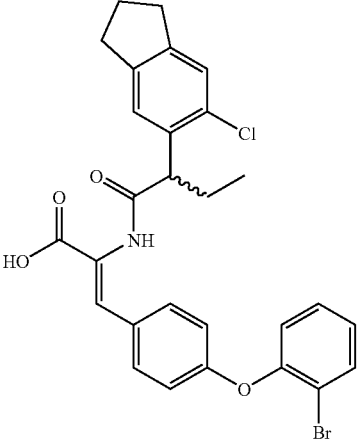<br>racemate | (2Z)-3-[4-(2-bromophenoxy)phenyl]-2-[2-(6-chloro-2,3-dihydro-1H-inden-5-yl)butanoyl]amino}acrylic acid; |
| 579. | 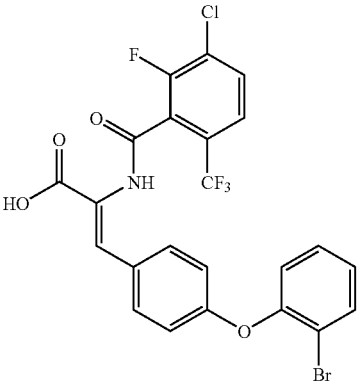 | (2Z)-3-[4-(2-bromophenoxy)phenyl]-2-{[3-chloro-2-fluoro-6-(trifluoromethyl)benzoyl]amino}acrylic acid; or V00116704 |
| 580. | 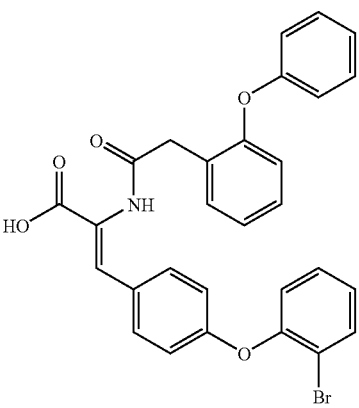 | (2Z)-3-[4-(2-bromophenoxy)phenyl]-2-{[(2-phenoxyphenyl)acetyl]amino}acrylic acid; |

-continued

| Compound Number | Structure | Name |
|---|---|---|
| 581. | 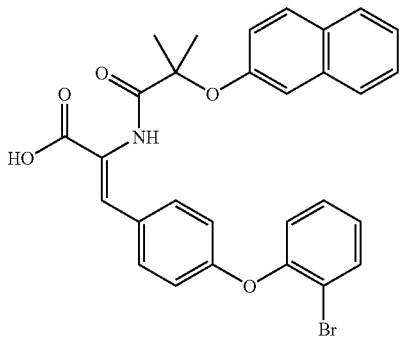 | (2Z)-3-[4-(2-bromophenoxy)phenyl]-2-{[2-methyl-2-(2-naphthyloxy)propanoyl]amino}acrylic acid; |
| 582. | 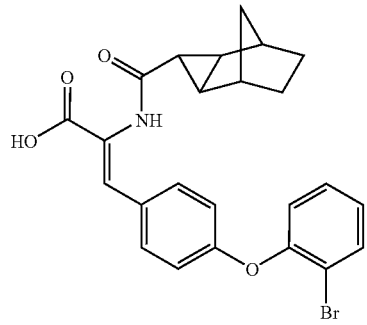 | (2Z)-3-[4-(2-bromophenoxy)phenyl]-2-[(tricyclo[3.2.1.0$^{2,4}$]oct-3-ylcarbonyl)amino]acrylic acid; |
| 583. | 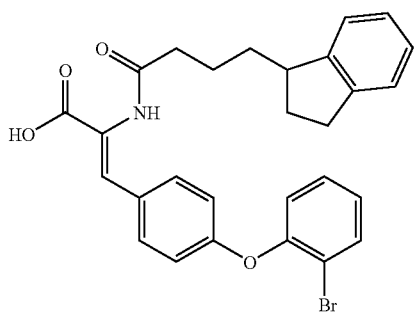<br>racemate | (2Z)-3-[4-(2-bromophenoxy)phenyl]-2-{[4-(2,3-dihydro-1H-inden-1-yl)butanoyl]amino}acrylic acid; |
| 584. | 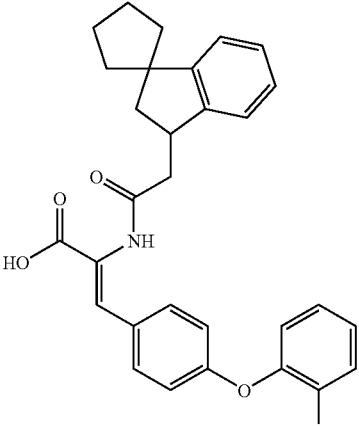<br>stereochemistry not determined | (2Z)-3-[4-(2-bromophenoxy)phenyl]-2-[(2',3'-dihydrospiro[cyclopentane-1,1'-inden]-3'-ylacetyl)amino]acrylic acid; |

-continued

| Compound Number | Structure | Name |
|---|---|---|
| 585. | 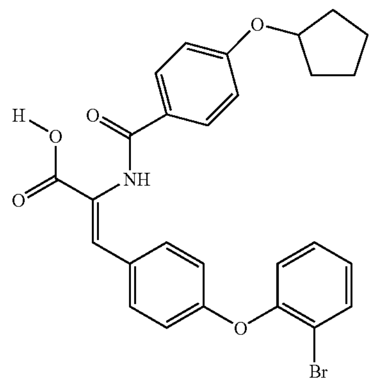 | (2Z)-3-[4-(2-bromophenoxy)phenyl]-2-{[4-(cyclopentyloxy)benzoyl]amino}acrylic acid; |
| 586. | 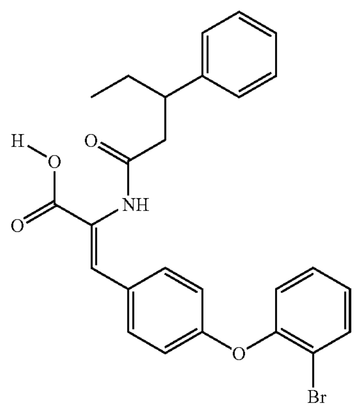 | (2Z)-3-[4-(2-bromophenoxy)phenyl]-2-[(3-phenylpentanoyl)amino]acrylic acid; |
| 587. | 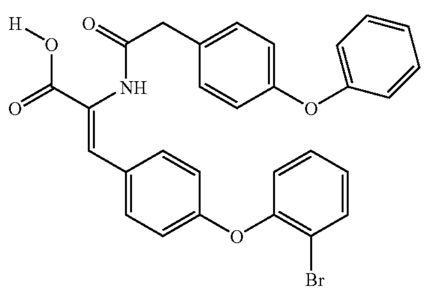 | (2Z)-3-[4-(2-bromophenoxy)phenyl]-2-{[(4-phenoxyphenyl)acetyl]amino}acrylic acid; or V00116652 |
| 588. | 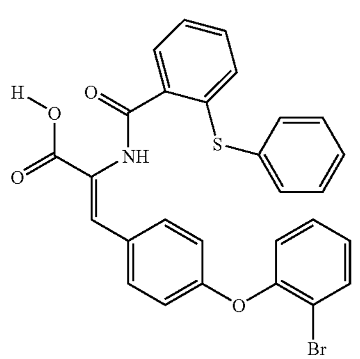 | (2Z)-3-[4-(2-bromophenoxy)phenyl]-2-{[2-(phenylthio)benzoyl]amino}acrylic acid; |

-continued

| Compound Number | Structure | Name |
| --- | --- | --- |
| 589. | 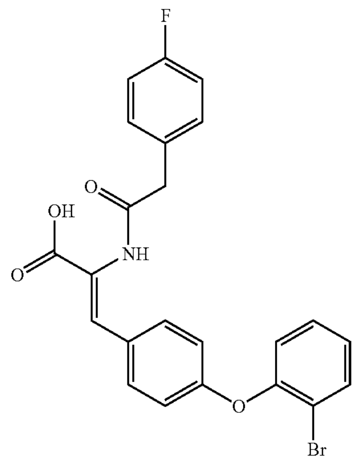 | (2Z)-3-[4-(2-bromophenoxy)phenyl]-2-{[(4-fluorophenyl)acetyl]amino}acrylic acid; |
| 590. | 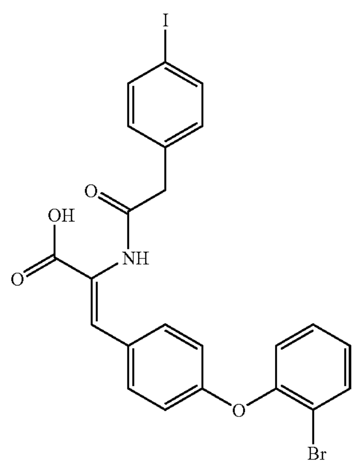 | (2Z)-3-[4-(2-bromophenoxy)phenyl]-2-{[(4-iodophenyl)acetyl]amino}acrylic acid; |
| 591. | 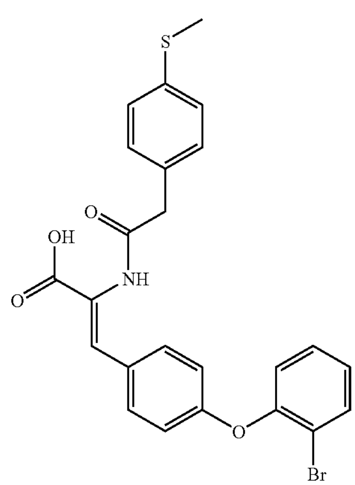 | (2Z)-3-[4-(2-bromophenoxy)phenyl]-2-({[4-(methylthio)phenyl]acetyl}amino)acrylic acid; |

-continued

| Compound Number | Structure | Name |
|---|---|---|
| 592. | 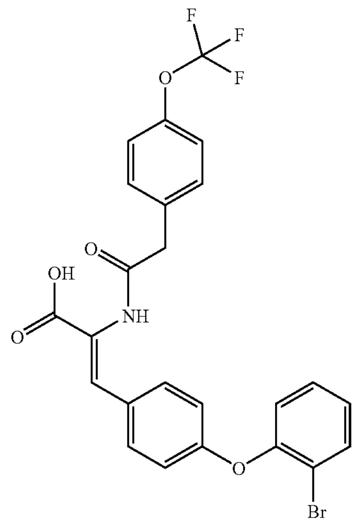 | (2Z)-3-[4-(2-bromophenoxy)phenyl]-2-({[4-(trifluoromethoxy)phenyl]acetyl}amino)acrylic acid; |
| 593. | 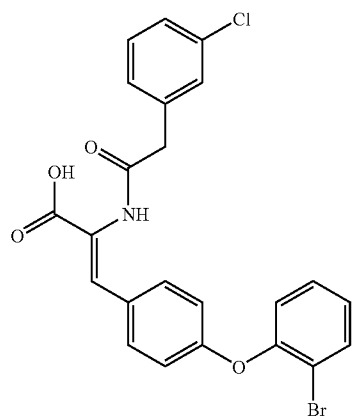 | (2Z)-3-[4-(2-bromophenoxy)phenyl]-2-{[(3-chlorophenyl)acetyl]amino}acrylic acid; |
| 594. | 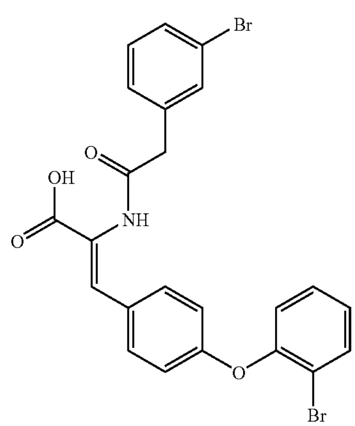 | (2Z)-3-[4-(2-bromophenoxy)phenyl]-2-{[(3-bromophenyl)acetyl]amino}acrylic acid; |

-continued

| Compound Number | Structure | Name |
|---|---|---|
| 595. | 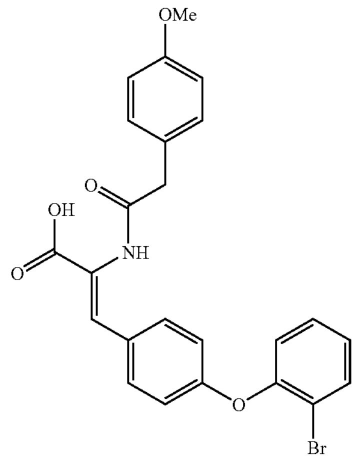 | (2Z)-3-[4-(2-bromophenoxy)phenyl]-2-{[(4-methoxyphenyl)acetyl]amino}acrylic acid; |
| 596. | 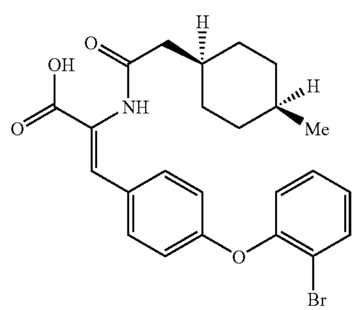 | (2Z)-3-[4-(2-bromophenoxy)phenyl]-2-{[(4-methylcyclohexyl)acetyl]amino}acrylic acid; or V00116660 |
| 597. | 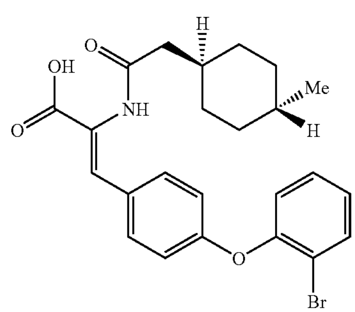 | (2Z)-3-[4-(2-bromophenoxy)phenyl]-2-{[(4-methylcyclohexyl)acetyl]amino}acrylic acid; or V00116660 |
| 598. | 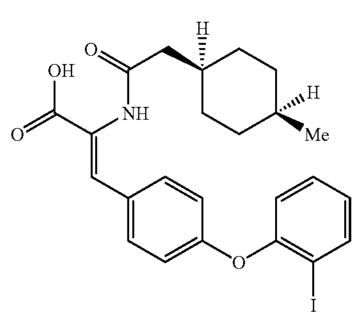 | (2Z)-3-[4-(2-iodophenoxy)phenyl]-2-{[(4-methylcyclohexyl)acetyl]amino}acrylic acid; |

-continued

| Compound Number | Structure | Name |
|---|---|---|
| 599. | 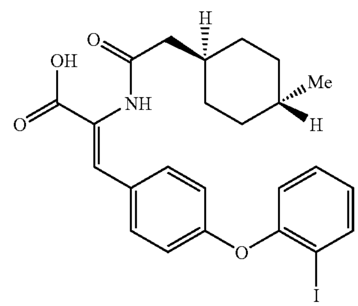 | (2Z)-3-[4-(2-iodophenoxy)phenyl]-2-{[(4-methylcyclohexyl)acetyl]amino}acrylic acid; |
| 600. | 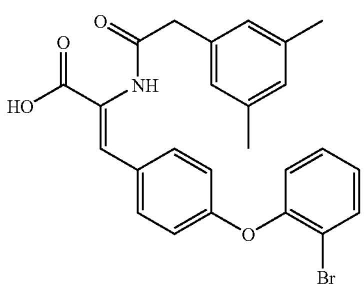 | (2Z)-3-[4-(2-bromophenoxy)phenyl]-2-{[(3,5-dimethylphenyl)acetyl]amino}acrylic acid; or V00116651 |
| 601. | 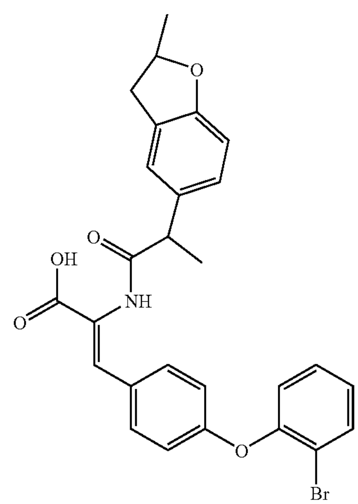 | (2Z)-3-[4-(2-bromophenoxy)phenyl]-2-{[2-(2-methyl-2,3-dihydro-1-benzofuran-5-yl)propanoyl]amino}acrylic acid; |
| 602. | 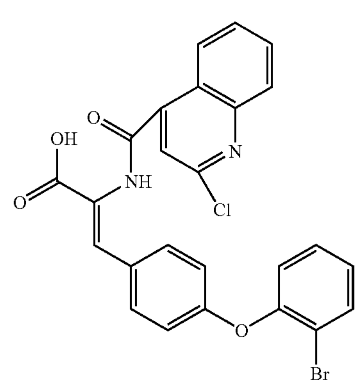 | (2Z)-3-[4-(2-bromophenoxy)phenyl]-2-{[(2-chloroquinolin-4-yl)carbonyl]amino}acrylic acid; |

-continued

| Compound Number | Structure | Name |
|---|---|---|
| 603. | 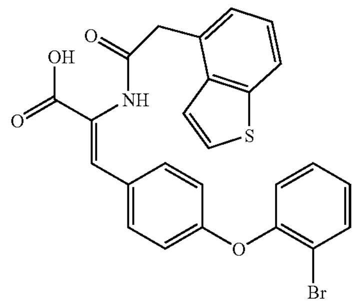 | (2Z)-2-[(1-benzothien-4-ylacetyl)amino]-3-[4-(2-bromophenoxy)phenyl]acrylic acid; |
| 604. | mixture of diastereomers | (2Z)-3-[4-(2-bromophenoxy)phenyl]-2-{[(2-methylcyclohexyl)carbonyl]amino}acrylic acid; or V00116669 |
| 605. | Racemic | (2Z)-3-[4-(2-bromophenoxy)phenyl]-2-{[2-methyl-2-(2-methyl-2,3-dihydro-1-benzofuran-5-yl)propanoyl]amino}acrylic acid; |
| 606. | 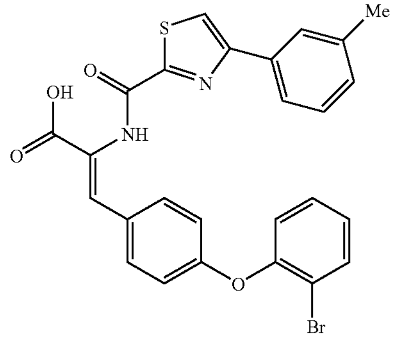 | (2Z)-3-[4-(2-bromophenoxy)phenyl]-2-({[4-(3-methylphenyl)-1,3-thiazol-2-yl]carbonyl}amino)acrylic acid; |

| Compound Number | Structure | Name |
|---|---|---|
| 607. | 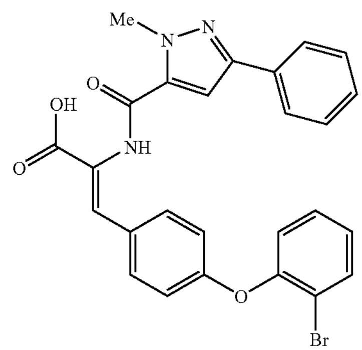 | (2Z)-3-[4-(2-bromophenoxy)phenyl]-2-{[(1-methyl-3-phenyl-1H-pyrazol-5-yl)carbonyl]amino}acrylic acid; |
| 608. | 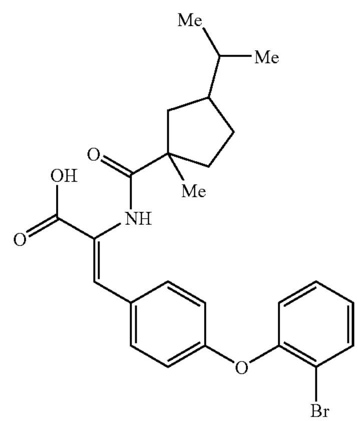 | (2Z)-3-[4-(2-bromophenoxy)phenyl]-2-{[(3-isopropyl-1-methylcyclopentyl)carbonyl]amino}acrylic acid; |
| 609. | 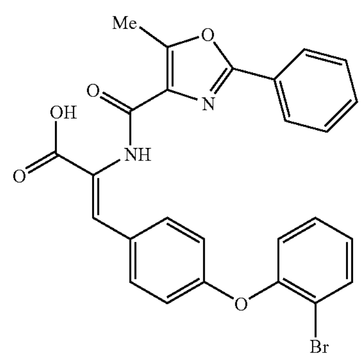 | (2Z)-3-[4-(2-bromophenoxy)phenyl]-2-{[(5-methyl-2-phenyl-1,3-oxazol-4-yl)carbonyl]amino}acrylic acid; |
| 610. | 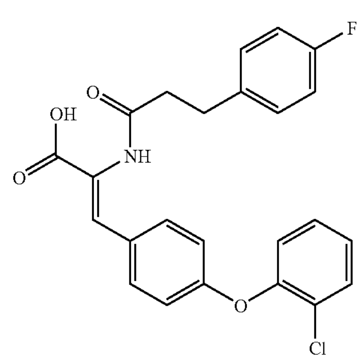 | (2Z)-3-[4-(2-chlorophenoxy)phenyl]-2-{[3-(4-fluorophenyl)propanoyl]amino}acrylic acid; |

-continued

| Compound Number | Structure | Name |
|---|---|---|
| 611. | 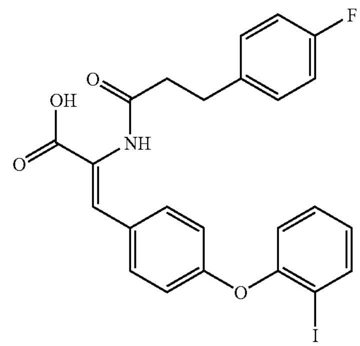 | (2Z)-2-{[3-(4-fluorophenyl)propanoyl]amino}-3-[4-(2-iodophenoxy)phenyl]acrylic acid; |
| 612. | 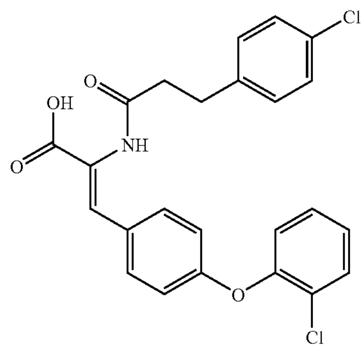 | (2Z)-3-[4-(2-chlorophenoxy)phenyl]-2-{[3-(4-chlorophenyl)propanoyl]amino}acrylic acid; |
| 613. | 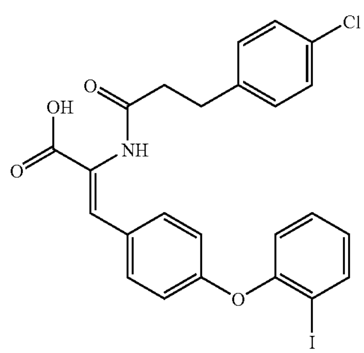 | (2Z)-2-{[3-(4-chlorophenyl)propanoyl]amino}-3-[4-(2-iodophenoxy)phenyl]acrylic acid; |
| 614. | 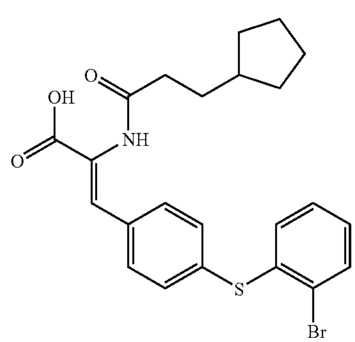 | (2Z)-3-{4-[(2-bromophenyl)thio]phenyl}-2-[(3-cyclopentylpropanoyl)amino]acrylic acid; |

-continued

| Compound Number | Structure | Name |
|---|---|---|
| 615. | 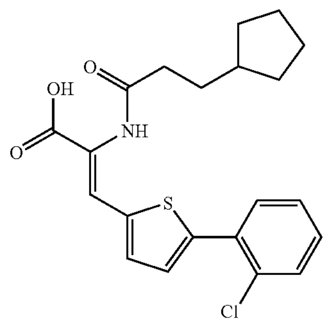 | (2Z)-3-[5-(2-chlorophenyl)thien-2-yl]-2-[(3-cyclopentylpropanoyl)amino]acrylic acid; |
| 616. | 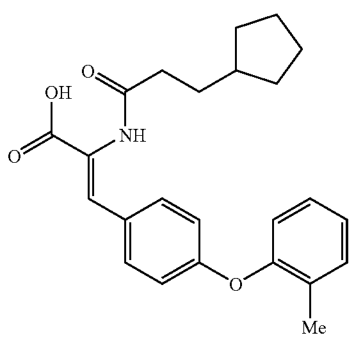 | (2Z)-2-[(3-cyclopentylpropanoyl)amino]-3-[4-(2-methylphenoxy)phenyl]acrylic acid; |
| 617. | A | sodium (2Z)-2-[(3-cyclopentylpropanoyl)amino]-3-[4-(2-methylphenoxy)phenyl]acrylate; |
| 618. | 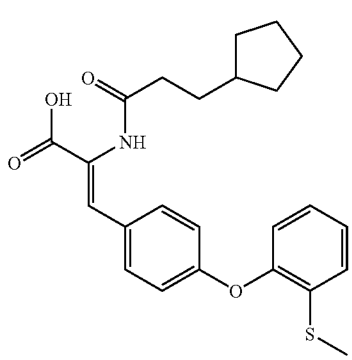 | (2Z)-2-[(3-cyclopentylpropanoyl)amino]-3-{4-[2-(methylthio)phenoxy]phenyl}acrylic acid; |

-continued
| Compound Number | Structure | Name |
|---|---|---|
| 619. | 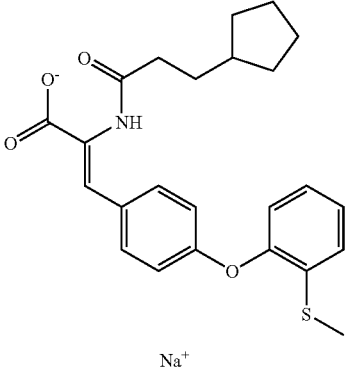 | sodium (2Z)-2-[(3-cyclopentylpropanoyl)amino]-3-{4-[2-(methylthio)phenoxy]phenyl}acrylate; |
| 620. | 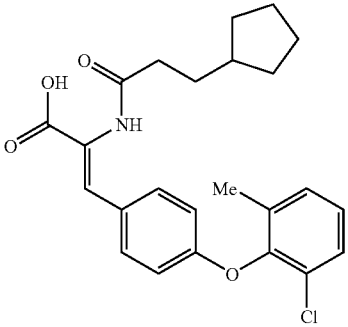 | (2Z)-3-[4-(2-chloro-6-methylphenoxy)phenyl]-2-[(3-cyclopentylpropanoyl)amino]acrylic acid; |
| 621. | 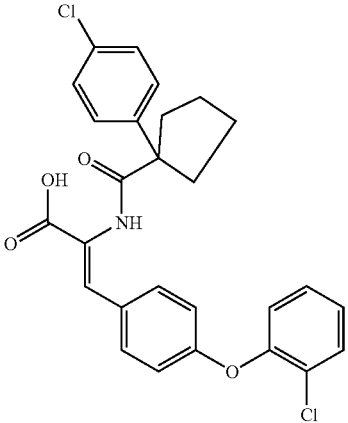 | (2Z)-3-[4-(2-chlorophenoxy)phenyl]-2-({[1-(4-chlorophenyl)cyclopentyl]carbonyl}amino)acrylic acid; |

-continued

| Compound Number | Structure | Name |
|---|---|---|
| 622. | 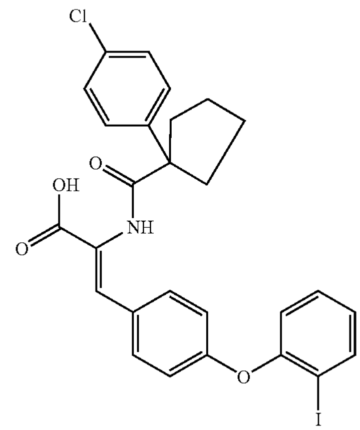 | (2Z)-2-({[1-(4-chlorophenyl)cyclopentyl]carbonyl}amino)-3-[4-(2-iodophenoxy)phenyl]acrylic acid; |
| 623. | 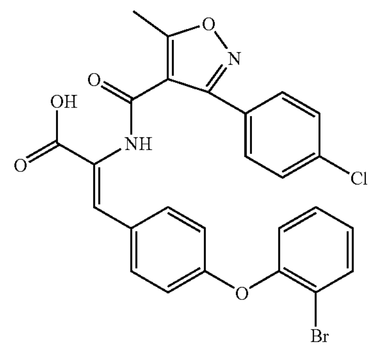 | (2Z)-3-[4-(2-bromophenoxy)phenyl]-2-({[3-(4-chlorophenyl)-5-methylisoxazol-4-yl]carbonyl}amino)acrylic acid; |
| 624. | 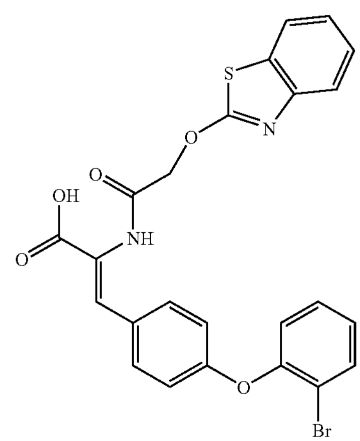 | (2Z)-2-{[(1,3-benzothiazol-2-yloxy)acetyl]amino}-3-[4-(2-bromophenoxy)phenyl]acrylic acid; |
| 625. | 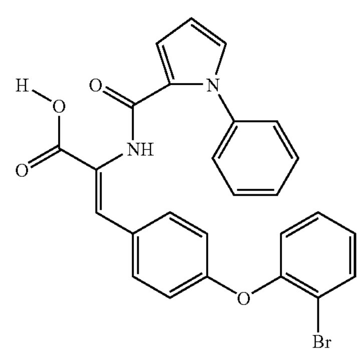 | (2Z)-3-[4-(2-bromophenoxy)phenyl]-2-{[(1-phenyl-1H-pyrrol-2-yl)carbonyl]amino}acrylic acid; |

-continued

| Compound Number | Structure | Name |
|---|---|---|
| 626. | 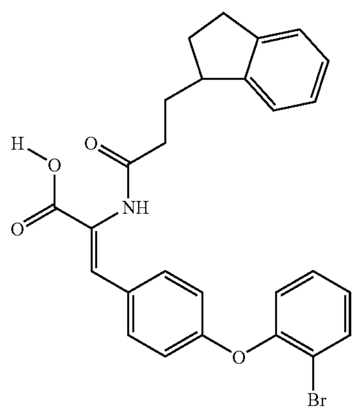 | (2Z)-3-[4-(2-bromophenoxy)phenyl]-2-{[3-(2,3-dihydro-1H-inden-1-yl)propanoyl]amino}acrylic acid; |
| 627. | ⓘ indicates text missing or illegible when filed | (2Z)-N-(aminosulfonyl)-3-[4-(2-bromophenoxy)phenyl]-2-[(3-cyclopentylpropanoyl)amino]acrylamide; |
| 628. | 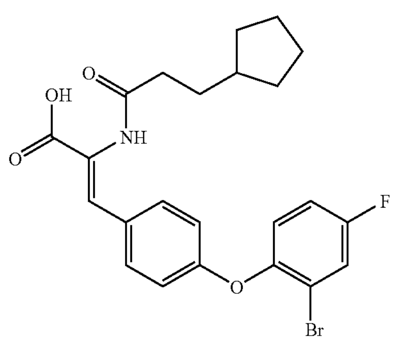 | (2Z)-3-[4-(2-bromo-4-fluorophenoxy)phenyl]-2-[(3-cyclopentylpropanoyl)amino]acrylic acid; |
| 629. | A | sodium (2Z)-3-[4-(2-bromo-4-fluorophenoxy)phenyl]-2-[(3-cyclopentylpropanoyl)amino]acrylate; |

-continued

| Compound Number | Structure | Name |
|---|---|---|
| 630. | 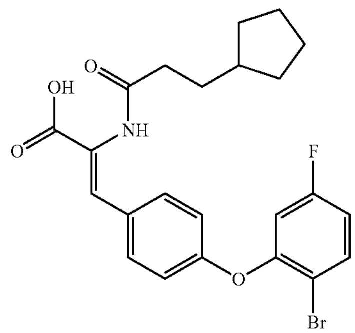 | (2Z)-3-[4-(2-bromo-5-fluorophenoxy)phenyl]-2-[(3-cyclopentylpropanoyl)amino]acrylic acid; |
| 631. | 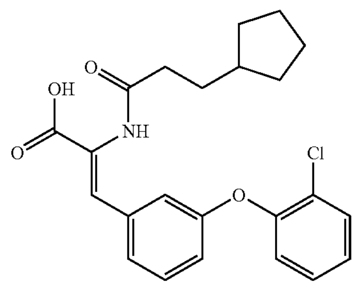 | (2Z)-3-[3-(2-chlorophenoxy)phenyl]-2-[(3-cyclopentylpropanoyl)amino]acrylic acid; |
| 632. | 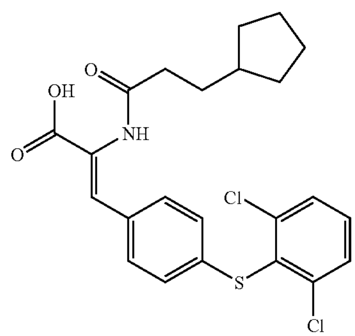 | (2Z)-2-[(3-cyclopentylpropanoyl)amino]-3-{4-[(2,6-dichlorophenyl)thio]phenyl}acrylic acid; |
| 633. | 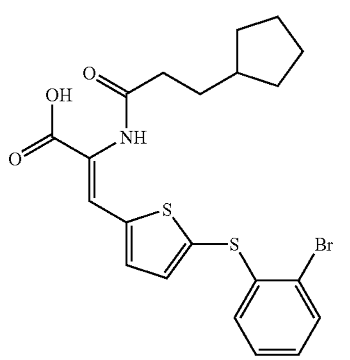 | (2Z)-3-{5-[(2-bromophenyl)thio]thien-2-yl}-2-[(3-cyclopentylpropanoyl)amino]acrylic acid; |

-continued

| Compound Number | Structure | Name |
|---|---|---|
| 634. | 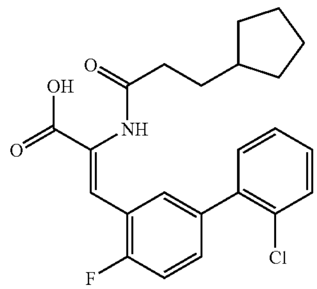 | (2Z)-3-(2'-chloro-4-fluoro-1,1'-biphenyl-3-yl)-2-[(3-cyclopentylpropanoyl)amino]acrylic acid; |
| 635. | 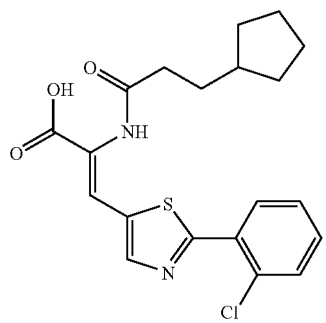 | (2Z)-3-[2-(2-chlorophenyl)-1,3-thiazol-5-yl]-2-[(3-cyclopentylpropanoyl)amino]acrylic acid; |
| 636. | 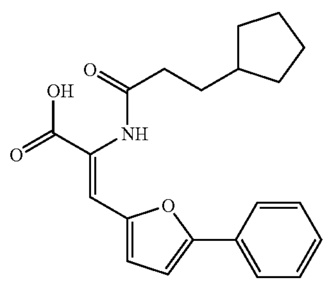 | (2Z)-2-[(3-cyclopentylpropanoyl)amino]-3-(5-phenyl-2-furyl)acrylic acid; |
| 637. | 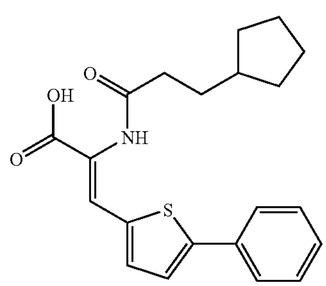 | (2Z)-2-[(3-cyclopentylpropanoyl)amino]-3-(5-phenylthien-2-yl)acrylic acid; |
| 638. | 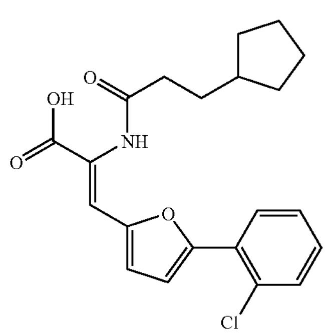 | (2Z)-3-[5-(2-chlorophenyl)-2-furyl]-2-[(3-cyclopentylpropanoyl)amino]acrylic acid; |

-continued

| Compound Number | Structure | Name |
|---|---|---|
| 639. | 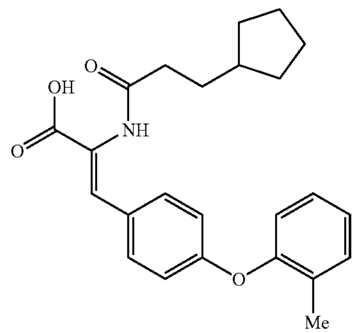 | (2Z)-2-[(3-cyclopentylpropanoyl)amino]-3-[4-(2-methoxyphenoxy)phenyl]acrylic acid; |
| 640. | 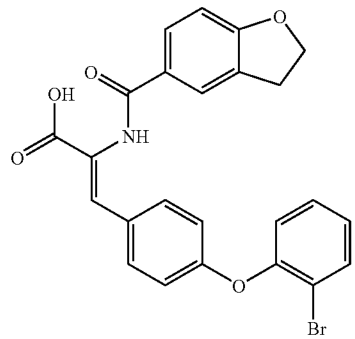 | (2Z)-3-[4-(2-bromophenoxy)phenyl]-2-[(2,3-dihydro-1-benzofuran-5-ylcarbonyl)amino]acrylic acid; |
| 641. | 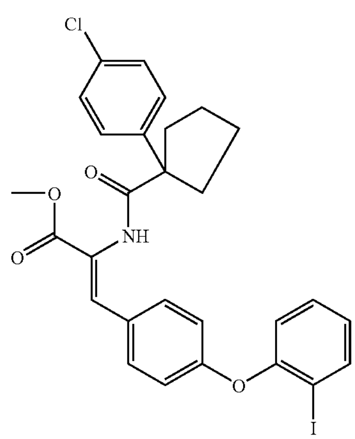 | methyl (2Z)-2-({[1-(4-chlorophenyl)cyclopentyl]carbonyl}amino)-3-[4-(2-iodophenoxy)phenyl]acrylate; |
| 642. | 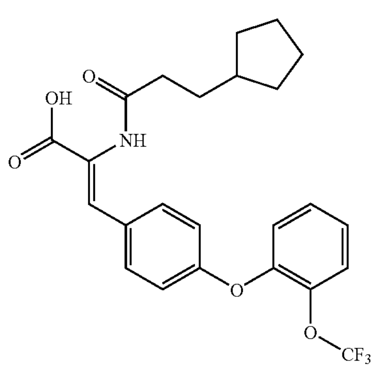 | (2Z)-2-[(3-cyclopentylpropanoyl)amino]-3-{4-[2-(trifluoromethoxy)phenoxy]phenyl}acrylic acid; |

-continued

| Compound Number | Structure | Name |
|---|---|---|
| 643. | 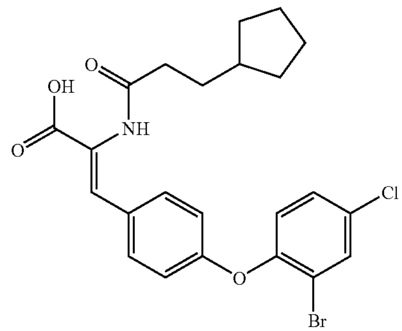 | (2Z)-3-[4-(2-bromo-4-chlorophenoxy)phenyl]-2-[(3-cyclopentylpropanoyl)amino]acrylic acid; |
| 644. | 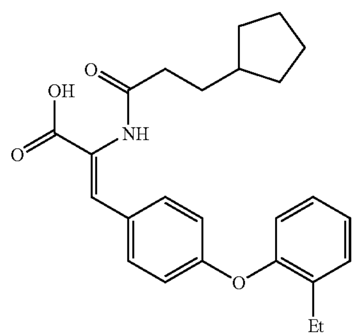 | (2Z)-2-[(3-cyclopentylpropanoyl)amino]-3-[4-(2-ethylphenoxy)phenyl]acrylic acid; |
| 645. | 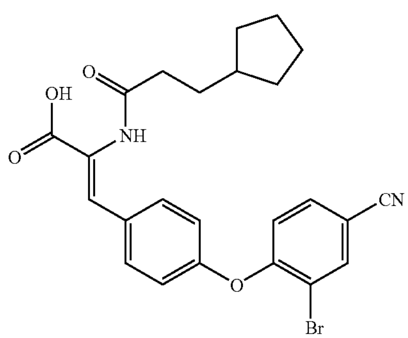 | (2Z)-3-[4-(2-bromo-4-cyanophenoxy)phenyl]-2-[(3-cyclopentylpropanoyl)amino]acrylic acid; |
| 646. | 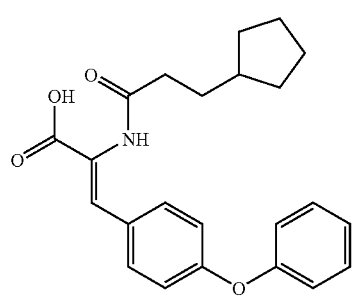 | (2Z)-2-[(3-cyclopentylpropanoyl)amino]-3-(4-phenoxyphenyl)acrylic acid; |

-continued

| Compound Number | Structure | Name |
|---|---|---|
| 647. | 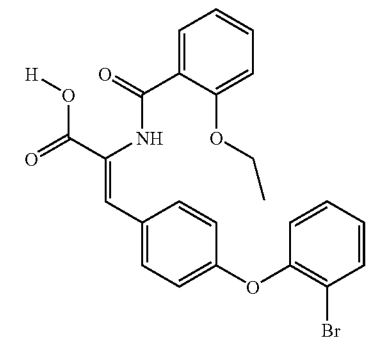 | (2Z)-3-[4-(2-bromophenoxy)phenyl]-2-[(2-ethoxybenzoyl)amino]acrylic acid; or V00116680 |
| 648. | 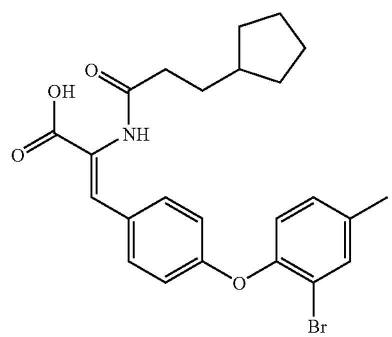 | (2Z)-3-[4-(2-bromo-4-methylphenoxy)phenyl]-2-[(3-cyclopentylpropanoyl)amino]acrylic acid; |
| 649. | Racemate | O-(2-chlorophenyl)-N-(3-cyclopentylpropanoyl)tyrosine; |
| 650. | 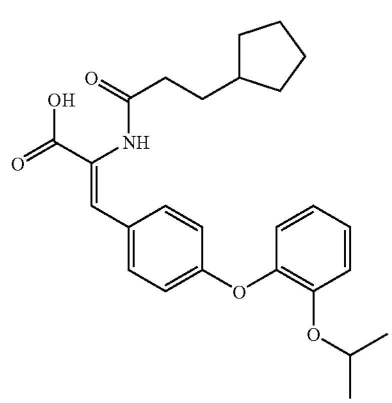 | (2Z)-2-[(3-cyclopentylpropanoyl)amino]-3-[4-(2-isopropoxyphenoxy)phenyl]acrylic acid; |

| Compound Number | Structure | Name |
|---|---|---|
| 651. | 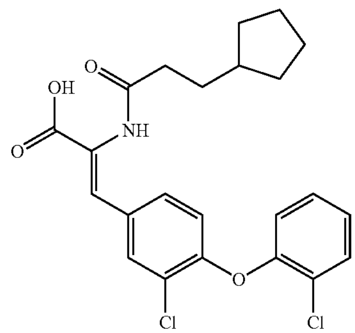 | (2Z)-3-[3-chloro-4-(2-chlorophenoxy)phenyl]-2-[(3-cyclopentylpropanoyl)amino]acrylic acid; |
| 652. | 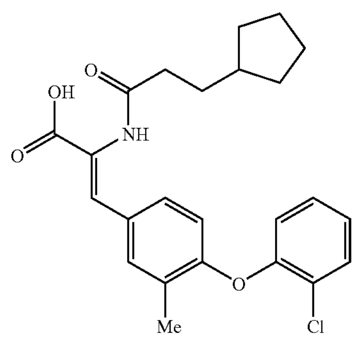 | (2Z)-3-[4-(2-chlorophenoxy)-3-methylphenyl]-2-[(3-cyclopentylpropanoyl)amino]acrylic acid; |
| 653. | 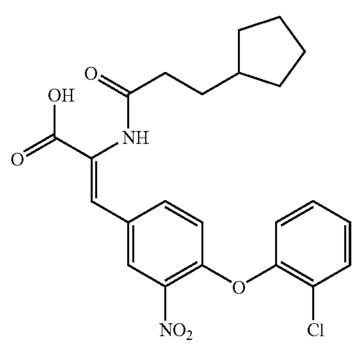 | (2Z)-3-[4-(2-chlorophenoxy)-3-nitrophenyl]-2-[(3-cyclopentylpropanoyl)amino]acrylic acid; |
| 654. | 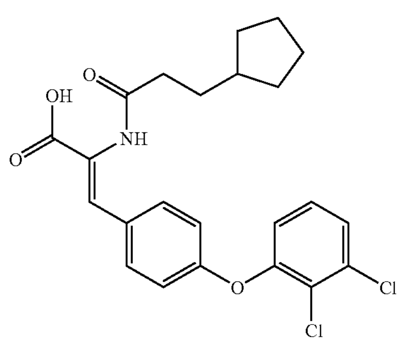 | (2Z)-2-[(3-cyclopentylpropanoyl)amino]-3-[4-(2,3-dichlorophenoxy)phenyl]acrylic acid; |

| Compound Number | Structure | Name |
|---|---|---|
| 655. | 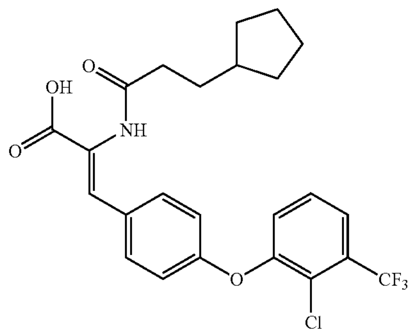 | (2Z)-3-{4-[2-chloro-3-(trifluoromethyl)phenoxy]phenyl}-2-[(3-cyclopentylpropanoyl)amino]acrylic acid; |
| 656. | 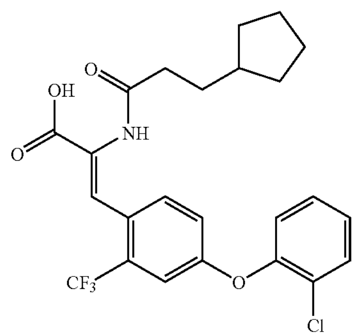 | (2Z)-3-[4-(2-chlorophenoxy)-2-(trifluoromethyl)phenyl]-2-[(3-cyclopentylpropanoyl)amino]acrylic acid; |
| 657. | 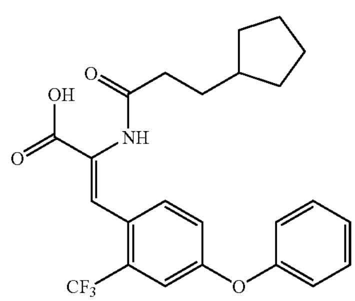 | (2Z)-2-[(3-cyclopentylpropanoyl)amino]-3-[4-phenoxy-2-(trifluoromethyl)phenyl]acrylic acid; |
| 658. | 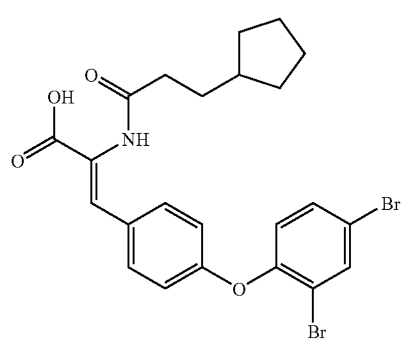 | (2Z)-2-[(3-cyclopentylpropanoyl)amino]-3-[4-(2,4-dibromophenoxy)phenyl]acrylic acid; |

-continued

| Compound Number | Structure | Name |
|---|---|---|
| 659. | 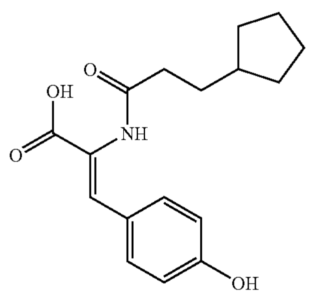 | (2Z)-2-[(3-cyclopentylpropanoyl)amino]-3-(4-hydroxyphenyl)acrylic acid; |
| 660. | 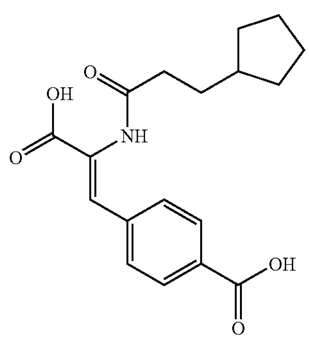 | 4-{(Z)-2-carboxy-2-[(3-cyclopentylpropanoyl)amino]vinyl}benzoic acid; |
| 661. | 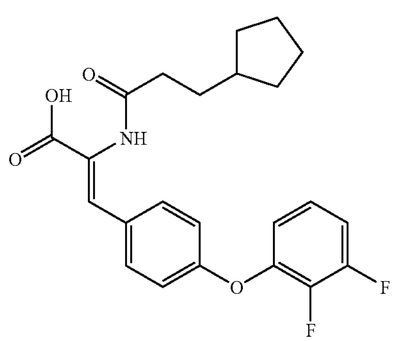 | (2Z)-2-[(3-cyclopentylpropanoyl)amino]-3-[4-(2,3-difluorophenoxy)phenyl]acrylic acid; |
| 662. | 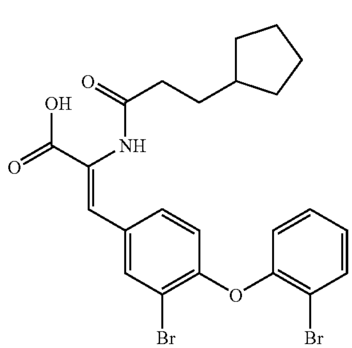 | (2Z)-3-[3-bromo-4-(2-bromophenoxy)phenyl]-2-[(3-cyclopentylpropanoyl)amino]acrylic acid; |

-continued

| Compound Number | Structure | Name |
|---|---|---|
| 663. | 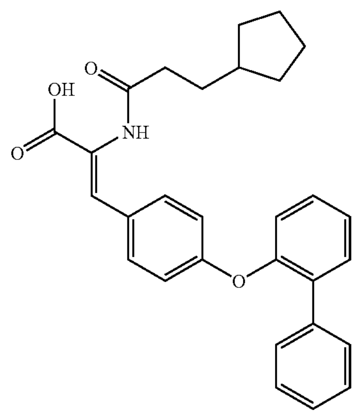 | (2Z)-3-[4-(1,1'-biphenyl-2-yloxy)phenyl]-2-[(3-cyclopentylpropanoyl)amino]acrylic acid; |
| 664. | 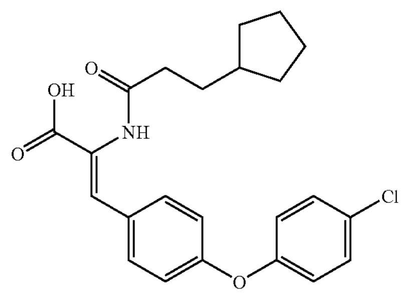 | (2Z)-3-[4-(4-chlorophenoxy)phenyl]-2-[(3-cyclopentylpropanoyl)amino]acrylic acid; |
| 665. | 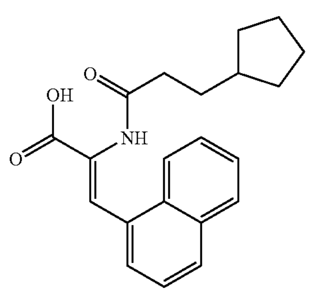 | (2Z)-2-[(3-cyclopentylpropanoyl)amino]-3-(1-naphthyl)acrylic acid; |
| 666. | 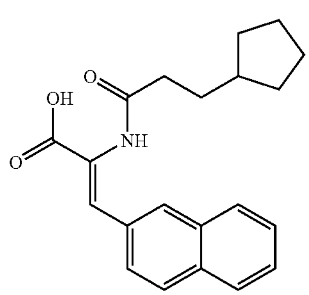 | (2Z)-2-[(3-cyclopentylpropanoyl)amino]-3-(2-naphthyl)acrylic acid; |

-continued

| Compound Number | Structure | Name |
|---|---|---|
| 667. | 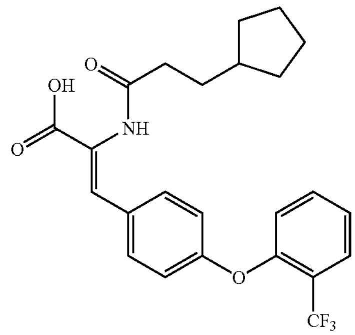 | (2Z)-2-[(3-cyclopentylpropanoyl)amino]-3-{4-[2-(trifluoromethyl)phenoxy]phenyl}acrylic acid; |
| 668. | 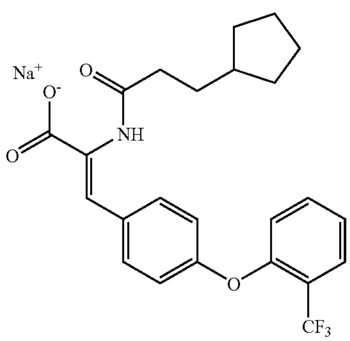 | sodium (2Z)-2-[(3-cyclopentylpropanoyl)amino]-3-{4-[2-(trifluoromethyl)phenoxy]phenyl}acrylate; |
| 669. | 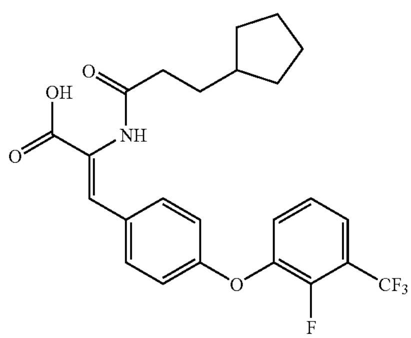 | (2Z)-2-[(3-cyclopentylpropanoyl)amino]-3-{4-[2-fluoro-3-(trifluoromethyl)phenoxy]phenyl}acrylic acid; |
| 670. | 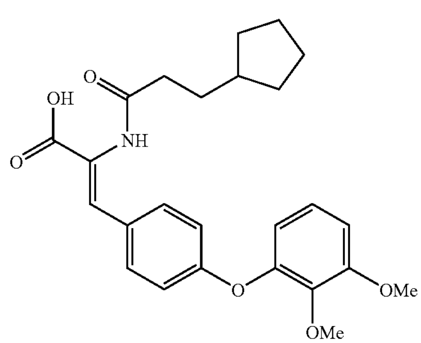 | (2Z)-2-[(3-cyclopentylpropanoyl)amino]-3-[4-(2,3-dimethoxyphenoxy)phenyl]acrylic acid; |

| Compound Number | Structure | Name |
|---|---|---|
| 671. | 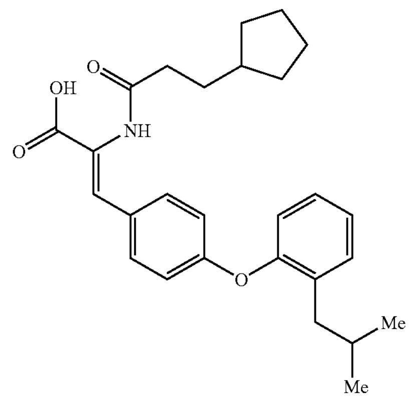 | (2Z)-2-[(3-cyclopentylpropanoyl)amino]-3-[4-(2-isobutylphenoxy)phenyl]acrylic acid; |
| 672. | 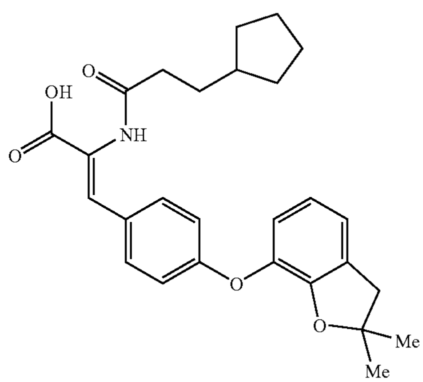 | (2Z)-2-[(3-cyclopentylpropanoyl)amino]-3-{4-[(2,2-dimethyl-2,3-dihydro-1-benzofuran-7-yl)oxy]phenyl}acrylic acid; |
| 673. | 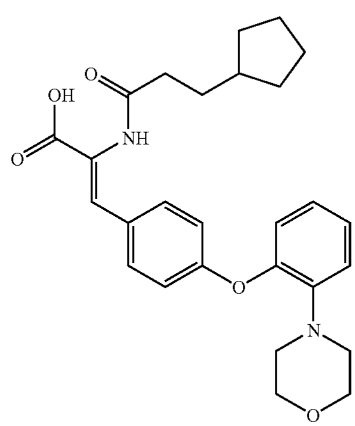 | (2Z)-2-[(3-cyclopentylpropanoyl)amino]-3-[4-(2-morpholin-4-ylphenoxy)phenyl]acrylic acid |
| 674. | 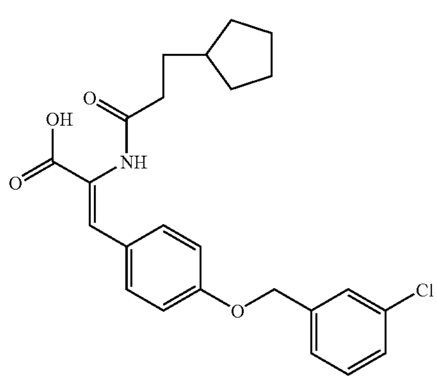 | (2Z)-3-{4-[(3-chlorobenzyl)oxy]phenyl}-2-[(3-cyclopentylpropanoyl)amino]acrylic acid; |

-continued

| Compound Number | Structure | Name |
|---|---|---|
| 675. | 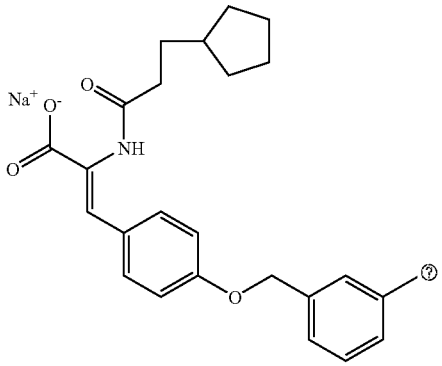 A  ⓘ indicates text missing or illegible when filed | sodium (2Z)-3-{4-[(3-chlorobenzyl)oxy]phenyl}-2-[(3-cyclopentylpropanoyl)amino]acrylate; |
| 676. | 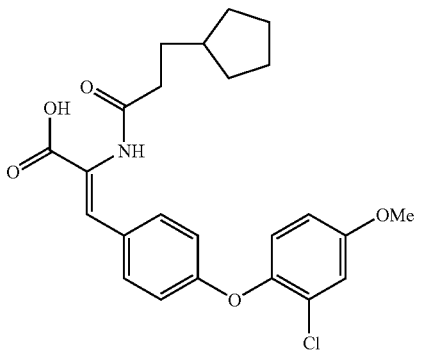 | (2Z)-3-[4-(2-chloro-4-methoxyphenoxy)phenyl]-2-[(3-cyclopentylpropanoyl)amino]acrylic acid; |
| 677. | 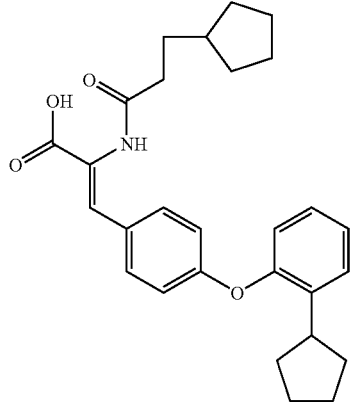 | (2Z)-3-[4-(2-cyclopentylphenoxy)phenyl]-2-[(3-cyclopentylpropanoyl)amino]acrylic acid; |
| 678. | 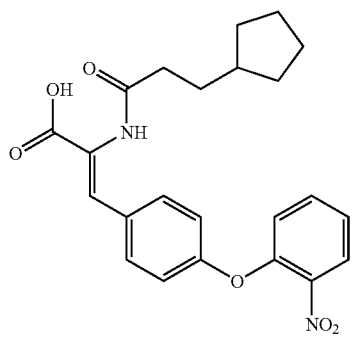 | (2Z)-2-[(3-cyclopentylpropanoyl)amino]-3-[4-(2-nitrophenoxy)phenyl]acrylic acid; |

-continued

| Compound Number | Structure | Name |
|---|---|---|
| 679. | 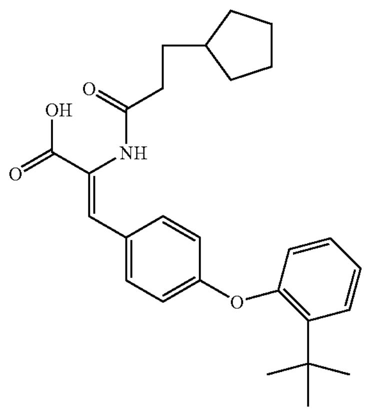 | (2Z)-3-[4-(2-tert-butylphenoxy)phenyl]-2-[(3-cyclopentylpropanoyl)amino]acrylic acid; |
| 680. | 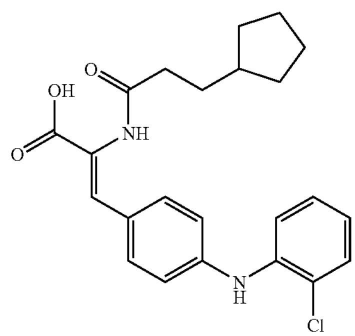 | (2Z)-3-{4-[(2-chlorophenyl)amino]phenyl}-2-[(3-cyclopentylpropanoyl)amino]acrylic acid; |
| 681. | 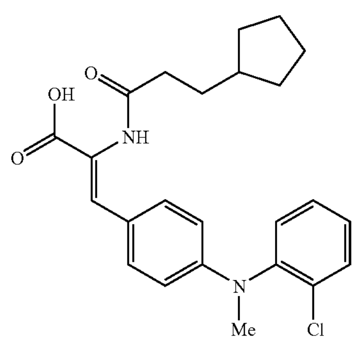 | (2Z)-3-{4-[(2-chlorophenyl)(methyl)amino]phenyl}-2-[(3-cyclopentylpropanoyl)amino]acrylic acid; |
| 682. | 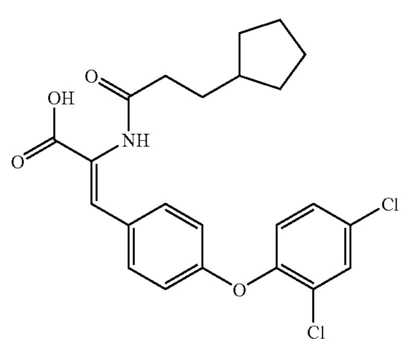 | (2Z)-3-[4-(4-chloro-2-methylphenoxy)phenyl]-2-[(3-cyclopentylpropanoyl)amino]acrylic acid; |

-continued

| Compound Number | Structure | Name |
|---|---|---|
| 683. | 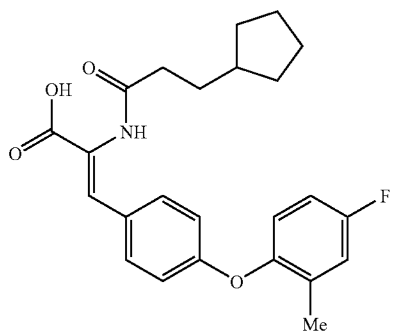 | (2Z)-2-[(3-cyclopentylpropanoyl)amino]-3-[4-(4-fluoro-2-methylphenoxy)phenyl]acrylic acid; |
| 684. | 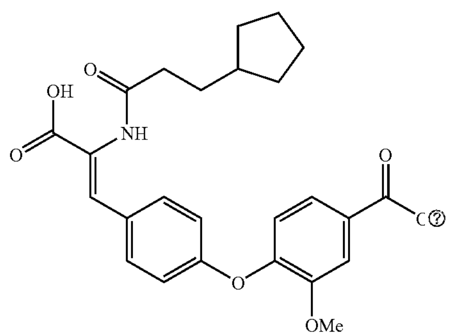 | 4-(4-{(Z)-2-carboxy-2-[(3-cyclopentylpropanoyl)amino]vinyl}phenoxy)-3-methoxybenzoic acid; |
| 685. | 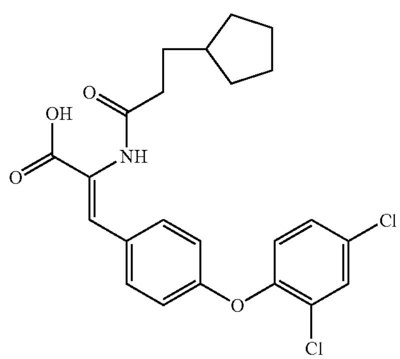 | (2Z)-2-[(3-cyclopentylpropanoyl)amino]-3-[4-(2,4-dichlorophenoxy)phenyl]acrylic acid; |
| 686. | 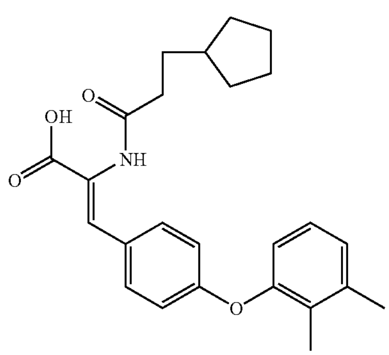 | (2Z)-2-[(3-cyclopentylpropanoyl)amino]-3-[4-(2,3-dimethylphenoxy)phenyl]acrylic acid; |

⊙ indicates text missing or illegible when filed

-continued

| Compound Number | Structure | Name |
| --- | --- | --- |
| 687. | A | sodium (2Z)-2-[(3-cyclopentylpropanoyl)amino]-3-[4-(2,3-dimethylphenoxy)phenyl]acrylate; |
| 688. | Racemic | (2Z)-2-(benzoylamino)-3-{4-[(2-oxocyclohexyl)oxy]phenyl}acrylic acid; |
| 689. | Stereoisomeric mixture | (2Z)-2-(benzoylamino)-3-{4-[(2-hydroxycyclohexyl)oxy]phenyl}acrylic acid; |
| 690. | 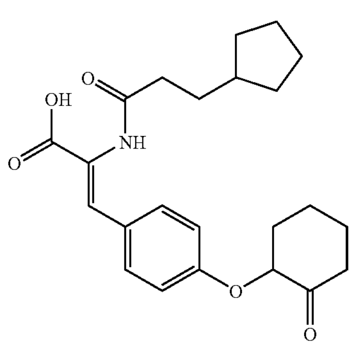 | (2Z)-2-[(3-cyclopentylpropanoyl)amino]-3-{4-[(2-oxocyclohexyl)oxy]phenyl}acrylic acid; |

-continued
| Compound Number | Structure | Name |
|---|---|---|
| 691. | 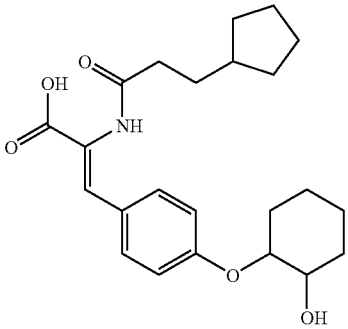<br>Stereoisomeric mixture | (2Z)-2-[(3-cyclopentylpropanoyl)amino]-3-{4-[(2-hydroxycyclohexyl)oxy]phenyl}acrylic acid; |
| 692. | 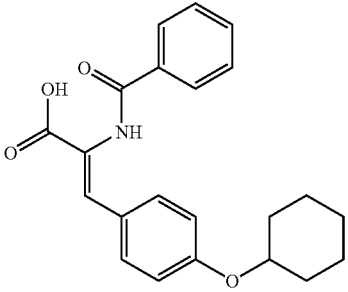 | (2Z)-2-(benzoylamino)-3-[4-(cyclohexyloxy)phenyl]acrylic acid; |
| 693. | 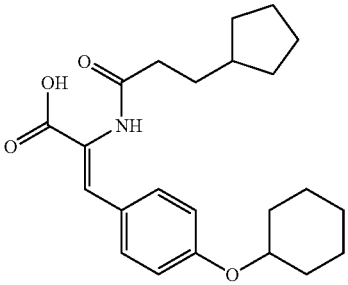 | (2Z)-3-[4-(cyclohexyloxy)phenyl]-2-[(3-cyclopentylpropanoyl)amino]acrylic acid; |
| 694. | 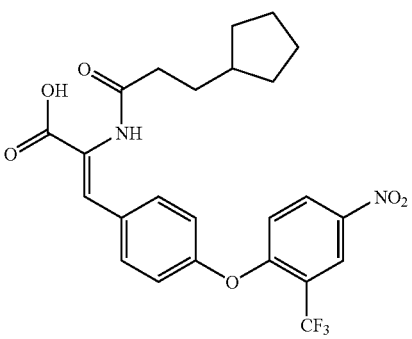 | (2Z)-2-[(3-cyclopentylpropanoyl)amino]-3-{4-[4-nitro-2-(trifluoromethyl)phenoxy]phenyl}acrylic acid; |

-continued

| Compound Number | Structure | Name |
|---|---|---|
| 695. | 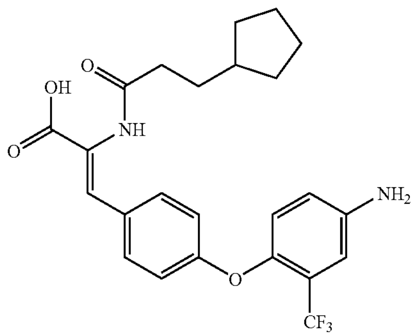 | (2Z)-3-{4-[4-amino-2-(trifluoromethyl)phenoxy]phenyl}-2-[(3-cyclopentylpropanoyl)amino]acrylic acid; |
| 696. | A ⓘ indicates text missing or illegible when filed | sodium (2Z)-3-{4-[4-amino-2-(trifluoromethyl)phenoxy]phenyl}-2-[(3-cyclopentylpropanoyl)amino]acrylate; |
| 697. | 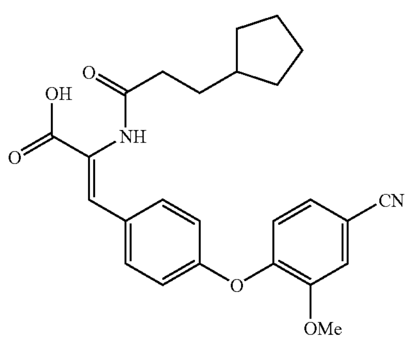 | (2Z)-3-[4-(4-cyano-2-methoxyphenoxy)phenyl]-2-[(3-cyclopentylpropanoyl)amino]acrylic acid; |
| 698. | 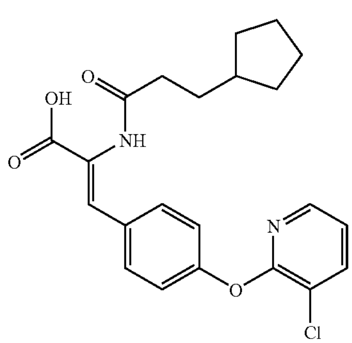 | (2Z)-3-{4-[(3-chloropyridin-2-yl)oxy]phenyl}-2-[(3-cyclopentylpropanoyl)amino]acrylic acid; |

-continued

| Compound Number | Structure | Name |
|---|---|---|
| 699. | 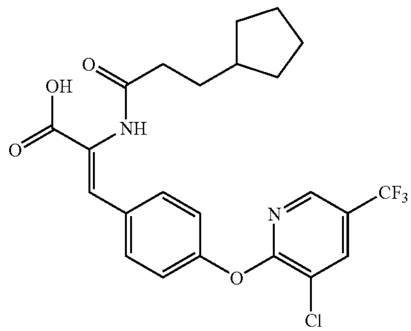 | (2Z)-3-(4-{[3-chloro-5-(trifluoromethyl)pyridin-2-yl]oxy}phenyl)-2-[(3-cyclopentylpropanoyl)amino]acrylic acid; |
| 700. | 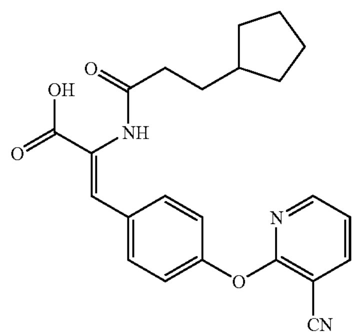 | (2Z)-3-{4-[(3-cyanopyridin-2-yl)oxy]phenyl}-2-[(3-cyclopentylpropanoyl)amino]acrylic acid; |
| 701. | 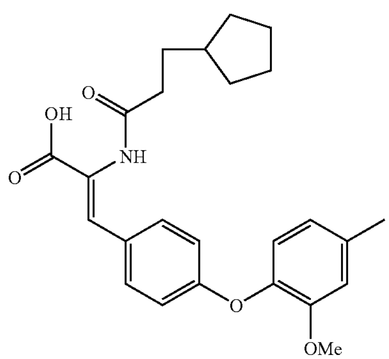 | (2Z)-2-[(3-cyclopentylpropanoyl)amino]-3-[4-(2-methoxy-4-methylphenoxy)phenyl]acrylic acid; |
| 702. | 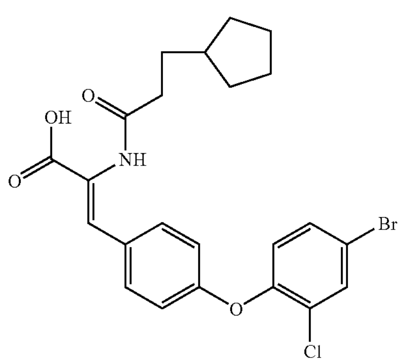 | (2Z)-3-[4-(4-bromo-2-chlorophenoxy)phenyl]-2-[(3-cyclopentylpropanoyl)amino]acrylic acid; |

-continued

| Compound Number | Structure | Name |
|---|---|---|
| 703. | 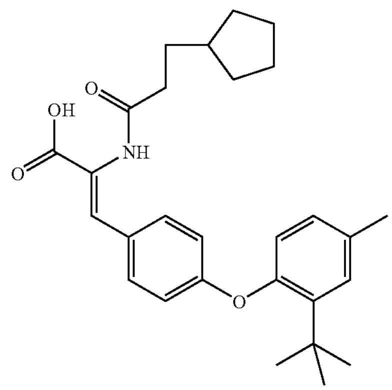 | (2Z)-3-[4-(2-tert-butyl-4-methylphenoxy)phenyl]-2-[(3-cyclopentylpropanoyl)amino]acrylic acid; |
| 704. | 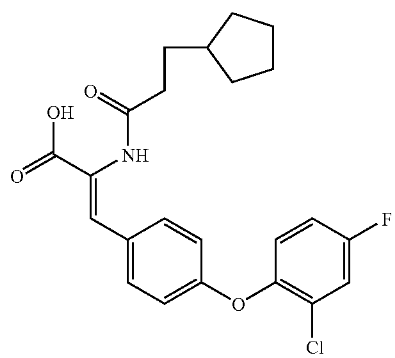 | (2Z)-3-[4-(2-chloro-4-fluorophenoxy)phenyl]-2-[(3-cyclopentylpropanoyl)amino]acrylic acid; |
| 705. | 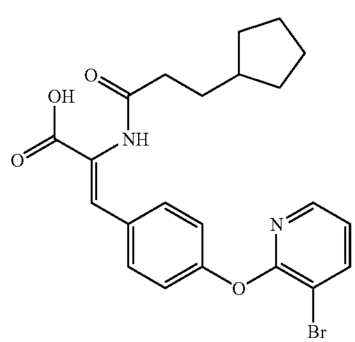 | (2Z)-3-{4-[(3-bromopyridin-2-yl)oxy]phenyl}-2-[(3-cyclopentylpropanoyl)amino]acrylic acid; |
| 706. | 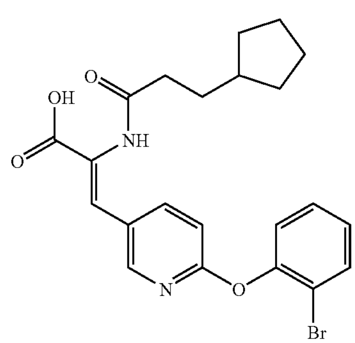 | (2Z)-3-[6-(2-bromophenoxy)pyridin-3-yl]-2-[(3-cyclopentylpropanoyl)amino]acrylic acid; |

-continued

| Compound Number | Structure | Name |
|---|---|---|
| 707. | 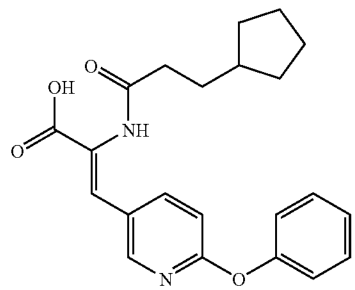 | (2Z)-2-[(3-cyclopentylpropanoyl)amino]-3-(6-phenoxypyridin-3-yl)acrylic acid; |
| 708. | 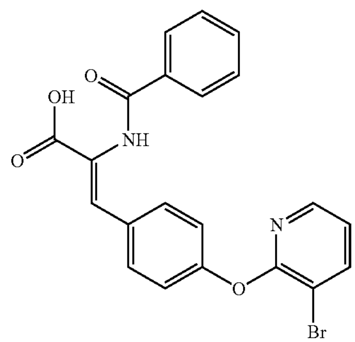 | (2Z)-2-(benzoylamino)-3-{4-[(3-bromopyridin-2-yl)oxy]phenyl}acrylic acid; |
| 709. | 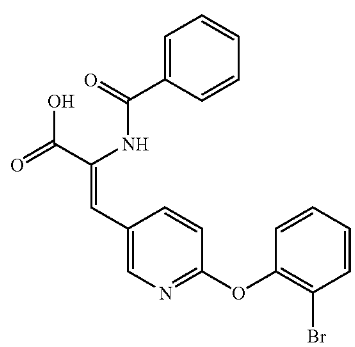 | (2Z)-2-(benzoylamino)-3-[6-(2-bromophenoxy)pyridin-3-yl]acrylic acid; |
| 710. | 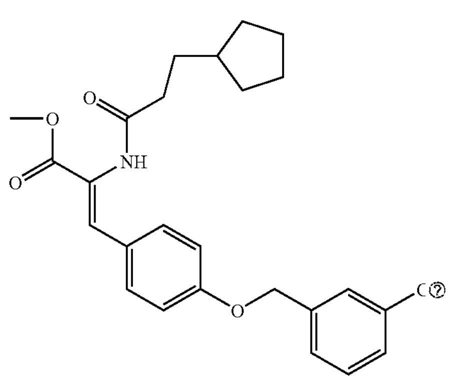 | methyl (2Z)-2-[(3-cyclopentylpropanoyl)amino]-3-{4-[(3-methoxybenzyl)oxy]phenyl}acrylate |

⓷ indicates text missing or illegible when filed

| Compound Number | Structure | Name |
|---|---|---|
| 711. | 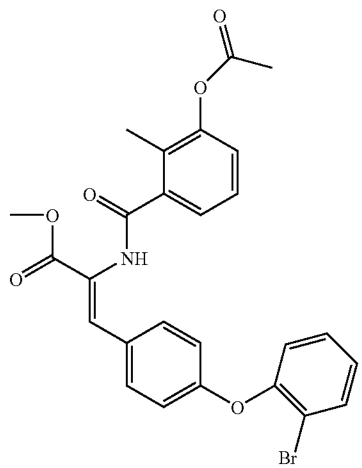 | methyl (2Z)-2-{[3-(acetyloxy)-2-methylbenzoyl]amino}-3-[4-(2-bromophenoxy)phenyl]acrylate |
| 712. | 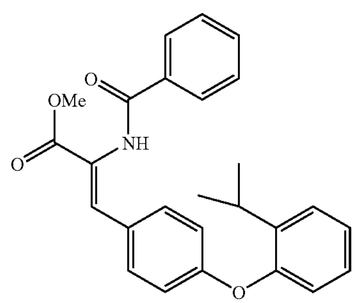 | methyl (2Z)-2-(benzoylamino)-3-[4-(2-isopropylphenoxy)phenyl]acrylate |
| 713. | 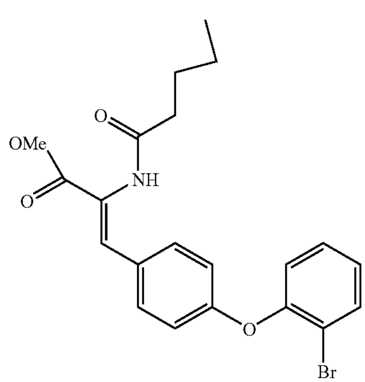 | methyl (2Z)-3-[4-(2-bromophenoxy)phenyl]-2-(pentanoylamino)acrylate |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of formula 1:

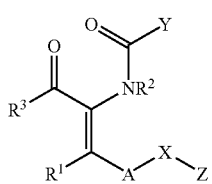

Formula 1 wherein: X represents a covalent bond or is selected from the group $NR^2$, S, O, C=O, $C(R^2)(R^{1'2})$, $CF_2$, $CCl_2$, $CR^2OR^{1'2}$, $CR^2NR^{1'2}$, SO, and $SO_2$;

Y is selected from the group substituted or unsubstituted alkyl, substituted or unsubstituted heteroalkyl, substituted or unsubstituted aryl, substituted or unsubstituted heteroaryl and substituted or unsubstituted heteroalkyl;

Z is selected from the group substituted or unsubstituted aryl and substituted or unsubstituted heteroaryl;

any two adjacent substiuents of Y or Z may be taken together to form a fused carbocyclic or heterocyclic ring of 5 to 7 members;

$R^1$ is selected from the group H, alkyl, hetero-$C_1$–$C_8$-alkyl, halogen, CN, halo $C_1$–$C_8$-alkyl, aryl, heteroaryl, cyclo-$C_1$–$C_8$-alkyl and ara-$C_1$–$C_8$-alkyl;

$R^2$ is H, $C_1$–$C^8$-alkyl, $C_1$–$C^8$-alkenyl, hetero $C_1$–$C_8$ alkyl, $C_1$–$C_8$ cycloalkyl, heterocyclo $C_1$–$C_8$ alkyl, aryl, ara $C_1$–$C_8$ alkyl, heteroaryl or heteroaralkyl;

$R^3$ is selected from the group H, OH, OR2, $N(R^2)(R^{1'2})$ and $N(R^2)$-T-W where T represents a substituted or unsubstituted alkyl or cycloalkyl group of 1–8 carbons;

W is selected from the group OH, $N(R^2)(R^{1'2})$, $CON(R^2)(R^{1'2})$, $OCON(R^2)(R^{1'2})$, $NCON(R^2)(R^{1'2})$ and $CO_2R^2$;

A represents a substituted or unsubstituted heteroaromatic ring of 5 or 6 members;

the substituents X and R1-double bond ($R^1C=$) are connected to A in a 1,2 1,3 or 1,4 spatial relationship; and the substituents A and $COR^3$ have an E (trans) configuration with respect to the double bond to which they are attached.

2. A pharmaceutical composition, comprising a pharmaceutically acceptable carrier and a therapeutically effective amount of a compound according to claim 1.

* * * * *